(12) United States Patent
Duncia et al.

(10) Patent No.: US 6,984,651 B2
(45) Date of Patent: *Jan. 10, 2006

(54) PIPERIDINE AMIDES AS MODULATORS OF CHEMOKINE RECEPTOR ACTIVITY

(75) Inventors: John V. Duncia, Hockessin, DE (US); Joseph B. Santella, Springfield, PA (US); Dean A. Wacker, Chadds Ford, PA (US); Wenqing Yao, Kennett Square, PA (US); Changsheng Zheng, Wilmington, DE (US)

(73) Assignee: Bristol-Myers Squibb Pharma, Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/635,946

(22) Filed: Aug. 7, 2003

(65) Prior Publication Data

US 2004/0082790 A1 Apr. 29, 2004

Related U.S. Application Data

(62) Division of application No. 09/885,550, filed on Jun. 29, 2001, now Pat. No. 6,638,950.
(60) Provisional application No. 60/213,066, filed on Jun. 21, 2000.

(51) Int. Cl.
*A61K 31/44* (2006.01)
*C07D 401/12* (2006.01)

(52) U.S. Cl. .................. 514/343; 514/381; 514/397; 514/406; 514/422; 514/428; 544/333; 546/197; 546/199; 546/276.4; 548/250; 548/314.7; 548/364.1; 548/517; 548/518; 548/567

(58) Field of Classification Search ............... 514/343, 514/381, 397, 406, 422, 428; 544/333; 548/250, 548/314.7, 364.1, 517, 518, 567; 546/197, 546/199, 276.4

See application file for complete search history.

(56) References Cited

U.S. PATENT DOCUMENTS

| | | | |
|---|---|---|---|
| 4,613,695 A | 9/1986 | Carlsson et al. | |
| 5,352,796 A | 10/1994 | Hoeger et al. | |
| 5,668,151 A | 9/1997 | Poindexter et al. | |
| 5,847,148 A | 12/1998 | Jacobsen et al. | |
| 5,880,128 A | 3/1999 | Doll et al. | |
| 5,994,364 A | 11/1999 | Njoroge et al. | |
| 5,998,447 A | 12/1999 | Stilz et al. | |

FOREIGN PATENT DOCUMENTS

| | | |
|---|---|---|
| DE | 2614189 | 10/1977 |
| EP | 0685463 | 2/1994 |
| EP | 0842943 | 11/1997 |
| EP | 0842945 | 11/1997 |
| EP | 659743 | 6/1998 |
| EP | 0903349 | 3/1999 |
| EP | 915088 | 5/1999 |
| WO | 92/03410 | 3/1992 |
| WO | 9301167 | 1/1993 |
| WO | 93/06108 | 4/1993 |
| WO | 93/21172 | 10/1993 |
| WO | 95/09859 | 4/1995 |
| WO | 95/13069 | 5/1995 |
| WO | 95/24186 | 9/1995 |
| WO | 96/14317 | 5/1996 |
| WO | 96/16981 | 6/1996 |
| WO | 97/09329 | 3/1997 |
| WO | 97/12876 | 4/1997 |
| WO | 9714689 | 4/1997 |
| WO | 97/23458 | 7/1997 |
| WO | 97/24325 | 7/1997 |
| WO | 98/04247 | 2/1998 |
| WO | 98/11092 | 3/1998 |
| WO | 98/25604 | 6/1998 |
| WO | 98/31359 | 7/1998 |
| WO | 98/31669 | 7/1998 |
| WO | WO 98/53814 | 12/1998 |
| WO | 99/50238 | 10/1999 |
| WO | WO 99/54321 | 10/1999 |
| WO | 00/00477 | 1/2000 |
| WO | 00/35449 | 6/2000 |
| WO | 00/35451 | 6/2000 |
| WO | 00/35452 | 6/2000 |
| WO | 00/35453 | 6/2000 |
| WO | 00/35454 | 6/2000 |
| WO | 00/35876 | 6/2000 |
| WO | 00/35877 | 6/2000 |
| WO | WO 01/00206 | 1/2001 |

OTHER PUBLICATIONS

Wyngaarden et al. "Cecil textbook of medicine" Saunders, p. 1397–98 (1983).*

Ikegami et al. "Preparation of azepine . . . " CA 135:137529 (2001).*

Atwal et al., "Binding of ATP–Sensitive Potassium Channel (KATP) Openers to Cardiac Membranes: Correlation of Binding Affinities with Cardioprotective and Smooth Muscle Relaxing Potencies", J. Med. Chem., vol. 41, pp. 271–275, 1998.

(Continued)

*Primary Examiner*—Celia Chang
(74) *Attorney, Agent, or Firm*—Mary VanAtten

(57) ABSTRACT

The present application describes modulators of CCR3 of formula (I):

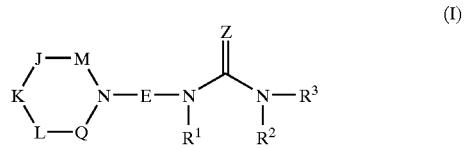

or pharmaceutically acceptable salt forms thereof, useful for the prevention of asthma and other allergic diseases.

13 Claims, No Drawings

OTHER PUBLICATIONS

Michael Gutschow, "One–Pot Reactions of N–(Mesyloxy)phthalimides with Secondary Amines to 2–Ureidobenzamides, 2–Ureidobenzoic Acids, Ethyl 2–Ureidobenzoates, or Isatoic Anhydrides", J. Org. Chem, vol. 64, pp. 5109–5115, 1999.

Jacobsen et al., Synthesis of a Series of Stromelysin–Selective Thiadiazole Urea Matrix Metalloprotease Inhibitors, Journal of Medicinal Chemistry, 1999, pp. 1525–1536, vol. 42, No. 9.

Freidinger et al., Novel Glutamic Acid Derived Cholecystokinin Receptor Ligands, Journal of Medicinal Chemistry, 1990, pp. 591–595, vol. 33, No. 2.

Capet et al., "Pyrrolidinines derivatives with a strong binding affinity for CCK and gastrin receptors", CA 122:31320 (1994).

Adams et al., "Early trauma polymorphonuclear neutrophil responses to chemokines are associated with development of sepsis, pneumonia, and organ failure", CA 136:261758 (2001).

Stedman's medical dictionary (2000), p. 897–898.

Harrison's principles of internal medicine (1994), p. 494–495.

* cited by examiner

PIPERIDINE AMIDES AS MODULATORS OF CHEMOKINE RECEPTOR ACTIVITY

CROSS-REFERENCE TO RELATED APPLICATION

This case is a divisional of Ser. No. 09/885,550 filed Jun. 20, 2001 now U.S. Pat. No. 6,638,950, which claims benefit to Provisional Application 60/213,066 filed Jun. 21 2000.

FIELD OF THE INVENTION

This invention relates generally to modulators of chemokine receptor activity, pharmaceutical compositions containing the same, and methods of using the same as agents for treatment and prevention of inflammatory diseases such as asthma and allergic diseases, as well as autoimmune pathologies such as rheumatoid arthritis and atherosclerosis.

BACKGROUND OF THE INVENTION

Chemokines are chemotactic cytokines, of molecular weight 6–15 kDa, that are released by a wide variety of cells to attract and activate, among other cell types, macrophages, T and B lymphocytes, eosinophils, basophils and neutrophils (reviewed in Luster, New Eng. J. Med., 338, 436–445 (1998) and Rollins, Blood, 90, 909–928 (1997)). There are two major classes of chemokines, CXC and CC, depending on whether the first two cysteines in the amino acid sequence are separated by a single amino acid (CXC) or are adjacent (CC). The CXC chemokines, such as interleukin-8 (IL-8), neutrophil-activating protein-2 (NAP-2) and melanoma growth stimulatory activity protein (MGSA) are chemotactic primarily for neutrophils and T lymphocytes, whereas the CC chemokines, such as RANTES, MIP-1α, MIP-1β, the monocyte chemotactic proteins (MCP-1, MCP-2, MCP-3, MCP-4, and MCP-5) and the eotaxins (-1, -2, and -3) are chemotactic for, among other cell types, macrophages, T lymphocytes, eosinophils, dendritic cells, and basophils. There also exist the chemokines lymphotactin-1, lymphotactin-2 (both C chemokines), and fractalkine (a CXXXC chemokine) that do not fall into either of the major chemokine subfamilies.

The chemokines bind to specific cell-surface receptors belonging to the family of G-protein-coupled seven-transmembrane-domain proteins (reviewed in Horuk, Trends Pharm. Sci., 15, 159–165 (1994)) which are termed "chemokine receptors." On binding their cognate ligands, chemokine receptors transduce an intracellular signal through the associated trimeric G proteins, resulting in, among other responses, a rapid increase in intracellular calcium concentration, changes in cell shape, increased expression of cellular adhesion molecules, degranulation, and promotion of cell migration. There are at least ten human chemokine receptors that bind or respond to CC chemokines with the following characteristic patterns: CCR-1 (or "CKR-1" or "CC-CKR-1") [MIP-1α, MCP-3, MCP-4, RANTES] (Ben-Barruch, et al., Cell, 72, 415–425 (1993), Luster, New Eng. J. Med., 338, 436–445 (1998)); CCR-2A and CCR-2B (or "CKR-2A"/"CKR-2B" or "CC-CKR-2A"/"CC-CKR-2B") [MCP-1, MCP-2, MCP-3, MCP-4, MCP-5] (Charo et al., Proc. Natl. Acad. Sci. USA, 91, 2752–2756 (1994), Luster, New Eng. J. Med., 338, 436–445 (1998)); CCR-3 (or "CKR-3" or "CC-CKR-3") [eotaxin-1, eotaxin-2, RANTES, MCP-3, MCP-4] (Combadiere, et al., J. Biol. Chem., 270, 16491–16494 (1995), Luster, New Eng. J. Med., 338, 436–445 (1998)); CCR-4 (or "CKR-4" or "CC-CKR-4") [TARC, MIP-1α, RANTES, MCP-1] (Power et al., J. Biol. Chem., 270, 19495–19500 (1995), Luster, New Eng. J. Med., 338, 436–445 (1998)); CCR-5 (or "CKR-5" OR "CC-CKR-5") [MIP-1α, RANTES, MIP-1β] (Sanson, et al., Biochemistry, 35, 3362–3367 (1996)); CCR-6 (or "CKR-6" or "CC-CKR-6") [LARC] (Baba et al., J. Biol. Chem., 272, 14893–14898 (1997)); CCR-7 (or "CKR-7" or "CC-CKR-7") [ELC] (Yoshie et al., J. Leukoc. Biol. 62, 634–644 (1997)); CCR-8 (or "CKR-8" or "CC-CKR-8") [I-309, TARC, MIP-1β] (Napolitano et al., J. Immunol., 157, 2759–2763 (1996), Bernardini et al., Eur. J. Immunol., 28, 582–588 (1998)); and CCR-10 (or "CKR-10" or "CC-CKR-10") [MCP-1, MCP-3] (Bonini et al, DNA and Cell Biol., 16, 1249–1256 (1997)).

In addition to the mammalian chemokine receptors, mammalian cytomegaloviruses, herpesviruses and poxviruses have been shown to express, in infected cells, proteins with the binding properties of chemokine receptors (reviewed by Wells and Schwartz, Curr. Opin. Biotech., 8, 741–748 (1997)). Human CC chemokines, such as RANTES and MCP-3, can cause rapid mobilization of calcium via these virally encoded receptors. Receptor expression may be permissive for infection by allowing for the subversion of normal immune system surveillance and response to infection. Additionally, human chemokine receptors, such as CXCR4, CCR2, CCR3, CCR5 and CCR8, can act as co-receptors for the infection of mammalian cells by microbes as with, for example, the human immunodeficiency viruses (HIV).

Chemokine receptors have been implicated as being important mediators of inflammatory, infectious, and immunoregulatory disorders and diseases, including asthma and allergic diseases, as well as autoimmune pathologies such as rheumatoid arthritis and atherosclerosis. For example, the chemokine receptor CCR-3 plays a pivotal role in attracting eosinophils to sites of allergic inflammation and in subsequently activating these cells. The chemokine ligands for CCR-3 induce a rapid increase in intracellular calcium concentration, increased expression of cellular adhesion molecules, cellular degranulation, and the promotion of eosinophil migration. Accordingly, agents which modulate chemokine receptors would be useful in such disorders and diseases. In addition, agents which modulate chemokine receptors would also be useful in infectious diseases such as by blocking infection of CCR3 expressing cells by HIV or in preventing the manipulation of immune cellular responses by viruses such as cytomegaloviruses.

A substantial body of art has accumulated over the past several decades with respect to substituted piperidines and pyrrolidines. These compounds have implicated in the treatment of a variety of disorders.

WO 98/25604 describes spiro-substituted azacycles which are useful as modulators of chemokine receptors:

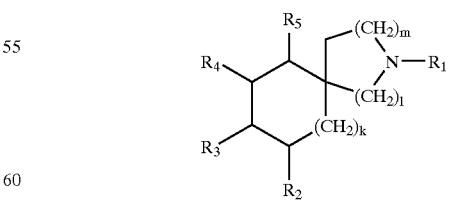

wherein $R_1$ is $C_{1-6}$ alkyl, optionally substituted with functional groups such as —$NR^6CONHR^7$, wherein $R^6$ and $R^7$ may be phenyl further substituted with hydroxy, alkyl, cyano, halo and haloalkyl. Such spiro compounds are not considered part of the present invention.

WO 95/13069 is directed to certain piperidine, pyrrolidine, and hexahydro-1H-azepine compounds of general formula:

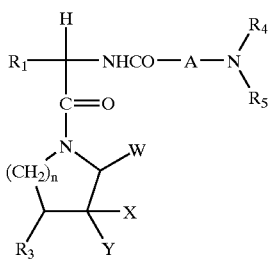

wherein A may be substituted alkyl or Z-substituted alkyl, with $Z=NR_{6a}$ or O. Compounds of this type are claimed to promote the release of growth hormone in humans and animals.

WO 93/06108 discloses pyrrolobenzoxazine derivatives as 5-hydroxytryptamine (5-HT) agonists and antagonists:

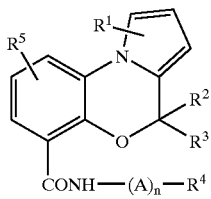

wherein A is lower alkylene and $R^4$ may be phenyl optionally substituted with halogen.

U.S. Pat. No. 5,668,151 discloses Neuropeptide Y (NPY) antagonists comprising 1,4-dihydropyridines with a piperidinyl or tetrahydropyridinyl-containing moiety attached to the 3-position of the 4-phenyl ring:

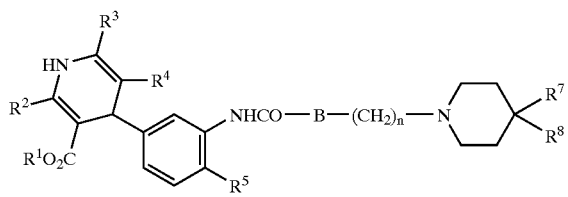

wherein B may be NH, $NR^1$, O, or a bond, and $R^7$ may be substituted phenyl, benzyl, phenethyl and the like.

Patent publication EP 0 903 349 A2 discloses CCR-3 receptor antagonists comprising cyclic amines of the following structure:

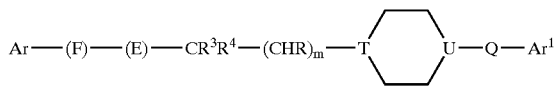

wherein T and U may be both nitrogen or one of T and U is nitrogen and the other is carbon and E may be —$NR^6CONR^5$— and others.

These reference compounds are readily distinguished structurally by either the nature of the urea functionality, the attachment chain, or the possible substitution of the present invention. The prior art does not disclose nor suggest the unique combination of structural fragments which embody these novel piperidine amides as having activity toward the chemokine receptors.

SUMMARY OF THE INVENTION

Accordingly, one object of the present invention is to provide novel agonists or antagonists of CCR-3, or pharmaceutically acceptable salts or prodrugs thereof.

It is another object of the present invention to provide pharmaceutical compositions comprising a pharmaceutically acceptable carrier and a therapeutically effective amount of at least one of the compounds of the present invention or a pharmaceutically acceptable salt or prodrug form thereof.

It is another object of the present invention to provide a method for treating inflammatory diseases and allergic disorders comprising administering to a host in need of such treatment a therapeutically effective amount of at least one of the compounds of the present invention or a pharmaceutically acceptable salt or prodrug form thereof.

It is another object of the present invention to provide novel piperidine amides for use in therapy.

It is another object of the present invention to provide the use of novel piperidine amides for the manufacture of a medicament for the treatment of allergic disorders.

These and other objects, which will become apparent during the following detailed description, have been achieved by the inventors' discovery that compounds of formula (I):

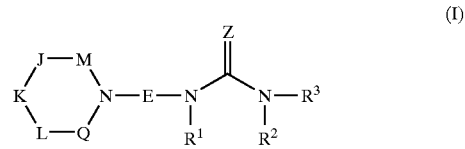

or stereoisomers or pharmaceutically acceptable salts thereof, wherein E, Z, M, J, K, L, Q, $R^1$, $R^2$, and $R^3$ are defined below, are effective modulators of chemokine activity.

DETAILED DESCRIPTION OF PREFERRED EMBODIMENTS

[1] Thus, in a first embodiment, the present invention provides novel compounds of formula (I):

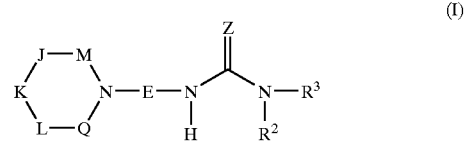

or stereoisomers or pharmaceutically acceptable salts thereof, wherein:

M is absent or selected from $CH_2$, $CHR^5$, $CHR^{13}$, $CR^{13}R^{13}$, and $CR^5R^{13}$;

Q is selected from $CH_2$, $CHR^5$, $CHR^{13}$, $CR^{13}R^{13}$, and $CR^5R^{13}$;

K is selected from $CH_2$, $CHR^5$ and $CHR^6$;

J and L are independently selected from $CH_2$, $CHR^5$, $CHR^6$, $CR^6R^6$ and $CR^5R^6$;

with the provisos:

1) at least one of M, J, K, L, or Q contains an $R^5$; and
2) when M is absent, J is selected from $CH_2$, $CHR^5$, $CHR^{13}$, and $CR^5R^{13}$;

Z is selected from O, S, $NR^{1a}$, $C(CN)_2$, $CH(NO_2)$, and CHCN;

$R^{1a}$ is selected from H, $C_{1-6}$ alkyl, $C_{3-6}$ cycloalkyl, $CONR^{1b}R^{1b}$, $OR^{1b}$, CN, $NO_2$, and $(CH_2)_n$phenyl;

$R^{1b}$ is independently selected from H, $C_{1-3}$ alkyl, $C_{3-6}$ cycloalkyl, and phenyl;

E is $-(C=O)-(CR^9R^{10})_v-(CR^{11}R^{12})-$, $-(SO_2)-(CR^9R^{10})_v-(CR^{11}R^{12})-$,

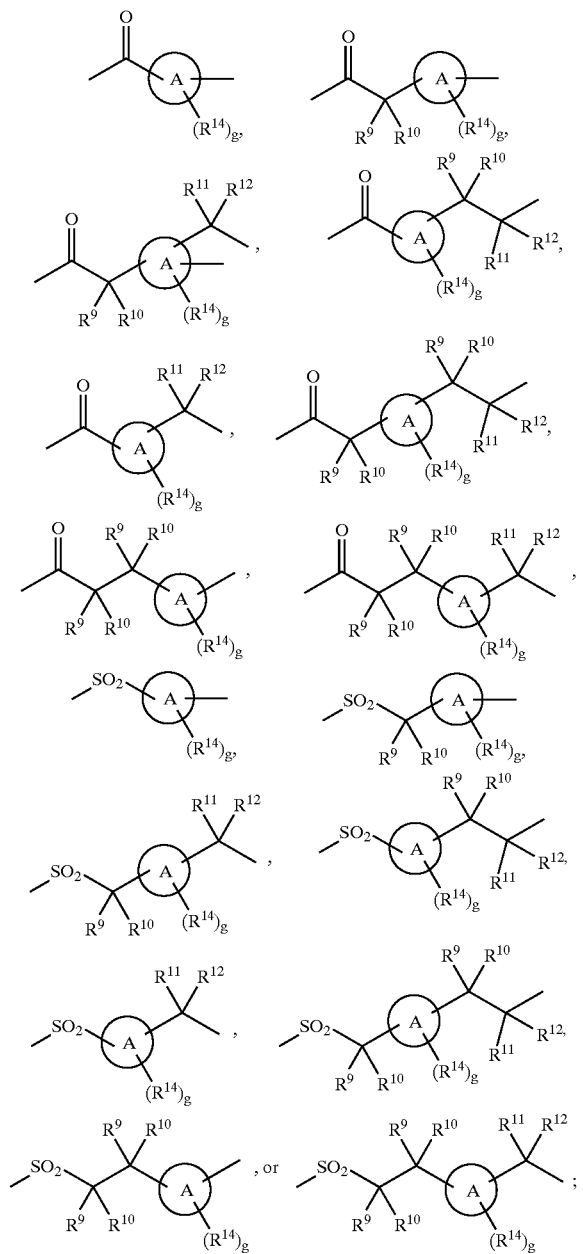

Ring A is a $C_{3-8}$ carbocyclic residue;

$R^2$ is selected from H, $C_{1-8}$ alkyl, $C_{3-8}$ alkenyl, $C_{3-8}$ alkynyl, and a $(CH_2)_r-C_{3-10}$ carbocyclic residue substituted with 0–5 $R^a$;

$R^a$, at each occurrence, is selected from $C_{1-4}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rNR^bR^b$, $(CH_2)_rOH$, $(CH_2)_r$ $OR^c$, $(CH_2)_rSH$, $(CH_2)_rSR^c$, $(CH_2)_rC(O)R^b$, $(CH_2)_rC(O)$ $NR^bR^b$, $(CH_2)_rNR^bC(O)R^b$, $(CH_2)_rC(O)OR^b$, $(CH_2)_rOC(O)R^c$, $(CH_2)_rCH(=NR^b)NR^bR^b$, $(CH_2)_rNHC(=NR^b)$ $NR^bR^b$, $(CH_2)_rS(O)_pR^c$, $(CH_2)_rS(O)_2NR^bR^b$, $(CH_2)_r$ $NR^bS(O)_2R^c$, and $(CH_2)_r$phenyl;

$R^b$, at each occurrence, is selected from H, $C_{1-6}$ alkyl, $C_{3-6}$ cycloalkyl, and phenyl;

$R^c$, at each occurrence, is selected from $C_{1-6}$ alkyl, $C_{3-6}$ cycloalkyl, and phenyl;

$R^3$ is selected from a $(CH_2)_rN(CH_3)_2$, $(CR^{3'}R^{3"})_r-C_{3-8}$ carbocyclic residue substituted with 0–5 $R^{15}$; a $(CR^{3'}R^{3"})_r$ $-C_{9-10}$ carbocyclic residue substituted with 0–4 $R^{15}$; and a $(CR^{3'}R^{3"})_r$-5–10 membered heterocyclic system containing 1–4 heteroatoms selected from N, O, and S, substituted with 0–3 $R^{15}$;

$R^{3'}$ and $R^{3"}$, at each occurrence, are selected from H, $C_{1-6}$ alkyl, $(CH_2)_rC_{3-6}$ cycloalkyl, and phenyl;

$R^5$ is selected from a $(CR^{5'}R^{5"})_r-C_{3-10}$ carbocyclic residue substituted with 0–5 $R^{16}$ and a $(CR^{5'}R^{5"})_r$-5–10 membered heterocyclic system containing 1–4 heteroatoms selected from N, O, and S, substituted with 0–3 $R^{16}$;

$R^{5'}$ and $R^{5"}$, at each occurrence, are selected from H, $C_{1-6}$ alkyl, $(CH_2)_rC_{3-6}$ cycloalkyl, and phenyl;

$R^6$, at each occurrence, is selected from $C_{1-6}$ alkyl, $C_{2-8}$ alkenyl, $C_{2-8}$ alkynyl, $(CH_2)_rC_{3-6}$ cycloalkyl, $(CF_2)_rCF_3$, CN, $(CH_2)_rNR^{6a}R^{6a'}$, $(CH_2)_rOH$, $(CH_2)_rOR^{6b}$, $(CH_2)_r$ SH, $(CH_2)_rSR^{6b}$, $(CH_2)_rC(O)OH$, $(CH_2)_rC(O)R^{6b}$, $(CH_2)_rC(O)NR^{6a}R^{6a'}$, $(CH_2)_rNR^{6d}C(O)R^{6a}$, $(CH_2)_rC(O)$ $OR^{6b}$, $(CH_2)_rOC(O)R^{6b}$, $(CH_2)_rS(O)_pR^{6b}$, $(CH_2)_rS(O)_2$ $NR^{6a}R^{6a'}$, $(CH_2)_rNR^{6d}S(O)_2R^{6b}$, and $(CH_2)_r$phenyl substituted with 0–3 $R^{6c}$;

$R^{6a}$ and $R^{6a'}$, at each occurrence, are selected from H, $C_{1-6}$ alkyl, $C_{3-6}$ cycloalkyl, and phenyl substituted with 0–3 $R^{6c}$;

$R^{6b}$, at each occurrence, is selected from $C_{1-6}$ alkyl, $C_{3-6}$ cycloalkyl, and phenyl substituted with 0–3 $R^{6c}$;

$R^{6c}$, at each occurrence, is selected from $C_{1-6}$ alkyl, $C_{3-6}$ cycloalkyl, Cl, F, Br, I, CN, $NO_2$, $(CF_2)_rCF_3$, $(CH_2)_r$ $OC_{1-5}$ alkyl, $(CH_2)_rOH$, $(CH_2)_rSC_{1-15}$ alkyl, and $(CH_2)_r$ $NR^{6d}R^{6d}$;

$R^{6d}$, at each occurrence, is selected from H, $C_{1-6}$ alkyl, and $C_{3-6}$ cycloalkyl;

with the proviso that when any of J, K, or L is $CR^6R^6$ and $R^6$ is halogen, cyano, nitro, or bonded to the carbon to which it is attached through a heteroatom, the other $R^6$ is not halogen, cyano, or bonded to the carbon to which it is attached through a heteroatom;

$R^9$, is selected from H, $C_{1-6}$ alkyl, $C_{2-8}$ alkenyl, $C_{2-8}$ alkynyl, F, Cl, Br, I, $NO_2$, CN, $(CHR')OH$, $(CH_2)_rOR^{9d}$, $(CH_2)_r$ $SR^{9d}$, $(CH_2)_rNR^{9a}R^{9a'}$, $(CH_2)_rC(O)OH$, $(CH_2)_rC(O)R^{9b}$, $(CH_2)_rC(O)NR^{9a}R^{9a'}$, $(CH_2)_rNR^{9a}C(O)R^{9a}$, $(CH_2)_r$ $NR^{9a}C(O)H$, $(CH_2)_rC(O)OR^{9b}$, $(CH_2)_rOC(O)R^{9b}$, $(CH_2)_r$ $OC(O)NR^{9a}R^{9a'}$, $(CH_2)_rNR^{9a}C(O)OR^{9b}$, $(CH_2)_rS(O)_p$ $R^{9b}$, $(CH_2)_rS(O)_2NR^{9a}R^{9a'}$, $(CH_2)_rNR^{9a}S(O)_2R^{9b}$, $C_{1-6}$ haloalkyl, a $(CH_2)_r-C_{3-10}$ carbocyclic residue substituted with 0–5 $R^{9c}$, and a $(CH_2)_r$-5–10 membered heterocyclic system containing 1–4 heteroatoms selected from N, O, and S, substituted with 0–3 $R^{9c}$;

$R^{9a}$ and $R^{9a'}$, at each occurrence, are selected from H, $C_{1-6}$ alkyl, $C_{3-8}$ alkenyl, $C_{3-8}$ alkynyl, a $(CH_2)_r-C_{3-10}$ carbocyclic residue substituted with 0–5 $R^{9e}$, and a $(CH_2)_r$-5–10 membered heterocyclic system containing 1–4 heteroatoms selected from N, O, and S, substituted with 0–3 $R^{9e}$;

alternatively, $R^{9a}$ and $R^{9a'}$ along with the N to which they are attached, join to form a 5–6 membered heterocyclic system containing 1–2 heteroatoms selected from $NR^{9g}$, O, and S and optionally fused with a benzene ring or a 6-membered aromatic heterocycle;

$R^{9b}$, at each occurrence, is selected from $C_{1-6}$ alkyl, $C_{3-8}$ alkenyl, $C_{3-8}$ alkynyl, a $(CH_2)_r-C_{3-6}$ carbocyclic residue substituted with 0–2 $R^{9e}$, and a $(CH_2)_r$-5–6 membered heterocyclic system containing 1–4 heteroatoms selected from N, O, and S, substituted with 0–3 $R^{9e}$;

$R^{9c}$, at each occurrence, is selected from $C_{1-6}$ alkyl, $C_{2-8}$ alkenyl, $C_{2-8}$ alkynyl, $(CH_2)_r C_{3-6}$ cycloalkyl, Cl, Br, I, F, $(CF_2)_r CF_3$, $NO_2$, CN, $(CH_2)_r NR^{9f}R^{9f}$, $(CH_2)_r OH$, $(CH_2)_r OR^{9b}$, $(CH_2)_r SR^{9b}$, $(CH_2)_r C(O)OH$, $(CH_2)_r C(O)R^{9b}$, $(CH_2)_r C(O)NR^{9f}R^{9f}$, $(CH_2)_r NR^{9f}C(O)R^{9a}$, $(CH_2)_r C(O)OR^{9b}$, $(CH_2)_r OC(O)R^{9b}$, $(CH_2)_r C(=NR^{9f})NR^{9f}R^{9f}$, $(CH_2)_r S(O)_p R^{9b}$, $(CH_2)_r NHC(=NR^{9f})NR^{9f}R^{9f}$, $(CH_2)_r S(O)_2 NR^{9f}R^{9f}$, $(CH_2)_r NR^{9f}S(O)_2 R^{9b}$, and $(CH_2)_r$phenyl substituted with 0–3 $R^{9e}$;

$R^{9d}$, at each occurrence, is selected from $C_{1-6}$ alkyl, $C_{3-6}$ alkenyl, $C_{3-6}$ alkynyl, a $C_{3-10}$ carbocyclic residue substituted with 0–3 $R^{9c}$, and a 5–6 membered heterocyclic system containing 1–4 heteroatoms selected from the group consisting of N, O, and S substituted with 0–3 $R^{9c}$;

$R^{9e}$, at each occurrence, is selected from $C_{1-6}$ alkyl, $C_{2-8}$ alkenyl, $C_{2-8}$ alkynyl, $(CH_2)_r C_{3-6}$ cycloalkyl, Cl, F, Br, I, CN, $NO_2$, $(CF_2)_r CF_3$, $(CH_2)_r OC_{1-5}$ alkyl, OH, SH, $(CH_2)_r SC_{1-15}$ alkyl, $(CH_2)_r NR^{9f}R^{9f}$, and $(CH_2)_r$phenyl, wherein the phenyl on the $(CH_2)_r$phenyl is substituted with 0–5 substituents selected from F, Cl, Br, I, $NO_2$, $C_{1-6}$alkyl, OH, and $NR^{9f}R^{9f}$;

$R^{9f}$, at each occurrence, is selected from H, $C_{1-6}$ alkyl, and $C_{3-6}$ cycloalkyl;

$R^{9g}$ is selected from H, $C_{1-6}$ alkyl, $C_{3-6}$ cycloalkyl, $(CH_2)_r$phenyl, $C(O)R^{9f}$, $C(O)OR^{9h}$, and $SO_2R^{9h}$;

$R^{9h}$, at each occurrence, is selected from $C_{1-6}$ alkyl, and $C_{3-6}$ cycloalkyl;

$R^{10}$, is selected from H, $C_{1-6}$ alkyl, $C_{2-8}$ alkenyl, $C_{2-8}$ alkynyl, F, Cl, Br, I, $NO_2$, CN, $(CHR')_r OH$, $(CH_2)_r OR^{10d}$, $(CH_2)_r SR^{10d}$, $(CH_2)_r NR^{10a}R^{10a'}$, $(CH_2)_r C(O)OH$, $(CH_2)_r C(O)R^{10b}$, $(CH_2)_r C(O)NR^{10a}R^{10a'}$, $(CH_2)_r NR^{10a}C(O)R^{10a}$, $(CH_2)_r NR^{10a}C(O)H$, $(CH_2)_r C(O)OR^{10b}$, $(CH_2)_r OC(O)R^{10b}$, $(CH_2)_r OC(O)NR^{10a}R^{10a'}$, $(CH_2)_r NR^{10a}C(O)OR^{10b}$, $(CH_2)_r S(O)_p R^{10b}$, $(CH_2)_r S(O)_2 NR^{10a}R^{10a'}$, $(CH_2)_r NR^{10a}S(O)_2 R^{10b}$, $C_{1-6}$ haloalkyl, a $(CH_2)_r$—$C_{3-10}$ carbocyclic residue substituted with 0–5 $R^{10c}$, and a $(CH_2)_r$-5–10 membered heterocyclic system containing 1–4 heteroatoms selected from N, O, and S, substituted with 0–3 $R^{10c}$;

$R^{10a}$ and $R^{10a'}$, at each occurrence, are selected from H, $C_{1-6}$ alkyl, $C_{3-8}$ alkenyl, $C_{3-8}$ alkynyl, a $(CH_2)_r$—$C_{3-10}$ carbocyclic residue substituted with 0–5 $R^{10e}$, and a $(CH_2)_r$-5–10 membered heterocyclic system containing 1–4 heteroatoms selected from N, O, and S, substituted with 0–3 $R^{10e}$;

alternatively, $R^{10a}$ and $R^{10a'}$, along with the N to which they are attached, join to form a 5–6 membered heterocyclic system containing 1–2 heteroatoms selected from $NR^{10g}$, O, and S and optionally fused with a benzene ring or a 6-membered aromatic heterocycle;

$R^{10b}$, at each occurrence, is selected from $C_{1-6}$ alkyl, $C_{3-8}$ alkenyl, $C_{3-8}$ alkynyl, a $(CH_2)_r$—$C_{3-6}$ carbocyclic residue substituted with 0–2 $R^{10e}$, and a $(CH_2)_r$-5–6 membered heterocyclic system containing 1–4 heteroatoms selected from N, O, and S, substituted with 0–3 $R^{10e}$;

$R^{10c}$, at each occurrence, is selected from $C_{1-6}$ alkyl, $C_{2-8}$ alkenyl, $C_{2-8}$ alkynyl, $(CH_2)_r C_{3-6}$ cycloalkyl, Cl, Br, I, F, $(CF_2)_r CF_3$, $NO_2$, CN, $(CH_2)_r NR^{10f}R^{10f}$, $(CH_2)_r OH$, $(CH_2)_r OR^{10b}$, $(CH_2)_r SR^{10b}$, $(CH_2)_r C(O)OH$, $(CH_2)_r C(O)R^{10b}$, $(CH_2)_r C(O)NR^{10f}R^{10f}$, $(CH_2)_r NR^{10f}C(O)R^{10a}$, $(CH_2)_r C(O)OR^{10b}$, $(CH_2)_r OC(O)R^{10b}$, $(CH_2)_r C(=NR^{10f})NR^{10f}R^{10f}$, $(CH_2)_r S(O)_p R^{10b}$, $(CH_2)_r NHC(=NR^{10f})NR^{10f}R^{10f}$, $(CH_2)_r S(O)_2 NR^{10f}R^{10f}$, $(CH_2)_r NR^{10f}S(O)_2 R^{10b}$, and $(CH_2)_r$phenyl substituted with 0–3 $R^{10e}$;

$R^{10d}$, at each occurrence, is selected from $C_{1-6}$ alkyl, $C_{3-6}$ alkenyl, $C_{3-6}$ alkynyl, and a $C_{3-10}$ carbocyclic residue substituted with 0–3 $R^{10c}$;

$R^{10e}$, at each occurrence, is selected from $C_{1-6}$ alkyl, $C_{2-8}$ alkenyl, $C_{2-8}$ alkynyl, $(CH_2)_r C_{3-6}$ cycloalkyl, Cl, F, Br, I, CN, $NO_2$, $(CF_2)_r CF_3$, $(CH_2)_r OC_{1-5}$ alkyl, OH, SH, $(CH_2)_r SC_{1-5}$ alkyl, $(CH_2)_r NR^{10f}R^{10f}$, and $(CH_2)_r$phenyl;

$R^{10f}$, at each occurrence, is selected from H, $C_{1-6}$ alkyl, and $C_{3-6}$ cycloalkyl;

$R^{10g}$ is selected from H, $C_{1-6}$ alkyl, $C_{3-6}$ cycloalkyl, $(CH_2)_r$phenyl, $C(O)R^{10f}$, $SO_2R^{10h}$, and $C(O)O R^{10h}$;

$R^{10h}$, at each occurrence, is selected from H, $C_{1-6}$ alkyl, $C_{3-6}$ cycloalkyl;

alternatively, $R^9$ and $R^{10}$ join to form =O, a $C_{3-10}$ cycloalkyl, a 5–6-membered lactone or lactam, or a 4–6-membered saturated heterocycle containing 1–2 heteroatoms selected from O, S, and $NR^{10g}$ and optionally fused with a benzene ring or a 6-membered aromatic heterocycle;

with the proviso that when either of $R^9$ or $R^{10}$ is bonded to the carbon to which it is attached through a heteroatom, then the other of $R^9$ or $R^{10}$ is not halogen, cyano, or bonded to the carbon to which it is attached through a heteroatom;

$R^{11}$, is selected from H, $C_{1-6}$ alkyl, $C_{2-8}$ alkenyl, $C_{2-8}$ alkynyl, $(CR'R^{17})_q OH$, $(CH_2)_q SH$, $(CR'R^{17})_q OR^{11d}$, $(CH_2)_q SR^{11d}$, $(CR'R^{17})_q NR^{11a}R^{11a'}$, $(CH_2)_r C(O)OH$, $(CH_2)_q C(O)R^{11b}$, $(CH_2)_r C(O)NR^{11a}R^{11a'}$, $(CH_2)_q NR^{11a}C(O)R^{11a}$, $(CH_2)_q OC(O)NR^{11a}R^{11a'}$, $(CH_2)_q NR^{11a}C(O)OR^{11b}$, $(CH_2)_q NR^{11a}C(O)NHR^{11a}$, $(CH_2)_q C(O)OR^{11b}$, $(CH_2)_q OC(O)R^{11b}$, $(CH_2)_q S(O)_p R^{11b}$, $(CH_2)_q S(O)_2 NR^{11a}R^{11a'}$, $(CH_2)_q NR^{11a}S(O)_2 R^{11b}$, $C_{1-6}$ haloalkyl, a $(CH_2)_r$—$C_{3-10}$ carbocyclic residue substituted with 0–5 $R^{11c}$, and a $(R'R^{17})_r$-5–10 membered heterocyclic system containing 1–4 heteroatoms selected from N, O, and S, substituted with 0–3 $R^{11c}$;

$R^{11a}$ and $R^{11a'}$, at each occurrence, are selected from H, $C_{1-6}$ alkyl, $C_{3-8}$ alkenyl, $C_{3-8}$ alkynyl, a $(CH_2)_r$—$C_{3-10}$ carbocyclic residue substituted with 0–5 $R^{11e}$, and a $(CH_2)_r$-5–10 membered heterocyclic system containing 1–4 heteroatoms selected from N, O, and S, substituted with 0–3 $R^{11e}$;

alternatively, $R^{11a}$ and $R^{11a'}$ along with the N to which they are attached, join to form a 5–6 membered heterocyclic system containing 1–2 heteroatoms selected from $NR^{11g}$, O, and S and optionally fused with a benzene ring or a 6-membered aromatic heterocycle;

$R^{11b}$, at each occurrence, is selected from $C_{1-6}$ alkyl, $C_{3-8}$ alkenyl, $C_{3-8}$ alkynyl, a $(CH_2)_r$—$C_{3-6}$ carbocyclic residue substituted with 0–2 $R^{11e}$, and a $(CH_2)_r$-5–6 membered heterocyclic system containing 1–4 heteroatoms selected from N, O, and S, substituted with 0–3 $R^{11e}$;

$R^{11c}$, at each occurrence, is selected from $C_{1-6}$ alkyl, $C_{2-8}$ alkenyl, $C_{2-8}$ alkynyl, $(CH_2)_r C_{3-6}$ cycloalkyl, Cl, Br, I, F, $(CF_2)_r CF_3$, $NO_2$, CN, $(CH_2)_r NR^{11f}R^{11f}$, $(CH_2)_r OH$, $(CH_2)_r OC_{1-4}$ alkyl, $(CH_2)_r SC_{1-4}$ alkyl, $(CH_2)_r C(O)OH$, $(CH_2)_r C(O)R^{11b}$, $(CH_2)_r C(O)NR^{11f}R^{11f}$, $(CH_2)_r NR^{11f}C(O)R^{11a}$, $(CH_2)_r C(O)OC_{1-4}$ alkyl, $(CH_2)_r OC(O)R^{11b}$, $(CH_2)_r C(=NR^{11f})NR^{11f}R^{11f}$, $(CH_2)_r NHC(=NR^{11f})NR^{11f}R^{11f}$, $(CH_2)_r S(O)_p R^{11b}$, $(CH_2)_r S(O)_2 NR^{11f}R^{11f}$, $(CH_2)_r NR^{11f}S(O)_2 R^{11b}$, and $(CH_2)_r$phenyl substituted with 0–3 $R^{11e}$;

$R^{11d}$, at each occurrence, is selected from $C_{1-6}$ alkyl, $C_{3-6}$ alkenyl, $C_{3-6}$ alkynyl, and a $C_{3-10}$ carbocyclic residue substituted with 0–3 $R^{11c}$;

$R^{11e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{11f}$R$^{11f'}$, and (CH$_2$)$_r$phenyl, wherein the phenyl on the (CH$_2$)$_r$phenyl is substituted with 0–5 substituents selected from F, Cl, Br, I, NO$_2$, C$_{1-6}$alkyl, OH, and NR$^{9f}$R$^{9f}$;

R$^{11f}$, at each occurrence, is selected from H, C$_{1-6}$ alkyl, and C$_{3-6}$ cycloalkyl;

R$^{11g}$ is selected from H, C$_{1-6}$ alkyl, C$_{3-6}$ cycloalkyl, (CH$_2$)$_r$phenyl, C(O)R$^{11f}$, C(O)OR$^{11h}$, and SO$_2$R$^{11h}$;

R$^{11h}$, at each occurrence, is selected from C$_{1-6}$ alkyl, and C$_{3-6}$ cycloalkyl;

R$^{12}$, is selected from H, C$_{1-6}$ alkyl, C$_{2-8}$ alkenyl, C$_{2-8}$ alkynyl, (CHR')$_q$OH, (CH$_2$)$_q$SH, (CHR')$_q$OR$^{12d}$, (CH$_2$)$_q$SR$^{12d}$, (CHR')$_q$NR$^{12a}$R$^{12a'}$, (CH$_2$)$_r$C(O)OH, (CH$_2$)$_r$C(O)R$^{12b}$, (CH$_2$)$_r$C(O)NR$^{12a}$R$^{12a'}$, (CH$_2$)$_r$NR$^{12a}$C(O)R$^{12a'}$, (CH$_2$)$_r$OC(O)NR$^{12a}$R$^{12a'}$, (CH$_2$)$_r$NR$^{12a}$C(O)OR$^{12b}$, (CH$_2$)$_r$NR$^{12a}$C(O)NHR$^{12a}$, (CH$_2$)$_r$C(O)OR$^{12b}$, (CH$_2$)$_q$OC(O)R$^{12b}$, (CH$_2$)$_r$S(O)$_p$R$^{12b}$, (CH$_2$)$_q$S(O)$_2$NR$^{12a}$R$^{12a'}$, (CH$_2$)$_q$NR$^{12a}$S(O)$_2$R$^{12b}$, C$_{1-6}$ haloalkyl, a (CH$_2$)$_r$—C$_{3-10}$ carbocyclic residue substituted with 0–5 R$^{12c}$, and a (R'R$^{17}$)$_r$-5–10 membered heterocyclic system containing 1–4 heteroatoms selected from N, O, and S, substituted with 0–3 R$^{12c}$;

R$^{12a}$ and R$^{12a'}$, at each occurrence, are selected from H, C$_{1-6}$ alkyl, C$_{3-8}$ alkenyl, C$_{3-8}$ alkynyl, a (CH$_2$)$_r$—C$_{3-10}$ carbocyclic residue substituted with 0–5 R$^{12e}$, and a (CH$_2$)$_r$-5–10 membered heterocyclic system containing 1–4 heteroatoms selected from N, O, and S, substituted with 0–3 R$^{12e}$;

alternatively, R$^{12a}$ and R$^{12a'}$, along with the N to which they are attached, join to form a 5–6 membered heterocyclic system containing 1–2 heteroatoms selected from NR$^{12g}$, O, and S and optionally fused with a benzene ring or a 6-membered aromatic heterocycle;

R$^{12b}$, at each occurrence, is selected from C$_{1-6}$ alkyl, C$_{3-8}$ alkenyl, C$_{3-8}$ alkynyl, a (CH$_2$)$_r$—C$_{3-6}$ carbocyclic residue substituted with 0–2 R$^{12e}$, and a (CH$_2$)$_r$-5–6 membered heterocyclic system containing 1–4 heteroatoms selected from N, O, and S, substituted with 0–3 R$^{12e}$;

R$^{12c}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, Br, I, F, (CF$_2$)$_r$CF$_3$, NO$_2$, CN, (CH$_2$)$_r$NR$^{12f}$R$^{12f}$, (CH$_2$)$_r$OH, (CH$_2$)$_r$OC$_{1-4}$ alkyl, (CH$_2$)$_r$SC$_{1-4}$ alkyl, (CH$_2$)$_r$C(O)OH, (CH$_2$)$_r$C(O)R$^{12b}$, (CH$_2$)$_r$C(O)NR$^{12f}$R$^{12f}$, (CH$_2$)$_r$NR$^{12f}$C(O)R$^{12a}$, (CH$_2$)$_r$C(O)OC$_{1-4}$ alkyl, (CH$_2$)$_r$OC(O)R$^{12b}$, (CH$_2$)$_r$C(=NR$^{12f}$)NR$^{12f}$R$^{12f}$, (CH$_2$)$_r$NHC(=NR$^{12f}$)NR$^{12f}$R$^{12f}$, (CH$_2$)$_r$S(O)$_r$R$^{12b}$, (CH$_2$)$_r$S(O)$_2$NR$^{12f}$R$^{12f}$, (CH$_2$)$_r$NR$^{12f}$S(O)$_2$R$^{12b}$, and (CH$_2$)$_r$phenyl substituted with 0–3 R$^{12e}$;

R$^{12d}$, at each occurrence, is selected from methyl, CF$_3$, C$_{2-6}$ alkyl substituted with 0–3 R$^{12e}$, C$_{3-6}$ alkenyl, C$_{3-6}$ alkynyl, and a C$_{3-10}$ carbocyclic residue substituted with 0–3 R$^{12c}$;

R$^{12e}$, at each occurrence, is selected from C$_{1-6}$ alkyl, C$_{2-8}$ alkenyl, C$_{2-8}$ alkynyl, C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{12f}$R$^{12f}$, and (CH$_2$)$_r$phenyl;

R$^{12f}$, at each occurrence, is selected from H, C$_{1-6}$ alkyl, and C$_{3-6}$ cycloalkyl;

R$^{12g}$ is selected from H, C$_{1-6}$ alkyl, C$_{3-6}$ cycloalkyl, (CH$_2$)$_r$phenyl, C(O)R$^{12f}$, C(O)OR$^{12h}$, and SO$_2$R$^{12h}$;

R$^{12h}$, at each occurrence, is selected from C$_{1-6}$ alkyl, and C$_{3-6}$ cycloalkyl;

alternatively, R$^{11}$ and R$^{12}$ join to form a C$_{3-10}$ cycloalkyl, a 5–6 membered lactone or lactam, or a 4–6-membered saturated heterocycle containing 1–2 heteroatoms selected from O, S, and NR$^{11g}$ and optionally fused with a benzene ring or a 6-membered aromatic heterocycle;

R$^{13}$, at each occurrence, is selected from C$_{1-6}$ alkyl, C$_{2-8}$ alkenyl, C$_{2-8}$ alkynyl, C$_{3-6}$ cycloalkyl, (CF$_2$)$_w$CF$_3$, (CH$_2$)$_q$NR$^{13a}$R$^{13a'}$, (CHR')$_q$OH, (CH$_2$)$_q$OR$^{13b}$, (CH$_2$)$_q$SH, (CH$_2$)$_q$SR$^{13b}$, (CH$_2$)$_w$C(O)OH, (CH$_2$)$_w$C(O)R$^{13b}$, (CH$_2$)$_w$C(O)NR$^{13a}$R$^{13a'}$, (CH$_2$)$_q$NR$^{13d}$C(O)R$^{13a}$, (CH$_2$)$_w$C(O)OR$^{13b}$, (CH$_2$)$_q$OC(O)R$^{13b}$, (CH$_2$)$_w$S(O)$_p$R$^{13b}$, (CH$_2$)$_w$S(O)$_2$NR$^{13a}$R$^{13a'}$, (CH$_2$)$_q$NR$^{13d}$S(O)$_2$R$^{13b}$, and (CH$_2$)$_w$phenyl substituted with 0–3 R$^{13c}$;

R$^{13a}$ and R$^{13a'}$, at each occurrence, are selected from H, C$_{1-6}$ alkyl, C$_{3-6}$ cycloalkyl, and phenyl substituted with 0–3 R$^{13c}$;

R$^{13b}$, at each occurrence, is selected from C$_{1-6}$ alkyl, C$_{3-6}$ cycloalkyl, and phenyl substituted with 0–3 R$^{13c}$;

R$^{13c}$, at each occurrence, is selected from C$_{1-6}$ alkyl, C$_{3-6}$ cycloalkyl, Cl, F, Br, I, CN, NO$_2$, (CF$_2$)$_r$CF$_3$, (CH$_2$)$_r$OC$_{1-5}$ alkyl, (CH$_2$)$_r$OH, (CH$_2$)$_r$SC$_{1-15}$ alkyl, and (CH$_2$)$_r$NR$^{13d}$R$^{13d}$;

R$^{13d}$, at each occurrence, is selected from H, C$_{1-6}$ alkyl, and C$_{3-6}$ cycloalkyl;

R$^{14}$, at each occurrence, is selected from H, C$_{1-6}$ alkyl, C$_{2-8}$ alkenyl, C$_{2-8}$ alkynyl, (CH$_2$)$_r$C$_{3-6}$ cycloalkyl, Cl, Br, I, F, NO$_2$, CN, (CHR')$_r$NR$^{14a}$R$^{14a'}$, (CHR')$_r$OH, (CHR')$_r$O(CHR')$_r$R$^{14d}$, (CHR')$_r$SH, (CHR')$_r$C(O)H, (CHR')$_r$S(CHR')$_r$R$^{14d}$, (CHR')$_r$C(O)OH, (CHR')$_r$C(O)(CHR')$_r$R$^{14b}$, (CHR')$_r$C(O)NR$^{14a}$R$^{14a'}$, (CHR')$_r$NR$^{14f}$C(O)(CHR')$_r$R$^{14b}$b, (CHR')$_r$OC(O)NR$^{14a}$R$^{14a'}$, (CHR')$_r$NR$^{14f}$C(O)O(CHR')$_r$R$^{14b}$, (CHR')$_r$C(O)O(CHR')$_r$R$^{14d}$d, (CHR')$_r$OC(O)(CHR')$_r$R$^{14b}$, (CHR')$_r$C(=NR$^{14f}$)NR$^{14a}$R$^{14a'}$, (CHR')$_r$NHC(=NR$^{14f}$)NR$^{14f}$R$^{14f}$, (CHR')$_r$S(O)$_p$(CHR')$_r$R$^{14b}$, (CHR')$_r$S(O)$_2$NR$^{14a}$R$^{14a}$a', (CHR')$_r$NR$^{14f}$S(O)$_2$(CHR')$_r$R$^{14b}$, C$_{1-6}$ haloalkyl, C$_{2-8}$ alkenyl substituted with 0–3 R', C$_{2-8}$ alkynyl substituted with 0–3 R', (CHR')$_r$phenyl substituted with 0–3 R$^{14e}$, and a (CH$_2$)$_r$-5–10 membered heterocyclic system containing 1–4 heteroatoms selected from N, O, and S, substituted with 0–2 R$^{15e}$, or two R$^{14}$ substituents on adjacent atoms on ring A form to join a 5–6 membered heterocyclic system containing 1–3 heteroatoms selected from N, O, and S substituted with 0–2 R$^{15e}$;

R$^{14a}$ and R$^{14a'}$, at each occurrence, are selected from H, C$_{1-6}$ alkyl, C$_{3-8}$ alkenyl, C$_{3-8}$ alkynyl, a (CH$_2$)$_r$—C$_{3-10}$ carbocyclic residue substituted with 0–5 R$^{14e}$, and a (CH$_2$)$_r$-5–10 membered heterocyclic system containing 1–4 heteroatoms selected from N, O, and S, substituted with 0–2 R$^{14e}$;

R$^{14b}$, at each occurrence, is selected from C$_{1-6}$ alkyl, C$_{3-8}$ alkenyl, C$_{3-8}$ alkynyl, a (CH$_2$)$_r$—C$_{3-6}$ carbocyclic residue substituted with 0–3 R$^{14e}$, and (CH$_2$)$_r$-5–6 membered heterocyclic system containing 1–4 heteroatoms selected from N, O, and S, substituted with 0–2 R$^{14e}$;

R$^{14d}$, at each occurrence, is selected from C$_{3-8}$ alkenyl, C$_{3-8}$ alkynyl, methyl, CF$_3$, C$_{2-6}$ alkyl substituted with 0–3 R$^{14e}$, a (CH$_2$)$_r$—C$_{3-10}$ carbocyclic residue substituted with 0–3 R$^{14e}$, and a (CH$_2$)$_r$5–6 membered heterocyclic system containing 1–4 heteroatoms selected from N, O, and S, substituted with 0–3 R$^{14e}$;

R$^{14e}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{14f}$R$^{14f}$, and (CH$_2$)$_r$phenyl;

R$^{14f}$, at each occurrence, is selected from H, C$_{1-6}$ alkyl, C$_{3-6}$ cycloalkyl, and phenyl;

R$^{15}$, at each occurrence, is selected from C$_{1-8}$ alkyl, (CH$_2$)$_r$C$_{3-6}$ cycloalkyl, Cl, Br, I, F, NO$_2$, CN, (CR'R$^{17}$)$_r$NR$^{15a}$R$^{15a'}$, (CR'R$^{17}$)$_r$OH, (CR'R$^{17}$)$_r$O(CHR')$_r$R$^{15d}$, (CR'R$^{17}$)$_r$SH, (CR'R$^{17}$)$_r$C(O)H, (CR'R$^{17}$)$_r$S(CHR')$_r$R$^{15d}$, $(CR'R^{17})_rC(O)OH$, $(CR'R^{17})_rC(O)(CHR')_rR^{15b}$, $(CR'R^{17})_rC(O)NR^{15a}R^{15a'}$, $(CR'R^{17})_rNR^{15f}C(O)(CHR')_rR^{15b}$, $(CR'R^{17})_rOC(O)NR^{15a}R^{15a'}$, $(CR'R^{17})_rNR^{15f}C(O)O(CHR')_rR^{15b}$, $(CR'R^{17})_rNR^{15f}C(O)NR^{15f}R^{15f}$, $(CR'R^{17})_rC(O)O(CHR')_rR^{15d}$, $(CR'R^{17})_rOC(O)(CHR')_rR^{15b}$, $(CR'R^{17})_rC(=NR^{15f})NR^{15a}R^{15a'}$, $(CR'R^{17})_rNHC(=NR^{15f})NR^{15f}R^{15f}$, $(CR'R^{17})_rS(O)_p(CHR')_rR^{15b}$, $(CR'R^{17})_rS(O)_2NR^{15a}R^{15a'}$, $(CR'R^{17})_rNR^{15f}S(O)_2(CHR')_rR^{15b}$, $C_{1-6}$ haloalkyl, $C_{2-8}$ alkenyl substituted with 0–3 R', $C_{2-8}$ alkynyl substituted with 0–3 R', $(CR'R^{17})_r$phenyl substituted with 0–3 $R^{15e}$, and a $(CH_2)_r$-5–10 membered heterocyclic system containing 1–4 heteroatoms selected from N, O, and S, substituted with 0–2 $R^{15e}$;

$R^{15a}$ and $R^{15a'}$, at each occurrence, are selected from H, $C_{1-6}$ alkyl, $C_{3-8}$ alkenyl, $C_{3-8}$ alkynyl, a $(CH_2)_r$—$C_{3-10}$ carbocyclic residue substituted with 0–5 $R^{15e}$, and a $(CH_2)_r$-5–10 membered heterocyclic system containing 1–4 heteroatoms selected from N, O, and S, substituted with 0–2 $R^{15e}$;

alternatively, $R^{15a}$ and $R^{15a'}$, along with the N to which they are attached, join to form a 5–6 membered heterocyclic system containing 1–2 heteroatoms selected from $NR^{15h}$, O, and S and optionally fused with a benzene ring or a 6-membered aromatic heterocycle;

$R^{15b}$, at each occurrence, is selected from $C_{1-6}$ alkyl, $C_{3-8}$ alkenyl, $C_{3-8}$ alkynyl, a $(CH_2)_r$—$C_{3-6}$ carbocyclic residue substituted with 0–3 $R^{15e}$, and $(CH_2)_r$-5–6 membered heterocyclic system containing 1–4 heteroatoms selected from N, O, and S, substituted with 0–2 $R^{15e}$;

$R^{15d}$, at each occurrence, is selected from $C_{3-8}$ alkenyl, $C_{3-8}$ alkynyl, methyl, $CF_3$, $C_{2-6}$ alkyl substituted with 0–3 $R^{15e}$, a $(CH_2)_r$—$C_{3-10}$ carbocyclic residue substituted with 0–3 $R^{15e}$, and a $(CH_2)_r$5–6 membered heterocyclic system containing 1–4 heteroatoms selected from N, O, and S, substituted with 0–3 $R^{15e}$;

$R^{15e}$, at each occurrence, is selected from $C_{1-6}$ alkyl, 2-cyanoethyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{15f}R^{15f}$, $(CH_2)_r$phenyl, and a heterocycle substituted with 0–1 $R^{15g}$, wherein the heterocycle is selected from imidazole, thiazole, oxazole, pyrazole, 1,2,4-triazole, 1,2,3-triazole, isoxazole, and tetrazole;

$R^{15f}$, at each occurrence, is selected from H, $C_{1-6}$ alkyl, $C_{3-6}$ cycloalkyl, and phenyl;

$R^{15g}$ is selected from methyl, ethyl, acetyl, and $CF_3$;

$R^{15h}$ is selected from H, $C_{1-6}$ alkyl, $C_{3-6}$ cycloalkyl, $(CH_2)_r$ phenyl, $C(O)R^{15f}$, $C(O)OR^{15i}$, and $SO_2R^{15i}$;

$R^{15i}$, at each occurrence, is selected from $C_{1-6}$ alkyl, $C_{3-6}$ cycloalkyl;

$R^{16}$, at each occurrence, is selected from $C_{1-8}$ alkyl, $C_{2-8}$ alkenyl, $C_{2-8}$ alkynyl, $(CH_2)_rC_{3-6}$ cycloalkyl, Cl, Br, I, F, $NO_2$, CN, $(CHR')_rNR^{16a}R^{16a'}(CHR')_rOH$, $(CHR')_rO(CHR')_rR^{16d}$, $(CHR')_rSH$, $(CHR')_rC(O)H$, $(CHR')_rS(CHR')_rR^{16d}$, $(CHR')_rC(O)OH$, $(CHR')_rC(O)(CHR')_rR^{16b}$, $(CHR')_rC(O)NR^{16a}R^{16a'}$, $(CHR')_rNR^{16f}C(O)(CHR')_rR^{16b}$, $(CHR')_rC(O)(CHR')_rR^{16d}$, $(CHR')_rOC(O)(CHR')_rR^{16b}$, $(CHR')_rC(=NR^{16f})NR^{16a}R^{16a'}$, $(CHR')_rNHC(=NR^{16f})NR^{16f}R^{16f}$, $(CHR')_rS(O)_p(CHR')_rR^{16b}$, $(CHR')_rS(O)_2NR^{16a}R^{16a'}$, $(CHR')_rNR^{16f}S(O)_2(CHR')_rR^{16b}$, $C_{1-6}$ haloalkyl, $C_{2-8}$ alkenyl substituted with 0–3 R', $C_{2-8}$ alkynyl substituted with 0–3 R', and $(CHR')_r$ phenyl substituted with 0–3 $R^{16e}$;

$R^{16a}$ and $R^{16a'}$, at each occurrence, are selected from H, $C_{1-6}$ alkyl, $C_{3-8}$ alkenyl, $C_{3-8}$ alkynyl, a $(CH_2)_r$—$C_{3-10}$ carbocyclic residue substituted with 0–5 $R^{16e}$, and a $(CH_2)_r$-5–10 membered heterocyclic system containing 1–4 heteroatoms selected from N, O, and S, substituted with 0–2 $R^{16e}$;

$R^{16b}$, at each occurrence, is selected from $C_{1-6}$ alkyl, $C_{3-8}$ alkenyl, $C_{3-8}$ alkynyl, a $(CH_2)_rC_{3-6}$ carbocyclic residue substituted with 0–3 $R^{16e}$, and a $(CH_2)_r$-5–6 membered heterocyclic system containing 1–4 heteroatoms selected from N, O, and S, substituted with 0–2 $R^{16e}$;

$R^{16d}$, at each occurrence, is selected from $C_{3-8}$ alkenyl, $C_{3-8}$ alkynyl, methyl, $CF_3$, $C_{2-6}$ alkyl substituted with 0–3 $R^{16e}$, a $(CH_2)_r$—$C_{3-10}$ carbocyclic residue substituted with 0–3 $R^{16e}$, and a $(CH_2)_r$-5–6 membered heterocyclic system containing 1–4 heteroatoms selected from N, O, and S, substituted with 0–3 $R^{16e}$;

$R^{16e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{16f}R^{16f}$, and $(CH_2)_r$phenyl;

$R^{16f}$, at each occurrence, is selected from H, $C_{1-5}$ alkyl, and $C_{3-6}$ cycloalkyl, and phenyl; $R^{17}$, at each occurrence, is independently selected from H and methyl;

R', at each occurrence, is selected from H, $C_{1-6}$ alkyl, $C_{3-8}$ alkenyl, $C_{3-8}$ alkynyl, $(CH_2)_rC_{3-6}$ cycloalkyl, and $(CH_2)_r$ phenyl substituted with $R^{15e}$;

g is selected from 0, 1, 2, 3, and 4;
v is selected from 0, 1, and 2;
t is selected from 1 and 2;
w is selected from 0 and 1;
r is selected from 0, 1, 2, 3, 4, and 5;
q is selected from 1, 2, 3, 4, and 5; and
p is selected from 0, 1, and 2.

[2] In another embodiment, the present invention provides novel compounds of formula (I):

Z is selected from O, S, N(CN), and $N(CONH_2)$;
$R^2$ is selected from H and $C_{1-4}$ alkyl;
$R^6$, at each occurrence, is selected from $C_{1-4}$ alkyl, $C_{2-8}$ alkenyl, $C_{2-8}$ alkynyl, $(CH_2)_rC_{3-6}$ cycloalkyl, $(CF_2)_rCF_3$, CN, $(CH_2)_rOH$, $(CH_2)_rOR^{6b}$, $(CH_2)_rC(O)R^{6b}$, $(CH_2)_rC(O)NR^{6a}R^{6a'}$, $(CH_2)_rNR^{6d}C(O)R^{6a}$, and $(CH_2)_r$phenyl substituted with 0–3 $R^{6c}$;

$R^{6a}$ and $R^{6a'}$, at each occurrence, are selected from H, $C_{1-6}$ alkyl, $C_{3-6}$ cycloalkyl, and phenyl substituted with 0–3 $R^{6c}$;

$R^{6b}$, at each occurrence, is selected from $C_{1-6}$ alkyl, $C_{3-6}$ cycloalkyl, and phenyl substituted with 0–3 $R^{6c}$;

$R^{6c}$, at each occurrence, is selected from $C_{1-6}$ alkyl, $C_{3-6}$ cycloalkyl, Cl, F, Br, I, CN, $NO_2$, $(CF_2)_rCF_3$, $(CH_2)_rOC_{1-5}$ alkyl, $(CH_2)_rOH$, $(CH_2)_rSC_{1-5}$ alkyl, and $(CH_2)_rNR^{6d}R^{6d}$;

$R^{6d}$, at each occurrence, is selected from H, $C_{1-6}$ alkyl, and $C_{3-6}$ cycloalkyl;

$R^{13}$, at each occurrence, is selected from $C_{1-4}$ alkyl, $C_{3-6}$ cycloalkyl, $(CH_2)NR^{13a}R^{13a'}$, $(CHR')OH$, $(CH_2)OR^{13b}$, $(CH_2)_wC(O)R^{13b}$, $(CH_2)_nC(O)NR^{13a}R^{13a'}$, $(CH_2)NR^{13d}C(O)R^{13a}$, $(CH_2)_wS(O)_2NR^{13a}R^{13a'}$, $(CH_2)NR^{13d}S(O)_2R^{13b}$, and $(CH_2)_w$-phenyl substituted with 0–3 $R^{13c}$;

$R^{13a}$ and $R^{13a'}$, at each occurrence, are selected from H, $C_{1-6}$ alkyl, $C_{3-6}$ cycloalkyl, and phenyl substituted with 0–3 $R^{13c}$;

$R^{13b}$, at each occurrence, is selected from $C_{1-6}$ alkyl, $C_{3-6}$ cycloalkyl, and phenyl substituted with 0–3 $R^{13c}$;

$R^{13c}$, at each occurrence, is selected from $C_{1-6}$ alkyl, $C_{3-6}$ cycloalkyl, Cl, F, Br, I, CN, $NO_2$, $(CF_2)_rCF_3$, $(CH_2)_rOC_{1-5}$ alkyl, $(CH_2)_rOH$, and $(CH_2)_rNR^{13d}R^{13d}$;

$R^{13d}$, at each occurrence, is selected from H, $C_{1-6}$ alkyl, and $C_{3-6}$ cycloalkyl;

v is selected from 0, 1 and 2;
q is selected from 1, 2, and 3; and
r is selected from 0, 1, 2, and 3.

[3] In another embodiment the present invention provides novel compounds of formula (I):

E is —(C=O)—(CR$^9$R$^{10}$)$_v$—(CR$^{11}$R$^{12}$)—, —(SO$_2$)—(CR$^9$R$^{10}$)$_v$—(CR$^{11}$R$^{12}$)—,

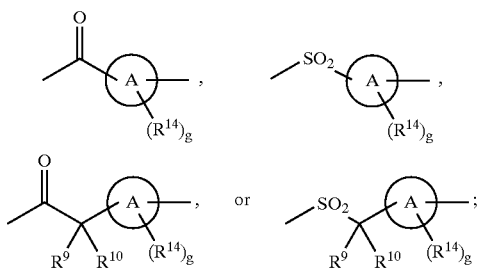

R$^3$ is selected from a (CH$_2$)$_2$N(CH$_3$)$_2$, (CR$^3$'H)$_r$-carbocyclic residue substituted with 0–5 R$^{15}$, wherein the carbocyclic residue is selected from phenyl, C$_{3-6}$ cycloalkyl, naphthyl, and adamantyl; and a (CR$^3$'H)$_r$-heterocyclic system substituted with 0–3 R$^{15}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl; and R$^5$ is selected from (CR$^5$'H)$_r$-phenyl substituted with 0–5 R$^{16}$; and a (CR$^5$'H)$_r$-heterocyclic system substituted with 0–3 R$^{16}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl.

[4] In another embodiment the present invention provides novel compounds of formula (I-i):

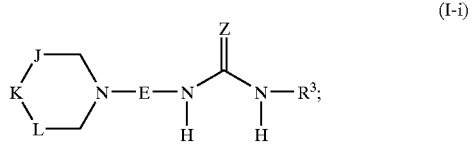

(I-i)

R$^{16}$, at each occurrence, is selected from C$_{1-8}$ alkyl, (CH$_2$)$_r$-C$_{3-6}$ cycloalkyl, CF$_3$, Cl, Br, I, F, (CH$_2$)$_r$NR$^{16a}$R$^{16a'}$, NO$_2$, CN, OH, (CH$_2$)$_r$OR$^{16d}$, (CH$_2$)$_r$C(O)R$^{16b}$, (CH$_2$)$_r$C(O)NR$^{16a}$R$^{16a'}$, (CH$_2$)$_r$NR$^{16f}$C(O)R$^{16b}$, (CH$_2$)$_r$S(O)$_p$R$^{16b}$, (CH$_2$)$_r$S(O)$_2$NR$^{16a}$R$^{16a'}$, (CH$_2$)$_r$NR$^{16f}$S(O)$_2$R$^{16b}$, and (CH$_2$)$_r$phenyl substituted with 0–3 R$^{16e}$;

R$^{16a}$ and R$^{16a'}$, at each occurrence, are selected from H, C$_{1-6}$ alkyl, C$_{3-6}$ cycloalkyl, and (CH$_2$)$_r$phenyl substituted with 0–3 R$^{16e}$;

R$^{16b}$, at each occurrence, is selected from C$_{1-6}$ alkyl, C$_{3-6}$ cycloalkyl, and (CH$_2$)$_r$phenyl substituted with 0–3 R$^{16e}$;

R$^{16d}$, at each occurrence, is selected from C$_{1-6}$ alkyl and phenyl;

R$^{16e}$, at each occurrence, is selected from C$_{1-6}$ alkyl, Cl, F, Br, I, CN, NO$_2$, (CF$_2$)$_r$CF$_3$, OH, and (CH$_2$)$_r$OC$_{1-5}$ alkyl; and R$^{16f}$, at each occurrence, is selected from H, and C$_{1-5}$ alkyl.

[5] In another embodiment the present invention provides novel compounds of formula (I-ii):

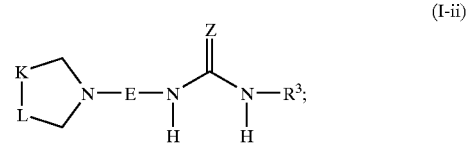

(I-ii)

R$^{16}$, at each occurrence, is selected from C$_{1-8}$ alkyl, (CH$_2$)$_r$-C$_{3-6}$ cycloalkyl, CF$_3$, Cl, Br, I, F, (CH$_2$)$_r$NR$^{16a}$R$^{16a'}$, NO$_2$, CN, OH, (CH$_2$)$_r$OR$^{16d}$, (CH$_2$)$_r$C(O)R$^{16b}$, (CH$_2$)$_r$C(O)NR$^{16a}$R$^{16a'}$, (CH$_2$)$_r$NR$^{16f}$C(O)R$^{16b}$, (CH$_2$)$_r$S(O)$_p$R$^{16b}$, (CH$_2$)$_r$S(O)$_2$NR$^{16a}$R$^{16a'}$, (CH$_2$)$_r$NR$^{16f}$S(O)$_2$R$^{16b}$, and (CH$_2$)$_r$phenyl substituted with 0–3 R$^{16e}$;

R$^{16a}$ and R$^{16a'}$, at each occurrence, are selected from H, C$_{1-6}$ alkyl, C$_{3-6}$ cycloalkyl, and (CH$_2$)$_r$phenyl substituted with 0–3 R$^{16e}$;

R$^{16b}$, at each occurrence, is selected from C$_{1-6}$ alkyl, C$_{3-6}$ cycloalkyl, and (CH$_2$)$_r$phenyl substituted with 0–3 R$^{16e}$;

R$^{16d}$, at each occurrence, is selected from C$_{1-6}$ alkyl and phenyl;

R$^{16e}$, at each occurrence, is selected from C$_{1-6}$ alkyl, Cl, F, Br, I, CN, NO$_2$, (CF$_2$)$_r$CF$_3$, OH, and (CH$_2$)$_r$OC$_{1-5}$ alkyl; and R$^{16f}$, at each occurrence, is selected from H, and C$_{1-5}$ alkyl.

[6] In another embodiment the present invention provides novel compounds of formula (I-i):

R$^5$ is CH$_2$phenyl substituted with 0–3 R$^{16}$;

E is —(C=O)—(CR$^9$R$^{10}$)$_v$—(CR$^{11}$R$^{12}$)—, or

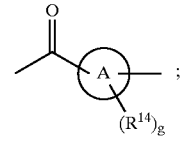

r is selected from 0, 1, and 2.

[7] In another embodiment the present invention provides novel compounds of formula (I-ii):

E is —(C=O)—(CR$^9$R$^{10}$)$_v$—(CR$^{11}$R$^{12}$)—, or

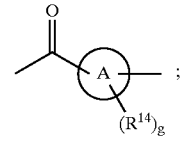

R$^5$ is CH$_2$phenyl substituted with 0–3 R$^{16}$; and r is selected from 0, 1, and 2.

[8] In another embodiment the present invention provides novel compounds of formula (I-i):

J is selected from CH$_2$ and CHR$^5$;
K is selected from CH$_2$ and CHR$^5$;
L is selected from CH$_2$ and CHR$^5$;

R$^3$ is a (CH$_2$)$_r$—C$_{3-10}$ carbocyclic residue substituted with 0–3 R$^{15}$, wherein the carbocyclic residue is selected from cyclopropyl, cyclobutyl, cyclopentyl, cyclohexyl, phenyl, naphthyl and adamantyl, and a (CR$^3$'H)$_r$-heterocyclic system substituted with 0–3 R$^{15}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl.

[9] In another embodiment the present invention provides novel compounds of formula (I-ii):

K is selected from $CH_2$ and $CHR^5$;
L is selected from $CH_2$ and $CHR^5$; and
$R^3$ is a $(CH_2)_r$—$C_{3-10}$ carbocyclic residue substituted with 0–3 $R^{15}$, wherein the carbocyclic residue is selected from cyclopropyl, cyclobutyl, cyclopentyl, cyclohexyl, phenyl, naphthyl and adamantyl, and a $(CR^3H)_r$-heterocyclic system substituted with 0–3 $R^{15}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl.

[10] In another embodiment the present invention provides novel compounds of formula (I):

M is absent or selected from $CH_2$;
Q is $CH_2$;
J is $CH_2$;
K and L are independently selected from $CH_2$ and $CHR^5$;
Z is O, S, NCN, or $NCONH_2$;
$R^1$ is H;
$R^2$ is H;
$R^3$ is selected from a $(CH_2)_r N(CH_3)_2$, a $(CH_2)_r$—$C_{3-10}$ carbocyclic residue substituted with 0–3 $R^{15}$, wherein the carbocyclic residue is selected from cyclopropyl, cyclobutyl, cyclopentyl, cyclohexyl, phenyl, naphthyl and adamantyl, and a $(CR^3H)_r$-heterocyclic system substituted with 0–3 $R^{15}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl; and
$R^5$ is selected from a $CH_2$-phenyl substituted with 0–5 $R^{16}$ and a $CH_2$-heterocyclic system substituted with 0–3 $R^{16}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl.

[11] In another embodiment, the present invention provides compounds of formula (II):

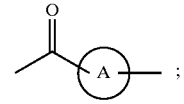

(II)

or stereoisomers or pharmaceutically acceptable salts thereof, wherein:

J, K, and L are independently selected from $CH_2$ and $CHR^5$;
Z is selected from O, and N(CN);
E is —(C=O)—$(CR^9R^{10})_v$—$CR^{11}R^{12}$—, or

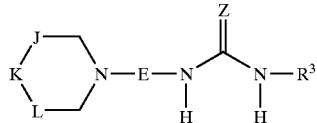

Ring A is cyclohexyl;
$R^3$ is selected from $(CH_2)_r N(CH_3)_2$, cyclopropyl, —$CH_2$-cyclopropyl, phenyl substituted with 0–2 $R^{15}$; and a $(CH_2)_r$-5–10 membered heterocyclic system containing 1–4 heteroatoms selected from N, O, and S, substituted with 0–2 $R^{15}$, wherein the heterocyclic system is selected from morpholinyl, pyridinyl, and thiazolyl;
$R^5$ is selected from a —$CH_2$-phenyl substituted with 0–2 $R^{16}$;
$R^9$ is selected from H, OH, $N(CO)CH_3$, and $NR^{9a}R^{9a'}$;
$R^{9a}$ and $R^{9a'}$, at each occurrence, are selected from H, methyl, ethyl, propyl, butyl, i-butyl;
alternatively, $R^9$ and $R^{10}$ join to form cyclohexyl;
$R^{11}$ is selected from H, methyl, $(CH_2)_r CONR^{11a}R^{11a'}$, $C(O)OR^{11b}$, and a $(CH_2)$-heterocyclic system, wherein the heterocyclic system is selected from morpholinyl and piperidinyl;
$R^{11a}$ and $R^{11a'}$ are independently selected from H, methyl, ethyl, propyl, i-propyl, butyl, i-butyl and t-butyl;
alternatively, $R^{11a}$ and $R^{11a'}$ along with the N to which they are attached, join to form a 5–6 membered heterocyclic system, wherein the heterocyclic system is selected from morpholinyl, piperidinyl, pyrrolidinyl, azapanyl, and N-methylpiperazinyl;
$R^{11b}$ is $CH_2$-phenyl; $R^{11g}$ is selected from H, methyl, ethyl, propyl, i-propyl, $C(O)OR^{11h}$, and $SO_2R^{11h}$;
$R^{11h}$ is selected from methyl, ethyl, propyl, i-propyl, butyl, i-butyl and t-butyl;
$R^{12}$ is H;
or alternatively, $R^{11}$ and $R^{12}$ join to form cyclopropyl, cyclopentyl, cyclohexyl, benzocyclopentyl, benzocyclohexyl, tetrahydropyan, tetrahydrofuran, or a 5–6-membered saturated heterocycle containing $NR^{11g}$ selected from pyrrolidine, and piperidine ring;
$R^{15}$, at each occurrence, is selected from methyl, ethyl, propyl, i-propyl, butyl, i-butyl, pentyl, $CF_3$, Cl, Br, I, F, $NO_2$, CN, OH, $OCH_3$, $C(O)OR^{15b}C(O)OH$, $C(O)CH_3$, $C(O)NR^{15a}R^{15a'}$ and a 5–6 membered heterocyclic system containing 1–4 heteroatoms selected from N, O, and S, substituted with 0–2 $R^{15e}$, wherein the heterocyclic system is selected from triazolyl, imidazolyl, tetrazolyl, pyrazolyl, oxazolyl, and isoxazolyl;
$R^{15a}$ and $R^{15a'}$ are selected from hydrogen, methyl, ethyl, propyl, i-propyl, butyl, t-butyl, and a heterocyclic system containing 1–4 heteroatoms selected from N, O, and S, substituted with 0–2 $R^{15e}$, wherein the heterocyclic system is selected from morpholinyl;
$R^{15b}$ is selected from methyl and benzyl;
$R^{15e}$ is selected from methyl, ethyl and 2-cyanoethyl;
$R^{16}$, at each occurrence, is selected from Cl, Br, I, and F,
v is 0 or 1; and
r is 0, 1, or 2.

[12] In another embodiment, the present invention provides compounds of formula (I), wherein the compound is selected from:

N-(3,5-diacetylphenyl)-N'-[3-[(3S)-3-[(4-fluorophenyl)methyl]piperidinyl]-3-oxopropyl]-urea;

N"-cyano-N-(3,5-diacetylphenyl)-N'-[3-[(3S)-3-[(4-fluorophenyl)methyl]piperidinyl]-3-oxopropyl]-guanidine;

N-(3-acetylphenyl)-N'-[(1S,2S)-2-[[(3S)-3-[(4-fluorophenyl)methyl]piperidinyl]carbonyl]cyclohexyl]-urea;

N-(3-acetylphenyl)-N'-[(1R,2R)-2-[[(3S)-3-[(4-fluorophenyl)methyl]piperidinyl]carbonyl]cyclohexyl]-urea;

N-[(1R,2R)-2-[[(3S)-3-[(4-fluorophenyl)methyl]piperidinyl]carbonyl]cyclohexyl]-N'-[3-(1-methyl-1H-tetrazol-5-yl)phenyl]-urea;

N-[(1R,2R)-2-[[(3S)-3-[(4-fluorophenyl)methyl]piperidinyl]carbonyl]cyclohexyl]-N'-[4-(1-methyl-1H-tetrazol-5-yl)phenyl]-urea;

N''-cyano-N-[(1R,2R)-2-[[(3S)-3-[(4-fluorophenyl)methyl]piperidinyl]carbonyl]cyclohexyl]-N'-[4-(1-methyl-1H-tetrazol-5-yl)phenyl]-guanidine;

N-[(1R,2R)-2-[[(3S)-3-[(4-fluorophenyl)methyl]piperidinyl]carbonyl]cyclohexyl]-N'-(4-pyridinyl)-urea;

N-[(1R,2R)-2-[[(3S)-3-[(4-fluorophenyl)methyl]piperidinyl]carbonyl]cyclohexyl]-N'-[2-(4-morpholinyl)ethyl]-urea;

N''-cyano-N-[(1R,2R)-2-[[(3S)-3-[(4-fluorophenyl)methyl]piperidinyl]carbonyl]cyclohexyl]-N'-[3-(1-methyl-1H-tetrazol-5-yl)phenyl]-guanidine;

N-[2-(dimethylamino)ethyl]-N'-[(1R,2R)-2-[[(3S)-3-[(4-fluorophenyl)methyl]piperidinyl]carbonyl]cyclohexyl]-urea;

N-(5-acetyl-4-methyl-2-thiazolyl)-N'-[(1R,2R)-2-[[(3S)-3-[(4-fluorophenyl)methyl]piperidinyl]carbonyl]cyclohexyl]-urea;

N-(3-acetylphenyl)-N'-[1-[[(3S)-3-[(4-fluorophenyl)methyl]piperidinyl]carbonyl]cyclohexyl]-urea;

N-[3,5-bis(1-methyl-1H-tetrazol-5-yl)phenyl]-N'-[(1R,2R)-2-[[(3S)-3-[(4-fluorophenyl)methyl]piperidinyl]carbonyl]cyclohexyl]-urea;

N-[3,5-di(1H-imidazol-1-yl)phenyl]-N'-[(1R,2R)-2-[[(3S)-3-[(4-fluorophenyl)methyl]piperidinyl]carbonyl]cyclohexyl]-urea;

N-[3,5-di(1H-1,2,4-triazol-1-yl)phenyl]-N'-[(1R,2R)-2-[[(3S)-3-[(4-fluorophenyl)methyl]piperidinyl]carbonyl]cyclohexyl]-urea;

N-(3-acetylphenyl)-N'-[1-[[(3S)-3-[(4-fluorophenyl)methyl]piperidinyl]carbonyl]cyclopentyl]-urea;

N-(3-acetylphenyl)-N'-[1-[[(3S)-3-[(4-fluorophenyl)methyl]piperidinyl]carbonyl]cyclopropyl]-urea;

N-(3-acetylphenyl)-N'-[2-[[(3S)-3-[(4-fluorophenyl)methyl]piperidinyl]carbonyl]-2,3-dihydro-1H-inden-2-yl]-urea;

N-(3-acetylphenyl)-N'-[2-[[(3S)-3-[(4-fluorophenyl)methyl]piperidinyl]carbonyl]-1,2,3,4-tetrahydro-2-naphthalenyl]-urea;

N-(5-acetyl-4-methyl-2-thiazolyl)-N'-[1-[[(3S)-3-[(4-fluorophenyl)methyl]piperidinyl]carbonyl]cyclopropyl]-urea;

N-(3-acetylphenyl)-N'-[2-[(3S)-3-[(4-fluorophenyl)methyl]piperidinyl]-2-oxoethyl]-urea;

N-[3,5-bis(1-ethyl-1H-tetrazol-5-yl)phenyl]-N'-[(1R,2R)-2-[[(3S)-3-[(4-fluorophenyl)methyl]piperidinyl]carbonyl]cyclohexyl]-urea;

N-[1-[[(3S)-3-[(4-fluorophenyl)methyl]piperidinyl]carbonyl]cyclopropyl]-N'-[3-(1-methyl-1H-tetrazol-5-yl)phenyl]-urea;

(alpha-1S,3S)-3-[(4-fluorophenyl)methyl]-alpha-[[[[3-(1-methyl-1H-tetrazol-5-yl)phenyl]amino]carbonyl]amino]-gamma-oxo-1-piperidinebutanoic acid, phenylmethyl ester;

(alpha-1S,3S)-3-[(4-fluorophenyl)methyl]-N-methyl-alpha-[[[[3-(1-methyl-1H-tetrazol-5-yl)phenyl]amino]carbonyl]amino]-gamma-oxo-1-piperidinebutanamide;

N-[(1S)-3-[(3S)-3-[(4-fluorophenyl)methyl]piperidinyl]-1-(4-morpholinylcarbonyl)-3-oxopropyl]-N'-[3-(1-methyl-1H-tetrazol-5-yl)phenyl]-urea;

3-[[[[(1R,2R)-2-[[(3S)-3-[(4-fluorophenyl)methyl]piperidinyl]carbonyl]cyclohexyl]amino]carbonyl]amino]-benzoic acid, ethyl ester;

3-[[[[(1R,2R)-2-[[(3S)-3-[(4-fluorophenyl)methyl]piperidinyl]carbonyl]cyclohexyl]amino]carbonyl]amino]benzoic acid;

N-[1-[[(3S)-3-[(4-fluorophenyl)methyl]piperidinyl]carbonyl]cyclopropyl]-N'-[3-(4-morpholinylcarbonyl)phenyl]-urea;

N-[(1R,2R)-2-[[(3S)-3-[(4-fluorophenyl)methyl]piperidinyl]carbonyl]cyclohexyl]-N'-[2-methoxy-5-(1-methyl-1H-tetrazol-5-yl)phenyl]-urea;

N-[3-[1-(2-cyanoethyl)-1H-tetrazol-5-yl]phenyl]-N'-[(1R,2R)-2-[[(3S)-3-[(4-fluorophenyl)methyl]piperidinyl]carbonyl]cyclohexyl]-urea;

N-[(1R,2R)-2-[[(3S)-3-[(4-fluorophenyl)methyl]piperidinyl]carbonyl]cyclohexyl]-N'-[3-(1H-tetrazol-5-yl)phenyl]-urea;

3-[[[[1-[[(3S)-3-[(4-fluorophenyl)methyl]piperidinyl]carbonyl]cyclopropyl]amino]carbonyl]amino]-4-methoxy-N-methyl-benzamide;

N-[1-[[(3S)-3-[(4-fluorophenyl)methyl]piperidinyl]carbonyl]cyclopropyl]-N'-[2-methoxy-5-(4-morpholinylcarbonyl)phenyl]-urea;

N-[(1S)-3-[(3S)-3-[(4-fluorophenyl)methyl]piperidinyl]-3-oxo-1-(1-pyrrolidinylcarbonyl)propyl]-N'-[3-(1-methyl-1H-tetrazol-5-yl)phenyl]-urea;

-(alpha-1S,3S)-N-(1,1-dimethylethyl)-3-[(4-fluorophenyl)methyl]-alpha-[[[[3-(1-methyl-1H-tetrazol-5-yl)phenyl]amino]carbonyl]amino]-gamma-oxo-1-piperidinebutanamide, N-[(1S)-3-[(3S)-3-[(4-fluorophenyl)methyl]piperidinyl]-3-oxo-1-(1-piperidinylcarbonyl)propyl]-N'-[3-(1-methyl-1H-tetrazol-5-yl)phenyl]-urea;

N-(3-acetylphenyl)-N'-[(2S)-2-amino-3-[(3S)-3-[(4-fluorophenyl)methyl]piperidinyl]-3-oxopropyl]-urea;

N-(3-acetylphenyl)-N'-[(2R)-2-amino-3-[(3S)-3-[(4-fluorophenyl)methyl]piperidinyl]-3-oxopropyl]-urea;

3-[[[[1-[[(3S)-3-[(4-fluorophenyl)methyl]piperidinyl]carbonyl]cyclopropyl]amino]carbonyl]amino]-4-methoxybenzamide;

N-[(1S)-3-[(3S)-3-[(4-fluorophenyl)methyl]piperidinyl]-1-[(4-methyl-1-piperazinyl)carbonyl]-3-oxopropyl]-N'-[3-(1-methyl-1H-tetrazol-5-yl)phenyl]-urea;

N-[(1S)-3-[(3S)-3-[(4-fluorophenyl)methyl]piperidinyl]-1-(4-morpholinylmethyl)-3-oxopropyl]-N'-[3-(1-methyl-1H-tetrazol-5-yl)phenyl]-urea;

N''-cyano-N-[(1S)-3-[(3S)-3-[(4-fluorophenyl)methyl]piperidinyl]-1-(4-morpholinylmethyl)-3-oxopropyl]-N'-[3-(1-methyl-1H-tetrazol-5-yl)phenyl]-guanidine 3-[(4-fluorophenyl)methyl]-N,N-dimethyl-alpha-[[[[3-(1-methyl-1H-tetrazol-5-yl)phenyl]amino]carbonyl]amino]-gamma-oxo-(alpha-1S,3S)-1-piperidinebutanamide N-{(1S)-1-({[(3-acetylanilino)carbonyl]amino}methyl)-2-[(3S)-3-(4-fluorobenzyl)piperidinyl]-2-oxoethyl}acetamide;

N-{(1R)-1-({[(3-acetylanilino)carbonyl]amino}methyl)-2-[(3S)-3-(4-fluorobenzyl)piperidinyl]-2-oxoethyl}acetamide;

3-[({[(1S)-3-[(3S)-3-(4-fluorobenzyl)-1-piperidinyl]-1-(4-morpholinylmethyl)-3-oxopropyl]amino}carbonyl)amino]-N-methylbenzamide;

N-(3-chlorophenyl)-N'-[(1S)-3-[(3S)-3-(4-fluorobenzyl)-1-piperidinyl]-1-(4-morpholinylmethyl)-3-oxopropyl]urea;

N-(3-cyanophenyl)-N'-[(1S)-3-[(3S)-3-(4-fluorobenzyl)-1-piperidinyl]-1-(4-morpholinylmethyl)-3-oxopropyl]urea;
N-[(1S)-3-[(3S)-3-(4-fluorobenzyl)-1-piperidinyl]-1-(4-morpholinylmethyl)-3-oxopropyl]-N'-(3-methoxyphenyl)urea;
N-cyclopropyl-N'-[(1S)-3-[(3S)-3-(4-fluorobenzyl)-1-piperidinyl]-1-(4-morpholinylmethyl)-3-oxopropyl]urea
N-(cyclopropylmethyl)-N'-[(1S)-3-[(3S)-3-(4-fluorobenzyl)-1-piperidinyl]-1-(4-morpholinylmethyl)-3-oxopropyl]urea;
benzyl 3-[({[(1S)-3-[(3S)-3-(4-fluorobenzyl)-1-piperidinyl]-1-(4-morpholinylmethyl)-3-oxopropyl]amino}carbonyl)amino]-4-methoxybenzoate;
N-(5-acetyl-4-methyl-1,3-thiazol-2-yl)-N'-[(1S)-3-[(3S)-3-(4-fluorobenzyl)-1-piperidinyl]-3-oxo-1-(1-piperidinylmethyl)propyl]urea;
N-[(1S,2R)-3-[(3S)-3-(4-fluorobenzyl)-1-piperidinyl]-2-methyl-1-(4-morpholinylcarbonyl)-3-oxopropyl]-N'-[3-(1-methyl-1H-tetraazol-5-yl)phenyl]urea;
3-[({[(1S,2R)-3-[(3S)-3-(4-fluorobenzyl)-1-piperidinyl]-2-methyl-1-(4-morpholinylcarbonyl)-3-oxopropyl]amino}carbonyl)amino]-N-methylbenzamide;
N-(3,5-diacetylphenyl)-N'-{(1R)-3-[(3S)-3-(4-fluorobenzyl)-1-piperidinyl]-1-methyl-3-oxopropyl}urea;
N-{(1R)-3-[(3S)-3-(4-fluorobenzyl)-1-piperidinyl]-1-methyl-3-oxopropyl}-N'-[3-(1-methyl-1H-tetraazol-5-yl)phenyl]urea;
N-{(2S)-3-[(3S)-3-(4-fluorobenzyl)-1-piperidinyl]-2-methyl-3-oxopropyl}-N'-[3-(1-methyl-1H-tetraazol-5-yl)phenyl]urea;
N-(3-acetylphenyl)-N'-{(1S)-1-{[tert-butyl(methyl)amino]methyl}-3-[(3S)-3-(4-fluorobenzyl)-1-piperidinyl]-3-oxopropyl}urea;
N-{(2R)-3-[(3S)-3-(4-fluorobenzyl)-1-piperidinyl]-2-methyl-3-oxopropyl}-N'-[3-(1-methyl-1H-tetraazol-5-yl)phenyl]urea;
(2S)-N-cyclopropyl-4-[(3S)-3-(4-fluorobenzyl)-1-piperidinyl]-2-[({[3-(1-methyl-1H-tetraazol-5-yl)phenyl]amino}carbonyl)amino]-4-oxobutanamide;
N-((1R)-2-[(3S)-3-(4-fluorobenzyl)-1-piperidinyl]-1-{[({[3-(1-methyl-1H-tetraazol-5-yl)phenyl]amino}carbonyl)amino]methyl}-2-oxoethyl)acetamide;
N-[(1S)-3-[(3S)-3-(4-fluorobenzyl)-1-piperidinyl]-1-(hexahydro-1H-azepin-1-ylcarbonyl)-3-oxopropyl]-N'-[3-(1-methyl-1H-tetraazol-5-yl)phenyl]urea;
N-(1-{2-[(3S)-3-(4-fluorobenzyl)-1-piperidinyl]-2-oxoethyl}cyclopropyl)-N'-[3-(1-methyl-1H-tetraazol-5-yl)phenyl]urea;
N-((1R)-2-[(3S)-3-(4-fluorobenzyl)-1-piperidinyl]-1-{[({[3-(1-methyl-1H-tetraazol-5-yl)phenyl]amino}carbonyl)amino]methyl}-2-oxoethyl)-2,2-dimethylpropanamide;
N-{(1R)-1-[({[(5-acetyl-4-methyl-1,3-thiazol-2-yl)amino]carbonyl}amino)methyl]-2-[(3S)-3-(4-fluorobenzyl)-1-piperidinyl]-2-oxoethyl}-2,2-dimethylpropanamide;
N-{(1S)-1-{[tert-butyl(methyl)amino]methyl}-3-[(3S)-3-(4-fluorobenzyl)-1-piperidinyl]-3-oxopropyl}-N'-[3-(1-methyl-1H-tetraazol-5-yl)phenyl]urea;
N-(5-acetyl-4-methyl-1,3-thiazol-2-yl)-N'-{(2R)-2-(diisobutylamino)-3-[(3S)-3-(4-fluorobenzyl)-1-piperidinyl]-3-oxopropyl}urea;
N-{(2R)-2-(diisobutylamino)-3-[(3S)-3-(4-fluorobenzyl)-1-piperidinyl]-3-oxopropyl}-N'-[3-(1-methyl-1H-tetraazol-5-yl)phenyl]urea;
N-(5-acetyl-4-methyl-1,3-thiazol-2-yl)-N'-{(1S)-1-{[tert-butyl(methyl)amino]methyl}-3-[(3S)-3-(4-fluorobenzyl)-1-piperidinyl]-3-oxopropyl}urea;
N-{(1R)-3-[(3S)-3-(4-fluorobenzyl)-1-piperidinyl]-1-methyl-3-oxopropyl}-N'-(4-pyridinyl)urea;
N-(5-acetyl-4-methyl-1,3-thiazol-2-yl)-N'-{(1R,2R)-3-[(3S)-3-(4-fluorobenzyl)-1-piperidinyl]-2-hydroxy-1-methyl-3-oxopropyl}urea;
N-(3,5-diacetylphenyl)-N'-{(1R,2R)-3-[(3S)-3-(4-fluorobenzyl)-1-piperidinyl]-2-hydroxy-1-methyl-3-oxopropyl}urea;
N-{3-[(dimethylamino)methyl]phenyl}-N'-((1R, 2R)-2-{[(3R)-3-(4-fluorobenzyl)-1-piperidinyl]carbonyl}cyclohexyl)urea;
3-({[(1-{[(3S)-3-(4-fluorobenzyl)-1-piperidinyl]carbonyl}cyclopropyl)amino]carbonyl}amino)benzamide;
N-(1-{[(3S)-3-(4-fluorobenzyl)-1-piperidinyl]carbonyl}cyclopropyl)-N'-[2-methoxy-5-(1-methyl-1H-tetraazol-5-yl)phenyl]urea;
N-(1-{[(3S)-3-(4-fluorobenzyl)-1-piperidinyl]carbonyl}cyclopropyl)-N'-[3-(5-methyl-1H-tetraazol-1-yl)phenyl]urea;
N-{(1R)-2-[(3S)-3-(4-fluorobenzyl)-1-piperidinyl]-1-methyl-2-oxoethyl}-N'-[3-(1-methyl-1H-tetraazol-5-yl)phenyl]urea; and
N-(3,5-diacetylphenyl)-N'-{(1S)-2-[(3S)-3-(4-fluorobenzyl)-1-piperidinyl]-1-methyl-2-oxoethyl}urea.

In another embodiment, the present invention provides a pharmaceutical composition, comprising a pharmaceutically acceptable carrier and a therapeutically effective amount of a compound of the present invention.

In another embodiment, the present invention provides a method for modulation of chemokine receptor activity comprising administering to a patient in need thereof a therapeutically effective amount of a compound of the present invention.

In another embodiment, the present invention provides a method for treating inflammatory disorders comprising administering to a patient in need thereof a therapeutically effective amount of a compound of the present invention In another embodiment, the present invention provides a method for treating or preventing disorders selected from asthma, allergic rhinitis, atopic dermatitis, inflammatory bowel diseases, idiopathic pulmonary fibrosis, bullous pemphigoid, helminthic parasitic infections, allergic colitis, eczema, conjunctivitis, transplantation, familial eosinophilia, eosinophilic cellulitis, eosinophilic pneumonias, eosinophilic fasciitis, eosinophilic gastroenteritis, drug induced eosinophilia, HIV infection, cystic fibrosis, Churg-Strauss syndrome, lymphoma, Hodgkin's disease, and colonic carcinoma.

In another embodiment, the compound of Formula (I) is

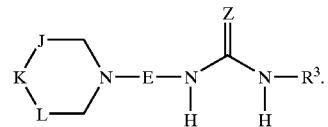

In another embodiment, the compound of Formula (I) is

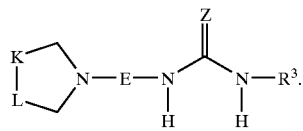

In another embodiment, J is $CH_2$, K is selected from $CH_2$ and $CHR^5$, and L is selected from $CH_2$ and $CHR^5$, wherein at least one of K or L contains an $R^5$.

In another embodiment, K is selected from $CHR^5$ and L is $CH_2$.

In another embodiment, L is selected from $CHR^5$ and K is $CH_2$.

In another embodiment,
E is $-(C=O)-(CR^9R^{10})_v-(CR^{11}R^{12})-$,

[chemical structures showing various E group embodiments with ring A substituted with $(R^{14})_g$ and carbonyl linkers with $R^9, R^{10}, R^{11}, R^{12}$ substituents]

In another embodiment
E is $-(C=O)-(CR^9R^{10})_v-(CR^{11}R^{12})-$,

[chemical structures]

In another embodiment
E is $-(C=O)-(CR^9R^{10})_v-(CR^{11}R^{12})-$, $-(SO_2)-(CR^9R^{10})_v-(CR^{11}R^{12})-$,

[chemical structures]

In another embodiment, E is $-(C=O)-(CR^9R^{10})_v-(CR^{11}R^{12})$.

In another embodiment, E is

[chemical structure with carbonyl, ring A, and $(R^{14})_g$]

In another embodiment, Z is selected from O and N(CN).

In another embodiment, Ring A is cyclohexyl, cyclopropyl, cyclobutyl, cyclopentyl, cycloheptyl, or phenyl.

In another embodiment, Ring A is cyclohexyl.

In another embodiment, $R^2$ is H.

In another embodiment, $R^3$ is selected from a $(CR^{3'}R^{3''})_r-C_{3-8}$ carbocyclic residue substituted with 0–5 $R^{15}$; a $(CR^{3'}R^{3''})_r-C_{9-10}$ carbocyclic residue substituted with 0–4 $R^{15}$; and a $(CR^{3'}R^{3''})_r$-5–10 membered heterocyclic system containing 1–4 heteroatoms selected from N, O, and S, substituted with 0–3 $R^{15}$.

In another embodiment, $R^3$ is selected from $(CH_2)_rN(CH_3)_2$.

In another embodiment, $R^3$ is selected from a $(CR^{3'}H)_r$-carbocyclic residue substituted with 0–5 $R^{15}$, wherein the carbocyclic residue is selected from phenyl, $(CH_2)-C_{3-6}$ cycloalkyl, naphthyl, and adamantyl; and a $(CR^{3'}H)_r$-heterocyclic system substituted with 0–3 $R^{15}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl.

In another embodiment, $R^3$ is selected from a phenyl substituted with 0–2 $R^{15}$; and a $(CH_2)_r$-5–10 membered heterocyclic system containing 1–4 heteroatoms selected from N, O, and S, substituted with 0–2 $R^{15}$, wherein the heterocyclic system is selected from pyridinyl, thiazolyl, and r is 0 or 1.

In another embodiment, $R^5$ is selected from $(CR^{5'}H)_r$-phenyl substituted with 0–5 $R^{16}$; and a $(CR^{5'}H)_r$-heterocyclic system substituted with 0–3 $R^{16}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl.

In another embodiment, $R^5$ is selected from a $CH_2-C_{3-10}$ carbocyclic residue substituted with 1–5 $R^{16}$ and a $CH_2$-heterocyclic system substituted with 0–3 $R^{15}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl.

In another embodiment, $R^5$ is $CH_2$-phenyl substituted with 0–3 $R^{16}$.

In another embodiment, $R^{11}$ and $R^{12}$ join to form cyclopropyl, cyclopentyl, cyclohexyl, benzocyclopentyl, benzocyclohexyl, tetrahydropyan, and tetrahydrofuran, or a 5–6-membered saturated heterocycle containing $NR^{11g}$ pyrrolidine, and piperidine ring.

In another embodiment, v is 0.

It is understood that any and all embodiments of the present invention may be taken in conjunction with any other embodiment to describe additional even more preferred embodiments of the present invention. Furthermore, any elements of an embodiment are meant to be combined with any and all other elements from any of the embodiments to describe additional embodiments.

Definitions

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced.

When any variable (e.g., $R^a$) occurs more than one time in any constituent or formula for a compound, its definition at each occurrence is independent of its definition at every other occurrence. Thus, for example, if a group is shown to be substituted with 0–2 $R^a$, then said group may optionally be substituted with up to two $R^a$ groups and $R^a$ at each occurrence is selected independently from the definition of $R^a$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "$C_{1-8}$ alkyl" is intended to include both branched and straight-chain saturated aliphatic hydrocarbon groups having the specified number of carbon atoms, examples of which include, but are not limited to, methyl, ethyl, n-propyl, i-propyl, n-butyl, i-butyl, sec-butyl, t-butyl, pentyl, and hexyl. $C_{1-8}$ alkyl, is intended to include $C_1$, $C_2$, $C_3$, $C_4$, $C_5$, $C_6$, $C_7$, and $C_8$ alkyl groups. "Alkenyl" is intended to include hydrocarbon chains of either a straight or branched configuration and one or more unsaturated carbon-carbon bonds which may occur in any stable point along the chain, such as ethenyl, propenyl, and the like. "Alkynyl" is intended to include hydrocarbon chains of either a straight or branched configuration and one or more unsaturated triple carbon-carbon bonds which may occur in any stable point along the chain, such as ethynyl, propynyl, and the like. "$C_{3-6}$ cycloalkyl" is intended to include saturated ring groups having the specified number of carbon atoms in the ring, including mono-, bi-, or poly-cyclic ring systems, such as cyclopropyl, cyclobutyl, cyclopentyl, cyclohexyl, and cycloheptyl in the case of $C_7$ cycloalkyl. $C_{3-6}$ cycloalkyl, is intended to include $C_3$, $C_4$, $C_5$, and $C_6$ cycloalkyl groups "Halo" or "halogen" as used herein refers to fluoro, chloro, bromo, and iodo; and "haloalkyl" is intended to include both branched and straight-chain saturated aliphatic hydrocarbon groups, for example $CF_3$, having the specified number of carbon atoms, substituted with 1 or more halogen (for example —$C_vF_w$ where v=1 to 3 and w=1 to (2v+1)).

As used herein, the term "5–6-membered cyclic ketal" is intended to mean 2,2-disubstituted 1,3-dioxolane or 2,2-disubstituted 1,3-dioxane and their derivatives.

As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin).

As used herein, the term "heterocycle" or "heterocyclic system" is intended to mean a stable 5, 6, or 7-membered monocyclic or bicyclic or 7, 8, 9, or 10-membered bicyclic heterocyclic ring which is saturated, partially unsaturated or unsaturated (aromatic), and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. As used herein, the term "aromatic heterocyclic system" is intended to mean a stable 5- to 7-membered monocyclic or bicyclic or 7- to 10-membered bicyclic heterocyclic aromatic ring which consists of carbon atoms and from 1 to 4 heterotams independently selected from the group consisting of N, O and S.

Examples of heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl., oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl. Preferred heterocycles include, but are not limited to, pyridinyl, thiophenyl, furanyl, indazolyl, benzothiazolyl, benzimidazolyl, benzothiaphenyl, benzofuranyl, benzoxazolyl, benzisoxazolyl, quinolinyl, isoquinolinyl, imidazolyl, indolyl, isoidolyl, piperidinyl, piperidonyl, 4-piperidonyl, piperonyl, pyrrazolyl, 1,2,4-triazolyl, 1,2,3-triazolyl, tetrazolyl, thiazolyl, oxazolyl, pyrazinyl, and pyrimidinyl. Also included are fused ring and spiro compounds containing, for example, the above heterocycles.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

Since prodrugs are known to enhance numerous desirable qualities of pharmaceuticals (e.g., solubility, bioavailability, manufacturing, etc. . . . ) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers which release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention.

"Stable compound" and "stable structure" are meant to indicate a compound that is sufficiently robust to survive isolation to a useful degree of purity from a reaction mixture, and formulation into an efficacious therapeutic agent.

Synthesis

The compounds of Formula I can be prepared using the reactions and techniques described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Wiley and Sons, 1991).

Generally, compounds described in the scope of this patent application can be synthesized by the route described in Scheme 1. Note that only one substitution pattern has been drawn for demonstration purposes, but more substitutents on the pyrrolidine or piperidine ring can be present as stipulated in the scope of this application. Thus, the appropriately substituted pyrrolidine (n=0) or piperidine (n=1) 1 is acylated or sulfonated by a N-protected acid chloride or sulfonylchloride 2, (X=Cl and where E represents a linkage described within the scope of this application in its fully elaborated form with the appropriate protecting groups as understood by one skilled in the art or in a precursor form which can be later elaborated into its final form by methods familiar to one skilled in the art) in the presence of base or an acid scavenger to yield the piperidinyl- or pyrrolidinylcarbonyl or piperidinyl- or pyrrolidinylsulfonyl protected amines 3. The coupling can be performed at −78° C. to room temperature to the reflux temperature of the solvent. Aqueous base such as NaOH, KOH, etc. may be employed under Schotten-Baumann conditions. Amine bases can also be employed such as Huenig's base or triethylamine in an inert solvent. Acid scavengers can also be employed such as but not limited to $K_2CO_3$, $Na_2CO3$, etc. Coupling can also be done via the free carboxylic acid and the pyrrolidine/piperidine base by a variety of methods familiar to one skilled in the art. Some of the coupling reagents include but are not limited to DCC (dicyclohexylcarbodiimide), EDC (N-ethyl,N'-dimethylaminopropylcarbodiimide), BOP (Benzotriazol-1-yloxy)tris(dimethylamino)phosphonium hexafluorophosphate), PyBOP (Benzotriazol-1-yloxy) tripyrrolidinophosphonium hexafluorophosphate), HATU (O-(7-Azabenzotriazol-1-yl)-N,N,N',N'-tetramethyluronium hexafluorophosphate), TBTU (O-(Benzotriazol-1-yl)-N,N,N',N'-tetramethyluronium tetrafluoroborate), etc., in an inert solvent such as DMF, THF, methylene chloride, etc. The non-diimide coupling reagents also might require the presence of a base such as triethylamine, Huenig's base, etc. The protecting group is subsequently removed to yield amine 4. Protecting groups include phthalimide which can be removed by hydrazine, a reaction familiar to one skilled in the art; bis-BOC which can be removed by either TFA or HCl dissolved in a suitable solvent, both procedures being familiar to one skilled in the art; a nitro group instead of an amine which can be reduced to yield an amine by conditions familiar to one skilled in the art; 2,4-dimethylpyrrole (S. P. Breukelman, et al. J. Chem. Soc. Perkin Trans. I, 1984, 2801); N-1,1,4,4-Tetramethyl-disilylazacyclopentane (STABASE) (S. Djuric, J. Venit, and P. Magnus Tet. Lett 1981, 22, 1787) and other protecting groups. Reaction with an isocyanate or isothiocyanate 5 (Z=O,S) yields urea or thiourea 6. Reaction with a chloroformate or chlorothioformate 7 (Z=O,S) such as o-, p-nitrophenyl-chloroformate or phenylchloroformate (or their thiocarbonyl equivalents), followed by displacement with an amine 9, also yields the corresponding urea or thiourea 6. Likewise, reaction of carbamate 8 (Y=H, or 2- or 4-NO2) with disubstituted amine 10 yields trisubstituted urea or thiourea 12. Reaction of the amine 4 with an N,N-disubstituted carbamoyl chloride 11 (or its thiocarbonyl equivalent) yields the corresponding N,N-disubstituted urea or thiourea 12. Amine 4 can also be reductively aminated to yield 13 by conditions familiar to one skilled in the art and by the following conditions: Abdel-Magid, A. F., et al. Tet. Lett. 1990, 31, (39) 5595–5598. This secondary amine can subsequently be reacted with isocyanates or isothiocyanates to yield trisubstituted ureas 14 or with carbamoyl chlorides to yield tetrasubstituted ureas 15.

SCHEME 1

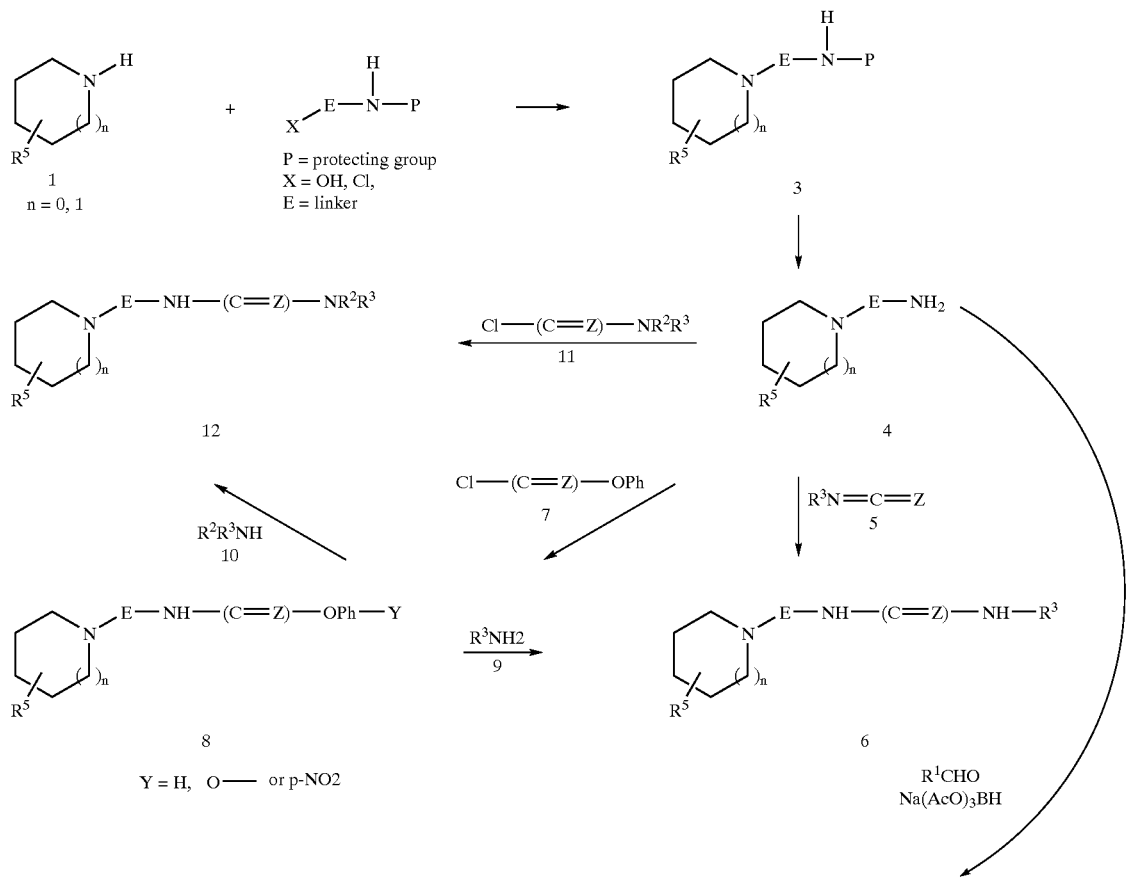

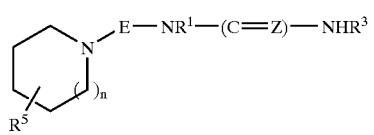

14

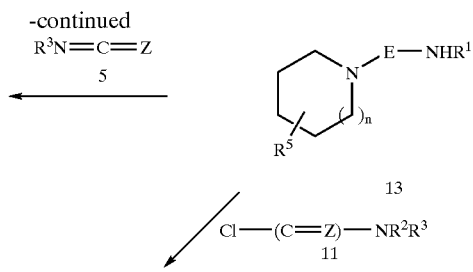

-continued

13

11

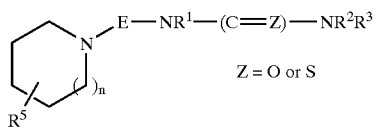

Z = O or S

15

One can also convert amine 4 or 13 into an isocyanate, isothiocyanate, carbamoyl chloride or its thiocarbonyl equivalent (isocyanate: Nowakowski, J. J Prakt. Chem/ Chem-Ztg 1996, 338 (7), 667–671; Knoelker, H.-J. et al., Angew. Chem. 1995, 107 (22), 2746–2749; Nowick, J. S. et al., J. Org. Chem. 1996, 61 (11), 3929–3934; Staab, H. A.; Benz, W.; Angew Chem 1961, 73; isothiocyanate: Strekowski L. et al., J. Heterocycl. Chem. 1996, 33 (6), 1685–1688; Kutschy, Pet al., Synlett. 1997, (3), 289–290) carbamoyl chloride: Hintze, F.; Hoppe, D.; Synthesis (1992) 12, 1216–1218; thiocarbamoyl chloride: Ried, W.; Hillenbrand, H.; Oertel, G.; Justus Liebigs Ann Chem 1954, 590) (these reactions are not shown in Scheme 1). These isocyanates, isothiocyantes, carbamoyl chlorides or thiocarbamoyl chlorides can then be reacted with $R^2R^3NH$ to yield di- or trisubstituted ureas or thioureas 12. An additional urea forming reaction involves the reaction of carbonyldiimidazole (CDI) (Romine, J. L.; Martin, S. W.; Meanwell, N. A.; Epperson, J. R.; Synthesis 1994 (8), 846–850) with 4 followed by reaction of the intermediate imidazolide with 9 or in the reversed sequence (9+CDI, followed by 4). Activation of imidazolide intermediates also facilitates urea formation (Bailey, R. A., et al., Tet. Lett. 1998, 39, 6267–6270). One can also use 13 and 10 with CDI. The urea forming reactions are done in an aprotic inert solvent such as THF, toluene, DMF, etc., at room temperature to the reflux temperature of the solvent and can employ the use of an acid scavenger or base when necessary such as carbonate and bicarbonate salts, triethylamine, DBU, Huenig's base, DMAP, etc. One can also make ureas (or thioureas) using the phenylcarbamates (or thiocarbamates) of amine $R^2R^3NH$, namely $R^2R^3N$—(C=O)—OPh (or $R^2R^3N$—(C=S)—OPh) (and substituted phenylcarbamates such as nitrophenylcarbamates), and reacting them with 4 or 13 to yield urea or thiourea 15 (this procedure is not shown in Scheme 1 but is similar in concept to 4 being converted to the carbamate 8 and then to the urea 6.

Substituted pyrrolidines and piperidines 1 can either be obtained commercially or be prepared as shown in Scheme 2. Commercially available N-benzylpiperid-3-one 16 can be debenzylated and protected with a BOC group employing reactions familiar to one skilled in the art. Subsequent Wittig reaction followed by reduction and deprotection yields piperidine 20 employing reactions familiar to one skilled in the art. Substituted pyrrolidines may be made by a similar reaction sequence. Other isomers and analogs around the piperidine ring can also be made by a similar reaction sequence. Chiral pyrrolidines/piperidines can be synthesized via asymmetric hydrogenation of 18 using chiral catalysts (see Parshall, G. W. Homogeneous Catalysis, John Wiley and Sons, New York: 1980, pp. 43–45; Collman, J. P., Hegedus, L. S. Principles and Applications of Organotransition Metal Chemistry, University Science Books, Mill Valley, Calif., 1980, pp. 341–348).

SCHEME 2

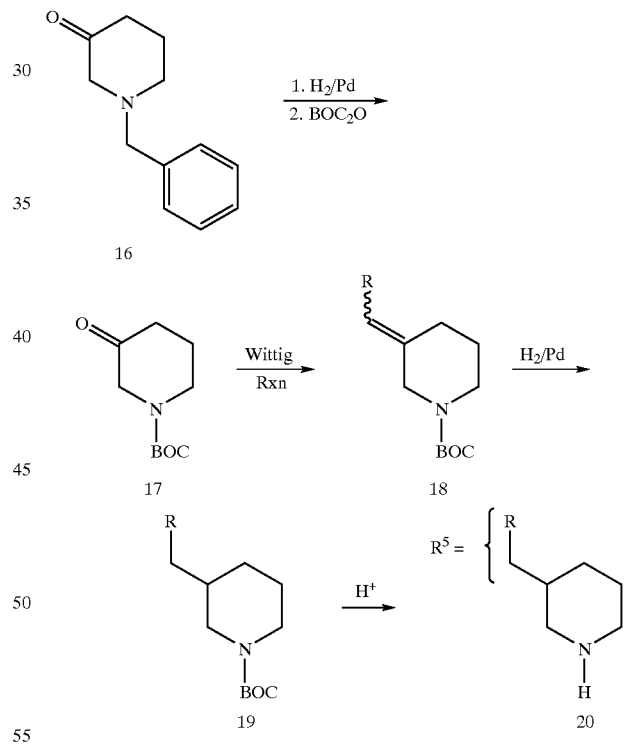

The cyanoguanidines (Z=N—CN) can be synthesized by the method of K. S. Atwal, et al. and references contained therein (J. Med. Chem. (1998) 41, 217–275). The nitroethylene analog (Z=C—NO2) can be synthesized by the method of F. Moimas, et al. (Synthesis 1985, 509–510) and references contained therein. The malononitrile analog (Z=C (CN)$_2$) may be synthesized by the method of S. Sasho, et al. (J. Med. Chem. 1993, 36, 572–579).

Guanidines (Z=NR$^{1a}$) can be synthesized by the methods outlined in Scheme 3. Compound 21 where Z=S can be methylated to yield the methylisothiourea 22. Displacement of the SMe group with amines yields substituted guanidines 23 (see H. King and I. M. Tonkin J. Chem. Soc. 1946, 1063 and references therein). Alternatively, reaction of thiourea 21 with amines in the presence of triethanolamine and "lac sulfur" which facilitates the removal of $H_2S$ yields substituted guanidines 23 (K. Ramadas, Tet. Lett. 1996, 37, 5161 and references therein). Finally, the use of carbonimidoyldichloride 24, or 25 followed by sequential displacements by amines yields the corresponding substituted guanidine 23 (S. Nagarajan, et al., Syn. Comm. 1992, 22, 1191–8 and references therein). In a similar manner, carbonimidoyldichlorides, $R^2$—N=C(Cl)$_2$ (not shown in Scheme 3) and $R^3$—N=C(Cl)$_2$ (not shown) can also be reacted sequentially with amines to yield di- and trisubstituted guanidine 23.

SCHEME 4

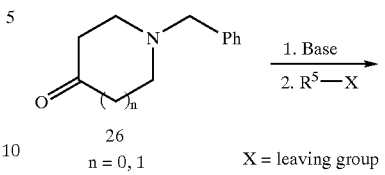

SCHEME 3

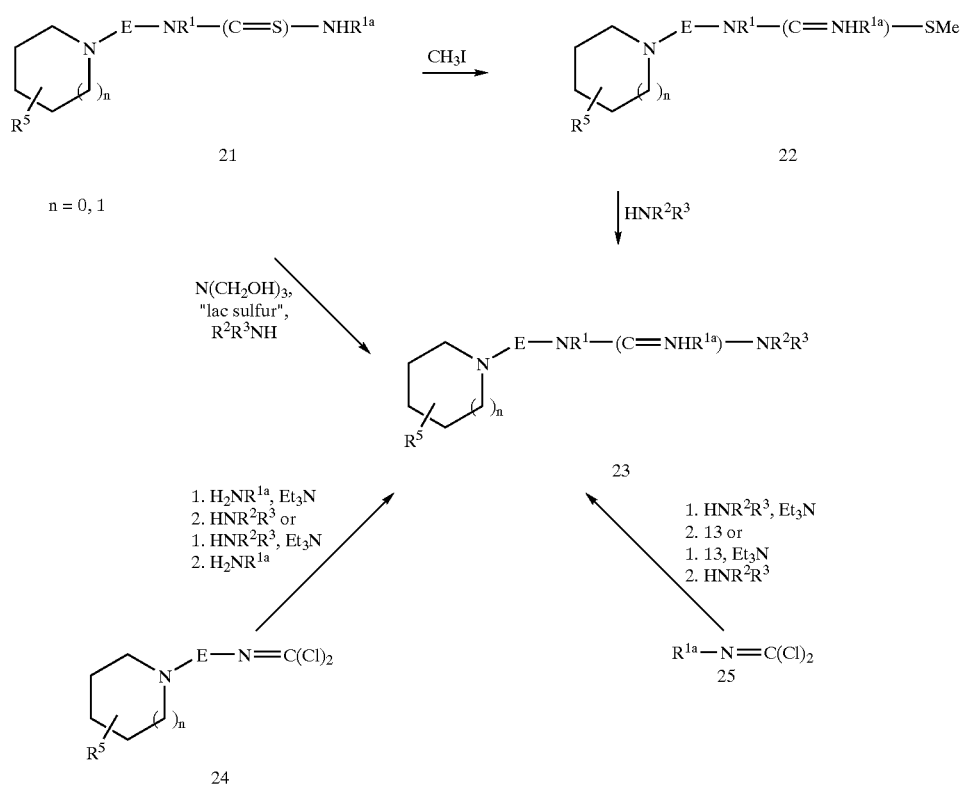

Multisubstituted pyrrolidines and piperidines may be synthesized by the methods outlined in Scheme 4. Monoalkylation of 26 via an enolate using LDA or potassium hexamethyldisilazane, or converting 26 first to an enamine, or by using other bases, all of which can be done in THF, ether, dioxane, benzene, or an appropriate an aprotic solvent at −78° C. to room temperature with an alkylating agent such as methyl iodide, benzyl bromide, etc. where X is leaving group such as Cl, Br, I, OTs, OMs, triflate, etc., yields product 27. This product can subsequently undergo alkylation again under thermodynamic or kinetic conditions and afterwards, if need be, can undergo two more alkylations to produce tri- and tetrasubstituted analogs of 27. The thermodynamic or kinetic conditions yield regioselectively alkylated products (for a discussion on thermodynamic vs. kinetic alkylations see H. House Modern Synthetic Reactions, W. A. Benjamin, Inc. (Menlo Park, Calif.: 1972) chapter 9).

-continued

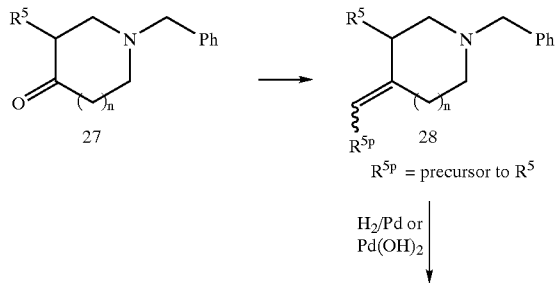

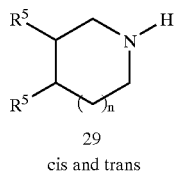

29
cis and trans

Subsequent Wittig olefination yields compound 28. Hydrogenation (asymmetric hydrogenation is an option here: Parshall, G. W. Homogeneous Catalysis, John Wiley and Sons, New York: 1980, pp. 43–45; Collman, J. P., Hegedus, L. S. Principles and Applications of Organotransition Metal Chemistry, University Science Books, Mill Valley, Calif., 1980, pp. 341–348) yields pyrrolidine or piperidine 29 which can be resolved into its relative and/or absolute isomers at this stage or later on in the synthesis either by crystallization, chromatographic techniques, or other methods familiar to one skilled in the art. The amine 29 an then be elaborated into the compounds of this invention by methods discussed previously (Scheme 1). The carbonyl-containing intermediate 27 in Scheme 4 can also be reduced to the methylene analog via a Wolff-Kishner reduction and modifications thereof, or by other methods familiar to one skilled in the art. The carbonyl group can also be reduced to an OH group, which can undergo displacement reactions familiar to one skilled in the art to synthesize the $R^6$ groups. This piperidine or pyrrolidine can be deprotected and elaborated to the compounds of this invention by methods discussed earlier. Thus, mono-, di-, tri-, or tetraalkylated carbonyl-containing pyrrolidines or piperidines can be synthesized, which in turn can be reduced to the corresponding —$CH_2$— analogs employing the Wolff-Kishner reduction or other methods.

SCHEME 5

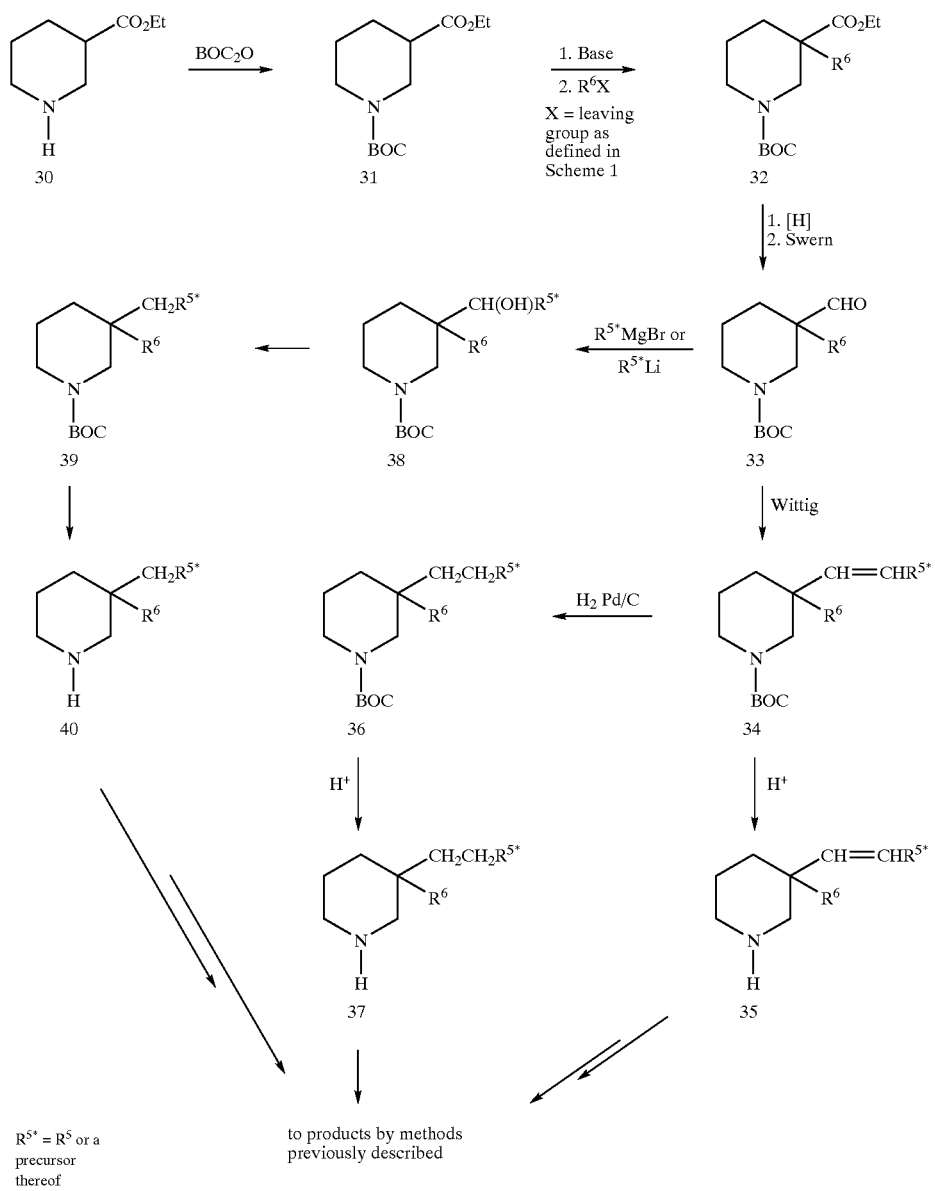

Another method for synthesizing gem-substituted pyrrolidines and piperidines is shown in Scheme 5. It is understood by one skilled in the art that some of the steps in this scheme can be rearranged. It is also understood that gem-disubstitution is only shown at only one position on the piperidine ring and that similar transformations may be performed on other carbon atoms as well, both for piperidine and pyrrolidine. Thus, 3-carboethoxypiperidine 30 may be BOC-protected and alkylated employing a base such as LDA, KHMDS, LHDMS, etc., in THF, ether, dioxane, etc. at −78° C. to room temperature, and an alkylating agent $R^6X$ where X is a halide (halide=Cl, Br, I), mesylate, tosylate or triflate, to yield 32. Reduction using DIBAL, for example, and if necessary followed by oxidation such as a Swern oxidation (S. L. Huang, K. Omura, D. Swern J. Org. Chem. 1976, 41, 3329–32) yields aldehyde 33. Wittig olefination (34) followed by deprotection yields 35 which may be elaborated as described previously into the compounds of this invention. Reduction of the Wittig adduct 34 yields 36 which may be deprotected to yield 37 which may be in turn elaborated as described previously into the compounds of this invention. Reaction of aldehyde 33 with an alkyllithium or Grignard reagent yields alcohol 38 which may be reduced catalytically or with $Et_3SiH/TFA$ (J. Org. Chem. 1969, 34, 4; J. Org. Chem. 1987, 52, 2226) if $R^{5*}$ ($R^{5*}=R^5$ or a precursor thereof) is aromatic to yield 39. If $R^{5*}$ is not aromatic, then the OH may be reduced by the method of Barton (Barton, D. H. R.; Jaszberenyi, J. C. Tet. Lett. 1989, 30, 2619 and other references therein). Once tosylated, the alcohol can also be displaced with dialkyllithium cuprates (not shown) (Hanessian, S.; Thavonekham, B.; DeHoff, B.; J. Org. Chem. 1989, 54, 5831). Deprotection if necessary yields 40 which may be elaborated as described previously into the compounds of this invention.

SCHEME 6

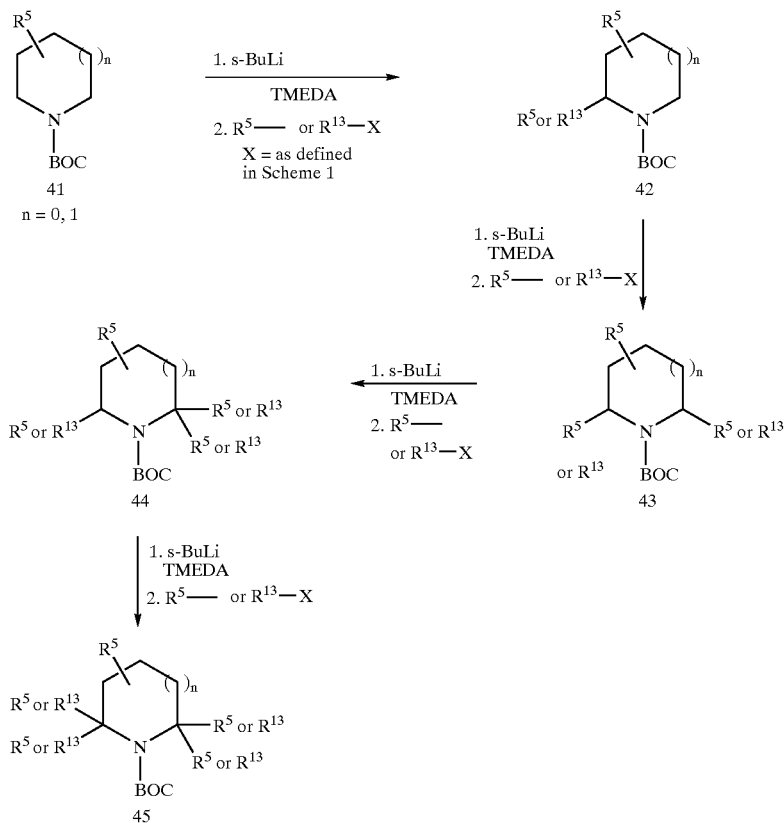

A method for the alkylation of alkyl groups, arylalkyl groups, allylic groups, propargylic groups, etc., and a variety of other electrophiles onto the pyrrolidinyl and/or piperidinyl alpha-carbons (alpha to the ring nitrogen atom) is represented by the work of Peter Beak, et al. as shown in Scheme 6. It is understood by one skilled in the art that the $R^5$ and $R^{13}$ groups are either in their precursor, protected, or final form. Only one $R^5$ group is shown to be substituted on piperidine/pyrrolidine 41. However it is understood by one skilled in the art that additional functionality may be present on the ring in either precursor, protected, or final form. Thus lithiation with an alkyllithium reagent such as n-BuLi or s-BuLi as shown, followed by quenching with an electrophilic species such as $R^5X$ or $R^{13}X$ where X is a leaving group such as Cl, Br, I, OMs, OTs, triflate, etc., and $R^5$ and $R^{13}$ are in their precursor, protected, or final form, yields monoalkylated piperidine/pyrrolidine 42. This alkylation may occur either stereoselectively (P. Beak and W. K. Lee J. Org. Chem. 1990, 55, 2578–2580) or enantioselectively if sparteine is included as a source of chirality (P. Beak, et al., J. Am. Chem. Soc. 1994, 116, 3231–3239). The alkylation process may be repeated up to three more times as shown in Scheme 6 to result in di-, tri-, and tetrasubstitution at the alpha-positions.

Compounds where $R^9$ and $R^{10}$ form a cyclic 3,4,5,6, or 7-membered ring can be synthesized by the methods disclosed in Scheme 7. These same methods may also be used to synthesize gem-disubstituted compounds in which $R^9$ can be different from $R^{10}$ by step-wise alkylation of the malonate derivative. Of course, this scheme may be used to synthesize compounds where $R^{10}$=H and $R^9$=$R^{10}$ also. For example, a cyclohexyl-fused malonate may be synthesized by Michael addition and alkylation of I(CH$_2$)$_4$CH=CCO$_2$Me with dimethyl malonate employing NaH/DMF (Desmaele, D.; Louvet, J.-M.; Tet Lett 1994, 35 (16), 2549–2552) or by a double Michael addition (Reddy, D. B., et al., Org. Prep. Proced. Int. 24 (1992) 1, 21–26) (Downes, A. M.; Gill, N. S.; Lions, F.; J Am Chem or by an alkylation followed by a second intromolecular alkylation employing an iodoaldehyde (Suami, T.; Tadano, K.; Kameda, Y.; Iimura, Y.; Chem Lett 1984, 1919), or by an alkylation followed by a second intramolecular alkylation employing an alkyl dihalide (Kohnz, H.; Dull, B.; Mullen, K.; Angew Chem 1989, 101 (10), 1375), etc.

$R^{11}$ and $R^{12}$ by methods familiar to one skilled in the art. Alcohol 49 can also be displaced via its tosylate, mesylate, or triflate with cyanide ion to form a nitrile. This nitrile can optionally be mono or bisalkylated at the alpha carbon and then be reduced to an amine to yield an analog of 50 with an extra carbon atom. The nitrile can also be hydrolyzed to a carboxylic acid which can be converted to an amine via Curtius rearrangement followed by hydrolysis to result in 50 with no substitution or mono- or disubstitution at the alpha carbon atom. Ester 48 can be hydrolyzed to a carboxylic acid. Curtius rearrangement followed by hydrolysis yields 50 where there is one less carbon atom. All of these generated amines can be reacted as in Scheme 1 to yield compounds of this invention.

Scheme 8 describes another method for the synthesis of compounds where $R^9$ and $R^{10}$ are taken together to form cycloalkyl groups. Aminoalcohols 52 are found in the literature (CAS Registry Nos. for n=0,1,2,3, respectively:

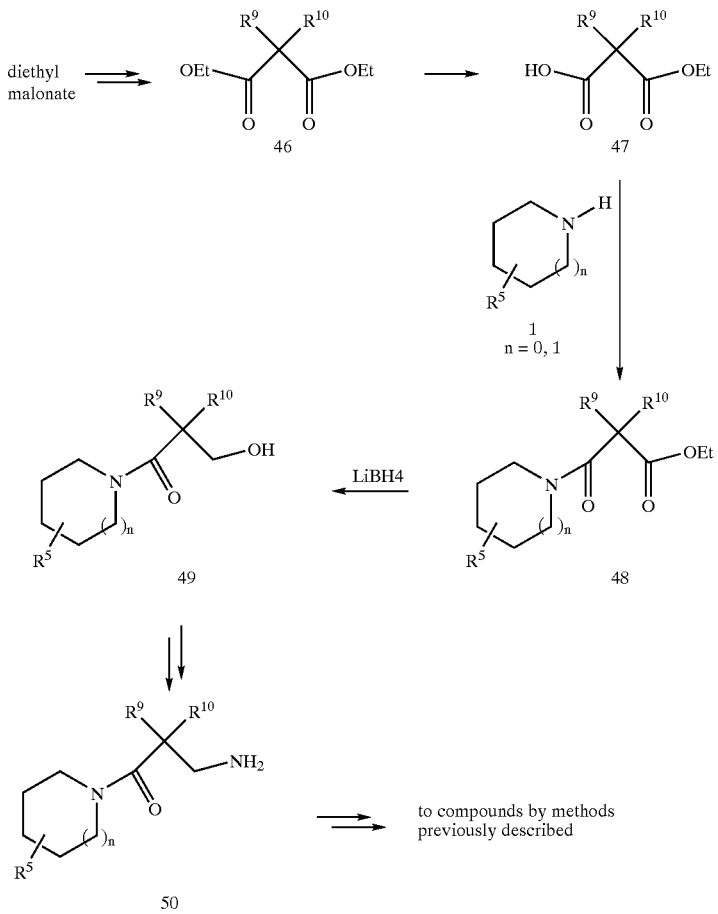

Subsequent monosaponification (Pallai, P. V., Richman, S., Struthers, R. S., Goodman, M. Int. J. Peptide Protein Res. 1983, 21, 84–92; M. Goodman Int. J. Peptide Protein Res. 19831, 17, 72–88), standard coupling with pyrrolidine/piperidine 1 yields 48. Reduction with LiBH4 yields 49 which can be then converted to amine 50 and then to the compounds of this invention by procedures as discussed previously or by other procedures which are familiar to one skilled in the art. Alcohol 49 can also be converted to an aldehyde which would allow the introduction of substituents 45434-02-4, 2041-56-7, 2239-31-8, 2041-57-8). They can easily be protected, as with a BOC group (or CBZ, or any other compatible protecting group) by known procedures familiar to one skilled in the art to yield alcohols 53. The alcohols can then be oxidized by methods familiar to one skilled in the art and activated for coupling as described previously and coupled to pyrrolidine/piperidine 1 by the conditions described in Scheme 1 to yield 55. Subsequent deprotection yields amine 56 which can be elaborated to the compounds of this invention as described previously.

SCHEME 8

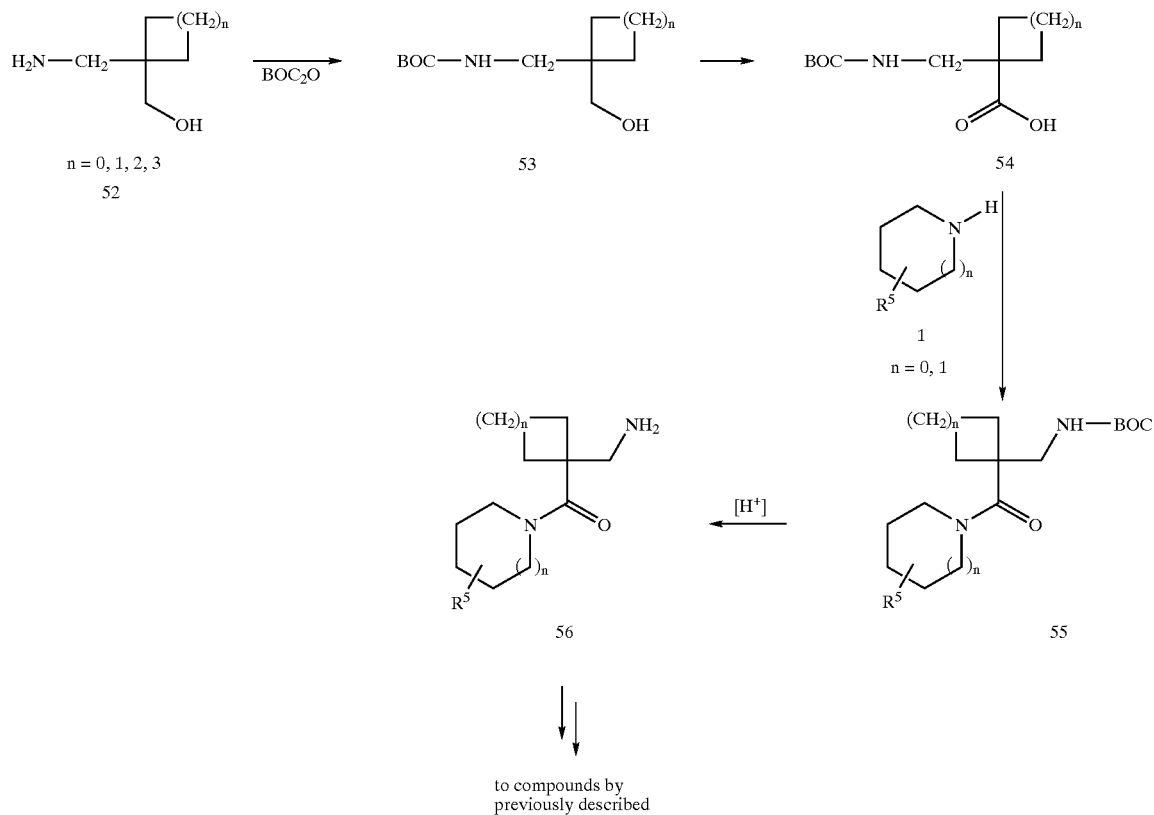

A method to introduce cycloalkyl groups at $R^{11}R^{12}$ is shown in Scheme 9. Protection of the nitrogen of compounds 57 which are commercially available yields 58 (the protecting group may be BOC, CBZ, or any other compatible protecting group) by procedures familiar to one skilled in the art. These can be then coupled as discussed previously to 1 and deprotected and elaborated to the compounds of this invention. Esterification by any one of a number procedures familiar to one skilled in the art (for example A. Hassner and V. Alexanian, Tet. Lett, 1978, 46, 4475–8) followed by reduction with DIBAL (or alternatively reduction to the alcohol with, for example, $LiBH_4$, followed by Swern oxidation (op. cit.) yields aldehyde 59. One carbon homologation via the Wittig reaction followed by hydrolysis of the vinyl ether yields aldehyde 61. Oxidation followed by standard coupling to 1 yields 62 followed by deprotection yields amine 63 which can be elaborated to the compounds of this invention by the methods previously discussed.

SCHEME 9

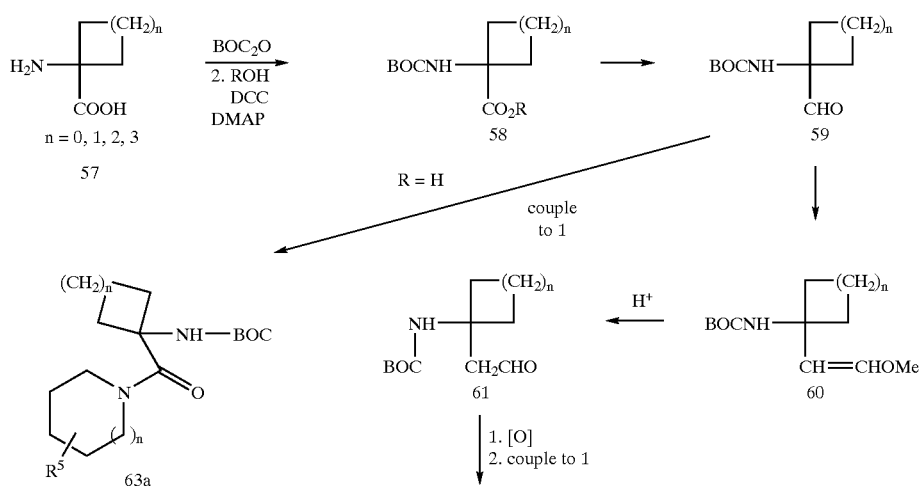

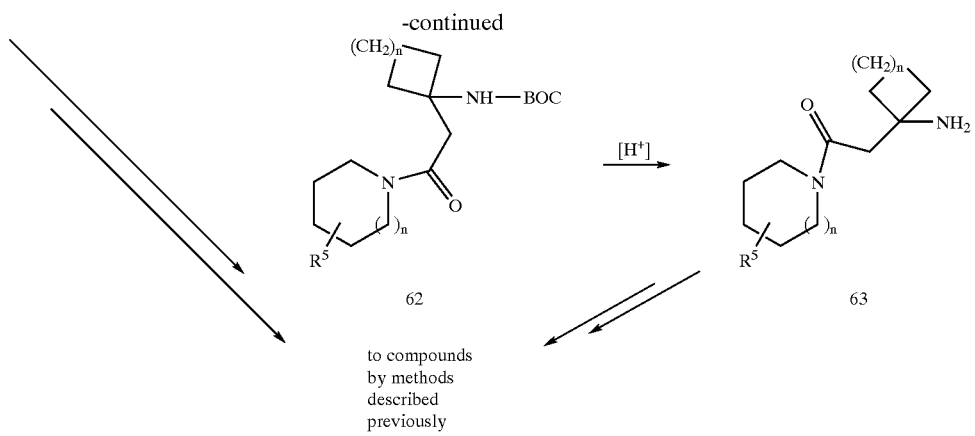

Aminoalkylsulfonyl chlorides may be synthesized by the methods described in Scheme 10. Protected alcohol 64 is converted into the acetylthio derivative 65 via Sn2 displacement chemistry familiar to one skilled in the art. For instance, 64 can be converted into a tosylate, mesylate, triflate, etc., and displaced with KSAc in a suitable solvent such as an alcohol, DMF, DMSO, etc. Another alternative is the Mitsunobu reaction. Alternatively, the acetylthio group may be added to a double bond via radical chemistry (Abbenante, G.; Prager, R. H. Aust. J. Chem. 1992, 45, 1801–1810). Conversion of 65 into sulfonylchloride 66 may be achieved using chlorine gas and water in an inert solvent such as for example, methylene chloride (Abbenante, G.; Prager, R. H. Aust. J. Chem. 1992, 45, 1801–1810). Coupling (67) and deprotection (68) and formation of the urea or urea isostere on the right hand side as discussed previously in Scheme 1 and elsewhere in this application yields compounds of this invention.

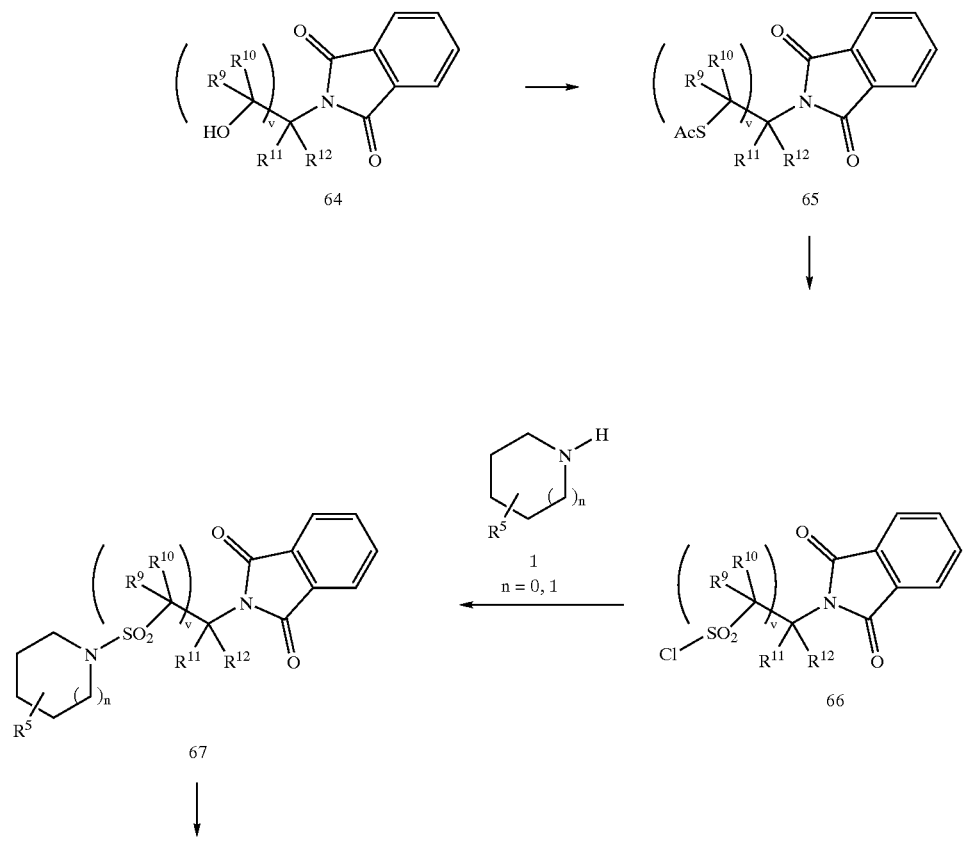

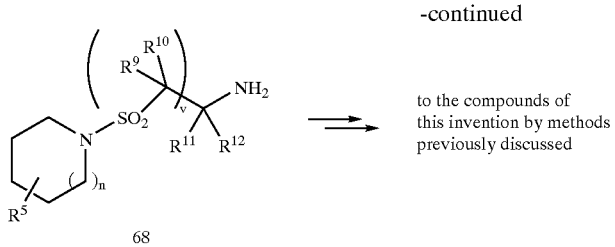

68

A method for the synthesis of N-substituted heterocycles at $R^5$ is shown in Scheme 11. The heterocycle can be deprotonated with NaH or by other bases familiar to one skilled in the art, in a solvent such as DMF, THF, or another appropriate aprotic solvent and reacted with piperidine or pyrrolidine 69 at room temperature to the reflux temperature of the solvent.

Deprotection and elaboration as described before yields compounds where $R^5$ contains an N-substituted heterocycle. If the nitrogen atom of the heterocycle is sufficiently nucleophilic, then an acid scavenger, such as $K_2CO_3$, $KHCO_3$, $Na_2CO_3$, $NaHCO_3$, amongst others, can be used in place of NaH, employing THF, DMF, or methyl ethyl ketone as solvents. In this case hydroxylic solvents may be used as well, such as methanol, ethanol, etc. from room temperature to the reflux temperature of the solvent. Compound 69 as well as its other positional isomers are available, for example, from commercially available 4-hydroxymethylpiperidine, 2-, 3- and 4-carboethoxypiperidine, L- or D-proline ethyl ester, or from methyl 1-benzyl-5-oxo-3-pyrrolidinecarboxylate by methods familiar to one skilled in the art and as discussed previously in this application.

SCHEME 11

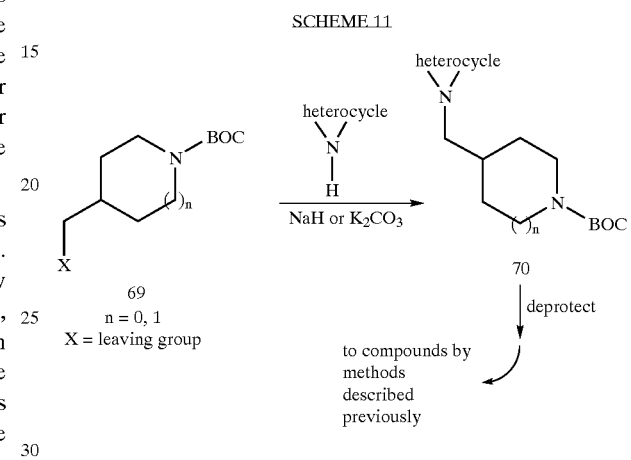

A method for the synthesis of C-substituted heterocycles at $R^5$ is shown in Scheme 12. Many heterocycles such as the ones shown in Scheme 12, but not limited thereto, can be metallated with strong bases such as LDA, n-BuLi, sec-BuLi, t-BuLi, etc. to yield the corresponding anionic species. These anions may also be generated via halogen-metal exchange employing n-BuLi, or other alkyllithium reagents. These reactions may be performed in THF, ether, dioxane, DME, benzene, etc. at −78° C. to room temperature.

SCHEME 12

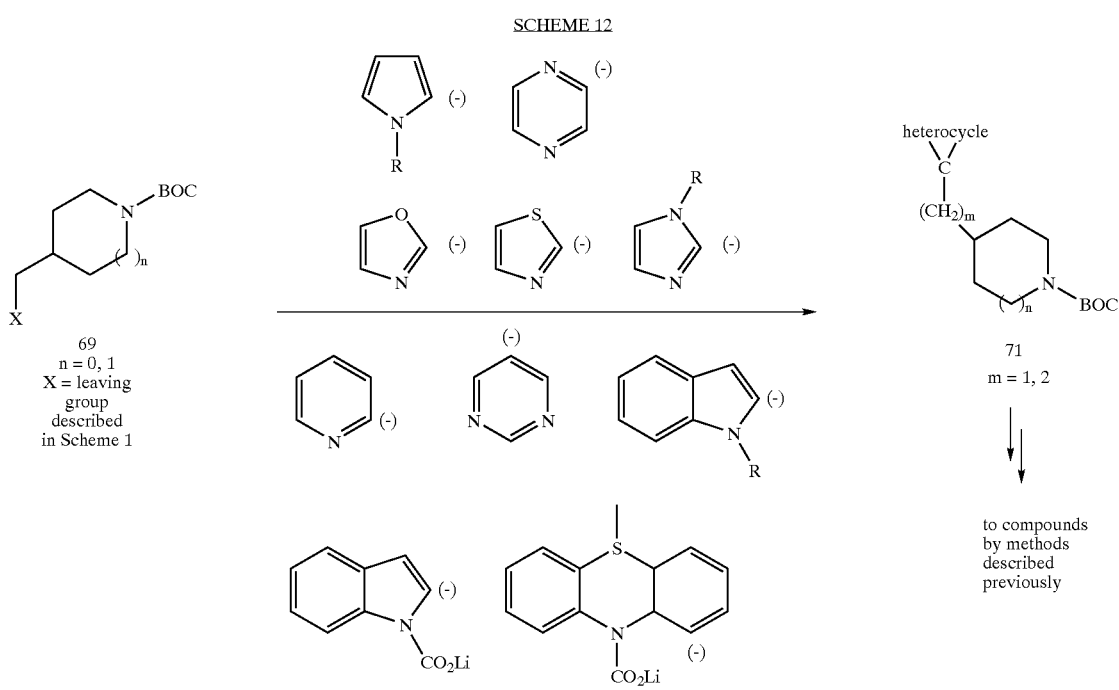

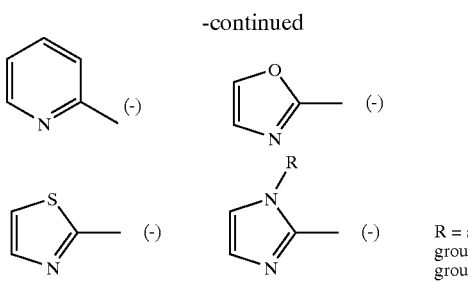

etc.

For reviews of these metallations and halogen-metal exchange reactions see Organometallics in Organic Synthesis, FMC Corp., Lithium Division, 1993, pp. 17–39; Lithium Link, FMC Corp., Spring 1993, pp. 2–17; n-Butyllithium in Organic Synthesis, Lithium Corp. of America, 1982, pp. 8–16; G. Heinisch, T. Langer, P. Lukavsky, J. Het. Chem. 1997, 34, 17–19. The anions can then be quenched with electrophile 69 or its positional isomers to yield the corresponding C-alkylated heterocyclic pyrrolidine or piperidine 71.

Org. Chem. 1969, 34, 4; J. Org. Chem. 1987, 52, 2226) amongst others familiar to one skilled in the art. It is understood by one skilled in the art that the aldehyde group can be located in other positions instead of, for example, the 4-position of piperidine in compound 72 as depicted in Scheme 13. It is to be understood that other heterocycles may also be used besides the ones shown in Scheme 12 and 13.

The anions of the methyl-substituted heterocycles may also be reacted with a BOC-protected piperidone or pyrroli-

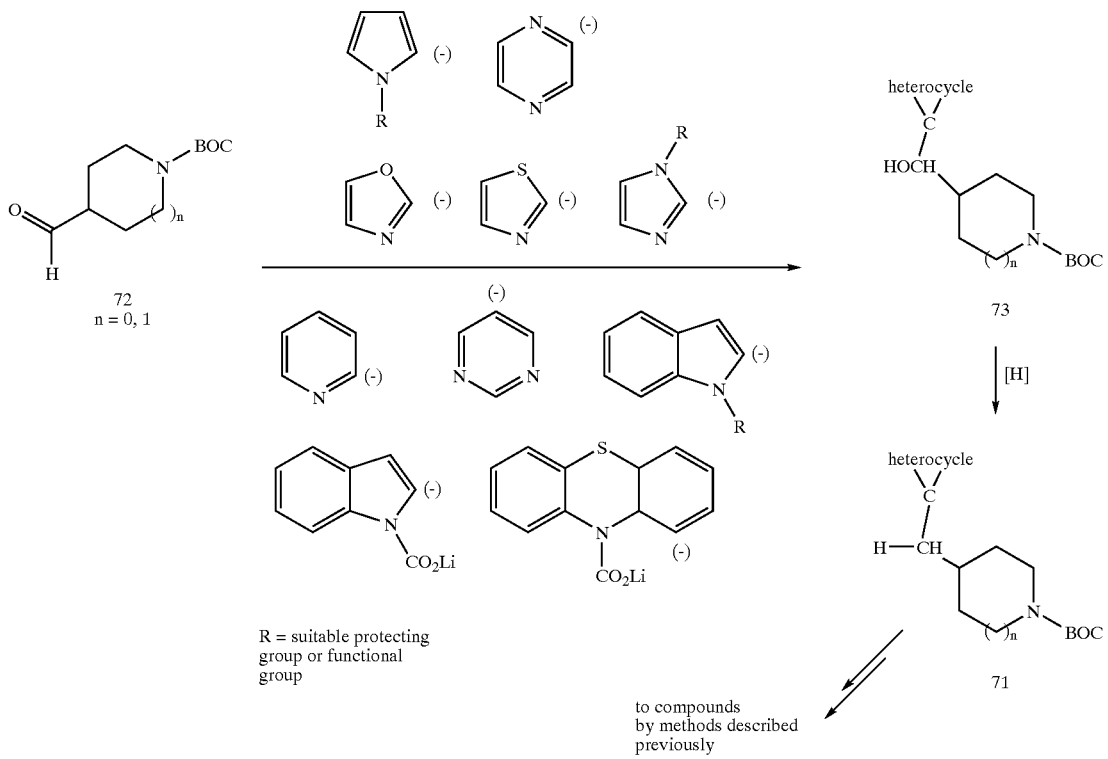

SCHEME 13

Another method for the synthesis of C-substituted heterocyclic-methylpyrrolidines or piperidines is shown in Scheme 13. The protected aldehyde 72 is reacted with the anion of the heterocycle (its generation as described previously) at −78° C. to room temperature with or without CeCl₃ in an inert solvent such as THF, ether, dioxane, DME, benzene, etc. to yield carbinol 73. Catalytic hydrogenation of the alcohol yields the corresponding methylene compound 71. Other reduction methods include Et₃SiH/TFA (J.

done (74) to yield alcohols 75 as shown in Scheme 14 (see above reviews on metallations for references). The OH may be reduced by the method of Barton (Barton, D. H. R.; Jaszberenyi, J. C. Tet. Lett. 1989, 30, 2619 and other references therein) to yield piperidines and pyrrolidines 76. These can subsequently be taken on to the compounds of this invention as described previously. It is understood by one skilled in the art that the carbonyl group can be located in other positions instead of, for example, the 4-position of piperidine in compound 74 as depicted in Scheme 14. It is to be understood that other heterocycles may also be used besides the ones shown in Scheme 14.

SCHEME 14

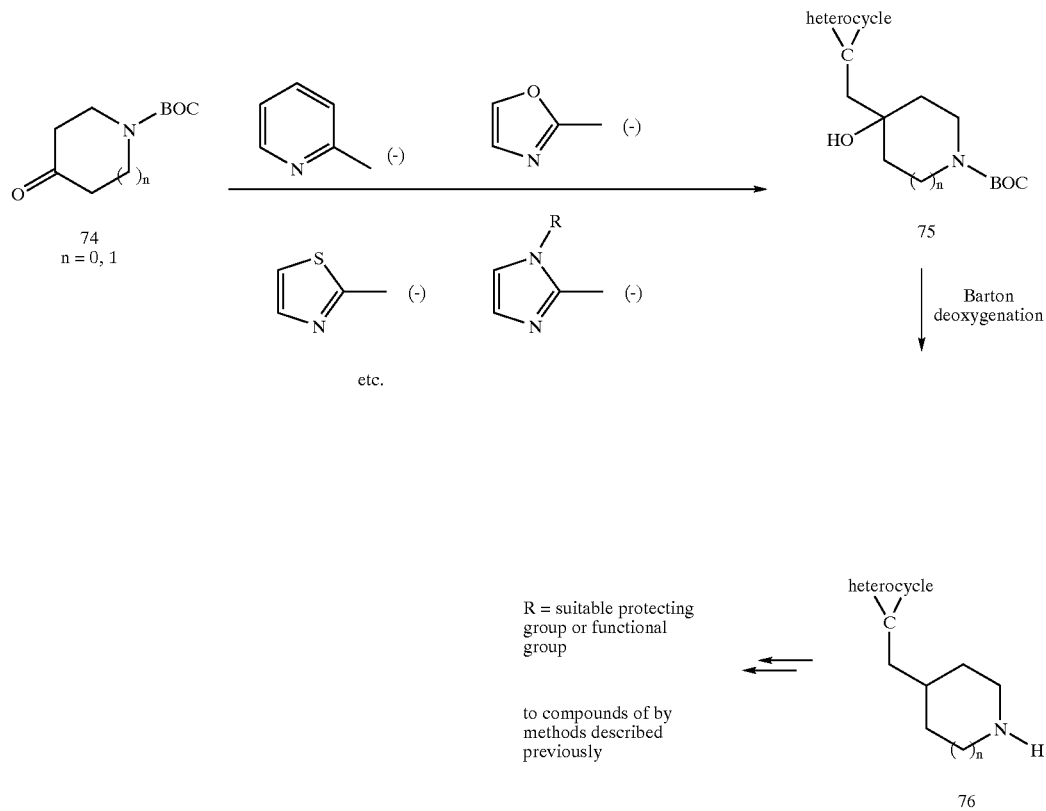

One may also react aryl (phenyl, naphthyl, etc.) anions, generated either by halogen-metal exchange or by ortho-directed metallation (Snieckus, V. Chem. Rev. 1990, 90, 879–933) using n- or s- or t-BuLi in an aprotic solvent such as THF, ether, etc., with or without TMEDA and allow them to react with compounds 69, 72, and 74 with subsequent elaboration to yield the compounds of this invention by the methods depicted in Schemes 11–14.

Another method for the preparation of C-substituted heterocycles is shown in Scheme 15. Protected piperidone 74 undergoes a Wittig reaction with heterocyclic phosphorous ylides to yield 77. Hydrogenation over a noble metal catalyst such as Pd in an alcoholic solvent or with an optically active transition metal catalyst (see asymmetric hydrogenation references of Parshall and Coleman, op. cit.) yields 76 which can be further elaborated into the compounds of this invention by the procedures described previously. It will be appreciated by one skilled in the art that the carbonyl group can be located in other positions instead of, for example, the 4-position of piperidine in compound 74 as depicted in Scheme 15. It is to be understood that other heterocycles may also be used besides the ones shown in Scheme 15.

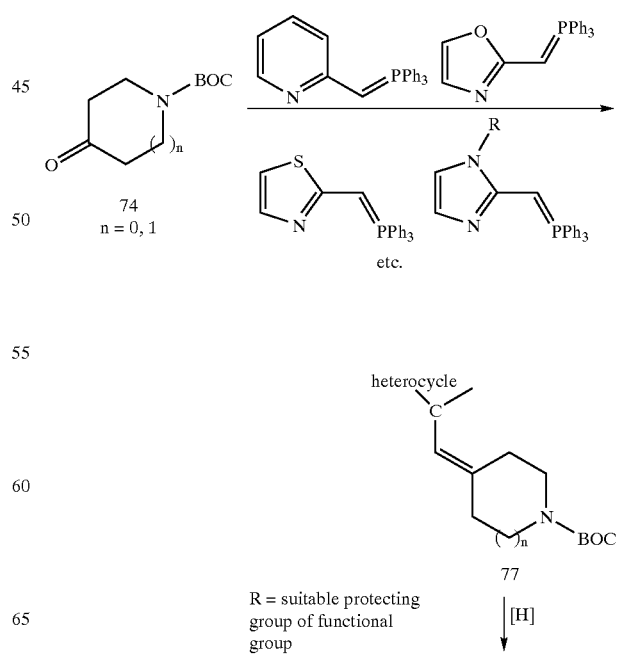

Scheme 15

-continued

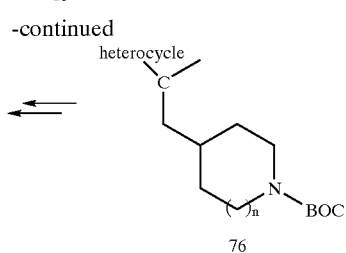

Syntheses of amines 9, 10, and the amines which are precursors to isocyanates, isothiocyanates 5 or of phenylcarbamates or thiocarbamates, all of which have been discussed in regards to Scheme 1, will now be discussed. For example, 3-nitrobenzeneboronic acid (79: Scheme 16) is commerically available and can undergo Suzuki couplings (Suzuki, A. Pure Appl. Chem. 1991, 63, 419) with a wide variety of substituted iodo- or bromo aryls (aryls such as phenyl, naphthalene, etc.), heterocycles, alkyls, akenyls (Moreno-manas, M., et al., J. Org. Chem., 1995, 60, 2396), or alkynes. It can also undergo coupling with triflates of aryls, heterocycles, etc. (Fu, J.-m, Snieckus, V. Tet. Lett. 1990, 31, 1665–1668). Both of the above reactions can also undergo carbonyl insertion in the presence of an atmosphere of carbon monoxide (Ishiyama, et al., Tet. Lett. 1993, 34, 7595). These nitro-containing compounds (81 and 83) can then be reduced to the corresponding amines either via catalytic hydrogenation, or via a number of chemical methods such as $Zn/CaCl_2$ (Sawicki, E. J Org Chem 1956, 21). The carbonyl insertion compounds (84) can also undergo reduction of the carbonyl group to either the CHOH or $CH_2$ linkages by methods already discussed ($NaBH_4$ or $Et_3SiH$, TFA, etc.). These amines can then be converted to isocyanate 5 via the following methods (Nowakowski, J. J Prakt Chem/Chem-Ztg 1996, 338 (7), 667–671; Knoelker, H.-J. et al., Angew Chem 1995, 107 (22), 2746–2749; Nowick, J. S. et al., J Org Chem 1996, 61 (11), 3929–3934; Staab, H. A.; Benz, W.; Angew Chem 1961, 73); to isothiocyanate 5 via the following methods (Strekowski L. et al., J Heterocycl Chem 1996, 33 (6), 1685–1688; Kutschy, Pet al., Synlett 1997, (3), 289–290); to carbamoyl chloride 11 (after 82 or 84 is reductively aminated with an $R^2$ group) (Hintze, F.; Hoppe, D.; Synthesis (1992) 12, 1216–1218); to thiocarbamoyl chloride 11 (after 82 or 84 is reductively aminated with an $R^2$ group) (Ried, W.; Hillenbrand, H.; Oertel, G.; Justus Liebigs Ann Chem 1954, 590); or just used as 9, or 10 (after 82 or 84 is reductively aminated with an $R^2$ group), in synthesizing the compounds of this invention by the methods depicted in Scheme 1.

Nitrobenzoic acids are precursors to N-monosubstituted nitrobenzamides which can be converted to tetrazoles by the method of Duncia, J. V. et al., J. Org. Chem., 1991, 56, 2395–2400, or by the method of Thomas, E., Synthesis (1993) 767–768 (and other methods familiar to one skilled in the art). These tetrazole-containing nitrobenzenes can be reduced to the corresponding anilines and coupled to make ureas and urea isosteres (i.e., Z is not oxygen in formula I) as in the discussion surrounding Scheme 1 to make compounds of the present invention. As in the above synthesis of tetrazole-substituted anilines, one can also make other heterocycle-substituted anilines in a similar de novo fashion using reactions familiar to one skilled in the art.

SCHEME 16

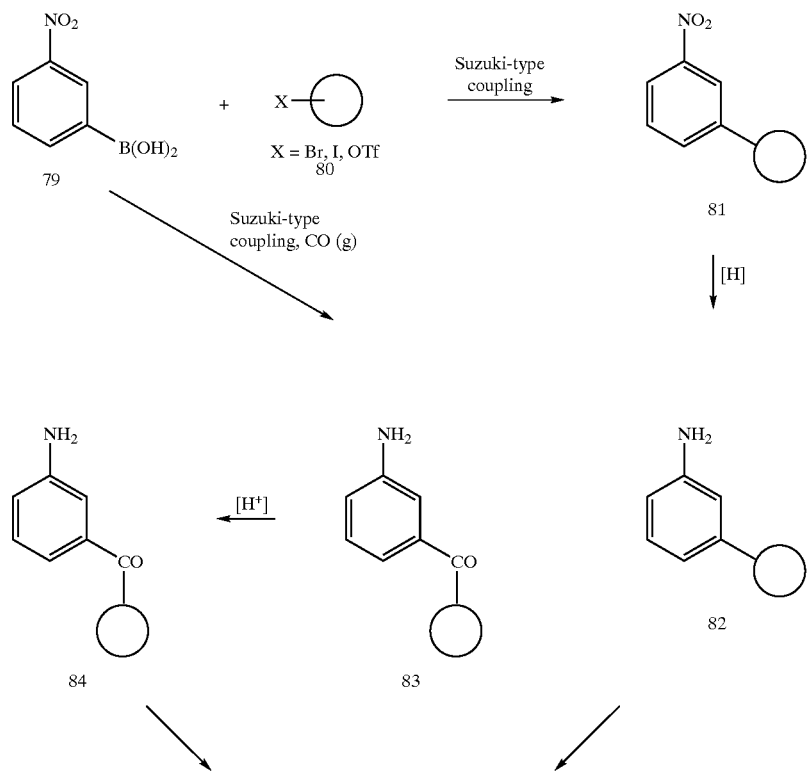

-continued
make isocyanate or isothiocyanate 5, or carbamoyl chlorides 11, or used as 9 or 10 to make the compounds of this invention as described for the compounds of Scheme 1

Likewise, protected aminobromobenzenes or triflates or protected aminobromoheterocycles or triflates 85 (Scheme 17) may undergo Suzuki-type couplings with arylboronic acids or heterocyclic boronic acids (86). These same bromides or triflates 85 may also undergo Stille-type coupling (Echavarren, A. M., Stille, J. K. J. Am. Chem. Soc., 1987, 109, 5478–5486) with aryl, vinyl, or heterocyclic stannanes 89. Bromides or triflates 85 may also undergo Negishi-type coupling with other aryl or heterocyclic bromides 90 (Negishi E. Accts. Chem. Res. 1982, 15, 340; M. Sletzinger, et al., Tet. Lett. 1985, 26, 2951). Deprotection of the amino group yields an amine which can be coupled to make a urea and other linkers containing Z as described above and for Scheme 1. Amino protecting groups include phthalimide, 2,4-dimethylpyrrole (S. P. Breukelman, et al. J. Chem. Soc. Perkin Trans. I, 1984, 2801); N-1,1,4,4-Tetramethyldisilyl-azacyclopentane (STABASE) (S. Djuric, J. Venit, and P. Magnus Tet. Lett 1981, 22, 1787) and others familiar to one skilled in the art.

to form an amine (Yamazaki, S.; Ukaji, Y.; Navasaka, K.; Bull Chem Soc Jpn 1986, 59, 525). Ketones and trifluoromethylketones undergo reductive amination in the presence of $TiCl_4$ followed by $NaCNBH_4$ to yield amines (Barney, C. L., Huber, E. W., McCarthy, J. R. Tet. Lett. 1990, 31, 5547–5550). Aldehydes and ketones undergo reductive amination with $Na(AcO)_3BH$ as mentioned previously to yield amines (Abdel-Magid, A. F., et al. Tet. Lett. 1990, 31, (39) 5595–5598). Amines may also be synthesized from aromatic and heterocyclic OH groups (for example, phenols) via the Smiles rearrangement (Weidner, J. J., Peet, N. P. J. Het. Chem., 1997, 34, 1857–1860). Azide and nitrile displacements of halides, tosylates, mesylates, triflates, etc. followed by LAH or other types or reduction methods yield amines. Sodium diformyl amide (Yinglin, H., Hongwen, H. Synthesis 1989 122), potassium phthalimide, and bis-BOC-amine anion can all displace halides, tosylates, mesylates, etc., followed by standard deprotection methods to yield amines, procedures which are familiar to one skilled in the art. Other

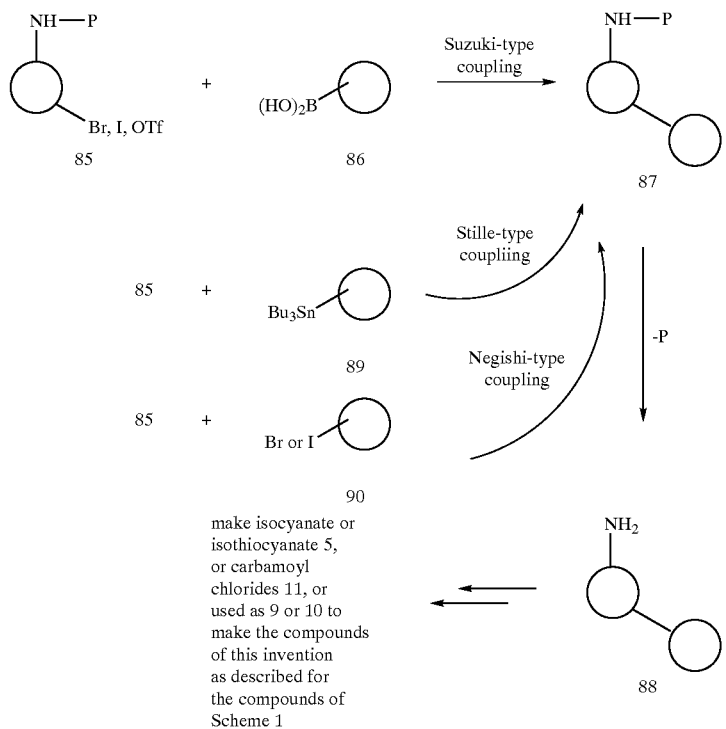

SCHEME 17

Many amines are commercially available and can be used as 9, 10, or used as precursors to isocyanates or isothiocyanates 5. There are numerous methods for the synthesis of non-commercially available amines familiar to one skilled in the art. For example, aldehydes and ketones may be converted to their O-benzyl oximes and then reduced with LAH methods to synthesize more elaborate amines involve the Pictet-Spengler reaction, imine/immonium ion Diels-Alder reaction (Larsen, S. D.; Grieco, P. A. J. Am. Chem. Soc. 1985, 107, 1768–69; Grieco, P. A., et al., J. Org. Chem. 1988, 53, 3658–3662; Cabral, J. Laszlo, P. Tet. Lett. 1989, 30, 7237–7238; amide reduction (with LAH or diborane, for example), organometallic addition to imines (Bocoum, A. et al., J. Chem. Soc. Chem. Comm. 1993, 1542–4) and others all of which are familiar to one skilled in the art.

Compounds containing an alcohol side-chain alpha to the nitrogen of the piperidine/pyrrolidine ring can be synthesized as shown in Scheme 18. Only the piperidine case is exemplified, and it is to be understood by one skilled in the art that the alpha-substituted pyrrolidines may be synthesized by a similar route. It is also understood that appropriate substituents may be present on the piperidine/pyrrolidine ring. A 4-benzylpiperidine 91 is protected with a BOC group. The BOC-piperidine 92 is then metallated under conditions similar to those Beak, et al. (P. Beak and W.-K. Lee, J. Org. Chem. 1990, 55, 2578–2580, and references therein) and quenched with an aldehyde to yield alcohol 93. The metallation may also be done enantioselectively using sparteine (P. Beak, S. T. Kerrick, S. Wu, J. Chu J. Am. Chem. Soc. 1994, 116, 3231–3239). This alcohol can be deprotonated with NaH and cyclized to carbamates 94 and 95 which permits structural assignments of the erythro and threo isomers. Protection of the hydroxyl group (93a) followed by deprotection with base yields piperidine 96. We have chosen piperidine only for demonstration purposes. Subsequent acylation or sulfonation by an E group, elaboration to the urea or its isostere and eventual deprotection of the hydroxyl group yields the compounds of this invention.

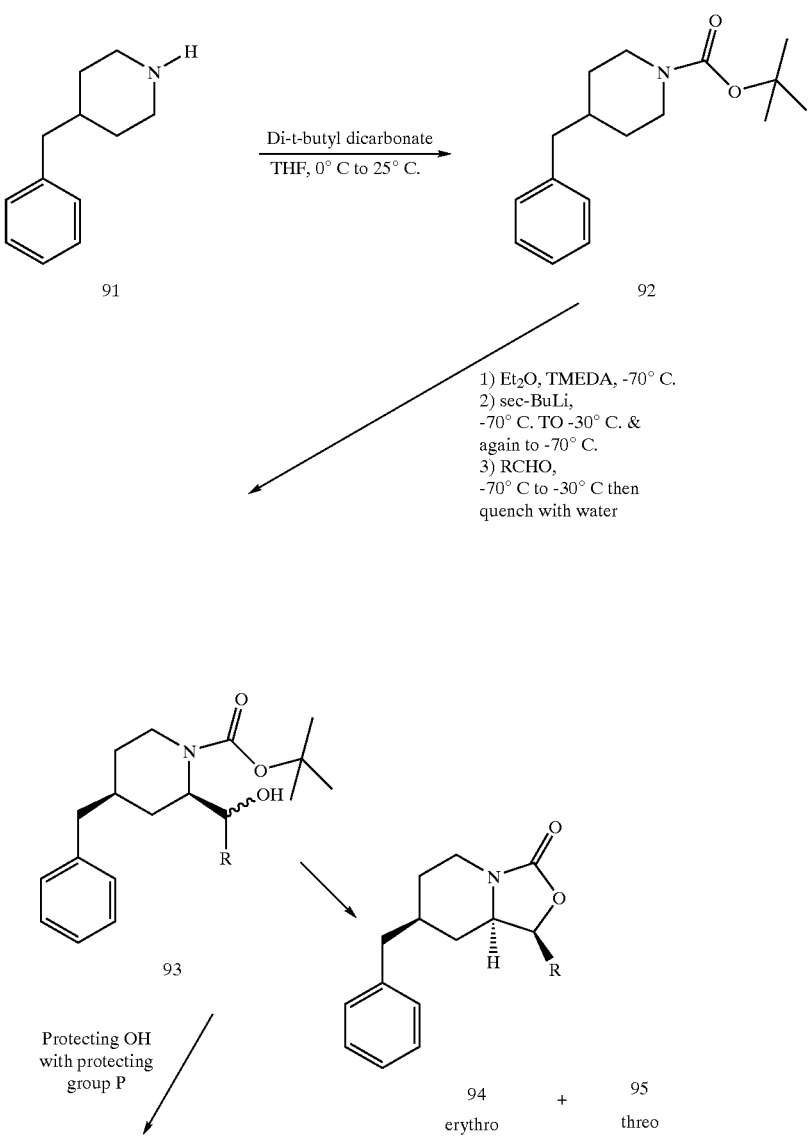

Scheme 18

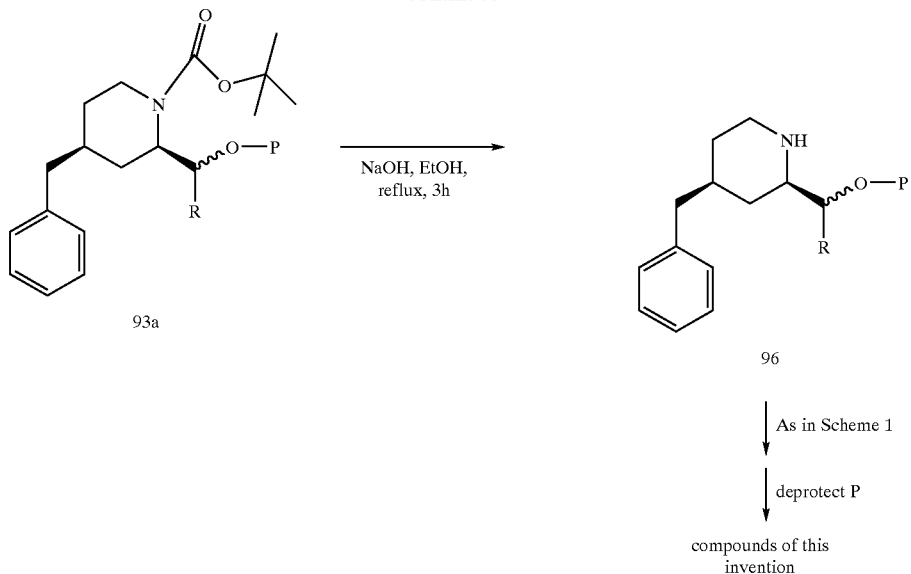

Compounds where Z=N—CN, CHNO$_2$, and C(CN)$_2$ can be synthesized by the methods shown in Scheme 19. Thus amine 100 reacts with malononitrile 99 neat or in an inert solvent at room temperature to the reflux temperature of the solvent, or at the melting point of the solid/solid mixture, to yield malononitrile 98. This in turn can undergo reaction with amine 97 under similar conditions stated just above to yield malononitrile 101. Likewise, a similar reaction sequence may be used to make 104 and 107 [for Z=C(CN)2], see for example P. Traxler, et al., J. Med. Chem. (1997), 40, 3601–3616; for Z=N—CN, see K. S. Atwal, J. Med. Chem. (1998) 41, 271; for Z=CHNO$_2$, see J. M. Hoffman, et al., J. Med. Chem. (1983) 26, 140–144). For all of the above-mentioned urea isosteres in Scheme 19, the reaction sequence can be reversed. For example, malononitrile 99 can react first with 97 followed by 100 to yield 101. The same holds true for nitroethylene 102 and cyanoguanidine intermediate 106.

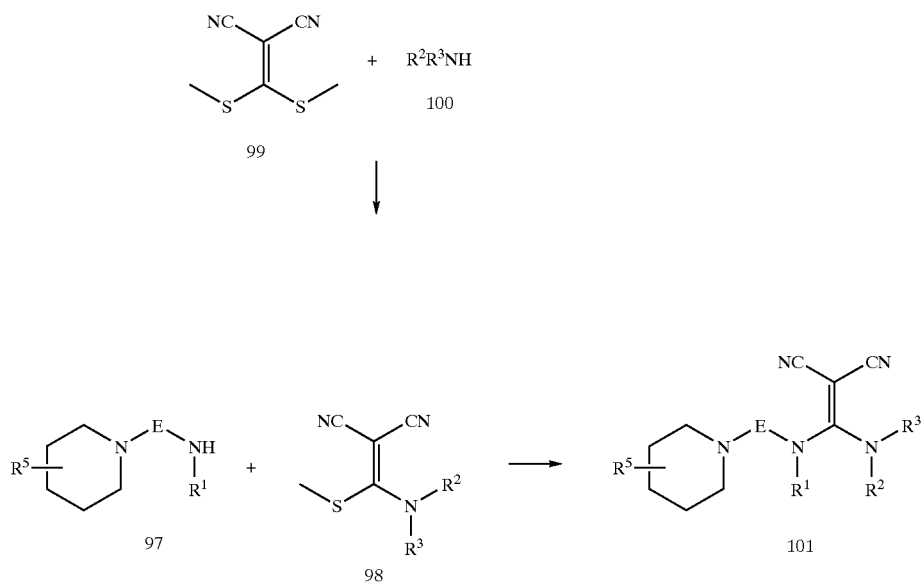

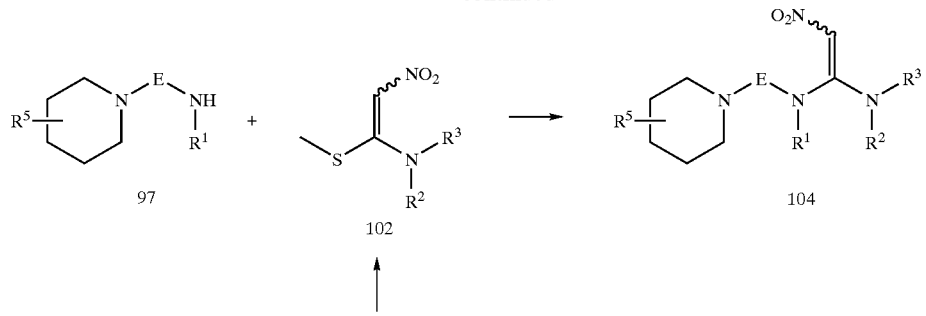

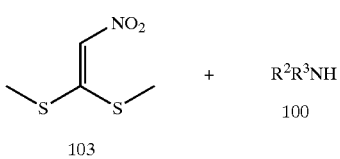

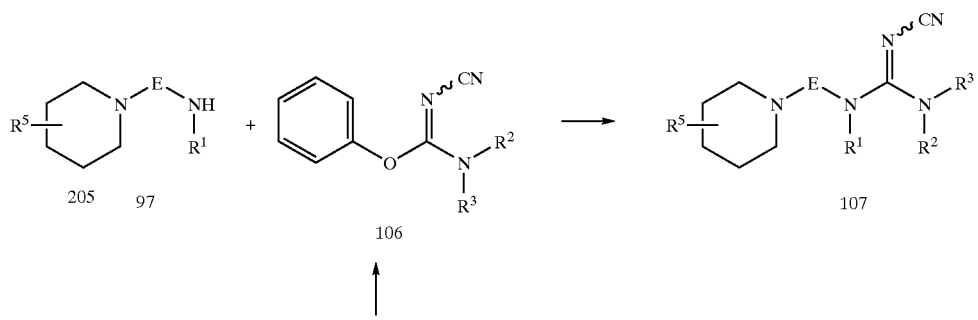

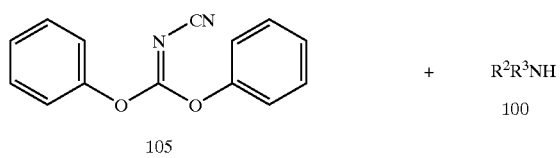

The synthesis of compounds wherein $R^{11}$ and $R^{12}$ are taken together to form a heterocyclic ring (such as in 108–111) is outlined in Scheme 20. Thus, 1-[(1,1-dimethylethoxy)carbonyl]-4-[[(phenylmethoxy)carbonyl]amino]-4-piperidineacetic acid 112 (Suzuki, T.; Imanishi, N.; Itahana, H.; Watanuki, S.; Ohta, M.; Mase, T. *Synthetic Comm.* 1998, 28, 701–712.) is coupled to (S)-3-(4-fluorobenzyl) piperidine using a common amide forming reagent such as BOP, HBTU or HATU to furnish the amide 113. The CBZ group of 113 can be removed by hydrogenation. Coupling with 3-acetylbenzene isocyanate furnishes 108. One can also use carbamic acid phenyl esters to furnish other urea analogs at this step. In addition, one can synthesize the other urea isosteres (cyanoguanidine, nitroethylene, etc.) covered in this application using the appropriate starting materials mentioned in Scheme 19 at this particular synthetic step. The BOC group of 108 is then removed by TFA or by other methods familiar to one skilled in the art to afford 109, followed by reductive amination to give 110. Reductive amination can also be performed with other aldehydes to yield analogs of compound 110. Compound 109 can be treated with methylsulfonyl chloride to provide methanesulfonamide 111. Likewise, other sulfonylchlorides can be also used at this step to yield a variety of different sulfonamide derivatives. Amine 109 can also be coupled (Schotten-Baumann reaction, using coupling reagents such as BOP, pyBOP, HATU, DCC, EDC, etc.) to a wide variety of carboxylic acids to yield amide derivatives (not shown).

Scheme 20
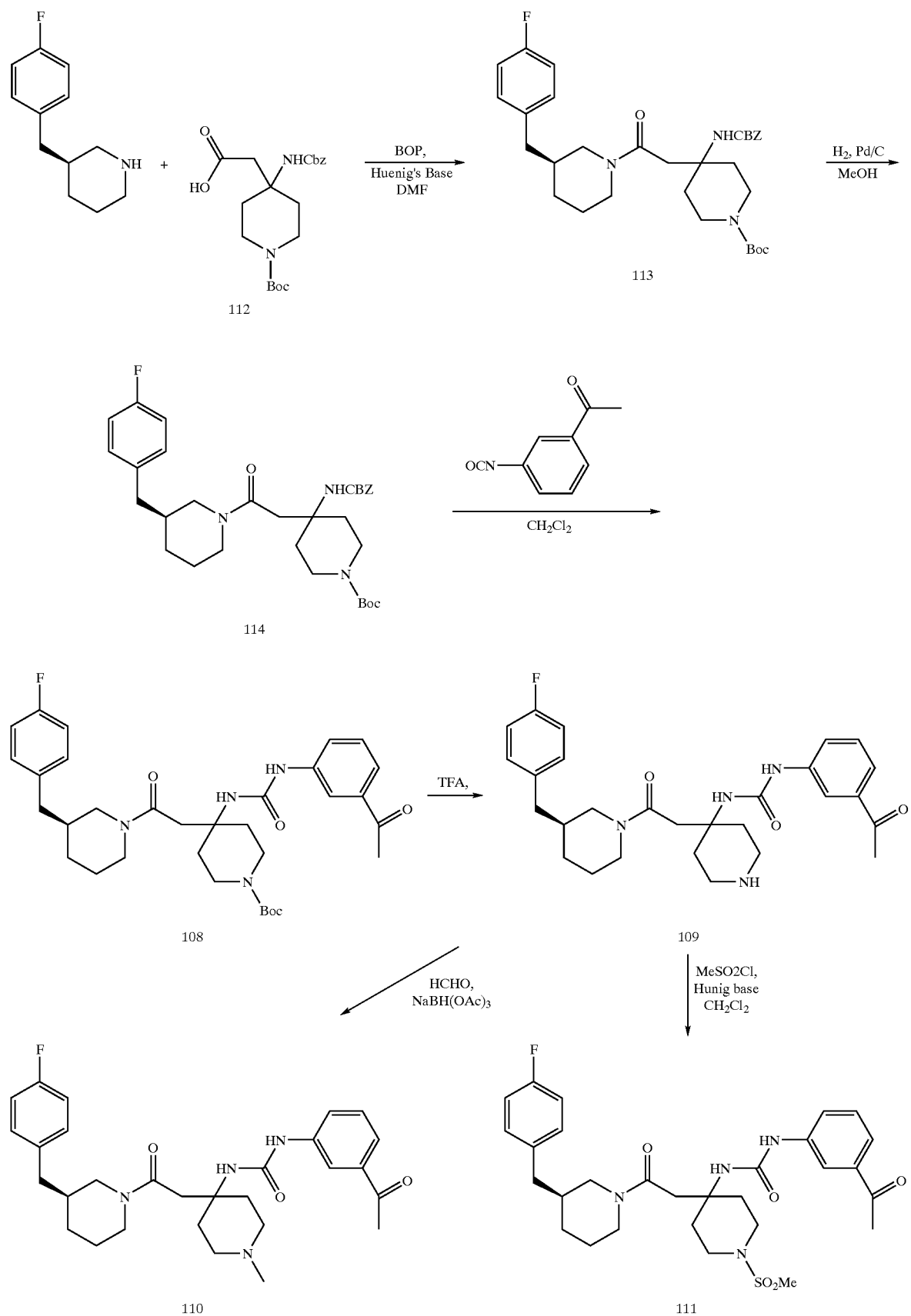

The synthesis of compounds wherein $R^{11}$ and $R^{12}$ is a carboxamide (such as in compound 115) is shown in Scheme 21. Note that if the protecting group on the COOH group of 116 is moved to the other COOH group, then compounds in which $R^9$ or $R^{10}$ is a carboxamide can be synthesized. Thus (S)-3-(4-fluorobenzyl)piperidine and CBZ-L-ASP(OH)—O-t-Bu is treated with a common amide formation reagent such as BOP, HATU, and TBTU to furnish the coupled product 117. The CBZ group of 117 was removed by hydrogenation. The free amine is then condensed with [3-(1-methyl-1H-tetrazol-5-yl)-phenyl]-carbamic acid phenyl ester to afford the 119. One can use other carbamic acid phenyl esters to furnish other urea analogs. One can also synthesize the other urea isosteres (cyanoguanidine, nitroethylene, etc.) covered in this application using the appropriate starting materials mentioned in Scheme 19 at this particular synthetic step. The tert-butyl group of 119 is then removed by TFA or by other methods familiar to one skilled in the art, followed by coupling with diethylamine in the presence of BOP (or other coupling reagent such as pyBOP, EDC, HATU, DCC, etc.) to afford the final product 115. Note that other amines besides diethylamine can be coupled to provide a wide variety of amides. Coupling with alcohols will yield a wide variety of esters.

Scheme 21

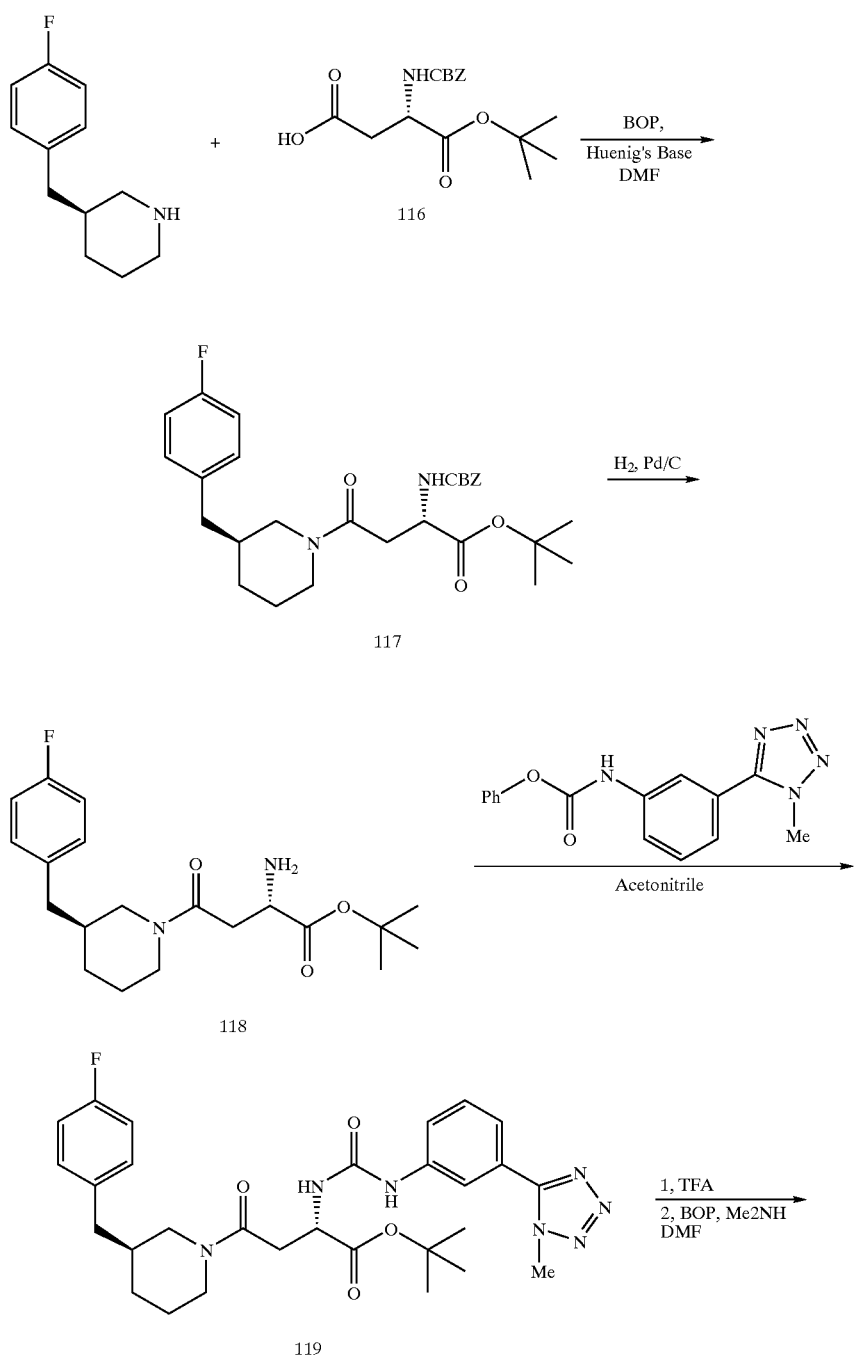

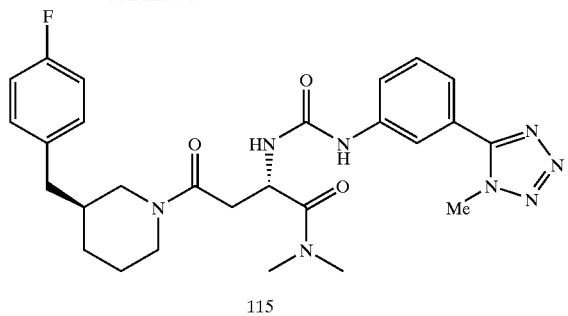

The synthesis of compounds wherein $R^{11}$ and $R^{12}$ is an amine (such as in 120) is outlined in Scheme 22. Note that if the protecting group on the COOH group of 121 is moved to the other COOH group, then compounds in which $R^9$ or $R^{10}$ is an amine can be synthesized. Thus CBZ-L-Asp (tert-butyl)-OH 121 is condensed with morpholine using an amide coupling reagent such as BOP (Note that other amines besides morpholine can be used at this step. In addition, other coupling reagents such as pyBOP, HATU, DCC, EDC, etc. can also be used). The resulting amide 122 is reduced to the corresponding amine, followed by treatment with TFA to afford the carboxylic acid 123. The acid is then coupled with (S)-3-(4-fluorobenzyl) piperidine using BOP (or any of the coupling reagents mentioned previously) to provide 124. The CBZ group of 124 is removed by hydrogenation. Condensation with [3-(1-methyl-1H-tetrazol-5-yl)-phenyl]-carbamic acid phenyl ester furnishes 120. One can use other carbamic acid phenyl esters to furnish other urea analogs. One can also synthesize the other urea isosteres (cyanoguanidine, nitroethylene, etc.) covered in this application using the appropriate starting materials mentioned in Scheme 19 at this particular synthetic step.

Scheme 22

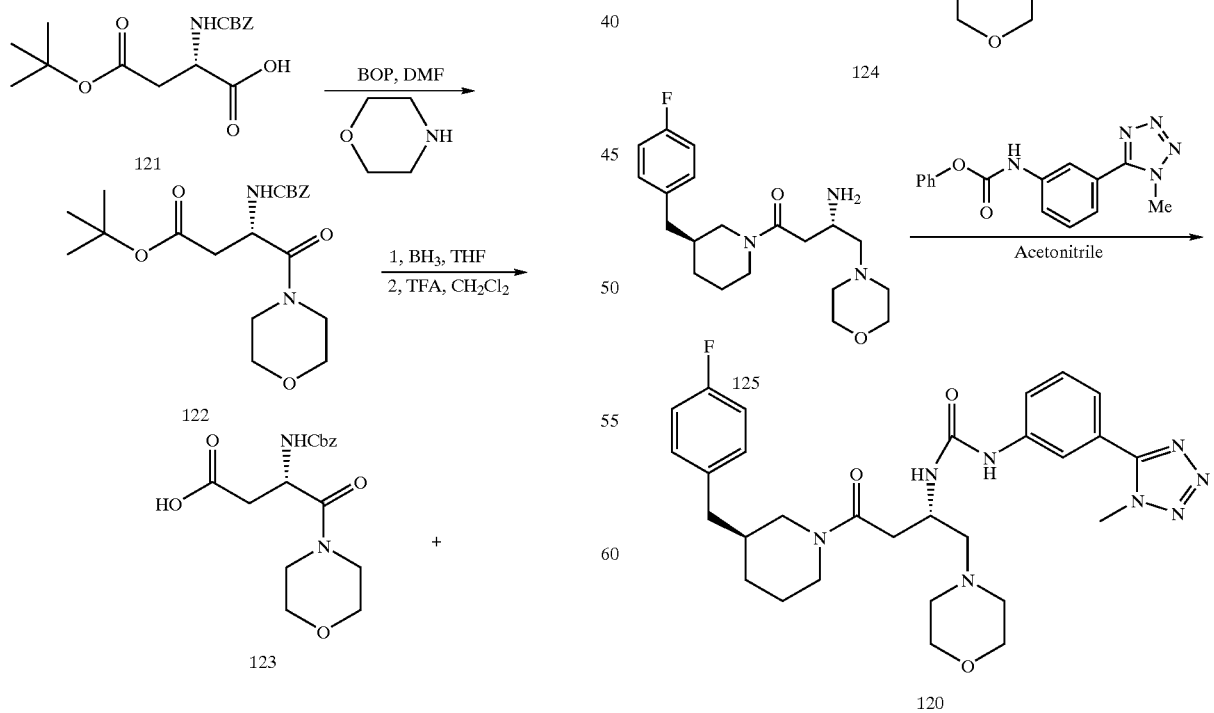

Scheme 23

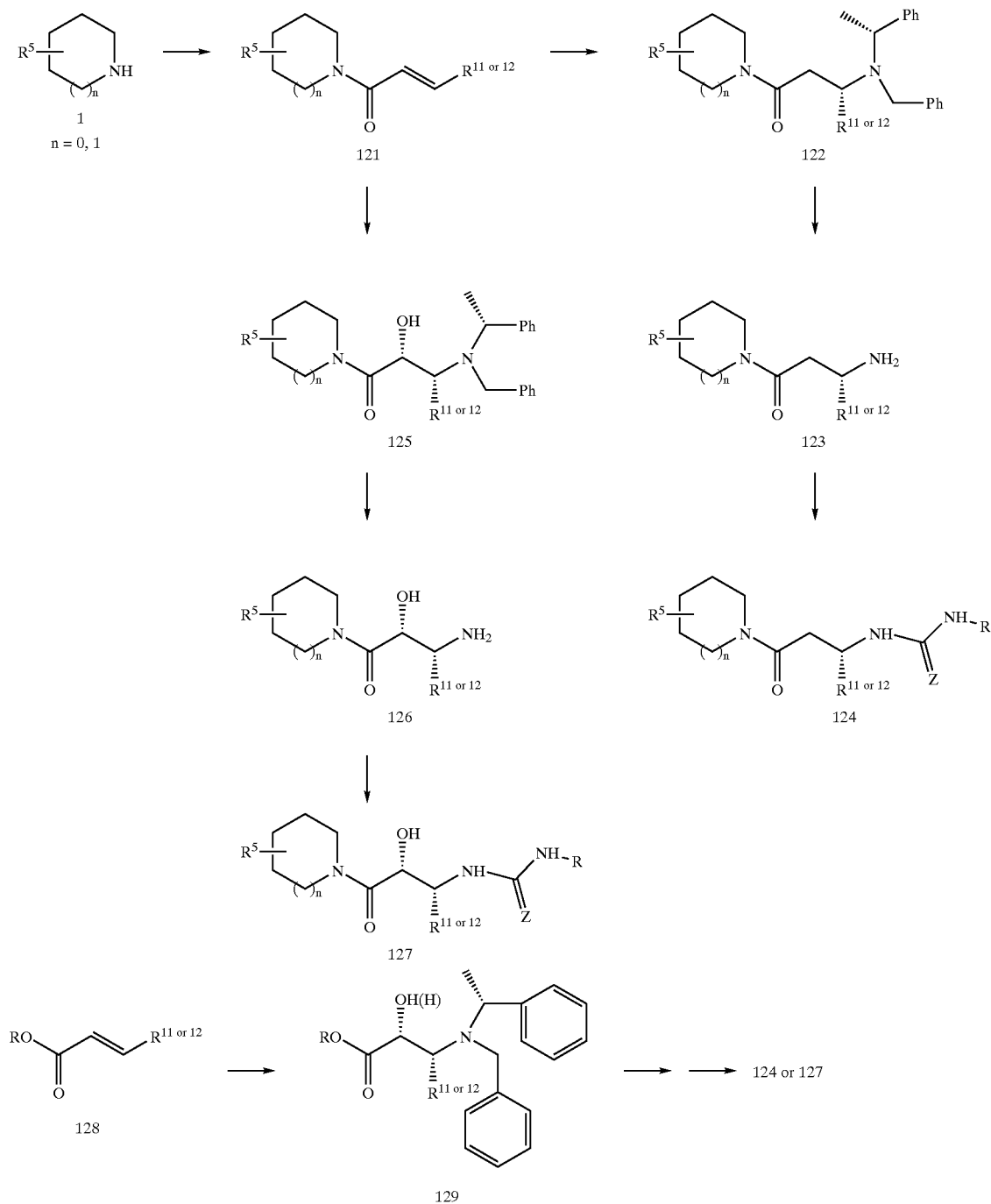

The synthesis of compounds 124 and 127 is described in Scheme 23. Coupling of pyrrolidine/piperidine 1 with a crotonic acid derivative using PyBOP or other peptide coupling reagents yields 121 where $R^{11}$ or $R^{12}$ contains a carbon atom which is directly attached to the olefin. It is to be understood that $R^{11}$ or $R^{12}$ is in its final form or in a protected form or in the form of a precursor. Michael-type addition of chiral benzyl-α-methyl benzyl)amine under the conditions of Davies et. al (M. E. Bunnage; A. N. Chernega; S. G. Davies; C. J. Goodwin J. Chem. Soc. P1, (1994) 2373–2384) yields 122. If the intermediate is quenched with a Davis oxaziridine reagent, then α-hydroxylated 125 is obtained. Catalytic hydrogenation over a noble metal catalyst such as $Pd(OH)_2$ yields amides 123 and 126. Coupling as described previously yields 124 and 127. The above sequence may also be performed on crotonate derivative 128 where R is an ester such as methyl, ethyl, t-butyl, etc., but not limited thereto. Eventually the ester is hydrolyzed and coupled to 1 to yield amides 122 and 125. Elaboration as described above yields 124 and 127.

SCHEME 24

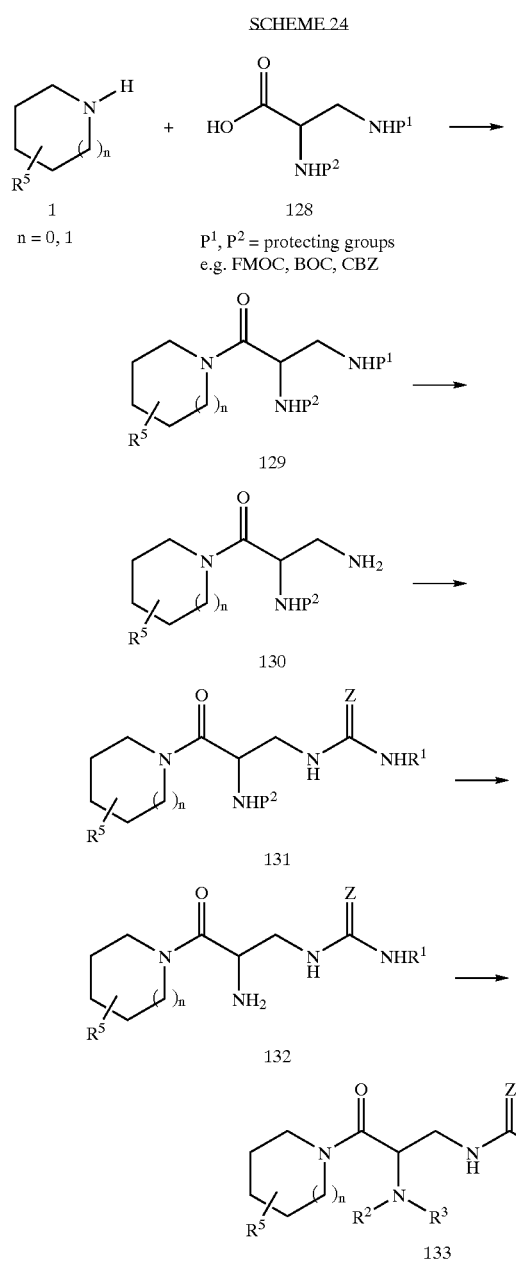

The synthesis of compounds wherein $R^9$ is a modified amino group ($R^{10}$=H) is shown in scheme 24. Compound 1 can be coupled to protected diaminopropionic acid 128 using a common amide forming reagent such as PyBOP, HATU or HBTU to furnish the amide 129. Selective removal of protecting group $p^1$ provides amine 130, which can be converted into 131 as urea (Z=O) or thiourea (Z=S) or other urea mimics (Z=N—CN, CHNO$_2$, and C(CN)$_2$) via the general methods described in Schemes 1 and 19. Deprotection of amino group in 131 provides amine 132. The free amine can be then converted into 133 as an amide, sulfonamide, secondary or tertiary amine, etc. by procedures familiar to one skilled in the art.

EXAMPLES

Example 1

Part A. Preparation of tert-Butyl 3-oxo-1-piperidinecarboxylate

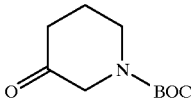

To a stirring solution of N-benzyl-3-piperidone hydrochloride hydrate (4.2 g, 18.6 mmol) and 10% palladium on carbon (0.8 g) in degassed methanol (200 mL) was added hydrogen gas to 55 psi. The reaction mixture was stirred for 16 hr and then filtered through a pad of Celite. The Celite was washed with methanol (200 mL). The filtrates were combined and concentrated in vacuo to a colorless oil. The oil was dissolved in tetrahydrofuran (200 mL) and then treated with di-t-butyl-dicarbonate (5.27 g, 24.1 mmol) and sat. aq. sodium bicarbonate (50 mL). The reaction was stirred for 4 hr and then concentrated in vacuo to a white solid. The solid was partioned between EtOAc and 1 N HCl. The organic layer was separated, washed with 1 N NaOH and brine, dried over Na$_2$SO$_4$, and evaporated in vacuo to a colorless oil. The oil was purified by flash chromatography (silica gel, hexane:EtOAc 3:1) to yield 2.93 g of product as a colorless oil. $^1$H NMR (300 MHz, CDCl$_3$) δ 3.99 (s, 2H), 3.58 (t, J=6.3 Hz, 2H), 2.46 (t, J=6.3 Hz, 2H), 1.97 (p, J=6.3 Hz, 2H), 1.45 (s, 9H).

Part B. Preparation of tert-Butyl 3-(4-fluorobenzylidene)-1-piperidinecarboxylate

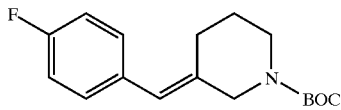

To a stirring solution of (4-fluorophenylmethyl) triphenylphosphonium chloride (17.68 g, 43.5 mmol) in dry THF (60 mL) at –78° C. was added 2.5 M n-butyllithium in hexane (14.6 mL, 36.5 mmol). The reaction was warmed to 0° C. for 1 hr and the piperidone from Part A (3.46 g, 17.4 mmol) in THF (60 mL) was added. The mixture was stirred at room temperature for 1 hr and the heated to reflux for 16 hr. The reaction was cooled to room temperature and quenched by the addition of sat. aq NH$_4$Cl. The reaction was extracted with EtOAc (3×100 mL). The organic layers were combined, washed with brine, dried over MgSO$_4$, and evaporated in vacuo to a pale yellow oil. The oil was purified by flash chromatography (silica gel, hexane:EtOAc 9:1) to yield 3.82 g of a mixture of E and Z isomers of product as a colorless oil. $^1$H NMR (300 MHz, CDCl$_3$) δ 7.22–7.14 (m, 2H), 7.04–6.98 (m, 2H), 6.36 (s, 0.33H), 6.28 (s, 0.67H), 4.14 (s, 1.34H), 4.00 (s, 0.66H) 3.50 (app t, J=5.5 Hz, 2H), 2.47 (t, J=5.1 Hz, 0.66H), 2.39 (t, J=5.1 Hz, 1.34H), 1.75–1.68 (m, 1.34H), 1.65–1.57 (m, 0.66H), 1.48 (s, 9H).

Part C. Preparation of tert-Butyl 3-(4-fluorobenzyl)-1-piperidinecarboxylate

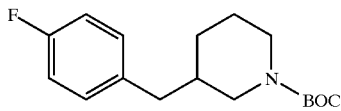

To a stirring solution of the olefin from Part B (3.82 g, 13.1 mmol) and 10% palladium on carbon (0.76 g) in degassed methanol (200 mL) was added hydrogen gas to 55 psi. The reaction was stirred for 16 h and then filtered through a pad of Celite. The celite was washed with methanol (200 mL). The filtrates were combined and concentrated in vacuo to yield 2.76 g of product as a colorless oil. $^1$H NMR (300 MHz, CDCl$_3$) δ 7.12–7.07 (m, 2H), 6.98–6.93 (m, 2H), 3.89 (dt, J=13.2 Hz, 4.0 Hz, 1H), 3.84–3.74 (m, 1H), 2.57–2.43 (m, 4H), 1.75–1.60 (m, 4H), 1.42 (s, 9H), 1.15–1.09 (m, 1H).

Part D-1. Preparation of 3-(4-fluorobenzyl)piperidine

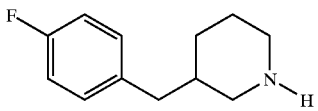

N-BOC-3-(4-fluorobenzyl)piperidine (5 g) was dissolved in 30 mL of 4N HCl in dioxane. Some initial gassing occurred which eventually subsided. After one hour, the mixture was neutralized with aqueous Na$_2$CO$_3$, and the dioxane was evaporated off. The residue was then extracted with ether. The combined ether extracts were dried over MgSO$_4$ and eveporated off to give 2.6 g of the free amine as a discolored oil. This crude material was used in to make the diastereomeric salts.

Part D-2. Resolution of 3-(4-fluorobenzyl)piperidine

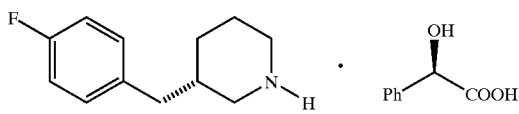

2.0 g of the crude racemic 3-(4-fluorobenzyl)piperidine was dissolved in 25 mL acetonitrile and heated to reflux. The solution was hazy. To this was added 1.56 g (1 equiv.) of (R)-(−) mandelic acid dissolved in 15 mL acetonitrile. Some initial precipitation occurred when the cooler solution was added but it did redissolve when refluxing resumed. The heat was turned off and small amounts of enantiomerically pure salt was added as the temperature dropped. At first the seed crystals dissolved, but when the temperature dropped to 75° C., they remained suspended in the stirred solution. After a few more degrees of cooling, crystal growth was obvious. Cooling was continued at the rate of 1 degree/min. At 50° C., the solution was filtered to recover 0.9 g of salt, which melted at 164° C. It was recrystallized from acetonitrile twice to give (S)-(+)-3-(4-fluorobenzyl)piperidine mandelic acid salt in 98% ee, and melting at 168–171° C.

The synthesis of 2-cbz-NH-cyclohexylmethanol is described in U.S. patent application Ser. No. 09/466,442, which is hereby incorporated by reference for its synthetic disclosure.

Part E-1: Preparation of trans-(1R,2R)-1-(benzyloxycarbonylamino)-2-hydroxymethyl-cyclohexane

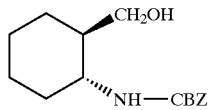

To a solution of trans-(1R,2R)-1-amino-2-hydroxymethyl-cyclohexane (R,R) amino alcohol [*J. Am. Chem. Soc.* 1996, 118, 5502–5503 and references therein] (1.9 g, 14.7 mmol) in CH$_2$Cl$_2$ (50 mL) is added 50 ml of an aqueous solution of Na$_2$CO$_3$ (2.4 g, 28.9 mmol). While stirring, benzyl chloroformate (2.51 g, 14.7 mmol) is added and the mixture is stirred at room temperature for 1 h. The organic layer is separated and washed with water and brine. The solution is concentrated on a rotary evaporator and the residue is chromatographed on silica gel (30% ethyl acetate/hexane) to give 3.1 g (12 mmol) of trans-(1R,2R)-1-(benzyloxycarbonylamino)-2-hydroxymethyl-cyclohexane as a white solid. $^1$H NMR (300 MHz, CDCl$_3$) δ 7.40–7.29 (m, 5H), 5.11 (s, 2H), 4.71 (bd, 1H), 3.76–3.71 (m, 1H), 3.53–3.28 (m, 3H), 2.00–1.95 (m, 1H), 1.90–1.09 (m, 8H). MS AP$^+$ (M+H)$^+$=264.3 (100%).

Part E-2 Preparation of (1R,2R)-2-(benzyloxycarbonylamino)cyclohexanecarboxaldehyde.

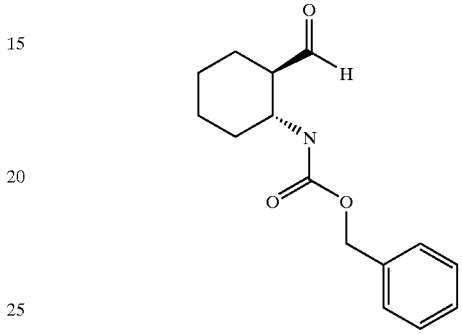

A solution of dimethyl sulfoxide (2.96 mL, 41.8 mmol, 2.2 eq.) in methylene chloride was added dropwise at −60° C. under N2 to a flask containing 2.0 M oxallyl chloride (18.99 mL, 38.0 mmol, 2 eq.) in methylene chloride and the contents then stirred for 15 minutes. A methylene chloride solution of trans-(1R,2R)-1-(benzyloxycarbonylamino)-2-hydroxymethyl-cyclohexane (5.00 g, 19.0 mmol, 1 eq.) was then added dropwise and the mixture stirred for 30 minutes. A solution of triethylamine (7.94 mL, 57.0 mmol, 3 eq.) in methylene chloride was subsequently added dropwise and the reaction allowed to warm to 0° C. The reaction was worked up by washing the methylene chloride layer 3 times with H$_2$O. The organic layer was dried over MgSO$_4$ then stripped to yield an oil which was purified over silica gel in 9:1 followed by 3:1 hexanes/ethyl acetate. Obtained 2.50 grams of an amber oil as product. Mass Spec detects 262 (M+H). NMR (300 MHz, CDCl$_3$) δ 9.60 (d, 1H, J=7 Hz), 7.50–7.20 (m, 5H), 5.20–5.00 (m, 3H), 4.90–4.70 (m, 1H), 4.00–3.70 (m, 1H), 2.20–1.00 (m, 8H).

Part F Preparation of (1R,2R)-2-(benzyloxycarbonylamino)cyclohexanecarboxylic acid

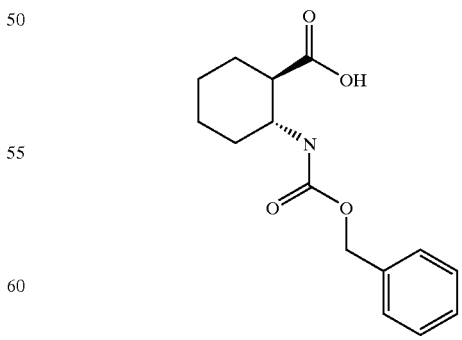

(1R,2R)-2(benzyloxycarbonylamino)cyclohexane-carboxaldehyde (500 mg, 1.91 mmol, 1 eq.), resorcinol (274, 2.49 mmol, 1.3 eq.), NaOAc/HOAc buffer (4 mL, pH=3.5, ionic strength=0.1), and acetonitrile (5 mL) were mixed and stirred under nitrogen at 0° C. Then a sodium chlorite (268 mg, 2.37 mmol, 1.24 eq.) solution in H₂O (4 mL) was added dropwise. The reaction was worked up after 16 hours by adjusting to pH=2 with 1N HCl. The acetonitrile was stripped and the aqueous mixture extracted 3 times with chloroform. The organic layers were dried (MgSO4) and stripped to yield an oil which was purified over silica gel in 3:1 hexanes/ethyl acetate followed by 1:1 hexanes/ethyl acetate followed by 100% ethyl acetate. Obtained 148 mg of white solids as product. Mass Spec detects 278 (M+H). NMR (300 MHz, CDCl₃) δ 7.40–7.20 (m, 5H), 5.20–4.80 (m, 3H), 3.90–3.60 (m, 1H), 2.40–2.20 (m, 1H), 2.20–1.80 (m, 2H), 1.80–1.00 (m, 8H).

Part G Preparation of (1R,2R)-2-(benzyloxycarbonylamino)cyclohexanecarboxylic acid, (S)-3-(4-fluorobenzyl) piperidine amide

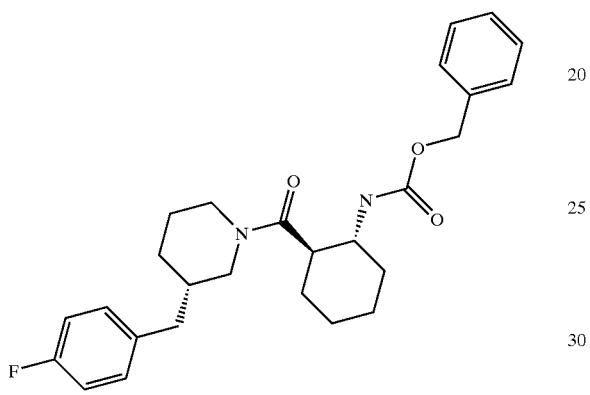

(S)-3-(4-fluorobenzyl)piperidine (obtained as the free base from Part D) (35 mg, 0.18 mmol, 1 eq.), (1R,2R)-2-(benzyloxycarbonylamino)cyclohexane carboxylic acid (50 mg, 0.18 mmol, 1 eq.), benzotriazol-1-yloxytripyrrolidinophosphonium hexafluorophosphate (BOP reagent) (103 mg, 0.198 mmol, 1.1 eq.) and methylene chloride (5 mL) were mixed at 25° C. under nitrogen. The reaction was cooled to 0° C. then triethylyamine (50 uL, 0.361 mmol, 2 eq.) in methylene chloride was added dropwise. Worked up after 16 hours by stripping off the solvent then purifying the residue over silica gel in 3:1 hexanes/ethyl acetate followed by 1:1 hexanes/ethyl acetate followed by 100% ethyl acetate. Obtained 50 mg of an off-white solid as product. Mass Spec detects 453 (M+H). NMR (300 MHz, CDCl₃) δ 7.40–7.20 (m, 5H), 7.20–6.90 (m, 4H), 5.20–4.80 (m, 3H), 4.60–4.40 (m, 1H), 3.90–3.40 (m, 2H), 3.00–2.20 (m, 3H), 2.00–1.80 (m, 1H), 1.80–1.00 (m, 10H).

Part H Preparation of (1R,2R)-2-aminocyclohexanecarboxylic acid, (S)-3-(4-fluorobenzylpiperidine amide

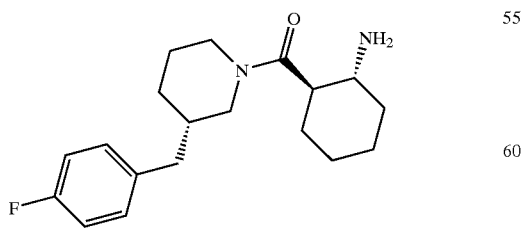

(1R,2R)-2-(benzyloxycarbonylamino)cyclohexanecarboxylic acid, (S)-3-(4-fluorobenzyl) piperidine amide (50 mg), 10% Pd/C (10 mg) and methanol were hydrogenated at 50 PSI overnight. The reaction was filtered through fiberglass filter paper under nitrogen. The filtrate was stripped to yield 34 mg of a colorless oil as product. Mass Spec detects 319 (M+H). NMR (300 MHz, CDCl₃) δ 7.20–7.03 (m, 2H), 7.03–6.90 (m, 2H), 4.60–4.30 (m, 1H), 3.90–3.60 (m, 1H), 3.20–2.90 (m, 2H), 2.80–2.20 (m, 4H), 2.10–0.80 (m, 15H).

Part I Preparation of (1R,2R)-2-(3-(acetyl)phenylaminocarbonylamino)cyclohexanecarboxylic acid, (S)-3-(4-fluorobenzyl)piperidine amide

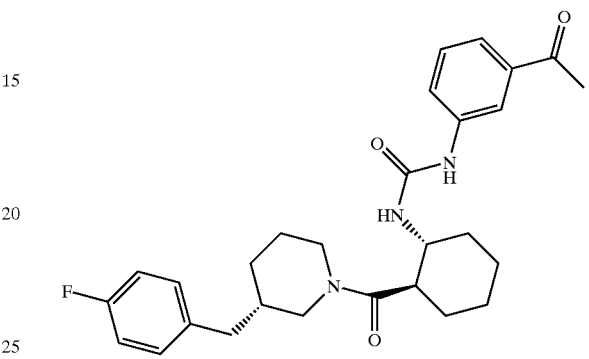

(1R,2R)-2-aminocyclohexanecarboxylic acid, (S)-3-(4-fluorobenzylpiperidine amide (25 mg, 0.00785 mmol, 1 eq.) was dissolved in 2 mL of THF at 25° C. under nitrogen. 3-Acetylphenyl isocyanate (11 μL, 0.00785 mmol, 1 eq.) was added and the contents stirred. Worked up after 3 hours by stripping off the solvent then purifying the crude over silica gel in 3:1 hexanes/ethyl acetate followed by 1:1 hexanes/ethyl acetate followed by 100% ethyl acetate. Obtained 33 mg of a white amorphous glass as product. Mass Spec detects 480 (M+H). NMR (300 MHz, CDCl₃) δ 9.20–8.80 (m, 1H), 8.20–7.90 (m, 1H), 7.80–7.50 (m, 2H), 7.40–7.30 (m, 1H), 7.20–6.70 (m, 4H), 4.80–4.20 (m, 2H), 4.00–3.50 (m, 2H), 3.30–2.90 (m, 1H), 2.80–2.20 (m, 8H), 2.20–1.00 (m, 11H).

Example 8

Part A. Preparation of N-Methyl-4-nitro-benzamide

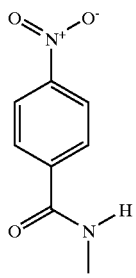

4-Nitrobenzoyl chloride (7.00 g, 38 mmol, 1 eq) was dissolved in 50 ml of THF and added to a 2.0 M solution of methylamine in THF (41.5 ml, 83 mmol, 2.2 eq.) at 0° C. Worked up after 3 hours by adding EtOAc and rinsing 3× with 1N NaOH, 1× with brine. The organic layer was dried over MgSO4, then stripped to obtain 2.25 g of off-white solids as product. NMR (300 MHz, DMSO d6) δ 8.80 (m, 1H), 8.33 (d, 2H, J=7 Hz), 8.06 (d, 2H, J=7 Hz). 2.86 (d, 3H, J=7 Hz).

Part B. Preparation of 1-Methyl-5-(4-nitro-phenyl)-1H-tetrazole

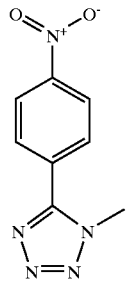

N-Methyl-4-nitro-benzamide (2.25 g, 12.5 mmol, 1 eq.) and PCl$_5$ (2.60 g, 12.5 mmol, 1 eq.) were melted together under house vacuum connected to a NaOH trap behind a safety shield. Melting occurred at 100° C. Heated at 130° C. for 1 hour then purified by kugelrohr distillation at 0.1 mmHg at 130° C. CAUTION: THE EXPLOSIVE PROPERTIES OF THIS COMPOUND ARE UNKNOWN). The iminoyl chloride (12.5 mmol 1 eq.) in DMF 10 ml was added to NaN$_3$ in 10 ml of DMF at 25° C. and stirred overnight. Worked up by adding EtOAc then rinsing 3× with H$_2$O. The organic layer was dried over MgSO4, then stripped to obtain yellow solids which were purified over silica gel in 3:1 hexanes/EtOAc to 100% EtOAc. Obtained 1.21 g of yellow solids as product. NMR (300 MHz, CDCl$_3$) δ 8.46 (d, 2H, J=7 Hz), 8.02 (d, 2H, J=7 Hz),4.27 (S, 3H).

Part C. Preparation of 4-(1-Methyl-1H-tetrazol-5-yl)-phenylamine

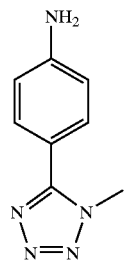

1-Methyl-5-(4-nitro-phenyl)-1H-tetrazole (470 mg), 20% Pd(OH)$_2$ (94 mg), and 1:1 MeOH/EtOAc (25 ml), were hydrogenated at 50 PSI for 1 hour. The reaction was filtered through fiberglass filter paper under nitrogen. The filtrate was stripped to yield 383 mg of yellow solids as product. Mass Spec detects 176 (M+H). NMR (300 MHz, CDCl$_3$) δ 7.57 (d, 2H, J=7 Hz), 6.80 (d, 2H, J=7 Hz), 4.14 (s, 3H), 4.03 (M, 2H).

Part D. Preparation of [4-(1-Methyl-1H-tetrazol-5-yl)-phenyl]-carbamic acid phenyl ester

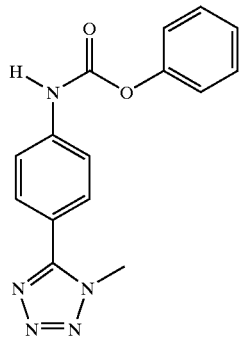

4-(1-Methyl-1H-tetrazol-5-yl)-phenylamine (190 mg, 1.08 mmol, 1 eq.), triethylamine (0.14 ml, 1.08 mmol, 1 eq.), in 10 ml of THF under nitrogen were cooled to 0° C. A 5 ml solution of phenyl chloroformate (0.14 ml, 1.08 mmol, 1 eq.), was added dropwise via an addition funnel. Worked up after 16 hours by adding EtOAc then rinsing 3× with H$_2$O. The organic layer was dried over MgSO4, then stripped to obtain yellow solids which were purified over silica gel in 3:1 hexanes/EtOAc to 100% EtOAc. Obtained 93 mg of white solids as product. Mass Spec detects 296 (M+H). NMR (300 MHz, DMSO-d$_6$) δ 10.65 (s, 2H), 7.86 (d, 2H, J=7 Hz), 7.76 (d, 2H, J=7 Hz), 7.44 (t, 2H, J=7 Hz), 7.28 (t, 2H, J=7 Hz), 4.18 s, 3H).

Part E. Preparation of 1-{2-[3-(4-Fluoro-benzyl)-pieridine-1-carbonyl]-cyclohexyl}-3-[4-(1-methyl-1H-tetrazol-5-yl)-phenyl]-urea

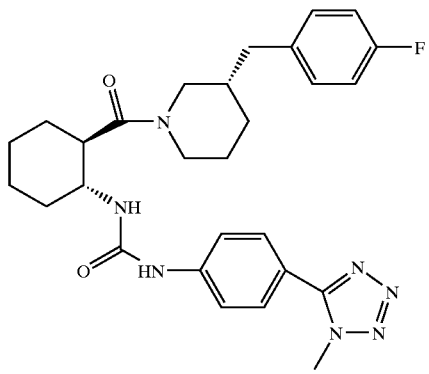

[4-(1-Methyl-1H-tetrazol-5-yl)-phenyl]-carbamic acid phenyl ester (28 mg, 0.00942 mmol, 1 eq.), (1R,2R)-2-aminocyclohexanecarboxylic acid, (S)-3-(4-fluorobenzylpiperidine amide, (see example 1) (30 mg, 0.00942 mmol, 1 eq.), in DMF at 25° C. under nitrogen were stirred overnight. Worked up by adding EtOAc then rinsing 3× with H$_2$O. The organic layer was dried over MgSO$_4$, then stripped to obtain solids which were stirred in 10 ml of 1:1 chloroform/diethyl ether. Solids which didn't dissolve were filtered and pumped under high vacuum to obtain 15 mg off off-white solids as product. Mass Spec detects 520 (M+H). $^1$H NMR (300 MHz, DMSO-d$_6$) δ 8.64 (s, 1H), 7.80–7.60 (m, 1H), 7.54 (d, 2H, J=7 Hz), 7.30–7.15 (m, 1H), 7.15–6.90 (m, 3H), 6.15–5.90 (m, 1H), 4.11 (s, 3H), 4.00–3.40 (m, 2H), 3.00–2.60 (m, 1H), 2.60–2.20 (m, 2H), 2.00–0.80 (m, 16H).

Example 2

Part A. Preparation of carbamimidic acid, N'-cyano-N-[4-(1-methyl-1H-tetrazol-5-yl)phenyl]-, phenyl ester

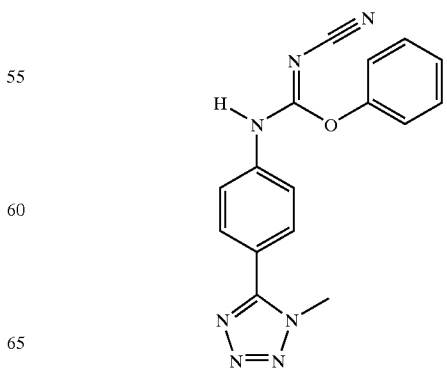

4-(1-Methyl-1H-tetrazol-5-yl)-phenylamine (500 mg, 2.85 mmol, 1 eq.) and diphenyl cyanocarbonimidate (680 mg, 2.85 mmol, 1 eq) were refluxed in 10 ml of acetonitrile under nitrogen overnight. Solids were present which were filtered and pumped under high vacuum to obtain 85 mg of white solids as product. $^1$H NMR (300 MHz, DMSO-$d_6$) δ 11.16 (s, 1H), 7.92 (d, 2H, J=7 Hz), 7.75 (d, 2H, J=7 Hz), 7.55–7.40 (M, 2H), 7.40–7.15 (M, 3H). 4.18 (S, 3H).

Part B Preparation of quanidine, N'-cyano-N-[(1R,2R)-2-[[(3R)-3-[(4-fluorophenyl)methyl]piperidinyl]carbonyl]cyclohexyl]-N'-[4-(1-methyl-1H-tetrazol-5-yl)phenyl]-

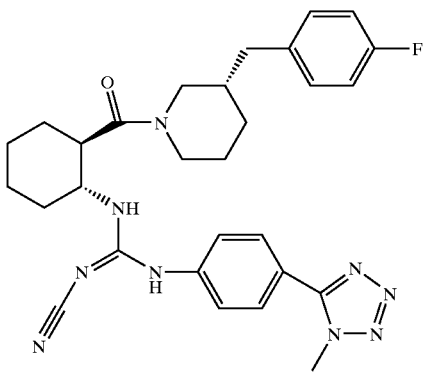

,N'-Cyano-N-[4-(1-methyl-1H-tetrazol-5-yl)phenyl]-carbamimidic acid phenyl ester (30 mg, 0.00942 mmol, 1 eq.), (1R,2R)-2-aminocyclohexanecarboxylic acid, (S)-3-(4-fluorobenzylpiperidine amide, (see example 1) (30 mg, 0.00942 mmol, 1 eq.), in DMF at 25° C. under nitrogen were stirred overnight. Worked up by adding EtOAc then rinsing 3× with H$_2$O. The organic layer was dried over MgSO$_4$, then stripped to obtain an oil which was purified over silica gel in 100% EtOAc to 4:1 CHCl$_3$/MeOH. Obtained 8 mg of an oil as product. Mass Spec detects 544 (M+H). $^1$H NMR (300 MHz, CDCl$_3$) δ 10.20–9.90 (m, 1H), 7.80–7.50 (M, 4H), 7.20–7.00 (M, 3H), 7.00–6.80 (M, 1H), 5.60–5.20 (M, 1H), 4.60–4.30 (M, 1H), 4.20 (d, 3H, J=7 Hz), 4.00–3.80 (M, 2H), 3.70–3.00 (M, 1H), 2.80–2.00 (M, 5H), 2.00–1.20 (M, 11H).

Example 3

Part A: Preparation of tert-1-{[(3S)-3-(4-fluorobenzyl)piperidinyl]carbonyl}cyclopropylcarbamate

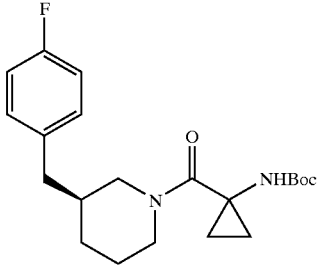

To a ice-water cooled solution of (S)-3-(4-fluorobenzyl) piperidine (100 mg, 0.517 mmol), Boc-1-aminocyclopropane-1-carboxylic acid (109.3 mg, 0.543 mmol) in DMF (2.2 mL) was added HATU reagent (204 mg, 0.543 mmol), followed by addition of Hunig base (0.142 mL, 0.815 mmol). The resulting mixture was then warmed to room temperature and stirred for 2 h. The reaction mixture was diluted in sat. NaHCO3 aq. solution, and extracted with ethyl acetate (25 mL). The organic layer was washed with sat. NaHCO3 aq. Solution, water and brine. The solution was then dried in MgSO4, concentrated. Mass: Spec(ES) detects 377.2 (M+H); $^1$H NMR (300 MHz, CDCl$_3$): δ 7.15–7.10 (m, 2H), 6.98 (t, 2H, J=8.8 Hz), 4.42–4.36 (m, 1H), 4.26–4.18 (m, 1H), 2.98–2.84 (m, 1H), 2.82 (s, 2H), 2.61–2.48 (m, 3H), 1.82–1.67 (m, 3H), 1.43 (s, 9H), 1.28–1.13 (m, 3H), 0.97 (bs, 1H).

Part B: Preparation of 1-{[(3S)-3-(4-fluorobenzyl)piperidinyl]carbonyl}cyclopropylamine

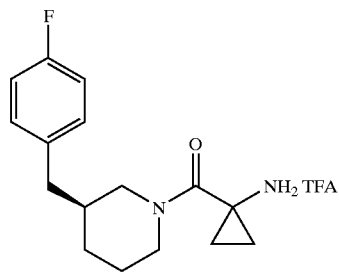

To a solution of tert-1-{[(3S)-3-(4-fluorobenzyl)piperidinyl]carbonyl}cyclopropylcarbamate (190 mg) in methylene chloride (1.5 mL) was added trifluoroacetic acid (1.5 mL) at room temperature. The resulting solution was stirred at RT for 1.0 h. The solvent was removed and dried in vacuum.

Part C: Preparation of N-(3-acetylphenyl)-N-(1-{[(3S)-3-(4-fluorobenzyl)piperidinyl]carbonyl}cyclopropylurea

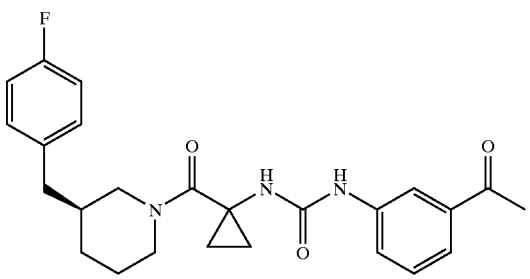

To an ice cooled solution of 1-{[(3S)-3-(4-fluorobenzyl)piperidinyl]carbonyl}cyclopropylamine TFA salt (20 mg, 0.0512 mmol) in methylene chloride (0.2 mL) was added hunig base till pH to 10–11. The resulting solution was then treated with 3-acetylphenyl isocyanate (8.3 mg). The mixture was stirred at ice bath for 1.0 h and concentrated. The residue was directly purified by RP-HPLC to give 26.1 mg of the product. Mass: Spec(ES) detects 438.1 (M+H). $^1$H NMR (300 MHz, DMSO-$d_6$): δ 7.97–7.96 (m, 1H), 7.61–7.51 (m, 2H), 7.37 (t, 1H, J=8.1 Hz), 7.16–7.11 (m, 2H), 7.00 (t, 2H, J=8.8 Hz), 4.12–4.02 (m, 4H), 2.65–2.51 (m, 1H), 2.50 (s, 3H), 2.39–2.29 (m, 1H), 1.57 (bs, 3H), 1.22–1.10 (m, 4H), 1.08–0.97 (m, 1H), 0.95–0.83 (m, 1H).

Example 3a
Part A. Preparation of piperidine, 3-[(4-fluorophenyl)methyl]-1-[(2E)-1-oxo-2-butenyl]-, (3S)-

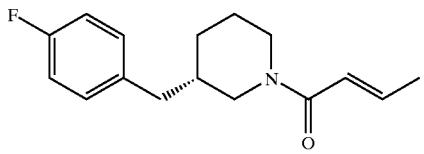

S-3-(4-Fluorophenylmethyl)piperidine (4.00 g, 20.7 mmol, 1 equiv.), crotonic acid (1.78 g, 20.7 mmol, 1 equiv.) and benzotriazol-1-yloxytripyrrolidinophosphonium hexafluorophosphate (PyBOP reagent) (11.85 g, 22.8 mmol, 1.1 equiv.) were dissolved in 75 ml of methylene chloride at 0° C. under $N_2$ and then triethylamine (5.57 ml, 41.4 mmol, 2 equiv.) was added last. The mixture warmed to 25° C. After 16 hours the reaction was stripped then purified over silica gel in 1:1 hexanes/EtOAc. Obtained 5.40 g of a colorless oil as product.

NMR (300 MHz, CDCl$_3$) δ 7.20–7.03 (m, 2H), 7.03–6.90 (m, 2H), 6.90–6.70 (m, 1H), 6.40–6.00 (m, 1H), 4.60–4.20 (m, 1H), 4.00–3.60 (m, 1H), 3.10–2.20 (m, 4H), 1.90–1.60 (m, 6H), 1.60–1.00 (m, 3H).

Mass Spec detects 262 (M+H).

Part B. 1-piperidineethanol, 3-[(4-fluorophenyl)methyl]-β-oxo-α-[(1R)-1-[[(1R)-1-phenylethyl](phenylmethyl)amino]ethyl]-, (α$^1$R,3S)-

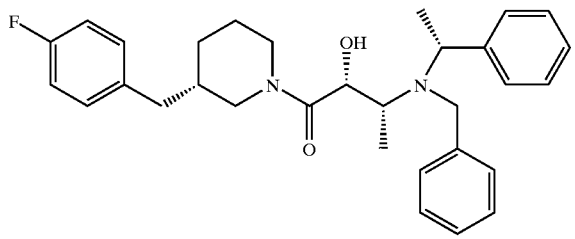

(R)-(+)-N-Benzyl-alpha-methylbenzylamine (6.92 (33.1 mmol, 1.6 equiv.) was dissolved in 50 ml of THF at 25° C. under $N_2$, cooled to 0° C. and 1.6 n-BuLi. in hexanes (19.37 ml, 31.0 mmol, 1.5 equiv.) was added dropwise thereto keeping the temperature below 10° C. The mixture was stirred for 45 minutes at 0° C., cooled to –70° C. after which piperidine, 3-[(4-fluorophenyl)methyl]-1-[(2E)-1-oxo-2-butenyl]-, (3S)- (5.40 g, 20.7 mmol, 1 equiv.) in THF was added dropwise keeping the temperature below –65° C. The mixture was then stirred an additional 1.5 hours at –70° C. (1S)-(+)-(10-Camphorsulfonyl)oxaziridine (7.58 g, 33.1 mmol, 1.6 equiv.) was added neat in 1 portion. The mixture stirred for 1 hour then allowed to warm to 0° C. The reaction was quenched with 50 ml of saturated NH$_4$Cl and the THF evaproated. Water was added and then extracted 3 times with methylene chloride. The organic layers were collected and dried to yield an amber oil which was purified over silica gel in 100% chloroform followed by 9:1 chloroform/EtOAc. Obtained an oil which was then stirred in Et$_2$O. The solids were filtered off and the Et$_2$O supernatant was stripped to yield 6.13 g of a tacky glass as product.

NMR (300 MHz, CDCl$_3$) δ 7.60–7.40 (m, 4H), 7.40–7.10 (m, 6H), 7.10–6.80 (m, 4H), 4.50–3.70 (m, 4H), 2.90–2.10 (m, 4H), 1.70–0.60 (m, 12H).

(Note: If the (1S)-(+)-(10-Camphorsulfonyl)oxaziridine is not added, the corresponding des-OH compound is synthesized).

Part C. Preparation of 1-piperidineethanol, α-[(1R)-1-aminoethyl]-3-[(4-fluorophenyl)methyl]-β-oxo-, (α$^1$R,3S)-

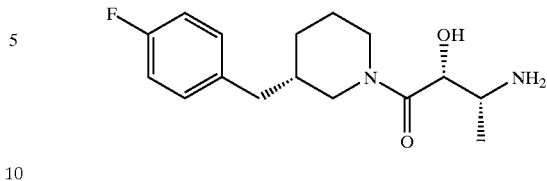

20% Pd(OH)$_2$ (200 mg), 1-piperidineethanol, 3-[(4-fluorophenyl)methyl]-β-oxo-α-[(1R)-1-[[(1R)-1-phenylethyl](phenylmethyl)amino]ethyl]-, (α$^1$R, 3S)- (500 mg, 1.02 nmol, 1 equiv.) and 10 ml of acetic acid in 10 ml of methanol were hydrogenated at 50 PSI overnight. The reaction was filtered through fiberglass filter paper under nitrogen. The filtrate was stripped to obtain a colorless oil. 20 ml of 1:1 hexanes/EtOAc were added followed by saturated NaHCO3 and the layers separated to remove impurities. To the aqueous was added 1N NaOH to adjust the pH=10 and then it was extracted 3 times with methylene chloride. The methylene chloride layers were combined, dried and stripped to give 360 mg of a near-colorless oil as product.

NMR (300 MHz, CDCl$_3$) δ 7.20–6.90 (m, 4H), 4.60–4.20 (m, 2H), 3.80–3.60 (m, 1H), 3.10–2.90 (m, 2H), 2.90–2.20 (m, 4H), 2.00–1.10 (m, 4H), 1.00–0.80 (m, 4H).

Mass Spec detects 295 M+H).

Part D. Preparation of urea, N-[(1R,2R)-3-[(3S)-3-[(4-fluorophenyl)methyl]-1-piperidinyl]-2-hydroxy-1-methyl-3-oxopropyl]-N'-[3-(1-methyl-1H-tetrazol-5-yl)phenyl]-

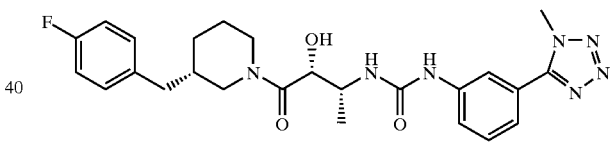

1-piperidineethanol, α-[(1R)-1-aminoethyl]-3-[(4-fluorophenyl)methyl]-β-oxo-, (α$^1$R,3S)- (50 mg, 0.10 mmol, 1 equiv.) and [3-(1-methyl-1H-tetrazol-5-yl)phenyl] carbamic acid phenyl ester (50 mg, 0.10 mmol, 1 equiv.) were stirred in 3 ml of acetonitrile at 25° C. under $N_2$. After 16 hours the reaction was stripped then purified over silica gel in 100% EtOAc. Obtained 60 mg of a white glass as product.

NMR (300 MHz, CDCl$_3$) δ 7.90–7.50 (m, 3H), 7.50–7.30 (m, 1H), 7.20–7.05 (m, 2H), 7.05–6.80 (m, 2H), 6.10–5.90 (m, 1H), 4.80–4.20 (m, 2H), 4.20–4.00 (m, 5H), 3.20–2.80 (m, 1H), 2.80–2.40 (m, 3H), 2.00–1.20 (m, 4H), 1.10–0.80 (m, 4H).

Mass Spec detects 496 (M+H).

Example 45

Preparation of: N-[(1S)-3-[(3S)-3-[(4-fluorophenylmethyl]-1-piperidinyl]-3-oxo-1-(1-piperidinylcarbonyl)propyl]-N'-[3-(1-methyl-1-H-tetrazol-5-yl)phenyl]-urea.

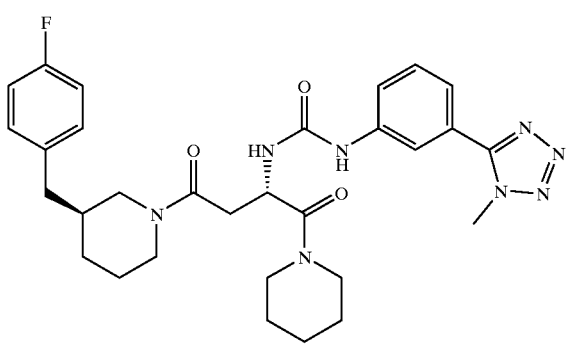

Step 1: To a solution of Boc-Asp(OH)—O-Bn (381.5 mg) in dry DMF (2.7 ml) at 0° C. was added HATU (448.6 mg) followed by Hunigs base (0.308 mL) and stirred for 5 minutes. S-3-(4-fluorobenzyl)-piperidine, dissolved in 2.0 ml dry DMF was added. The reaction was then stirred at 0° c. for 30 minutes, room temperature for 3 hours and then raised to 50° C. for 30 minutes. After cooling the reaction to room temperature, it was partitioned between saturated sodium chloride and ethyl acetate. The aqueous layer was re-extracted with EtOAc (4×40 mL). The organic layers were combined, washed with $H_2O$, 10% citric acid, brine, dried ($MgSO_4$), concentrated to give 606 mg of crude material, which was sufficiently pure to be used directly for the next step. (step 2). Electrospray ms spectrum m/e 499.2 (M+H).

Step 2: To a solution of the amide (606 mg; prepared above) in 5.0 ml $CH_2Cl_2$ was added trifluoroacetic acid (5.0 ml) and $H_2O$ (0.5 ml). The reaction mixture was stirred at room temperature for 50 minutes. The solvent was removed in vacuo to give 609 mg of a crude solid as a trifluoroacetate salt which was sufficiently pure for use directly in the next step.

Electrospray ms spectrum m/e 399.2 (M+H).

Step 3: To a stirring solution of the amine (609 mg; prepared above) in dry acetonitrile (4.0 ml), was [3-(1-methyl-1H-tetrazol-5-yl)phenyl]carbamic acid phenyl ester (292.3 mg) followed by Hunigs base (517 uL) and stirred overnight at room temperature. The solvent was removed in vacuo and resulting crude was purified by silica gel chromatography (0–5% MeOH/$CH_2Cl_2$) to give a solid. Electrospray ms spectrum m/e 600.2 (M+H).

Step 4: To a solution of the benzyl ester (11.0 gm; prepared above) in methanol (8.0 ml) was added a catalytic amount of Palladium (10% on carbon) and hydrogenated under a balloon of hydrogen (1 atmosphere) for 2 hours. The catalyst was filtered, washed with methanol and filtrate was concentrated in vacuo to give 800 mg of a crude acid, which was sufficiently pure to be used in the next step. Electrospray ms spectrum m/e 510.0 (M+H); 532.1 (M+Na).

Step 5: To a stirring solution of the acid (100 mg; prepared above) in dry DMF (0.65 ml) at 0° C. was added BOP (104 mg) followed by Hunigs base (0.1 ml). After stirring for 10 minutes, piperidine (97 uL) was added and reaction was stirred at room temperature overnight. The reaction was poured into a mixture of ice/saturated $NaHCO_3$ and extracted into EtOAc (4×50 ml). The combined organic layers were washed with 1N HCl, brine, dried ($MgSO_4$), and concentrated in vacuo to give a crude oil (170 mg). The crude material was purified by silica gel chromatography (0–5% MeOH/$CH_2Cl_2$) to give 16.8 mg of a final solid. Electrospray ms spectrum m/e 599.3 (M+H); $^1H$ NMR spectrum ($CD_3OD$): 7.95 (s, 1H), 7.5 (m, 3H), 7.2 (m, 2H), 7.0 (m, 2H) 5.2 (m, 1H) 4.2 (m, H) 4.2 (s, 3H) 3.8 (m, 6H), 3.4 (m, H), 3.2 (m, 2H), 3.0 (m, H), 2.85 (m, H), 2.7 (m, 3H), 2.5 (m, 4H), 1.6 (m, 4H), 1.4 (m, 2H).

Example: 55

Preparation of: N-[(1S)-3-[(3S)-3-[(4-fluorophenylmethyl]-1-piperidinyl]-3-oxo-1-(1-morpholine)butyl]-N'-[3-(N-methyl amide)phenyl]-urea

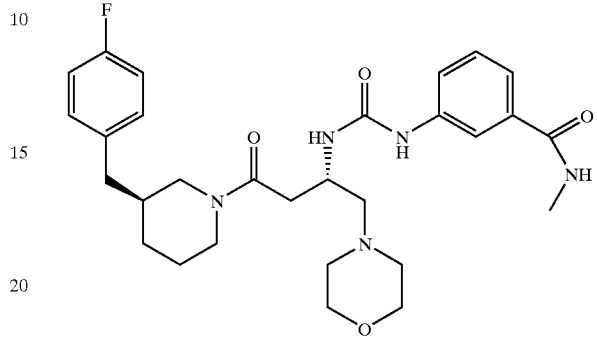

Step 1: To a stirring solution of Cbz-Asp(O-$^t$Bu)-OH in dry DMF (25 ml) was added BOP (8.16 gm) followed by Hunigs base (75 ml) at 0° C. This was stirred for 8–10 minutes before adding morpholine (3.25 ml) and stirred at room temperature overnight. The reaction was then poured onto 50% sodium bicarbonate and ice and extracted into ethyl actetate (3×150 ml). The organic layer was washed with 1N HCl, water and brine (once each) dried over Magnesium sulfate, filtered and the residual crude was purified by column chromatography on silica gel eluting with (50% Hexanes-Petroleum ether) to give a crystalline white solid (3.87 gm). Electrospray ms spectrum m/e 393.3 (M+H).

Step 2: To a solution of 930 mg of the amide prepared above, in dry tetrohydrofuran (6.0 mL) was added Borane-tetrahydrofuran complex (5.99 ml) dropwise at 0° C. over 10 minutes and the reaction was stirred overnight at room temperature. The reaction was cooled to 0° C. in an ice bath, quenched by the addition of water (5.0 mL) dropwise until all the gas evolution subsided. The THF was removed in vacuo, aqueous extracted into methylene chloride (3×100 mL) and the organic layers were combined, dried over magnesium sulfate, concentrated and purified by chromatography on silica gel (33% ethylacetate-hexanes). The resulting oil (400 mg) was carried on to the next step Electrospray ms spectrum m/e 379.3 (M+H).

Step 3: To a solution of 400 mg of the amide prepared above in methylene chloride (2.5 mL) and water (0.5 ml), was added trifluoroacetic acid (2.5 ml). The mixture was stirred for 50 minutes at room temperature. The solvent was then removed in vacuo, suspended in methylene chloride and removed in vacuo (twice) and the resulting solids were triturated (15% Ether-petroleum ether) to afford a fine white solid (480 mg).

Electrospray ms spectrum m/e 323.2 (M+H).

Step 4: HATU (584 mgm) and Hunigs base (1.1 ml) were added to a stirring solution of 558 mg of the amine prepared above, in dry DMF (3.5 ml) at 0° C. The mixture was stirred for 10 minutes, then S-3-(4-fluorobenzyl)-piperidine (260 mg) was added and the mixture stirred at room temperature overnight. The reaction was poured onto ice/Sat. $NaHCO_3$ and extracted into EtOAc (3×100 ml). The organic layers were combined, washed with water (20 ml), brine (25 ml), dried ($MgSO_4$), filtered and concentrated in vacuo. The resulting crude oil was purified by chromatography on silica gel (0–3% MeOH-CH$_2$Cl$_2$) to give a solid (525 mg). Electrosray ms spectrum m/e 498.2 (M+H).

Step 5: 10% Palladium on carbon (75 mg) was added to a solution of 520 mg of the amide prepared above, in MeOH (4.0 ml) and the mixture was hydrogenated under one atmosphere of hydrogen gas (balloon). The palladium catalyst was filtered, filtrate was concentrated in vacuo and the resulting white foam (370 mg) was sufficiently pure for use in the next step. Electrospray ms spectrum m/e 364.3 (M+H).

Step 6: To a stirring solution of the amine (25 mg; prepared above) in 0.227 ml dry DMF, was added [3-(N-methylcarboxamido)phenyl]carbamic acid phenyl ester (22.3 mg) and stirred overnight at room temperature. The mixture was poured into water (2.0 ml) and extracted into EtOAc (3×10 ml). The organic layers were combined, dried (MgSO4), filtered, concentrated and purified by silica gel chromatography (0–10% MeOH/EtOAc) to give a solid (21.4 mg) as a final product. Electrospray ms spectrum m/e 540.1 (M+H). $^1$H NMR (CD$_3$OD): 7.85 (s, H), 7.55 (m, H), 7.35 (m, 2H), 7.2 (m, 2H), 7.0 (m, 2H), 4.5 (m, H), 4.3 (m, H), 3.8 (m, 4H), 3.2 (m, 4H), 2.9 (s, 3H), 2.8 (m, H), 2.6 (m, H), 2.5 (m, 4H), 1.8 (m, 4H), 1.3 (m, 4H).

Example 63

Preparation of: N-[(1S)-3-[(3S)-3-[(4-fluorophenylmethyl]-1-piperidinyl]-3-oxo-2-methyl-1-(1-morphonylcarbonyl)propyl]-N'-[3-(1-methyl-1-H-tetrazol-5-yl)phenyl]-urea

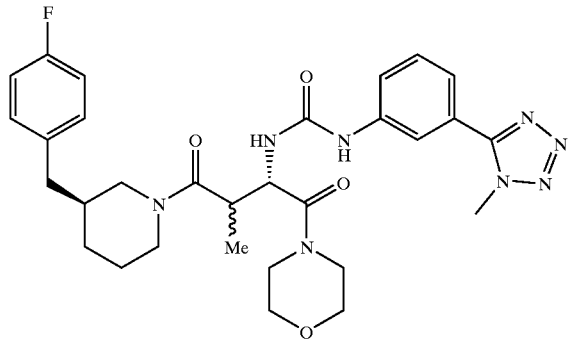

Step 1: K$_2$CO$_3$ (12.82 gm) and CH$_3$I (5.77 mL) were successively added to a stirring solution of N-Cbz-Asp(O-'Bu)-OH (15.0 gm) in dry DMF (116 ml) at room temperature. The mixture was stirred overnight at room temperature. The insoluble solids were filtered and the filtrate was diluted with water and extracted into EtOAc (3×200 mL). The organic layer was washed with water (3×50 mL), dried (MgSO4), filtered and concentrated in vacuo. The crude oil was purified by silica gel chromatography (15–33% of EtOAc-hexanes) and gave a final oil (16.0 gm). Electrospray ms spectrum m/e 360.3 (M+H).

Step 2: LiHMSD (18.67 ml) was added dropwise to a stirring solution of the ester (3.0 gm) prepared above, in dry THF (25 ml) at −78° C. The reaction was stirred at −78° C. for 1 hour then gradually raised to −30° C. It was re-cooled to −78° C. after which CH$_3$I was added dropwise over 3 minutes. The reaction was allowed to stir at −78° C. gradually rising to −20° C. over 2 hours. The reaction was quenched at −78° C. with 10% citric acid (10 ml), poured on to ice/sat. NaCl and extracted into EtOAc (3×100 mL). The organic layers were combined, dried (MgSO$_4$), filtered, concentrated in vacuo and purified by silica gel chromatography (15–25% EtOAc-hexanes). The resulting oil (2.9 gm) was sufficiently pure to be used for the next step. Electrospray ms spectrum m/e 378.2 (M+Na).

Step 3: To a solution of 2.0 gm of the ester prepared above in methylene chloride (18.2 mL) and water (2.0 mL) was added trifluoroacetic acid (20 ml). The mixture was stirred at room temperature for 90 minutes. The solvent was removed in vacuo, re-dissolved into CH$_2$Cl$_2$ and solvent removed in vacuo (3×), and the resulting product (1.6 gm) was sufficiently pure for use in the next step. Electrospray ms spectrum m/e 348.2 (M+H).

Step 4: HBTU (674 mgm) and Hunigs base (0.77 mL) was added to a stirring solution of the acid (500 mg, prepared above) in dry DMF (5.0 mL) at 0° C. The mixture was stirred for 10 minutes, then S-3-(4-fluorobenzyl)-piperidine (300 mg) was added and the mixture stirred at room temperature overnight. The reaction was poured onto ice/Sat. NaHCO$_3$ and extracted in to EtOAc (3×10 mL). The organic layers were combined, washed with water (20 mL), brine (25 ml), dried (MgSO$_4$), filtered and concentrated in vacuo. The resulting crude oil was purified by chromatography on silica gel (33–100% EtOAc-Hexanes) to give a solid (500 mg) to be used in the next step. Electrosray ms spectrum m/e 494.3 (M+Na).

Step 5: LiOH solution (1.9 ml, 2.5 M) was added to a solution of the amide (200 mg, prepared above) in MeOH (4.0 mL) at 0° C. and the mixture was stirred at room temperature overnight. The reaction was diluted with 2 ml water, washed with ether (1×5 mL). The aqueous layer was acidified with 1N HCl to pH 2–3 and extracted into EtOAc (3×30 mL). The combined organic layers were dried (MgSO$_4$), filtered and filtrate was concentrated in vacuo and the resulting white foam (169 mg) was sufficiently pure for use in the next step. Electrospray ms spectrum m/e 454.4 (M+H).

Step 6: To a stirring solution of the acid (165 mg, prepared above) in dry DMF (1.3 mL) was added BOP (207 mg) followed by Hunigs base (0.203 mL) at 0° C. This was stirred for 8–10 minutes then added morpholine (0.068 mL) and stirred at room temperature overnight. The reaction was then poured onto 50% NaHCO$_3$ and ice and extracted into EtOAc (3×150 mL). The combined organic layers were washed with 1N HCl, water, brine (once each), dried (MgSO$_4$), filtered, concentrated in vacuo. The crude material was purified by silica gel chromatography (0–5% of MeOH—CH$_2$Cl$_2$) to give a clear oil (190 mg). Electrospray ms spectrum m/e 526.3 (M+H).

Step 7: 10% Palladium on carbon (70 mg) was added to a solution of 190 mg of the amide prepared above in MeOH (2.0 mL) and the mixture was hydrogenated under one atmosphere of hydrogen gas (balloon) for 2.0 hour. The palladium catalyst was filtered, filtrate was concentrated in vacuo and the resulting white foam (120 mg) was sufficiently pure for use in the next step. Electrospray ms spectrum m/e 392.3 (M+H).

Step 8: To a stirring solution of the amine (20 mg; prepared above) in dry acetonitrile (0.17 mL), was [3-(1-methyl-1H-tetrazol-5-yl)phenyl]carbamic acid phenyl ester (18.8 mg) followed by Hunigs base (22 uL) and stirred overnight at room temperature. The solvent was removed in vacuo and resulting crude was purified by silica gel chromatography (0–5% MeOH/CH$_2$Cl$_2$) to give a solid (20.3 mg) as a final product. Electrospray ms spectrum m/e 600.2 (M+H). $^1$H NMR (CD$_3$OD): 7.95 (s, H), 7.5 (m, 3H), 7.2 (m, 2H), 7.0 (m, 2H), 5.1 (m, H), 4.4 (m, H), 4.2 (s, 3H), 4.0 (m, H), 3.4–3.9 (m, 9H), 3.2 (m, 2H), 2.8 (m, 2H), 2.6 (m, 4H), 1.8 (m, 2H), 1.4 (m, 2H), 1.2 (t, 3H).

Example 74

Part A. Preparation of benzyl (1R)-1-(aminomethyl)-2-[(3S)-3-(4-fluorobenzyl)-1-piperidinyl]-2-oxoethylcarbamate

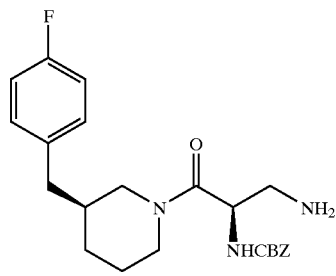

To a solution of (S)-3-(4-fluorobenzyl)piperidine (0.20 g, 0.52 mmol) in dry DMF (3 mL) was added PyBop (0.54 g, 1.04 mmol), Hunig's base (0.18 mL, 1.04 mmol) and N-α-Cbz-N-β-Boc-D-diaminopropionic acid (0.35 g, 1.0 mmol). The mixture was stirred at room temperature for overnight. The reaction mixture was subsequently diluted with ethyl acetate, washed with water, saturated Na$_2$CO$_3$ and brine. The organic layer was dried over MgSO$_4$ and concentrated under reduced pressure. The residue was purified over silica gel in 1:1 hexane/EtOAc to yield 0.43 g of intermediate. MS AP$^+$ (M+H)$^+$=514.3. The intermediate was then treated with 1:1 v:v mixture of CH$_2$Cl$_2$ and TFA at room temperature for 1 h. The solvent was then evaporated. The residue was dissolved in ethyl acetate and washed with saturated Na$_2$CO$_3$ and brine. The organic layer was dried over MgSO$_4$ and concentrated under reduced pressure to provide 0.34 g of product. MS AP$^+$ (2M+H)$^+$=827.8.

Part B. Preparation of benzyl (1R)-2-[(3S)-3-(4-fluorobenzyl)-1-piperidinyl]-1-{[({[3-(1-methyl-1H-tetraazo-5-yl)phenyl]amino}carbonyl)amino]methyl}-2-oxoethylcarbamate

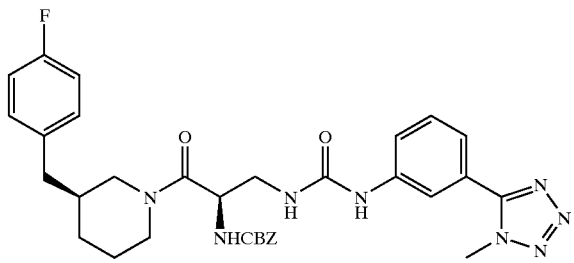

Benzyl (1R)-1-(aminomethyl)-2-[(3S)-3-(4-fluorobenzyl)-1-piperidinyl]-2-oxoethylcarbamate (0.17 g, 0.40 mmol), [4-(1-methyl-1H-tetrazol-5-yl)-phenyl]-carbamic acid phenyl ester (0.23 g, 0.78 mmol), in 3 ml of acetonitrile were stirred at room temperature overnight. Worked up by stripping off the solvent then purifying the crude over silica gel in 1:1 hexane/ethyl acetate followed by 100% ethyl acetate. Obtained 0.14 g of solids as product. Mass spectra detect 615.6 (M+H).

Part C. Preparation of N-{(2R)-2-amino-3-[(3S)-3-(4-fluorobenzyl)-1-piperidinyl]-3-oxopropyl}-N'-[3-(1-methyl-1H-tetraazol-5-yl)phenyl]urea

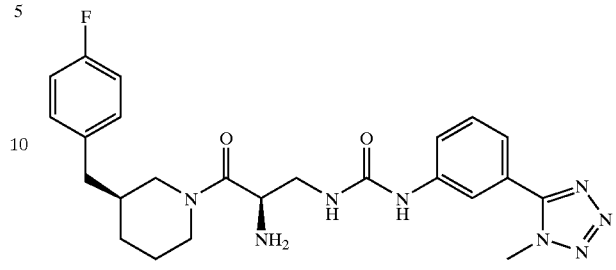

To a solution of benzyl (1R)-2-[(3S)-3-(4-fluorobenzyl)-1-piperidinyl]-1-{[({[3-(1-methyl-1H-tetraazo-5-yl)phenyl]amino}carbonyl)amino]methyl}-2-oxoethylcarbamate (0.14 g, 0.23 mmol) and 10% palladium on carbon (0.030 g) in degassed methanol (15 mL) was added hydrogen gas to 55 psi. The reaction was stirred for 12 h and then filtered through a pad of Celite. The celite was washed with methanol (10 mL). The filtrates were combined and concentrated in vacuo to yield 0.10 g of product. MS AP$^+$ (M+H)$^+$=481.

Part D. Preparation of N-((1R)-2-[(3S)-3-(4-fluorobenzyl)-1-piperidinyl]-1-{[({[3-(1-methyl-1H-tetraazole-5-yl)phenyl]amino]carbonyl)amino]methyl}-2-oxoethyl)-2,2-dimethylpropanamide

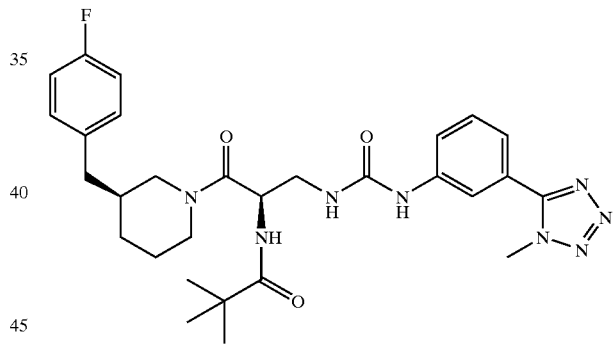

To a solution of N-{(2R)-2-amino-3-[(3S)-3-(4-fluorobenzyl)-1-piperidinyl]-3-oxopropyl}-N'-[3-(1-methyl-1H-tetraazol-5-yl)phenyl]urea (0.053 g, 0.11 mmol) in dry CH$_2$Cl$_2$ (2 mL) was added trimethylacetyl chloride (0.07 mL, 0.57 mmol) and stirred at room temperature for 3 h. PS-trisamine (0.33 g, 1.5 mmol, Argonaut Technologies Inc.) was added and stirred for 1 h. The reaction mixture was filtered and the polymer was washed with CH$_2$Cl$_2$, and the combined filtrate was concentrated under vacuum. The residue is further purified by RP-HPLC to afford 3.2 mg of product. Mass spectra detects 565.6 (M+H). $^1$H NMR (300 MHz, CD$_3$OD) δ 7.95 (s, 1H), 7.60–7.36 (m, 3H), 7.25–7.15 (m, 2H), 7.00–6.90 (m, 2H), 5.10–4.80 (m, 1H), 4.40 (m, 1H), 4.20 (s, 3H), 4.10–3.95 (m, 2H), 3.60–3.35 (m, 2H), 3.25–2.80 (m, 2H), 2.80–2.40 (m, 4H), 1.95–1.40 (m, 3H), 1.20 (s, 9H).

Example 77

Part A. Preparation of tert-Butyl (1R)-1-(aminomethyl)-2-[(3S)-3-(4-fluorobenzyl)-1-piperidinyl-2-oxoethylcarbamate

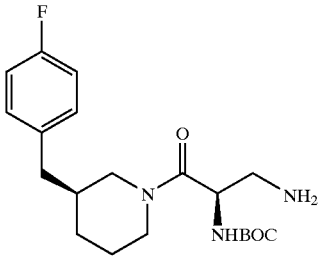

To a solution of (S)-3-(4-fluorobenzyl)piperidine (2.0 g, 10.2 mmol) in dry DMF (50 mL) was added PyBop (10.63 g, 20.43 mmol), Hunig's base (9.0 mL, 51 mmol) and N-α-Boc-N-β-Fmoc-D-diaminopropionic acid (8.71 g, 20.43 mmol). The mixture was stirred at room temperature for overnight. The reaction mixture was subsequently diluted with ethyl acetate, washed with water, saturated $Na_2CO_3$ and brine. The organic layer was dried over $MgSO_4$ and concentrated under reduced pressure. The residue was then treated with 1:3 v:v mixture of piperidine and DMF at room temperature for 2 h. The reaction mixture was subsequently diluted with ethyl acetate, washed with water, saturated $Na_2CO_3$ and brine. The organic layer was dried over $MgSO_4$ and concentrated under reduced pressure. The residue was purified over silica gel in 1:1 hexane/ethyl acetate followed by 100% ethyl acetate followed by 4:1:0.1 ethyl acetate/Methanol/triethylamine, providing 5.0 g of product. MS AP⁺ (M+H)⁺=380.3.

Part B. Preparation of N-(5-acetyl-4-methyl-1,3-thiazol-2-yl)-N'-[(2R)-2-amino-3-[(3S)-3-(4-fluorobenzyl)-1-piperidinyl]-3-oxopropyl}urea

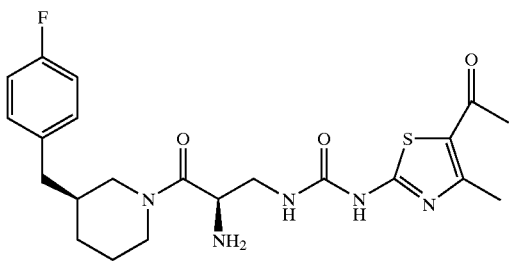

Tert-butyl (1R)-1-(aminomethyl)-2-[(3S)-3-(4-fluorobenzyl)-1-piperidinyl]-2-oxoethylcarbamate (0.15 g, 0.39 mmol), phenyl 5-acetyl-4-methyl-1,3-thiazol-2-ylcarbamate (0.22 g, 0.78 mmol), in 10 ml of acetonitrile were stirred at room temperature for overnight. Worked up by stripping off the solvent then purifying the crude over silica gel in 1:1 hexane/ethyl acetate followed by 100% ethyl acetate followed by 4:1:0.1 ethyl acetate/Methanol/ammonia. The purified intermediate was then treated with 1:1 v:v mixture of $CH_2Cl_2$ and TFA at room temperature for 1 h. The solvent was then evaporated to provide 0.09 g of product. MS AP⁺ (M+H)⁺=462.3.

Part C. Preparation of N-(5-acetyl-4-methyl-1,3-thiazol-2-yl)-N'-{(2R)-2-(diisobutylamino)-3-[(3S)-3-(4-fluorobenzyl)-1-piperidinyl]-3-oxopropyl}urea

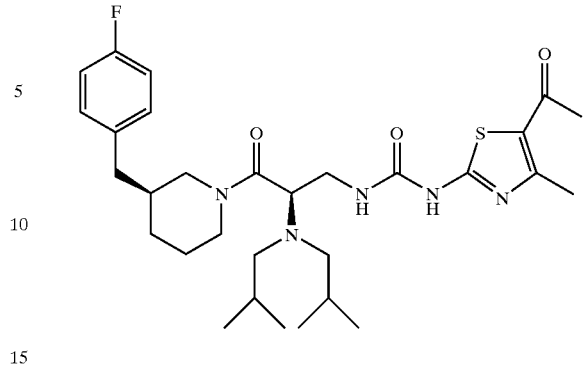

To a solution of N-(5-acetyl-4-methyl-1,3-thiazol-2-yl)-N'-{(2R)-2-amino-3-[(3S)-3-(4-fluorobenzyl)-1-piperidinyl]-3-oxopropyl}urea (0.089 g, 0.20 mmol) in $CH_2Cl_2$ (2 mL), isobutyl aldehyde (0.14 mL, 1.95 mmol), $NaBH(OAC)_3$ (0.27 g, 1.27 mmol) and AcOH (40 μL) were added and stirred at room temperature for overnight. The reaction mixture was concentrated and the residue was directly purified by RP-HPLC to give 24.1 mg of the product. Mass spectra detect 574.3 (M+H). ¹H NMR (300 MHz, $CD_3OD$) δ 7.20–6.90 (m, 4H), 4.50–4.30 (m, 2H), 4.00–3.50 (m, 4H), 3.30–2.80 (m, 4H), 2.60–2.40 (m, 2H), 2.55 (S, 3H), 2.45 (S, 3H), 2.20–1.00 (m, 10H), 1.05–0.90 (d, 12H, J=4 Hz).

Example 79

Part A. Preparation of butanoic acid, 3-[[(1,1-dimethylethoxy)carbonyl]amino]-4-hydroxy-, methyl ester, (3S)-

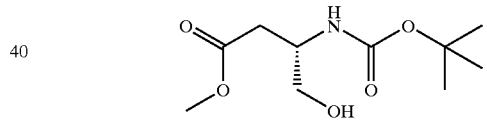

N-t-BOC-L-Aspartic acid Beta-Methyl Ester (Sigma) (2.00 g, 8.09 mmol, 1 equiv.) was dissolved in 25 ml of THF at 25° C. under $N_2$. 1.0M Borane in THF (24.27 ml, 24.3 mmol, 3 equiv.) was added dropwise at 0° C. over 10 minutes. The reaction was stirred 1 hour at 0° C. and then carefully quenched with the dropwise addition of MeOH followed by 2 ml of acetic acid. The mixture was stripped to obtain an oil which was treated with 10 ml of $H_2O$ followed by adjusting the pH to 8–9 with NaHCO3 then extracted 3 times with EtOAc. The organic layers were combined, dried and stripped to give a colorless oil which was purified over silica gel in 3:1 hexanes/EtOAc to 100% EtOAc. Obtained 1.08 g of a colorless oil as product.

NMR (300 MHz, $CDCl_3$) δ 5.40 (m, 1H,), 4.00–3.80 (m, 1H), 3.42 (s, 3H), 3.45–3.35 (m, 1H), 3.20–3.10 (m, 1H), 2.38 (d, 2H, J=7 Hz), 1.63 (s, 9H).

Mass Spec detects 234 (M+H).

Part B. Preparation of butanoic acid, 3-[[(1,1-dimethylethoxy)carbonyl]amino]-4-((methylsulfonyl)oxy]-, methyl ester, (3S)-

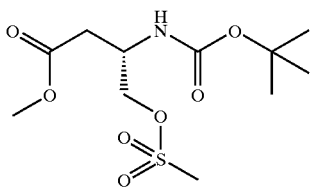

To a solution of butanoic acid, 3-[[(1,1-dimethylethoxy) carbonyl]amino]-4-hydroxy-, methyl ester, (3S)- (500 mg, 2.14 mmol, 1 equiv.) in 10 ml of Et₂O at 25° C. under N₂ were added triethylamine (0.39 ml, 2.79 mmol, 1.3 equiv.) followed by methanesulfonyl chloride (0.18 ml, 2.36 mmol, 1.1 equiv.). The reaction was stirred overnight. The liquid was decanted away from solids and then the liquid was stripped to obtain an oil which was purified over silica gel (1:1 hexanes/EtOAc). Obtained 464 mg of a colorless oil as product.

NMR (300 MHz, CDCl₃) δ 5.30–5.15 (m, 1H), 4.20–4.10 (m, 3H), 3.77 (s, 3H), 3.47 (s, 3H), 3.13 (d, 2H, J=7 Hz), 2.37 (s, 9H).

Part C. Preparation of butanoic acid, 3-[[(1,1-dimethylethoxy)carbonyl]amino]-4-iodo-, methyl ester, (3S)-

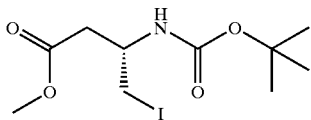

Butanoic acid, 3-([[(1,1-dimethylethoxy)carbonyl]amino]-4-[(methylsulfonyl)oxy]-, methyl ester, (3S)- (0.46 g, 1.48 mmol, 1 equiv.) was dissolved in 10 ml of acetone at 25° C. under N₂ and NaI (1.11 g, 7.39 mmol, 5 equiv.) was added thereto. The mixture was refluxed for 1 hour. The solids were filtered and the filtrate was stripped to obtain an oil which was purified over silica gel in (3:1 hexanes/EtOAc). Obtained 164 mg of an amber oil as product.

NMR (300 MHz, CDCl₃) δ 5.20–5.00 (m, 1H), 4.00–3.80 (m, 1H), 3.70 (s, 3H), 3.50–3.30 (m, 2H), 2.80–2.60 (m, 2H), 1.43 (s, 9H).

Part D. Preparation of butanoic acid, 3-[[(1,1-dimethylethoxy)carbonyl]amino]-, methyl ester, (3R)-

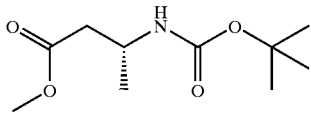

Butanoic acid, 3-[[(1,1-dimethylethoxy)carbonyl]amino]-4-iodo-, methyl ester, (3S)- (8.50 g, 24.8 mmol, 1 equiv.), triethylamine (3.45 ml, 24.8 mmol, 1 equiv.) and 2.00 g of 20% Pd(OH)₂ were mixed under nitrogen in 100 ml of methanol then hydrogenated at 50 PSI overnight in a Parr hydrogenator. The reaction was filtered through fiberglass filter paper under nitrogen. The filtrate was stripped to obtain an oil which was purified over silica gel in 100% chloroform to 1:1 hexanes/EtOAc. Obtained 5.30 g of an amber oil as product.

NMR (300 MHz, CDCl₃) δ 4.80–3.90 (m, 1H), 3.63 (s, 3H), 2.60–2.40 (m, 1H), 1.40 (s, 9H), 1.18 (d, 3H).

Part E. Preparation of butanoic acid, 3-[[(1,1-dimethylethoxy)carbonyl]amino]-, (3R)-

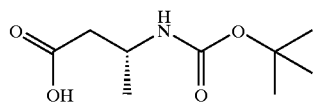

Butanoic acid, 3-[[(1,1-dimethylethoxy) carbonyl]amino]-, methyl ester, (3R)- (5.30 g, 24.4 mmol, 1 equiv.) was dissolved in 50 ml of THF at 25° C. and then 0.5N LiOH (97.6 ml, 48.8 mmol, 2 equiv.) was added. The reaction was worked up after 0.5 hour by adding 60 ml of 1N HCl to pH=3 then extracting 3 times with EtOAc. The organic layers were combined, dried and stripped to give 4.95 g of an oil as product.

NMR (300 MHz, CDCl₃) δ 4.10–3.90 (m, 1H), 2.60–2.50 (m, 2H), 1.42 (s, 9H), 1.24 (d, 3H, J=7 Hz).

Mass Spec detects 203 (M+H).

Part F. Preparation of carbamic acid, [(1R)-3-[(3S)-3-[(4-fluorophenyl)methyl]-1-piperidinyl]-1-methyl-3-oxopropyl]-, 1,1-dimethylethyl ester

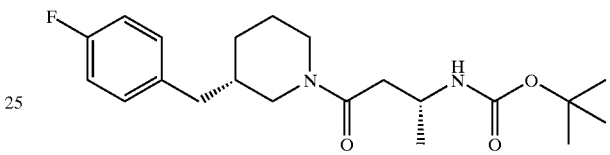

Butanoic acid, 3-[[(1,1-dimethylethoxy)carbonyl]amino]-, (3R)- (411 mg, 2.02 mmol, 1 equiv.), 4-fluorobenzyl)piperidine (obtained as the free base from XXX (391 mg, 2.02 mmol, 1 equiv.), and benzotriazol-1-yloxytripyrrolidinophosphonium hexafluorophosphate (PyBOP reagent) (1.16 g, 2.22 mmol, 1.1 equiv.) were mixed in methylene chloride at 0° C. under N₂ followed by the addition of triethylamine (0.56 ml, 4.04 mmol, 2 equiv.) which was added last. The contents were warmed to 25° C. After 16 hours the reaction was stripped then purified over silica gel in 1:1 hexanes/EtOAc. Obtained 750 mg of an amber oil as product.

NMR (300 MHz, CDCl₃) δ 7.20–7.00 (m, 2H), 7.00–6.80 (m, 2H), 5.40–5.20 (m, 1H), 4.40 (m, 1H), 4.00-3.60 (m, 2H), 3.10–2.20 (m, 6H), 1.90–1.40 (m, 3H), 1.41 s, 9H) 1.50–1.30 (m, 2H), 1.30–1.00 (m, 3H).

Part G. Preparation of 1-piperidinepropanamine, 3-[(4-fluorophenyl)methyl]-α-methyl-γ-oxo-, (α¹R, 3S)-

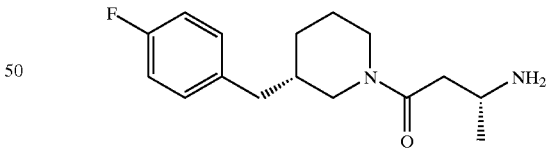

To a solution of carbamic acid, [(1R)-3-[(3S)-3-[(4-fluorophenyl)methyl]-1-piperidinyl]-1-methyl-3-oxopropyl]-, 1,1-dimethylethyl ester (750 mg) dissoved in 3 ml of methylene chloride at 25° C. under N₂ was added 1 ml of trifluoroacetic acid. The reaction was worked up after 4 hours by stripping off the solvent then rerotovapping the residue 2 times from methylene chloride. Then the residue was dissolved in methylene chloride and rinsed 3 times with 1N NaOH, 1 time with brine. The organic layer was dried and stripped to give 350 mg of an amber oil as product.

NMR (300 MHz, CDCl₃) δ 7.20–6.80 (m, 4H), 4.60–4.30 (m, 1H), 3.80–3.50 (m, 1H), 3.50–3.20 (m, 1H), 3.00–2.00 (m, 7H), 2.00–1.60 (m, 4H), 1.60–1.00 (m, 5H).

Part H. Preparation of urea, N-[(1R)-3-[(3S)-3-[(4-fluorophenyl)methyl]-1-piperidinyl]-1-methyl-3-oxopropyl]-N'-[3-(1-methyl-1H-tetrazol-5-yl)phenyl]-

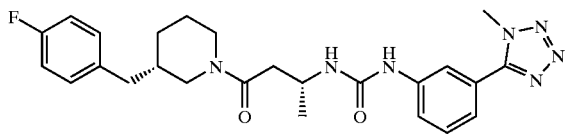

1-piperidinepropanamine, 3-[(4-fluorophenyl)methyl]-α-methyl-γ-oxo-, (α$^1$R,3S)- (30 mg, 0.108 mmol, 1 equiv.) and [3-(1-methyl-1H-tetrazol-5-yl)-phenyl]-carbamic acid phenyl ester (32 mg, 0.108 mmol, 1 equiv.) were stirred in acetonitrile at 25° C. under $N_2$. After 16 hours the reaction was stripped then purified over silica gel in 100% EtOAc followed by 4:1 chloroform/MeOH. Obtained 32 mg of a white glass as product.

NMR (300 MHz, CDCl$_3$) δ 7.82 (d, 1H, J=7 Hz), 7.60–7.40 (m, 1H), 7.40–7.15 (m, 3H), 7.10–6.90 (m, 2H), 6.90–6.7-(m, 2H), 4.50–4.20 (m, 2H), 3.90–3.60 (m, 1H), 3.20–2.20 (m, 9H), 2.00–1.60 (m, 4H), 1.60–1.40 (m, 1H), 1.30–1.00 (m, 3H).

Mass Spec detects 480 (M+H).

The following compounds in Table 1 were prepared by the above methods or by methods familiar to one skilled in the art:

TABLE 1

| Ex No. | E' | Z | R³ | (M + H) |
|---|---|---|---|---|
| 4 | —(CH₂)—(CH₂)— | O | 3,5-diacetylphenyl | 468 |
| 5 | —(CH₂)—(CH₂)— | N—(CN) | 3,5-diacetylphenyl | 492 |
| 1 | cis-cyclohexyl | O | 3-acetylphenyl | 480 |
| 6 | trans-cyclohexyl | O | 3-acetylphenyl | 480 |
| 7 | trans-cyclohexyl | O | 3-(1-methyl-1H-tetrazol-5-yl)phenyl | 520 |

TABLE 1-continued
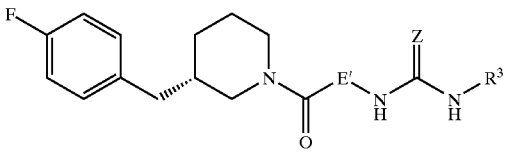
| Ex No. | E' | Z | R³ | (M + H) |
|---|---|---|---|---|
| 8 | 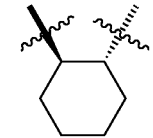 | O | 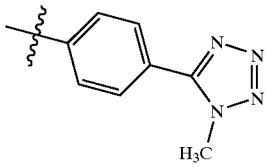 | 520 |
| 2 | 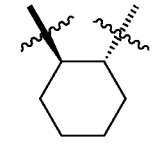 | N—CN | 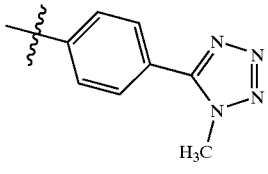 | 544 |
| 9 | 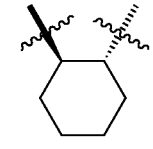 | O | 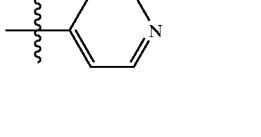 | 439 |
| 10 | 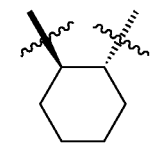 | O | 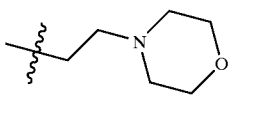 | 475 |
| 11 | " | N—CN | 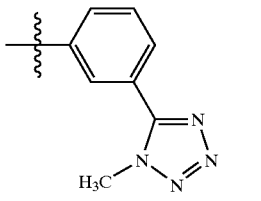 | 544 |
| 12 | " | O | 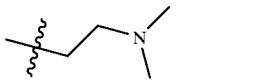 | 433 |
| 13 | " | O | 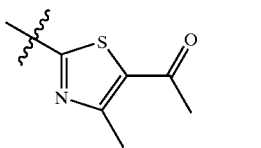 | 501 |

TABLE 1-continued
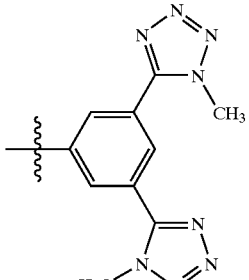
| Ex No. | E' | Z | R³ | (M + H) |
|---|---|---|---|---|
| 14 | " | O | 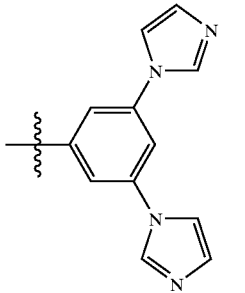 | 602 |
| 15 | " | O | 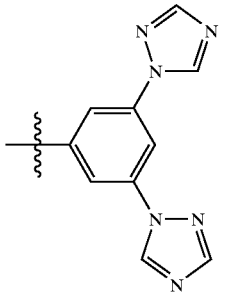 | 570 |
| 16 | " | O | 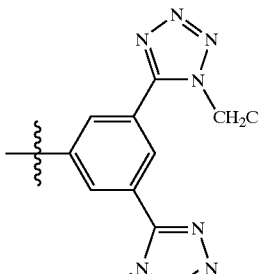 | 572 |
| 17 | " | O | (structure with ethyl tetrazoles) | 630 |

TABLE 1-continued
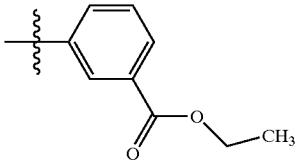
| Ex No. | E' | Z | R³ | (M + H) |
|---|---|---|---|---|
| 18 | " | O | 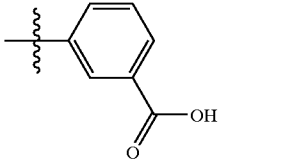 | 510 |
| 19 | " | O | 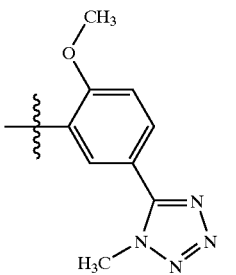 | 482 |
| 20 | " | O | 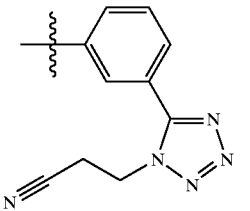 | 550 |
| 21 | " | O | 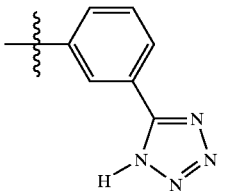 | 559 |
| 22 | " | O | 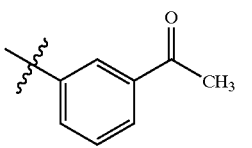 | 506 |
| 23 | 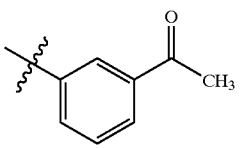 | O | | 480 |
| 24 | | O | | 466 |

TABLE 1-continued
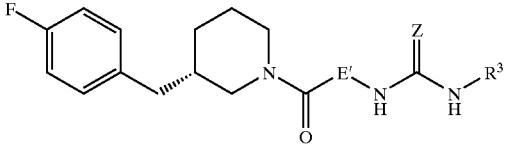
| Ex No. | E' | Z | R³ | (M + H) |
|---|---|---|---|---|
| 3 | 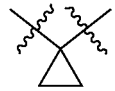 | O | 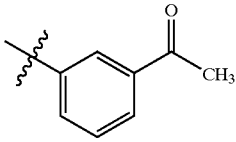 | 438 |
| 25 | " | O | 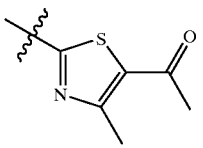 | 459 |
| 26 | 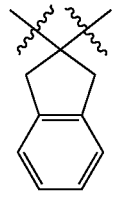 | O | 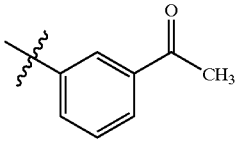 | 514 |
| 27 | 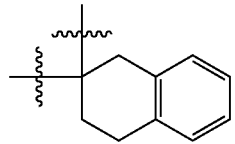 | O | 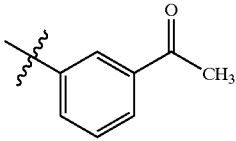 | 528 |
| 28 | —(CH$_2$)— | O | 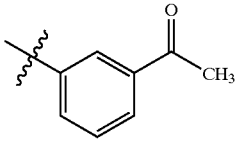 | 412 |
| 29 | 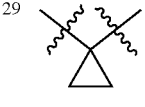 | O | 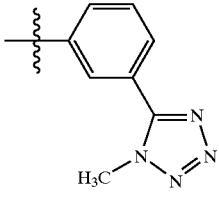 | 478 |
| 30 | " | O | 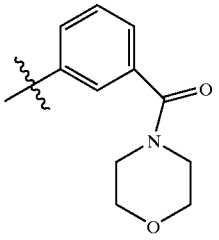 | 509 |

TABLE 1-continued
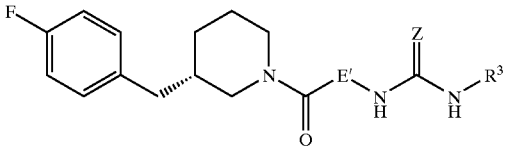
| Ex No. | E' | Z | R³ | (M + H) |
|---|---|---|---|---|
| 31 | " | O | 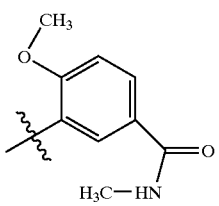 | 483 |
| 32 | " | O | 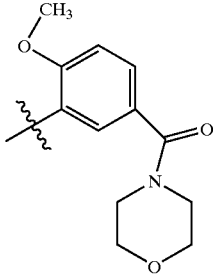 | 539 |
| 33 | —(CH₂)—(CH(CO₂CH₂Ph))—S-isomer | O | 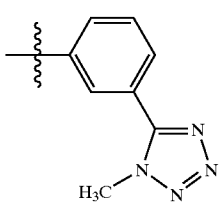 | 600 |
| 34 | —(CH₂)—(CH(CONHCH₃))—S-isomer | O | 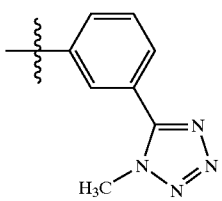 | 523 |
| 35 | 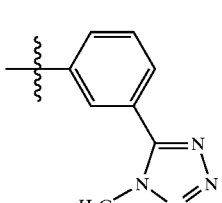 | O | 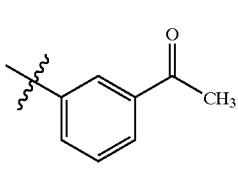 | 579 |
| 36 |  | O |  | 494 |

TABLE 1-continued

| Ex No. | E' | Z | R³ | (M + H) |
|---|---|---|---|---|
| 37 | (1,1-cyclohexyl-diyl) | O | 3-acetylphenyl | 494 |
| 38 | —C(CH₃)₂— | O | 3-acetylphenyl | 440 |
| 39 | 4,4-(1-Boc-piperidinyl) | O | 3-acetylphenyl | 595 |
| 40 | 4,4-(piperidinyl), NH | O | 3-acetylphenyl | 495 |
| 41 | 4,4-(1-methyl-piperidinyl) | O | 3-acetylphenyl | 509 |
| 42 | 4,4-(1-methanesulfonyl-piperidinyl) | O | 3-acetylphenyl | 573 |
| 43 | CH(CH₃)-C(O)-pyrrolidinyl | O | 3-(1-methyl-1H-tetrazol-5-yl)phenyl | 563 |

TABLE 1-continued

| Ex No. | E' | Z | R³ | (M + H) |
|---|---|---|---|---|
| 44 | -CH(CH₂C(O)NH-tBu)- | O | 3-(1-methyl-tetrazol-5-yl)phenyl | 565 |
| 45 | -CH(CH₂C(O)-piperidinyl)- | O | 3-(1-methyl-tetrazol-5-yl)phenyl | 577 |
| 46 | cyclopropylidene (1,1-disubstituted cyclopropane) | O | 4-methoxy-3-carbamoylphenyl | 469 |
| 47 | -CH(CH₂C(O)-(4-methylpiperazin-1-yl))- | O | 3-(1-methyl-tetrazol-5-yl)phenyl | 592 |
| 48 | -CH(NH₂)- (CH₂ on each side) | O | 3-acetylphenyl | 441 |
| 49 | -CH(NH₂)- (CH₂ on each side) | O | 3-acetylphenyl | 441 |
| 50 | -CH(NHAc)- (CH₂ on each side) | O | 3-acetylphenyl | 483 |

TABLE 1-continued

| Ex No. | E' | Z | R³ | (M + H) |
|---|---|---|---|---|
| 51 | CH(NHAc) branched | O | 3-acetylphenyl | 483 |
| 52 | CH₂-piperidinyl branched | O | 3-(1-methyltetrazol-5-yl)phenyl | 565 |
| 53 | CH₂-morpholinyl branched | N—CN | 3-(1-methyltetrazol-5-yl)phenyl | 589 |
| 54 | CH₂-C(O)N(CH₃)₂ branched | O | 3-(1-methyltetrazol-5-yl)phenyl | 537 |
| 55 | CH₂-morpholinyl branched | O | 3-(N-methylcarbamoyl)phenyl | 540 |
| 56 | CH₂-morpholinyl branched | O | 3-chlorophenyl | 518 |

TABLE 1-continued
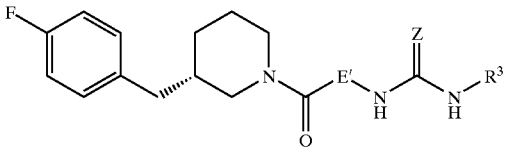
| Ex No. | E' | Z | R³ | (M + H) |
|---|---|---|---|---|
| 57 | 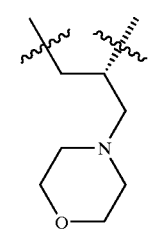 | O | 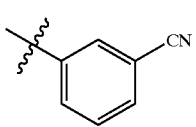 | 508 |
| 58 | 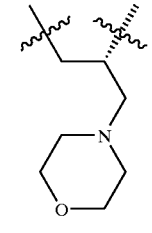 | O | 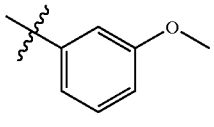 | 513 |
| 59 | 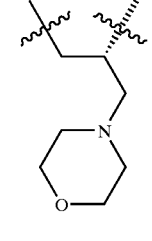 | O |  | 447 |
| 60 | 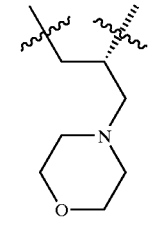 | O | 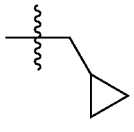 | 461 |
| 61 | 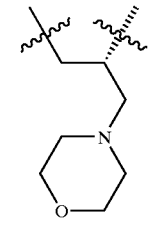 | O | 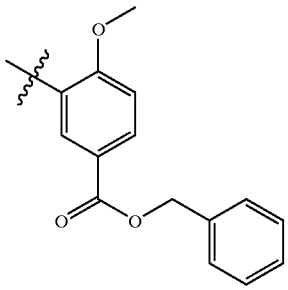 | 647 |

TABLE 1-continued

| Ex No. | E' | Z | R³ | (M + H) |
|---|---|---|---|---|
| 62 | [CH2-piperidinyl branched] | O | [4-methyl-5-acetyl-thiazol-2-yl] | 544 |
| 63 | [CH(CH2-morpholine-C(O))] | O | [3-(1-methyltetrazol-5-yl)phenyl] | 593 |
| 64 | [CH(CH2-morpholine-C(O))] | O | [3-(N-methylcarbamoyl)phenyl] | 568 |
| 65 | [CH(CH3) branched] | O | [3,5-diacetylphenyl] | 482 |
| 66 | [CH(CH3) branched] | O | [3-(1-methyltetrazol-5-yl)phenyl] | 480 |
| 67 | [CH(CH3) branched] | O | [3-(1-methyltetrazol-5-yl)phenyl] | 480 |

TABLE 1-continued

| Ex No. | E' | Z | R³ | (M + H) |
|---|---|---|---|---|
| 68 | | O | | 525 |
| 69 | | O | | 480 |
| 70 | | O | | 549 |
| 71 | | O | | 523 |
| 72 | | O | | 591 |
| 73 | | O | | 492 |
| 74 | | O | | 565 |

TABLE 1-continued

| Ex No. | E' | Z | R³ | (M + H) |
|---|---|---|---|---|
| 75 | (structure) | O | (structure) | 546 |
| 76 | (structure) | O | (structure) | 565 |
| 77 | (structure) | O | (structure) | 574 |
| 78 | (structure) | O | (structure) | 593 |
| 79 | (structure) | O | (structure) | 480 |
| 80 | (structure) | O | (structure) | 546 |

TABLE 1-continued

| Ex No. | E' | Z | R³ | (M + H) |
|---|---|---|---|---|
| 81 | (structure) | O | 4-pyridyl | 399 |
| 82 | (structure with OH) | O | (methyl-thiazolyl ketone) | 496 |
| 83 | (structure with OH) | O | (3,5-diacetylphenyl) | 498 |
| 84 | (cyclohexyl structure) | O | (3-(dimethylaminomethyl)phenyl) | 495 |
| 85 | (cyclopropyl structure) | O | (3-carbamoylphenyl) | 439 |
| 86 | (cyclopropyl structure) | O | (4-methoxy-3-(1-methyltetrazol-5-yl)phenyl) | 508 |
| 87 | (cyclopropyl structure) | O | (3-(5-methyltetrazol-1-yl)phenyl) | 478 |
| 88 | (structure) | O | (3-(1-methyltetrazol-5-yl)phenyl) | 466 |

TABLE 1-continued

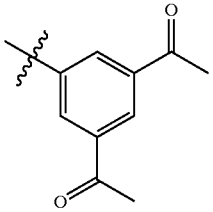

| Ex No. | E' | Z | R³ | (M + H) |
|---|---|---|---|---|
| 89 | 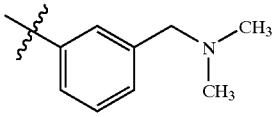 | O | 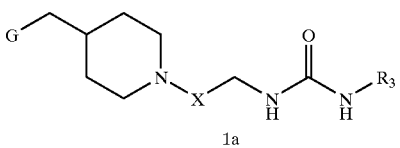 | 468 |
| | 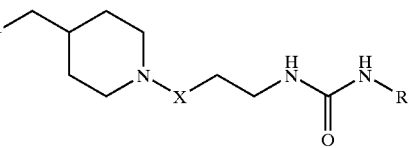 | O | 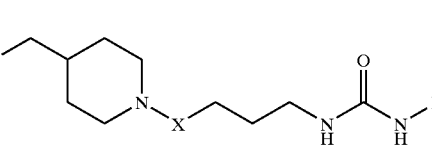 | 495 |

The following tables contain representative examples of the present invention, and may be prepared by procedures described above, or methods familiar to one skilled in the art. Each entry in each table is intended to be paired with each formulae at the start of the table. For example, Entry 1 in Table 4 is intended to be paired with each of formulae 1a-221, wherein each of formulae 1a-221 can obtain either X listed.

TABLE 2

$X = C{=}O, SO_2$

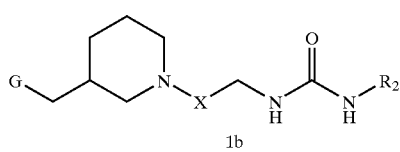

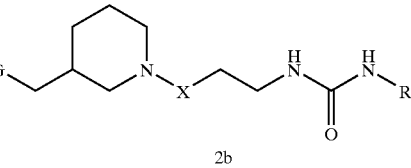

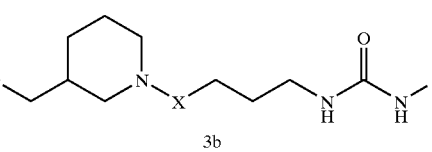

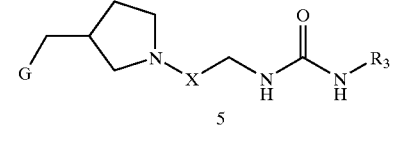

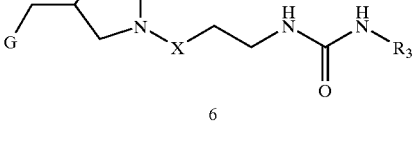

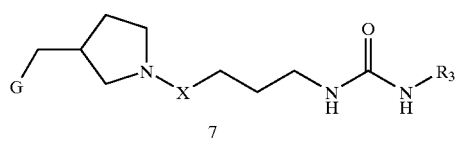
7
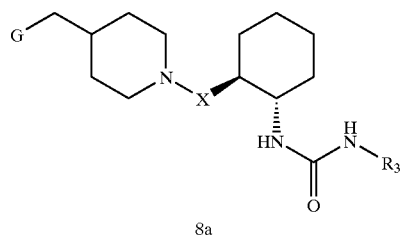
8a
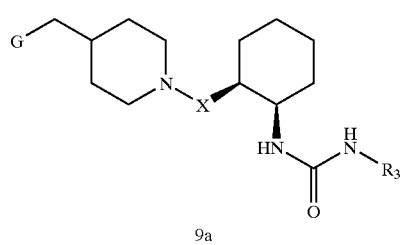
9a
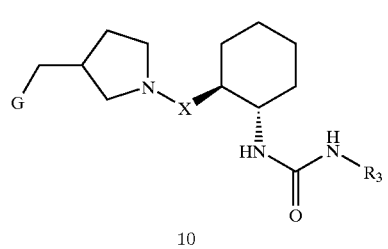
10
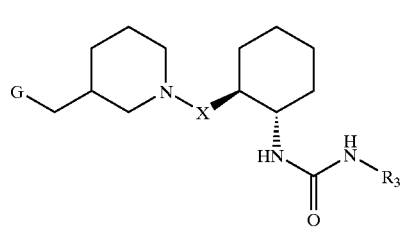
8b
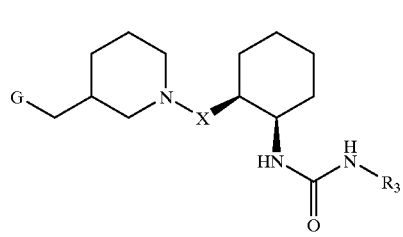
9b
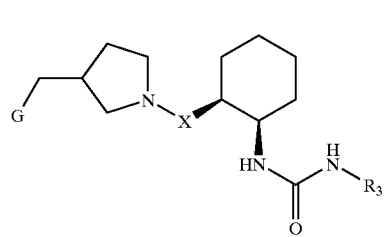
11
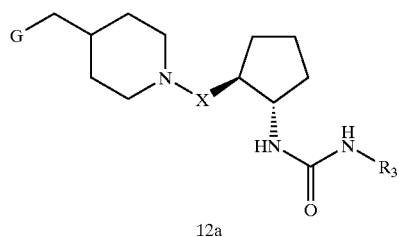
12a
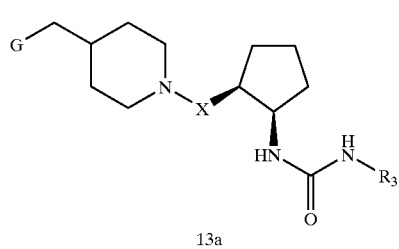
13a
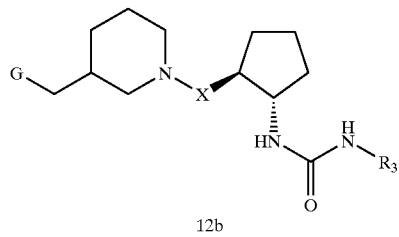
12b
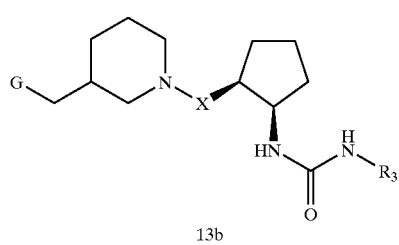
13b
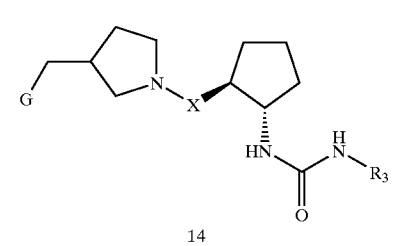
14
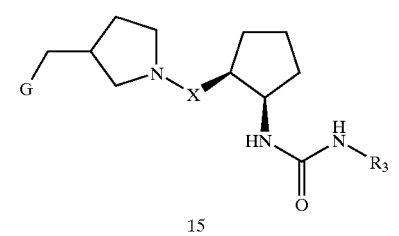
15

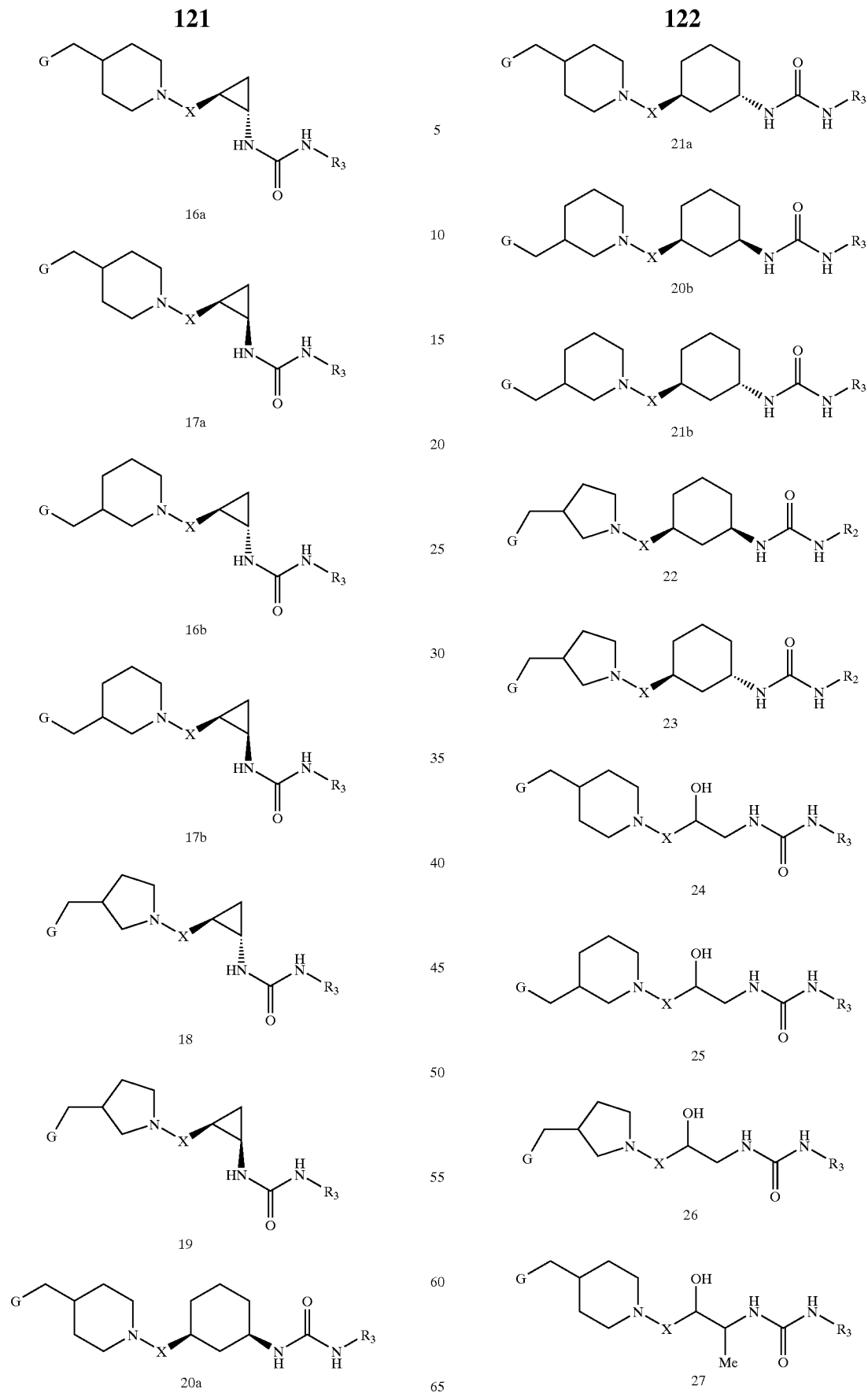

123
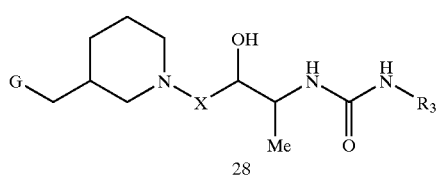
28
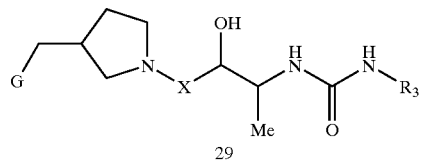
29
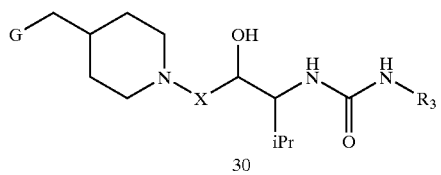
30
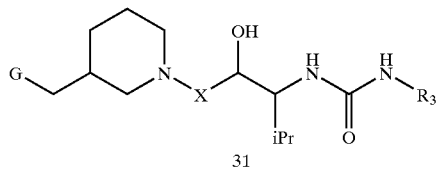
31
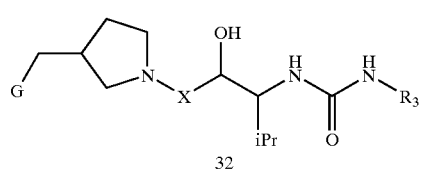
32
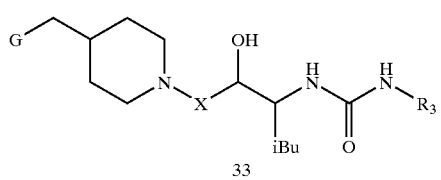
33
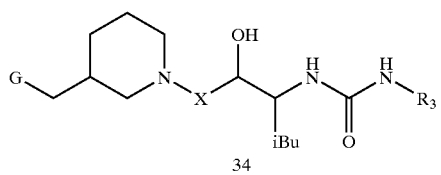
34
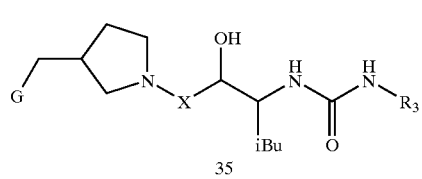
35
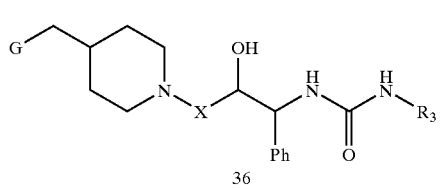
36
124
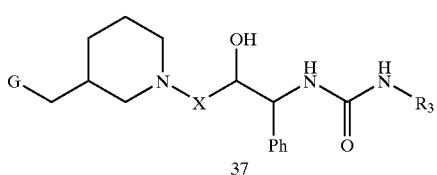
37
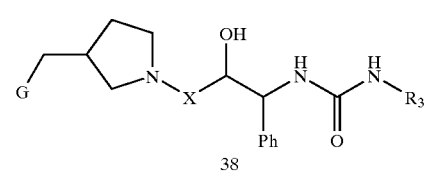
38
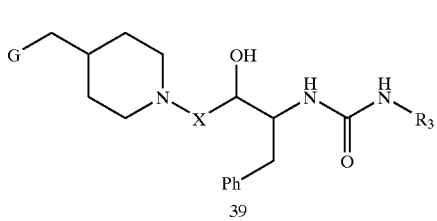
39
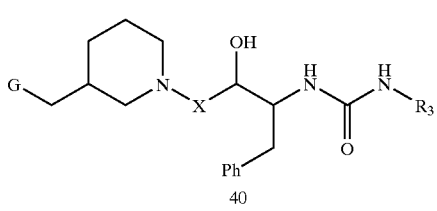
40
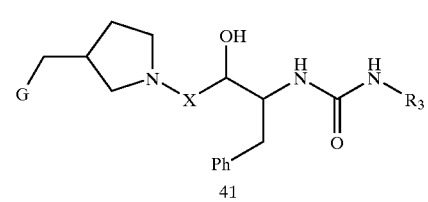
41
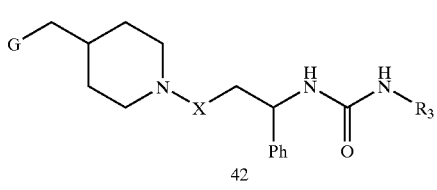
42
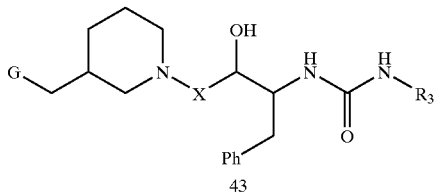
43
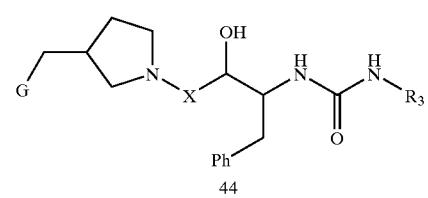
44

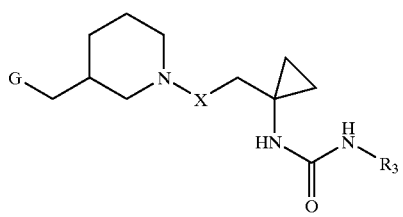
45
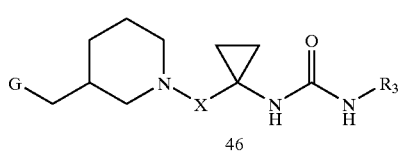
46
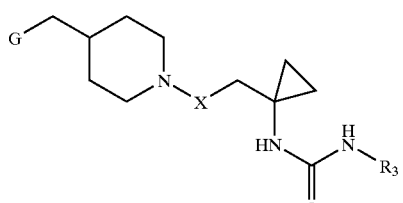
47
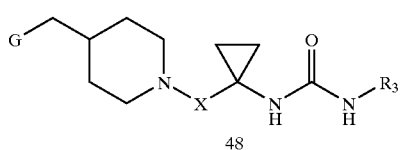
48
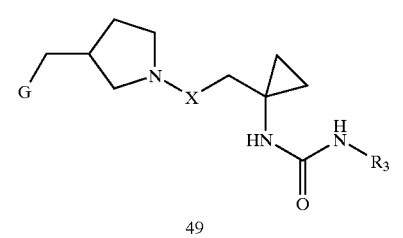
49
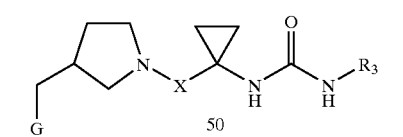
50
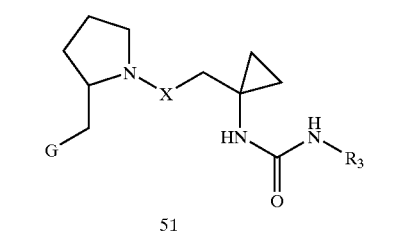
51
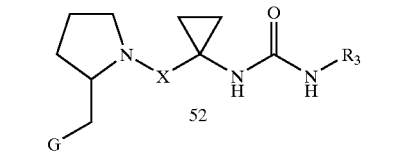
52
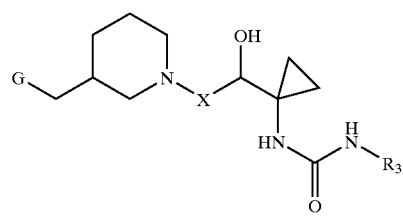
53
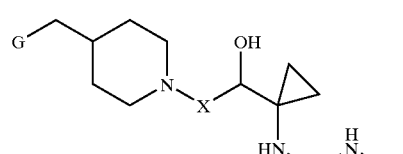
54
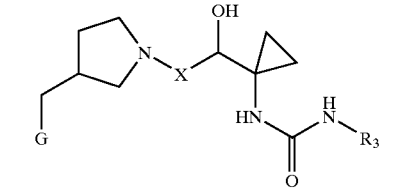
55
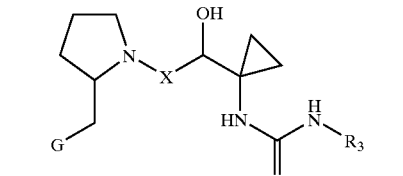
60
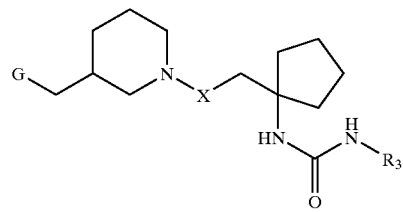
61
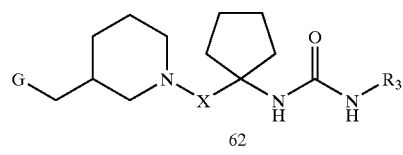
62
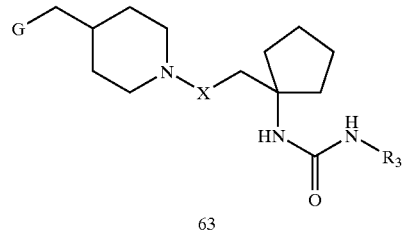
63

127
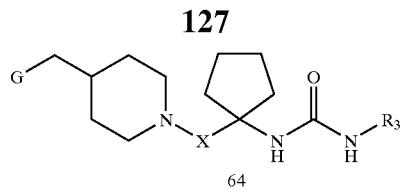
64
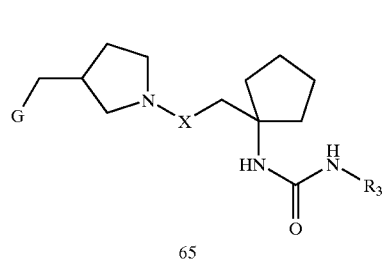
65
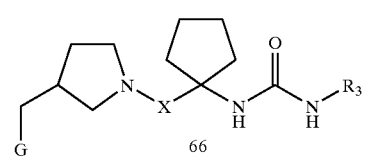
66
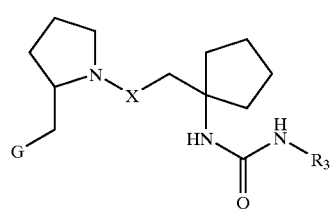
67
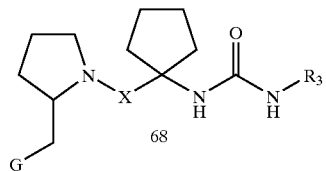
68
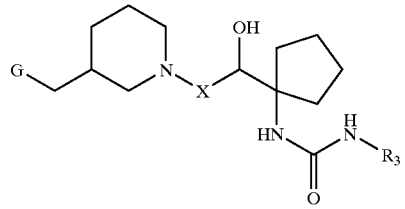
69
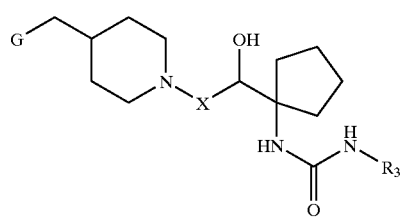
70
128
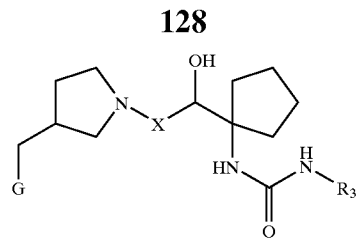
71
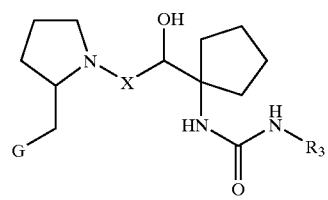
72
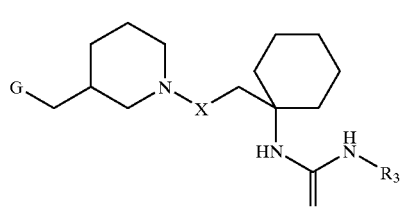
73
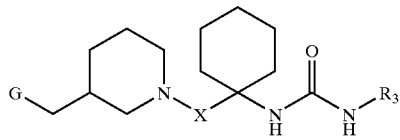
74
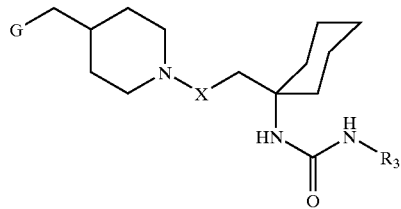
75
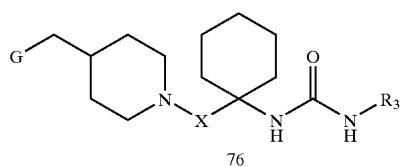
76
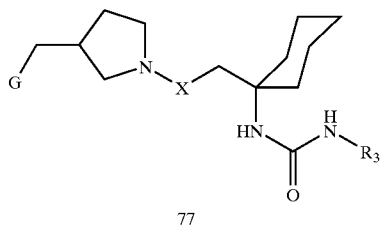
77

129
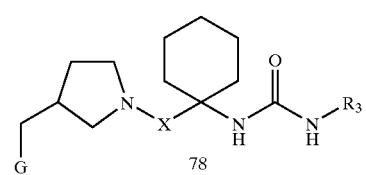
78
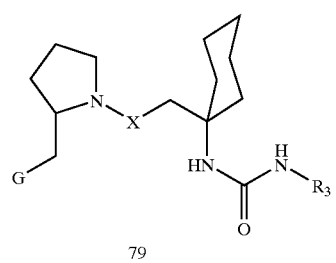
79
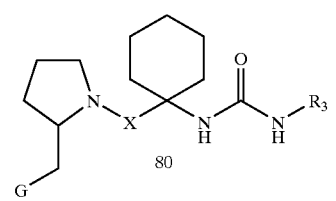
80
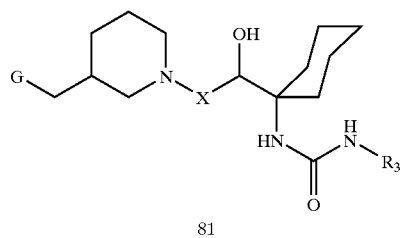
81
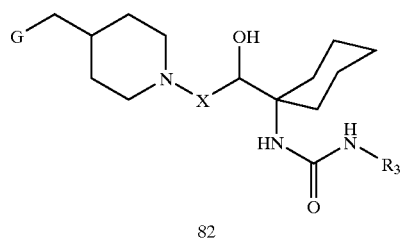
82
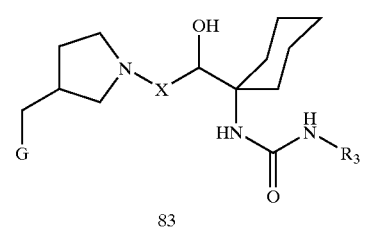
83
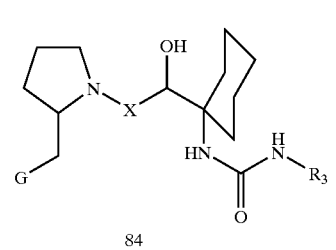
84
130
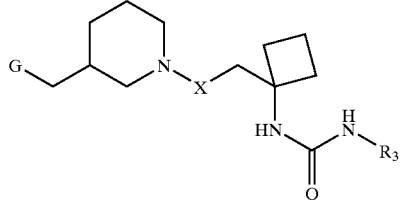
85
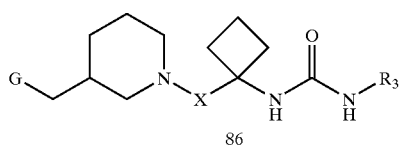
86
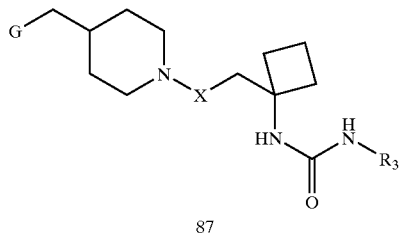
87
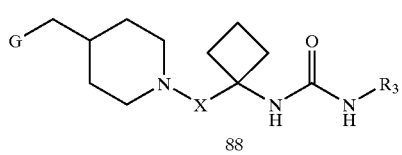
88
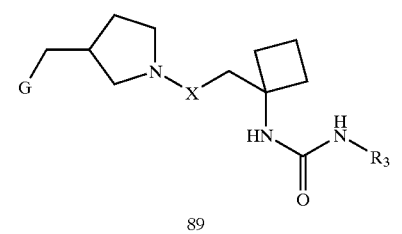
89
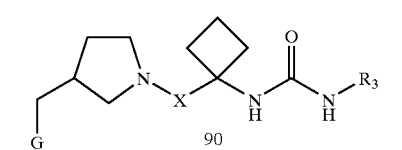
90
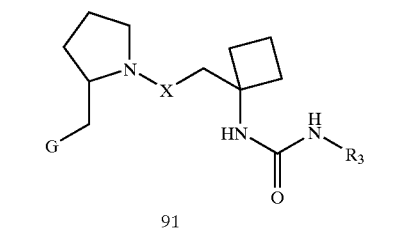
91
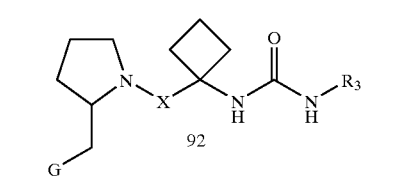
92

131                                           132
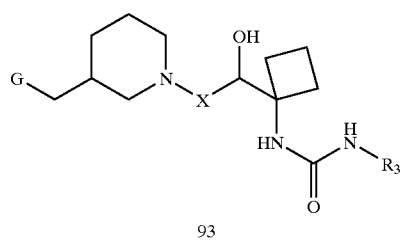
93
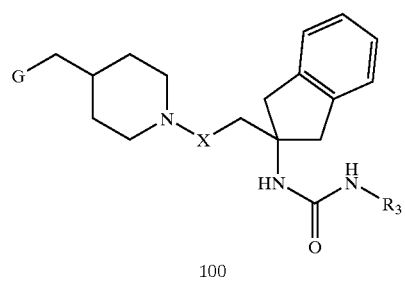
100
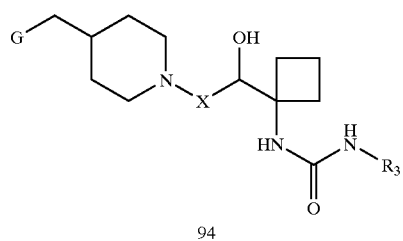
94
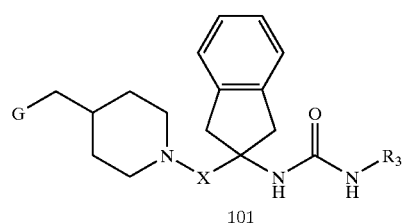
101
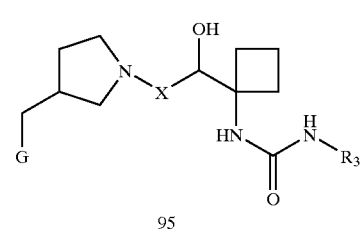
95
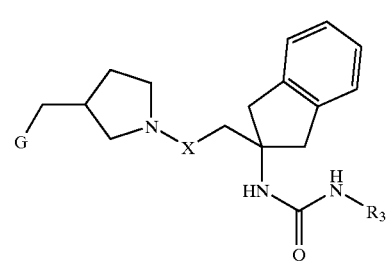
102
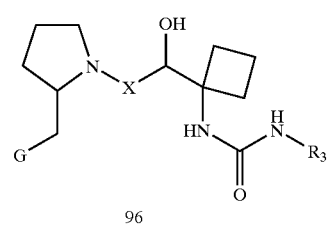
96
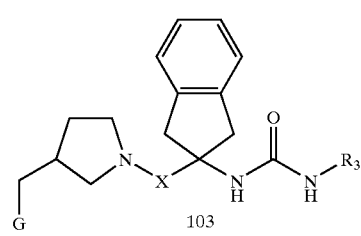
103
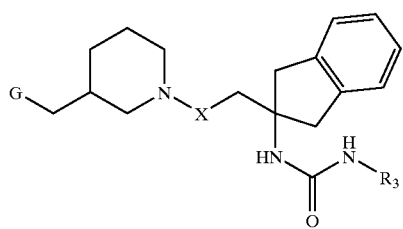
97
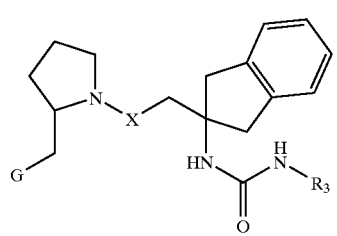
104
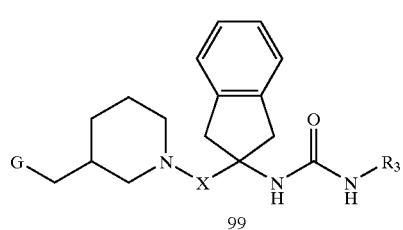
99
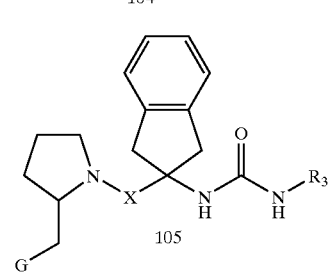
105

133
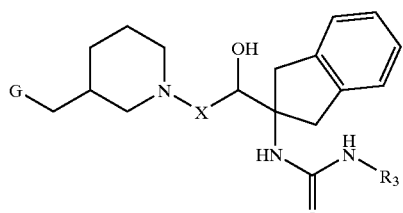
106
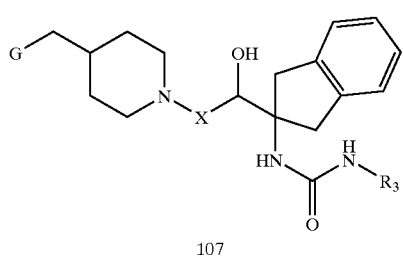
107
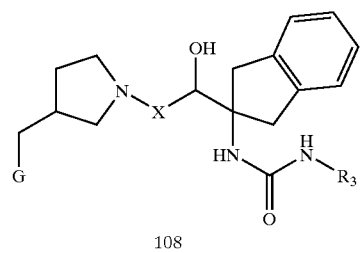
108
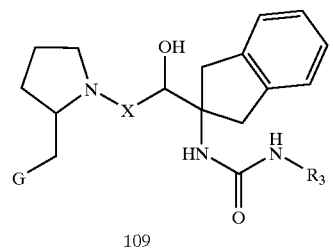
109
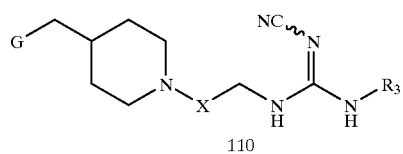
110
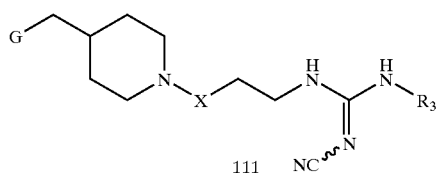
111
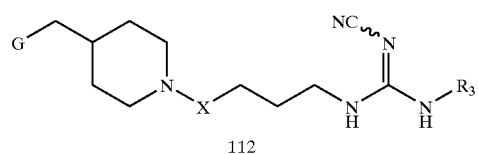
112
134
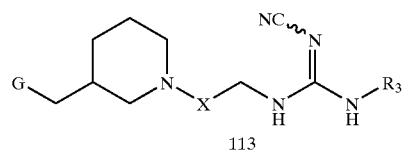
113
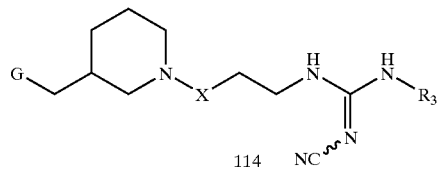
114
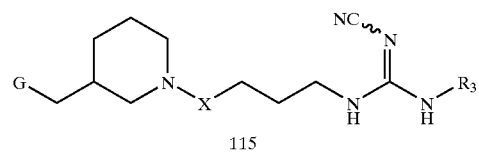
115
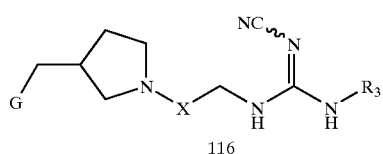
116
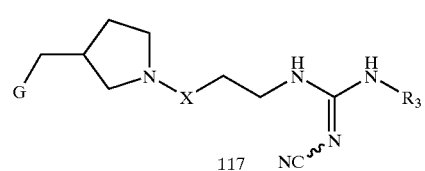
117
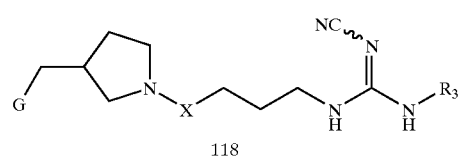
118
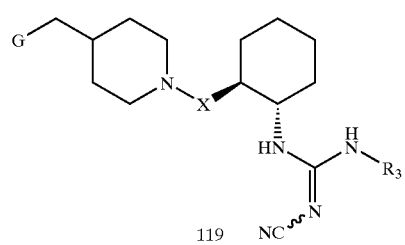
119
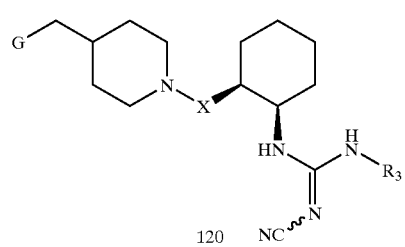
120

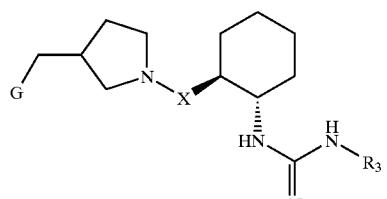
135
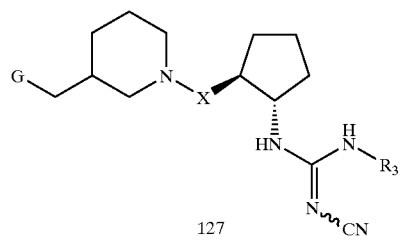
136

137
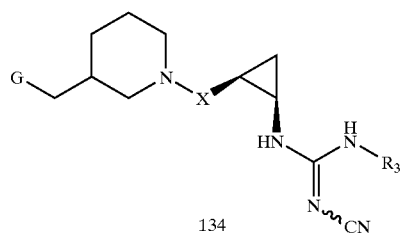
134
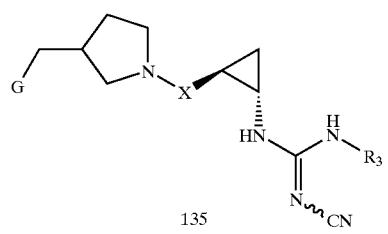
135
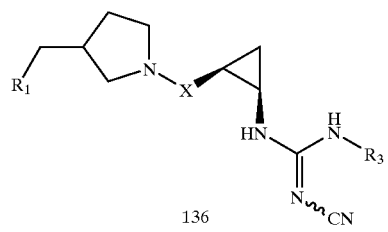
136
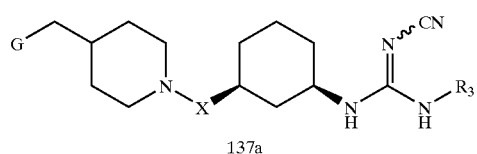
137a
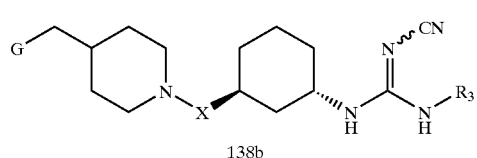
138b
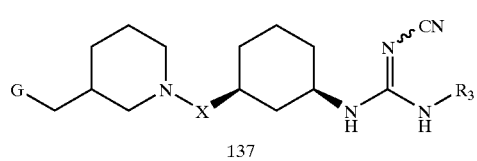
137
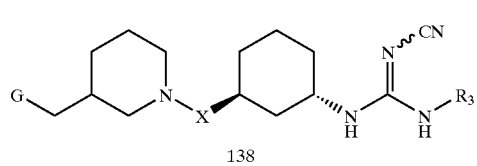
138
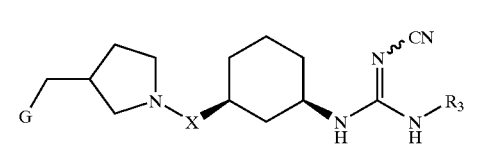
139
138
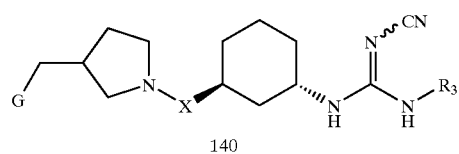
140
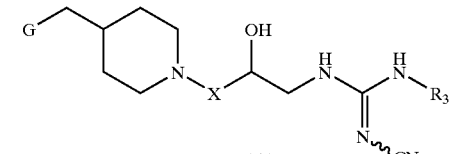
141
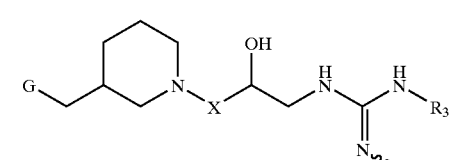
142
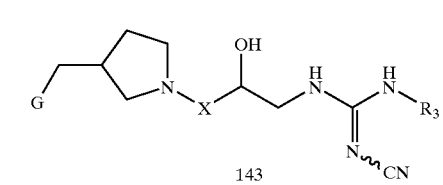
143
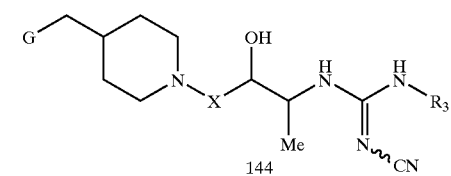
144
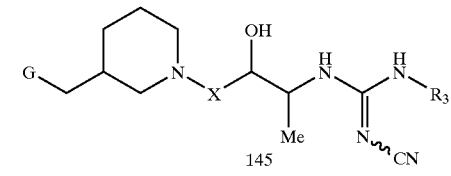
145
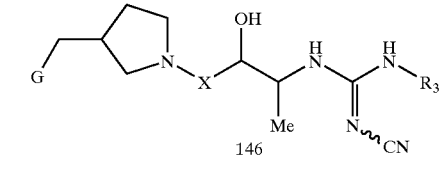
146
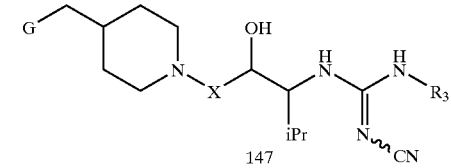
147
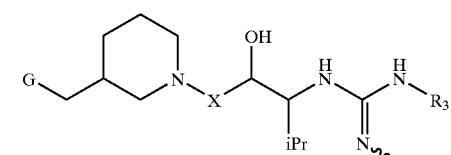
148

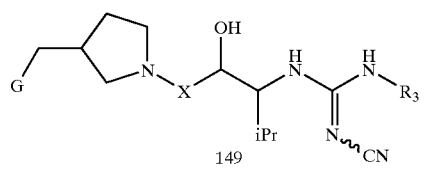
149
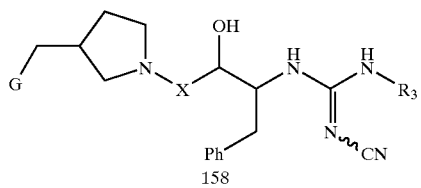
158
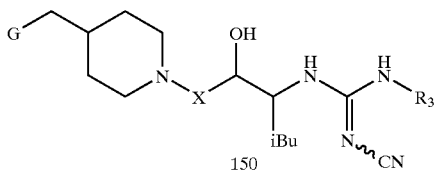
150
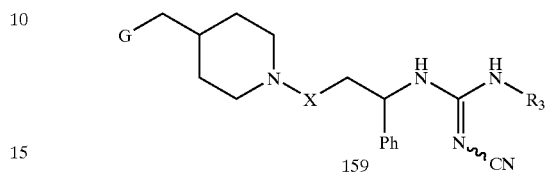
159
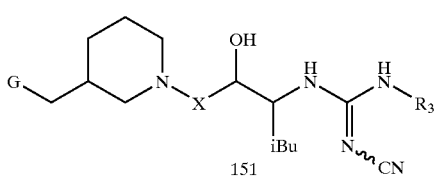
151
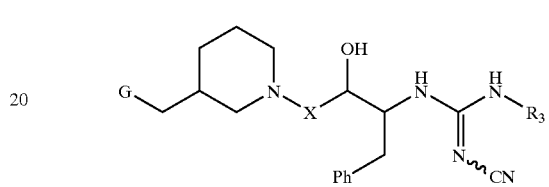
160
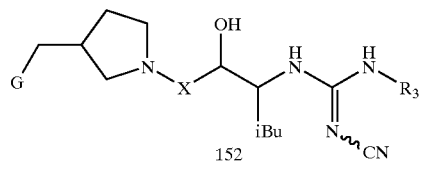
152
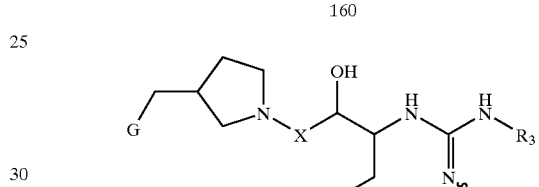
161
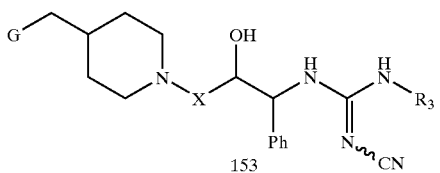
153
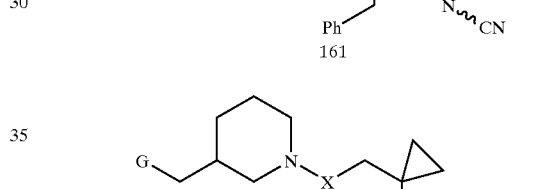
162
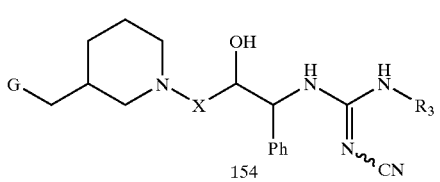
154
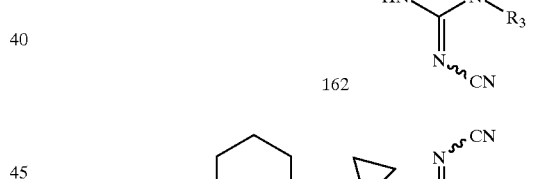
163
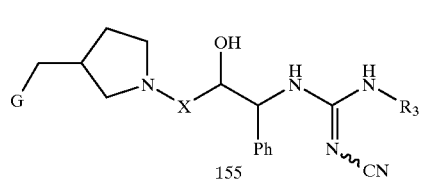
155
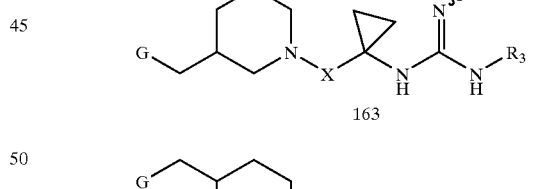
164
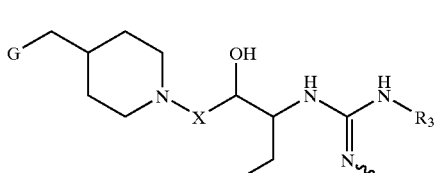
156
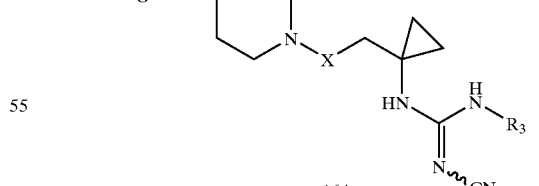
165
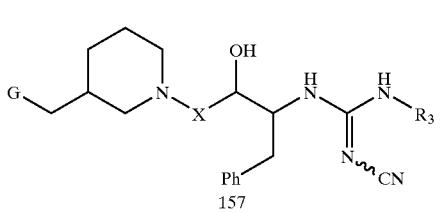
157

141
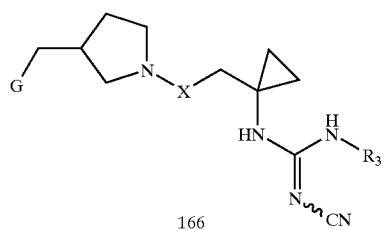
166
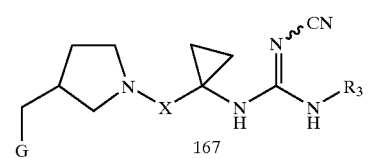
167
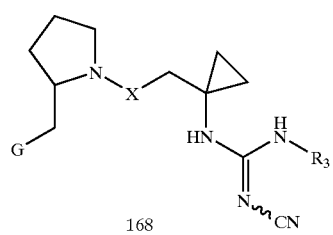
168
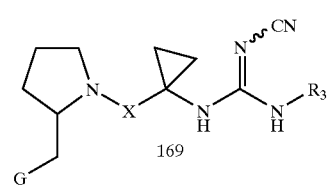
169
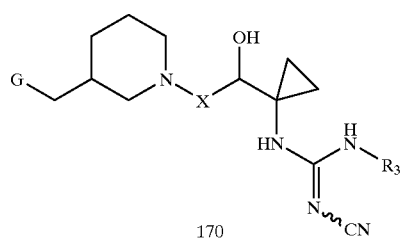
170
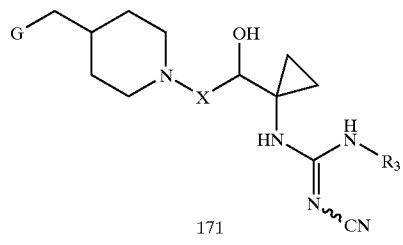
171
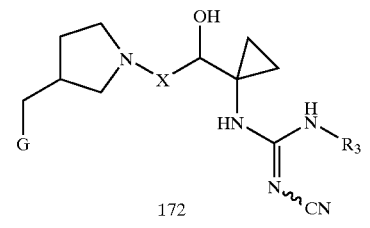
172
142
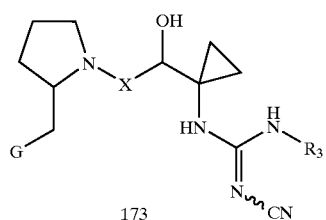
173
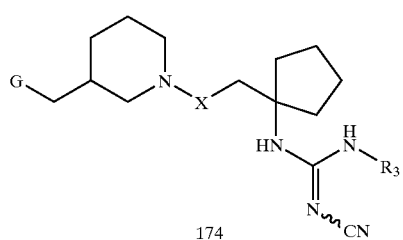
174
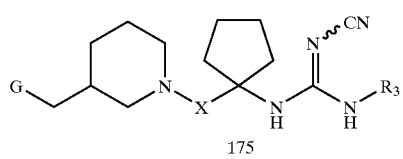
175
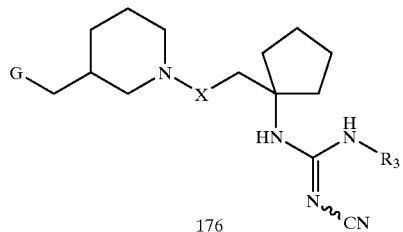
176
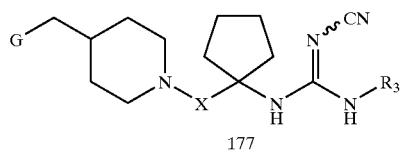
177
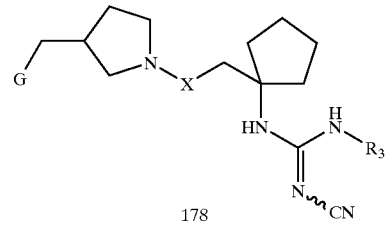
178
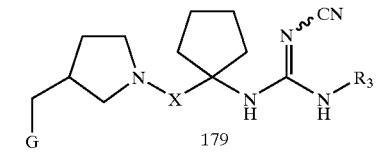
179
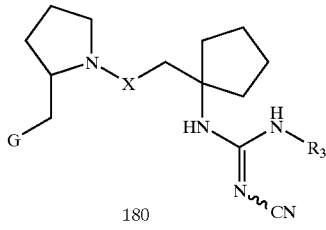
180

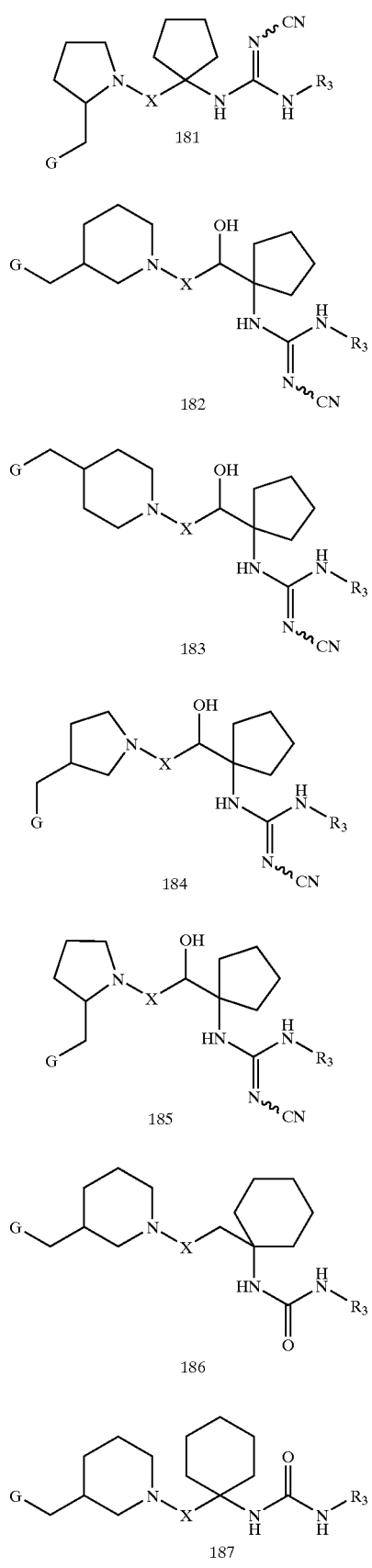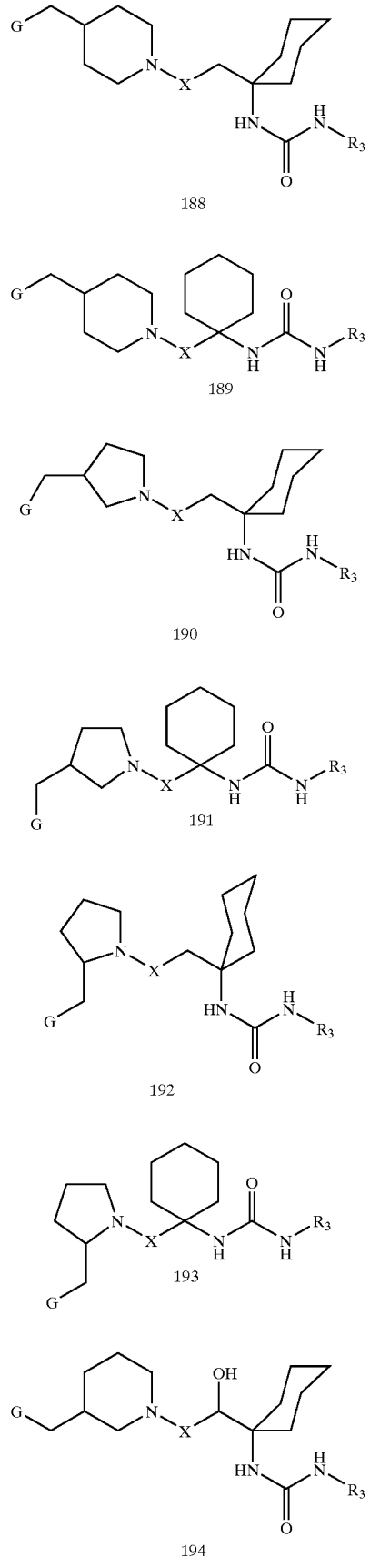

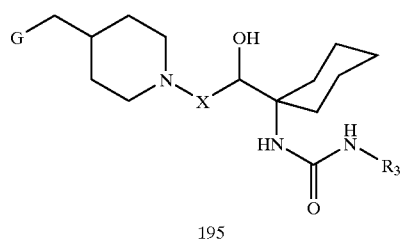
195
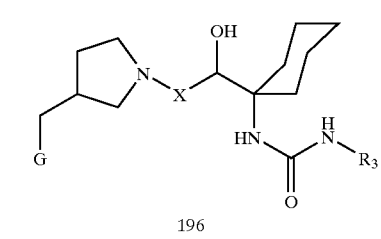
196
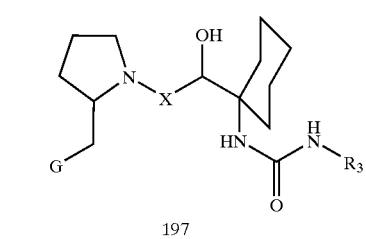
197
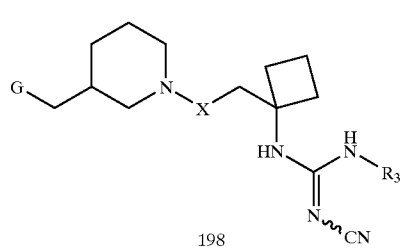
198
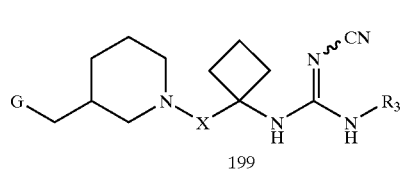
199
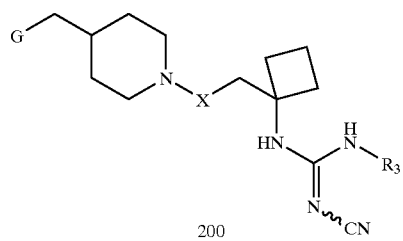
200
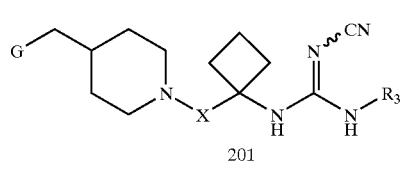
201
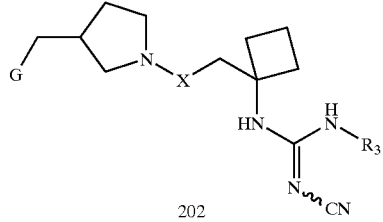
202
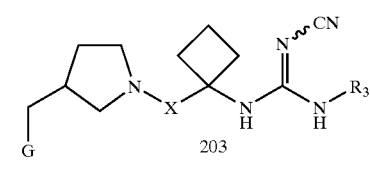
203
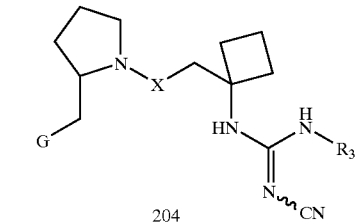
204
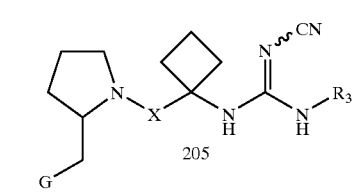
205
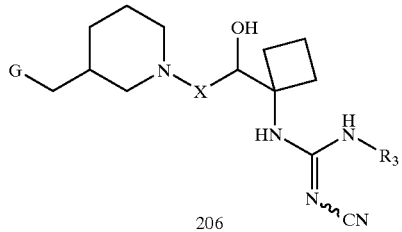
206
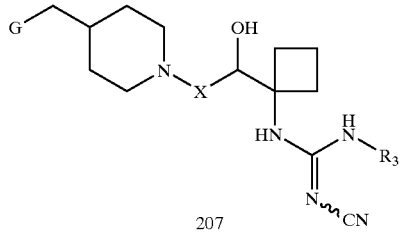
207
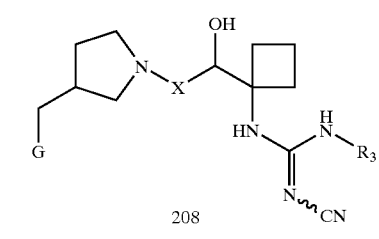
208

147
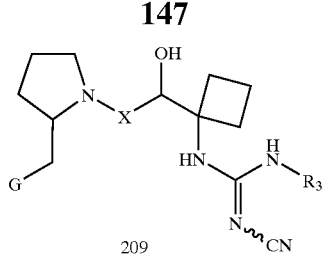
209
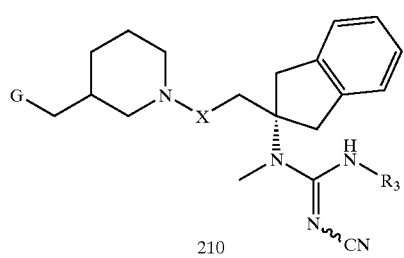
210
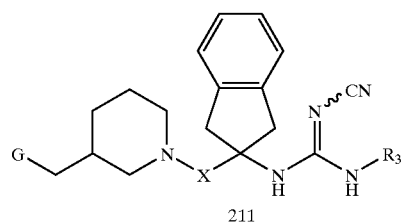
211
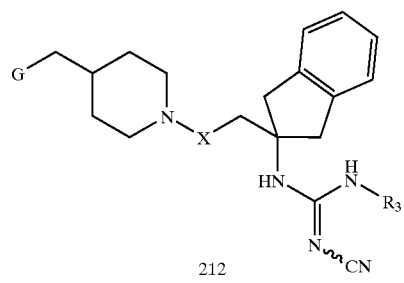
212
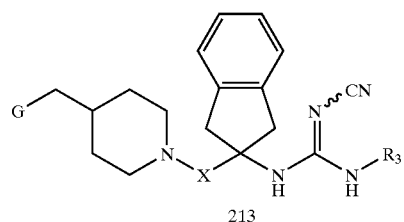
213
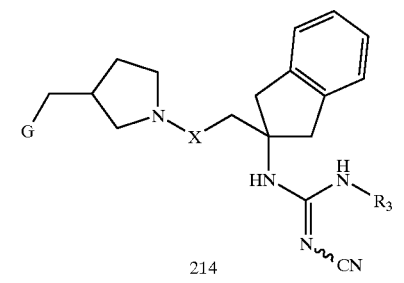
214
148
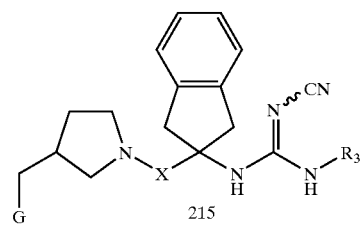
215
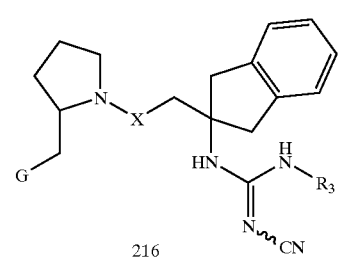
216
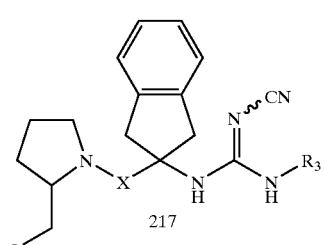
217
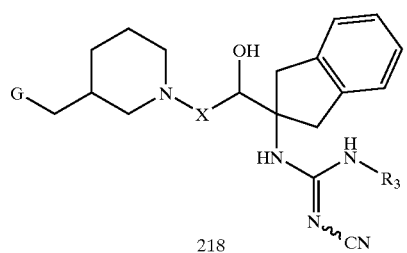
218
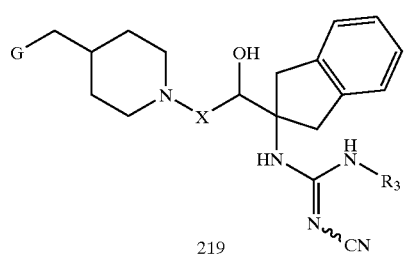
219
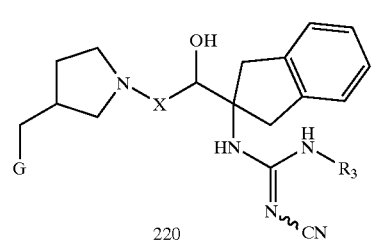
220

149
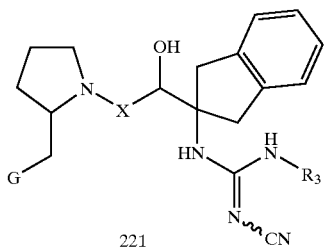
221
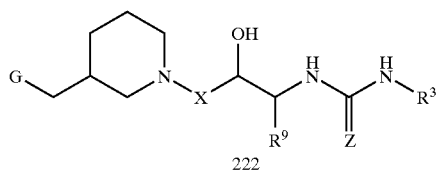
222
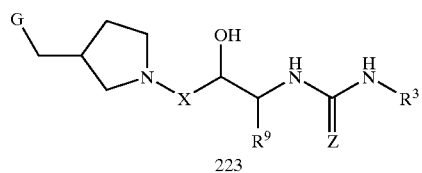
223
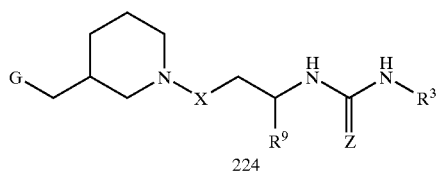
224
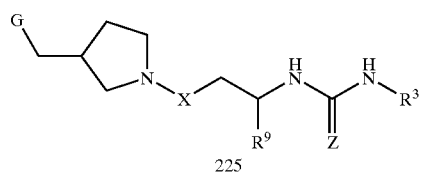
225
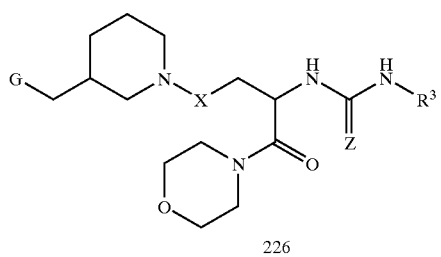
226
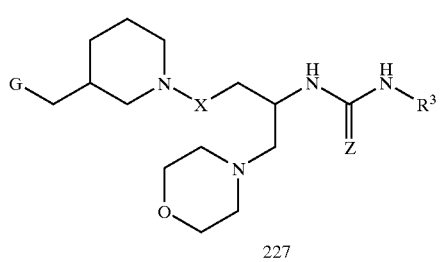
227
150
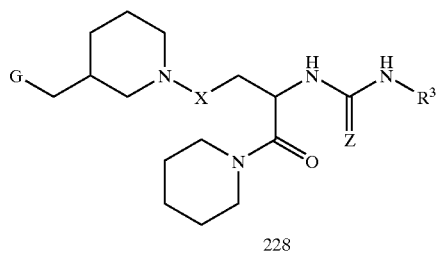
228
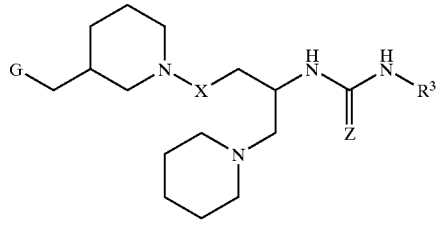
229
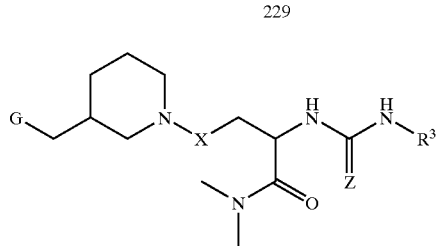
230
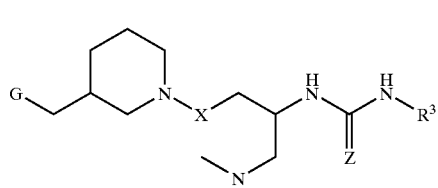
231
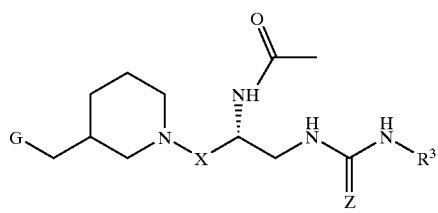
232
| Entry # | G | R3 |
|---|---|---|
| 1. | 4-F-Ph | Ph |
| 2. | 4-F-Ph | 3-CN-Ph |
| 3. | 4-F-Ph | 3-COCH3-Ph |
| 4. | 4-F-Ph | 3-CO2Me-Ph |
| 5. | 4-F-Ph | 3-CO2Et-Ph |
| 6. | 4-F-Ph | 3-CO2H-Ph |
| 7. | 4-F-Ph | 3-CONH2-Ph |
| 8. | 4-F-Ph | 3-CONHMe-Ph |
| 9. | 4-F-Ph | 3-F-Ph |
| 10. | 4-F-Ph | 3-Cl-Ph |
| 11. | 4-F-Ph | 3-Br-Ph |
| 12. | 4-F-Ph | 3-NO2-Ph |
| 13. | 4-F-Ph | 3-NH2-Ph |
| 14. | 4-F-Ph | 3-NHMe-Ph |
| 15. | 4-F-Ph | 3-NMe2-Ph |
| 16. | 4-F-Ph | 3-NHCOCH3-Ph |
| 17. | 4-F-Ph | 3-SO2NH2-Ph |

| | | |
|---|---|---|
| 18. | 4-F-Ph | 3-SO2NHMe-Ph |
| 19. | 4-F-Ph | 3-CF3-Ph |
| 20. | 4-F-Ph | 3-OCH3-Ph |
| 21. | 4-F-Ph | 3-OPh-Ph |
| 22. | 4-F-Ph | 3-OCF3-Ph |
| 23. | 4-F-Ph | 3-SCH3-Ph |
| 24. | 4-F-Ph | 3-SOCH3-Ph |
| 25. | 4-F-Ph | 3-SO2CH3-Ph |
| 26. | 4-F-Ph | 3-OH-Ph |
| 27. | 4-F-Ph | 3-CH2OH-Ph |
| 28. | 4-F-Ph | 3-CHOHCH3-Ph |
| 29. | 4-F-Ph | 3-COH(CH3)2-Ph |
| 30. | 4-F-Ph | 3-CHOHPh-Ph |
| 31. | 4-F-Ph | 3-CH3-Ph |
| 32. | 4-F-Ph | 3-C2H5-Ph |
| 33. | 4-F-Ph | 3-iPr-Ph |
| 34. | 4-F-Ph | 3-tBu-Ph |
| 35. | 4-F-Ph | 3-Ph-Ph |
| 36. | 4-F-Ph | 3-CH2Ph-Ph |
| 37. | 4-F-Ph | 3-CH2CO2Me-Ph |
| 38. | 4-F-Ph | 3-(1-piperidinyl)-Ph |
| 39. | 4-F-Ph | 3-(1-pyrrolidinyl)-Ph |
| 40. | 4-F-Ph | 3-(2-imidazolyl)-Ph |
| 41. | 4-F-Ph | 3-(1-imidazolyl)-Ph |
| 42. | 4-F-Ph | 3-(2-thiazolyl)-Ph |
| 43. | 4-F-Ph | 3-(3-pyrazolyl)-Ph |
| 44. | 4-F-Ph | 3-(1-pyrazolyl)-Ph |
| 45. | 4-F-Ph | 3-(1-tetrazolyl)-Ph |
| 46. | 4-F-Ph | 3-(5-tetrazolyl)-Ph |
| 47. | 4-F-Ph | 3-(2-pyridyl)-Ph |
| 48. | 4-F-Ph | 3-(2-thienyl)-Ph |
| 49. | 4-F-Ph | 3-(2-furanyl)-Ph |
| 50. | 4-F-Ph | 4-CN-Ph |
| 51. | 4-F-Ph | 4-COCH3-Ph |
| 52. | 4-F-Ph | 4-CO2Me-Ph |
| 53. | 4-F-Ph | 4-CO2Et-Ph |
| 54. | 4-F-Ph | 4-CO2H-Ph |
| 55. | 4-F-Ph | 4-CONH2-Ph |
| 56. | 4-F-Ph | 4-CONHMe-Ph |
| 57. | 4-F-Ph | 4-CONHPh-Ph |
| 58. | 4-F-Ph | 4-NHCONH2-Ph |
| 59. | 4-F-Ph | 4-F-Ph |
| 60. | 4-F-Ph | 4-Cl-Ph |
| 61. | 4-F-Ph | 4-Br-Ph |
| 62. | 4-F-Ph | 4-NO2-Ph |
| 63. | 4-F-Ph | 4-NH2-Ph |
| 64. | 4-F-Ph | 4-NHMe-Ph |
| 65. | 4-F-Ph | 4-NMe2-Ph |
| 66. | 4-F-Ph | 4-NHCOCH3-Ph |
| 67. | 4-F-Ph | 4-SO2NH2-Ph |
| 68. | 4-F-Ph | 4-SO2NHMe-Ph |
| 69. | 4-F-Ph | 4-CF3-Ph |
| 70. | 4-F-Ph | 4-OCH3-Ph |
| 71. | 4-F-Ph | 4-OPh-Ph |
| 72. | 4-F-Ph | 4-OCF3-Ph |
| 73. | 4-F-Ph | 4-SCH3-Ph |
| 74. | 4-F-Ph | 4-SOCH3-Ph |
| 75. | 4-F-Ph | 4-SO2CH3-Ph |
| 76. | 4-F-Ph | 4-OH-Ph |
| 77. | 4-F-Ph | 4-CH2OH-Ph |
| 78. | 4-F-Ph | 4-CHOHCH3-Ph |
| 79. | 4-F-Ph | 4-COH(CH3)2-Ph |
| 80. | 4-F-Ph | 4-CH3-Ph |
| 81. | 4-F-Ph | 4-C2H5-Ph |
| 82. | 4-F-Ph | 4-iPr-Ph |
| 83. | 4-F-Ph | 4-tBu-Ph |
| 84. | 4-F-Ph | 4-Ph-Ph |
| 85. | 4-F-Ph | 4-CH2Ph-Ph |
| 86. | 4-F-Ph | 4-CH2CO2Me-Ph |
| 87. | 4-F-Ph | 4-(1-piperidinyl)-Ph |
| 88. | 4-F-Ph | 4-(1-pyrrolidinyl)-Ph |
| 89. | 4-F-Ph | 4-(2-imidazolyl)-Ph |
| 90. | 4-F-Ph | 4-(1-imidazolyl)-Ph |
| 91. | 4-F-Ph | 4-(2-thiazolyl)-Ph |
| 92. | 4-F-Ph | 4-(3-pyrazolyl)-Ph |
| 93. | 4-F-Ph | 4-(1-pyrazolyl)-Ph |
| 94. | 4-F-Ph | 4-(1-tetrazolyl)-Ph |
| 95. | 4-F-Ph | 4-(5-tetrazolyl)-Ph |
| 96. | 4-F-Ph | 4-(2-pyridyl)-Ph |
| 97. | 4-F-Ph | 4-(2-thienyl)-Ph |
| 98. | 4-F-Ph | 4-(2-furanyl)-Ph |
| 99. | 4-F-Ph | 2-CN-Ph |
| 100. | 4-F-Ph | 2-COCH3-Ph |
| 101. | 4-F-Ph | 2-CO2Me-Ph |
| 102. | 4-F-Ph | 2-CO2Et-Ph |
| 103. | 4-F-Ph | 2-CO2H-Ph |
| 104. | 4-F-Ph | 2-CONH2-Ph |
| 105. | 4-F-Ph | 2-CONHMe-Ph |
| 106. | 4-F-Ph | 2-F-Ph |
| 107. | 4-F-Ph | 2-Cl-Ph |
| 108. | 4-F-Ph | 2-Br-Ph |
| 109. | 4-F-Ph | 2-NO2-Ph |
| 110. | 4-F-Ph | 2-NH2-Ph |
| 111. | 4-F-Ph | 2-NHMe-Ph |
| 112. | 4-F-Ph | 2-NMe2-Ph |
| 113. | 4-F-Ph | 2-NHCOCH3-Ph |
| 114. | 4-F-Ph | 2-SO2NH2-Ph |
| 115. | 4-F-Ph | 2-SO2NHMe-Ph |
| 116. | 4-F-Ph | 2-CF3-Ph |
| 117. | 4-F-Ph | 2-OCH3-Ph |
| 118. | 4-F-Ph | 2-OPh-Ph |
| 119. | 4-F-Ph | 2-OCF3-Ph |
| 120. | 4-F-Ph | 2-SCH3-Ph |
| 121. | 4-F-Ph | 2-SOCH3-Ph |
| 122. | 4-F-Ph | 2-SO2CH3-Ph |
| 123. | 4-F-Ph | 2-OH-Ph |
| 124. | 4-F-Ph | 2-CH2OH-Ph |
| 125. | 4-F-Ph | 2-CHOHCH3-Ph |
| 126. | 4-F-Ph | 2-COH(CH3)2-Ph |
| 127. | 4-F-Ph | 2-CHOHPh-Ph |
| 128. | 4-F-Ph | 2-CH3-Ph |
| 129. | 4-F-Ph | 2-C2H5-Ph |
| 130. | 4-F-Ph | 2-iPr-Ph |
| 131. | 4-F-Ph | 2-tBu-Ph |
| 132. | 4-F-Ph | 2-Ph-Ph |
| 133. | 4-F-Ph | 2-CH2Ph-Ph |
| 134. | 4-F-Ph | 2-CH2CO2Me-Ph |
| 135. | 4-F-Ph | 2-(1-piperidinyl)-Ph |
| 136. | 4-F-Ph | 2-(1-pyrrolidinyl)-Ph |
| 137. | 4-F-Ph | 2-(2-imidazolyl)-Ph |
| 138. | 4-F-Ph | 2-(1-imidazolyl)-Ph |
| 139. | 4-F-Ph | 2-(2-thiazolyl)-Ph |
| 140. | 4-F-Ph | 2-(3-pyrazolyl)-Ph |
| 141. | 4-F-Ph | 2-(1-pyrazolyl)-Ph |
| 142. | 4-F-Ph | 2-(1-tetrazolyl)-Ph |
| 143. | 4-F-Ph | 2-(5-tetrazolyl)-Ph |
| 144. | 4-F-Ph | 2-(2-pyridyl)-Ph |
| 145. | 4-F-Ph | 2-(2-thienyl)-Ph |
| 146. | 4-F-Ph | 2-(2-furanyl)-Ph |
| 147. | 4-F-Ph | 2,4-diF-Ph |
| 148. | 4-F-Ph | 2,5-diF-Ph |
| 149. | 4-F-Ph | 2,6-diF-Ph |
| 150. | 4-F-Ph | 3,4-diF-Ph |
| 151. | 4-F-Ph | 3,5-diF-Ph |
| 152. | 4-F-Ph | 2,4-diCl-Ph |
| 153. | 4-F-Ph | 2,5-diCl-Ph |
| 154. | 4-F-Ph | 2,6-diCl-Ph |
| 155. | 4-F-Ph | 3,4-diCl-Ph |
| 156. | 4-F-Ph | 3,5-diCl-Ph |
| 157. | 4-F-Ph | 3,4-diCF3-Ph |
| 158. | 4-F-Ph | 3,5-diCF3-Ph |
| 159. | 4-F-Ph | 5-Cl-2-MeO-Ph |
| 160. | 4-F-Ph | 5-Cl-2-Me-Ph |
| 161. | 4-F-Ph | 2-F-5-Me-Ph |
| 162. | 4-F-Ph | 2-F-5-NO2-Ph |
| 163. | 4-F-Ph | 3,4-OCH2O-Ph |
| 164. | 4-F-Ph | 3,4-OCH2CH2O-Ph |
| 165. | 4-F-Ph | 2-MeO-4-Me-Ph |
| 166. | 4-F-Ph | 2-MeO-5-Me-Ph |
| 167. | 4-F-Ph | 1-naphthyl |
| 168. | 4-F-Ph | 2-naphthyl |
| 169. | 4-F-Ph | 2-thienyl |
| 170. | 4-F-Ph | 3-thienyl |
| 171. | 4-F-Ph | 2-furanyl |
| 172. | 4-F-Ph | 3-furanyl |
| 173. | 4-F-Ph | 2-pyridyl |
| 174. | 4-F-Ph | 3-pyridyl |
| 175. | 4-F-Ph | 4-pyridyl |
| 176. | 4-F-Ph | 2-indolyl |
| 177. | 4-F-Ph | 3-indolyl |
| 178. | 4-F-Ph | 5-indolyl |
| 179. | 4-F-Ph | 6-indolyl |
| 180. | 4-F-Ph | 3-indazolyl |
| 181. | 4-F-Ph | 5-indazolyl |

| # | R1 | R2 |
|---|---|---|
| 182. | 4-F-Ph | 6-indazolyl |
| 183. | 4-F-Ph | 2-imidazolyl |
| 184. | 4-F-Ph | 3-pyrazolyl |
| 185. | 4-F-Ph | 2-thiazolyl |
| 186. | 4-F-Ph | 5-tetrazolyl |
| 187. | 4-F-Ph | 2-benzimidazolyl |
| 188. | 4-F-Ph | 5-benzimidazolyl |
| 189. | 4-F-Ph | 2-benzothiazolyl |
| 190. | 4-F-Ph | 5-benzothiazolyl |
| 191. | 4-F-Ph | 2-benzoxazolyl |
| 192. | 4-F-Ph | 5-benzoxazolyl |
| 193. | 4-F-Ph | 1-adamantyl |
| 194. | 4-F-Ph | 2-adamantyl |
| 195. | 4-F-Ph | t-Bu |
| 196. | 2-F-Ph | 3-CN-Ph |
| 197. | 2-F-Ph | 3-COCH3-Ph |
| 198. | 2-F-Ph | 3-CO2Me-Ph |
| 199. | 2-F-Ph | 3-CO2Et-Ph |
| 200. | 2-F-Ph | 3-CO2H-Ph |
| 201. | 2-F-Ph | 3-CONH2-Ph |
| 202. | 2-F-Ph | 3-F-Ph |
| 203. | 2-F-Ph | 3-Cl-Ph |
| 204. | 2-F-Ph | 3-NH2-Ph |
| 205. | 2-F-Ph | 3-SO2NH2-Ph |
| 206. | 2-F-Ph | 3-CF3-Ph |
| 207. | 2-F-Ph | 3-OCH3-Ph |
| 208. | 2-F-Ph | 3-OEt-Ph |
| 209. | 2-F-Ph | 3-OCF3-Ph |
| 210. | 2-F-Ph | 3-SO2CH3-Ph |
| 211. | 2-F-Ph | 3-OH-Ph |
| 212. | 2-F-Ph | 3-CH3-Ph |
| 213. | 2-F-Ph | 3-C2H5-Ph |
| 214. | 2-F-Ph | 4-CN-Ph |
| 215. | 2-F-Ph | 4-COCH3-Ph |
| 216. | 2-F-Ph | 4-CO2Me-Ph |
| 217. | 2-F-Ph | 4-CO2Et-Ph |
| 218. | 2-F-Ph | 4-CO2H-Ph |
| 219. | 2-F-Ph | 4-CONH2-Ph |
| 220. | 2-F-Ph | 4-F-Ph |
| 221. | 2-F-Ph | 4-Cl-Ph |
| 222. | 2-F-Ph | 4-NH2-Ph |
| 223. | 2-F-Ph | 4-SO2NH2-Ph |
| 224. | 2-F-Ph | 4-CF3-Ph |
| 225. | 2-F-Ph | 4-OCH3-Ph |
| 226. | 2-F-Ph | 4-OEt-Ph |
| 227. | 2-F-Ph | 4-OCF3-Ph |
| 228. | 2-F-Ph | 4-SO2CH3-Ph |
| 229. | 2-F-Ph | 4-OH-Ph |
| 230. | 2-F-Ph | 4-CH3-Ph |
| 231. | 2-F-Ph | 4-C2H5-Ph |
| 232. | 2-F-Ph | 2,4-diF-Ph |
| 233. | 2-F-Ph | 2,5-diF-Ph |
| 234. | 2-F-Ph | 3,4-diF-Ph |
| 235. | 2-F-Ph | 3,5-diF-Ph |
| 236. | 2-F-Ph | 2,4-diCl-Ph |
| 237. | 2-F-Ph | 2,5-diCl-Ph |
| 238. | 2-F-Ph | 3,4-diCl-Ph |
| 239. | 2-F-Ph | 3,5-diCl-Ph |
| 240. | 2-F-Ph | 3,4-OCH2O-Ph |
| 241. | 2-F-Ph | 3,4-OCH2CH2O-Ph |
| 242. | 2-F-Ph | 2-thienyl |
| 243. | 2-F-Ph | 2-furanyl |
| 244. | 2-F-Ph | 2-pyridyl |
| 245. | 2-F-Ph | 4-pyridyl |
| 246. | 2-F-Ph | 2-imidazolyl |
| 247. | 2-F-Ph | 3-pyrazolyl |
| 248. | 2-F-Ph | 2-thiazolyl |
| 249. | 2-F-Ph | 5-tetrazolyl |
| 250. | 2-F-Ph | 1-adamantyl |
| 251. | 2,4-diF-Ph | 3-CN-Ph |
| 252. | 2,4-diF-Ph | 3-COCH3-Ph |
| 253. | 2,4-diF-Ph | 3-CO2Me-Ph |
| 254. | 2,4-diF-Ph | 3-CO2Et-Ph |
| 255. | 2,4-diF-Ph | 3-CO2H-Ph |
| 256. | 2,4-diF-Ph | 3-CONH2-Ph |
| 257. | 2,4-diF-Ph | 3-F-Ph |
| 258. | 2,4-diF-Ph | 3-Cl-Ph |
| 259. | 2,4-diF-Ph | 3-NH2-Ph |
| 260. | 2,4-diF-Ph | 3-SO2NH2-Ph |
| 261. | 2,4-diF-Ph | 3-CF3-Ph |
| 262. | 2,4-diF-Ph | 3-OCH3-Ph |
| 263. | 2,4-diF-Ph | 3-OEt-Ph |
| 264. | 2,4-diF-Ph | 3-OCF3-Ph |
| 265. | 2,4-diF-Ph | 3-SO2CH3-Ph |
| 266. | 2,4-diF-Ph | 3-OH-Ph |
| 267. | 2,4-diF-Ph | 3-CH3-Ph |
| 268. | 2,4-diF-Ph | 3-C2H5-Ph |
| 269. | 2,4-diF-Ph | 4-CN-Ph |
| 270. | 2,4-diF-Ph | 4-COCH3-Ph |
| 271. | 2,4-diF-Ph | 4-CO2Me-Ph |
| 272. | 2,4-diF-Ph | 4-CO2Et-Ph |
| 273. | 2,4-diF-Ph | 4-CO2H-Ph |
| 274. | 2,4-diF-Ph | 4-CONH2-Ph |
| 275. | 2,4-diF-Ph | 4-F-Ph |
| 276. | 2,4-diF-Ph | 4-Cl-Ph |
| 277. | 2,4-diF-Ph | 4-NH2-Ph |
| 278. | 2,4-diF-Ph | 4-SO2NH2-Ph |
| 279. | 2,4-diE-Ph | 4-CF3-Ph |
| 280. | 2,4-diF-Ph | 4-OCH3-Ph |
| 281. | 2,4-diF-Ph | 4-OEt-Ph |
| 282. | 2,4-diF-Ph | 4-OCF3-Ph |
| 283. | 2,4-diF-Ph | 4-SO2CH3-Ph |
| 284. | 2,4-diF-Ph | 4-OH-Ph |
| 285. | 2,4-diF-Ph | 4-CH3-Ph |
| 286. | 2,4-diF-Ph | 4-C2H5-Ph |
| 287. | 2,4-diF-Ph | 2,4-diF-Ph |
| 288. | 2,4-diF-Ph | 2,5-diF-Ph |
| 289. | 2,4-diF-Ph | 3,4-diF-Ph |
| 290. | 2,4-diF-Ph | 3,5-diF-Ph |
| 291. | 2,4-diF-Ph | 2,4-diCl-Ph |
| 292. | 2,4-diF-Ph | 2,5-diCl-Ph |
| 293. | 2,4-diF-Ph | 3,4-diCl-Ph |
| 294. | 2,4-diF-Ph | 3,5-diCl-Ph |
| 295. | 2,4-diF-Ph | 3,4-OCH2O-Ph |
| 296. | 2,4-diF-Ph | 3,4-OCH2CH2O-Ph |
| 297. | 2,4-diF-Ph | 2-thienyl |
| 298. | 2,4-diF-Ph | 2-furanyl |
| 299. | 2,4-diF-Ph | 2-pyridyl |
| 300. | 2,4-diF-Ph | 4-pyridyl |
| 301. | 2,4-diF-Ph | 2-imidazolyl |
| 302. | 2,4-diF-Ph | 3-pyrazolyl |
| 303. | 2,4-diF-Ph | 2-thiazolyl |
| 304. | 2,4-diF-Ph | 5-tetrazolyl |
| 305. | 2,4-diF-Ph | 1-adamantyl |
| 306. | 4-Cl-Ph | Ph |
| 307. | 4-Cl-Ph | 3-CN-Ph |
| 308. | 4-Cl-Ph | 3-COCH3-Ph |
| 309. | 4-Cl-Ph | 3-CO2Me-Ph |
| 310. | 4-Cl-Ph | 3-CO2Et-Ph |
| 311. | 4-Cl-Ph | 3-CO2H-Ph |
| 312. | 4-Cl-Ph | 3-CONH2-Ph |
| 313. | 4-Cl-Ph | 3-CONHMe-Ph |
| 314. | 4-Cl-Ph | 3-F-Ph |
| 315. | 4-Cl-Ph | 3-Cl-Ph |
| 316. | 4-Cl-Ph | 3-Br-Ph |
| 317. | 4-Cl-Ph | 3-NO2-Ph |
| 318. | 4-Cl-Ph | 3-NH2-Ph |
| 319. | 4-Cl-Ph | 3-NHMe-Ph |
| 320. | 4-Cl-Ph | 3-NMe2-Ph |
| 321. | 4-Cl-Ph | 3-NHCOCH3-Ph |
| 322. | 4-Cl-Ph | 3-SO2NH2-Ph |
| 323. | 4-Cl-Ph | 3-SO2NHMe-Ph |
| 324. | 4-Cl-Ph | 3-CF3-Ph |
| 325. | 4-Cl-Ph | 3-OCH3-Ph |
| 326. | 4-Cl-Ph | 3-OPh-Ph |
| 327. | 4-Cl-Ph | 3-OCF3-Ph |
| 328. | 4-Cl-Ph | 3-SCH3-Ph |
| 329. | 4-Cl-Ph | 3-SOCH3-Ph |
| 330. | 4-Cl-Ph | 3-SO2CH3-Ph |
| 331. | 4-Cl-Ph | 3-OH-Ph |
| 332. | 4-Cl-Ph | 3-CH2OH-Ph |
| 333. | 4-Cl-Ph | 3-CHOHCH3-Ph |
| 334. | 4-Cl-Ph | 3-COH(CH3)2-Ph |
| 335. | 4-Cl-Ph | 3-CHOHPh-Ph |
| 336. | 4-Cl-Ph | 3-CH3-Ph |
| 337. | 4-Cl-Ph | 3-C2H5-Ph |
| 338. | 4-Cl-Ph | 3-iPr-Ph |
| 339. | 4-Cl-Ph | 3-tBu-Ph |
| 340. | 4-Cl-Ph | 3-Ph-Ph |
| 341. | 4-Cl-Ph | 3-CH2Ph-Ph |
| 342. | 4-Cl-Ph | 3-CH2CO2Me-Ph |
| 343. | 4-Cl-Ph | 3-(1-piperidinyl)-Ph |
| 344. | 4-Cl-Ph | 3-(1-pyrrolidinyl)-Ph |
| 345. | 4-Cl-Ph | 3-(2-imidazolyl)-Ph |

| | | |
|---|---|---|
| 346. | 4-Cl-Ph | 3-(1-imidazolyl)-Ph |
| 347. | 4-Cl-Ph | 3-(2-thiazolyl)-Ph |
| 348. | 4-Cl-Ph | 3-(3-pyrazolyl)-Ph |
| 349. | 4-Cl-Ph | 3-(1-pyrazolyl)-Ph |
| 350. | 4-Cl-Ph | 3-(1-tetrazolyl)-Ph |
| 351. | 4-Cl-Ph | 3-(5-tetrazolyl)-Ph |
| 352. | 4-Cl-Ph | 3-(2-pyridyl)-Ph |
| 353. | 4-Cl-Ph | 3-(2-thienyl)-Ph |
| 354. | 4-Cl-Ph | 3-(2-furanyl)-Ph |
| 355. | 4-Cl-Ph | 4-CN-Ph |
| 356. | 4-Cl-Ph | 4-COCH3-Ph |
| 357. | 4-Cl-Ph | 4-CO2Me-Ph |
| 358. | 4-Cl-Ph | 4-CO2Et-Ph |
| 359. | 4-Cl-Ph | 4-CO2H-Ph |
| 360. | 4-Cl-Ph | 4-CONH2-Ph |
| 361. | 4-Cl-Ph | 4-CONHMe-Ph |
| 362. | 4-Cl-Ph | 4-CONHPh-Ph |
| 363. | 4-Cl-Ph | 4-NHCONH2-Ph |
| 364. | 4-Cl-Ph | 4-F-Ph |
| 365. | 4-Cl-Ph | 4-Cl-Ph |
| 366. | 4-Cl-Ph | 4-Br-Ph |
| 367. | 4-Cl-Ph | 4-NO2-Ph |
| 368. | 4-Cl-Ph | 4-NH2-Ph |
| 369. | 4-Cl-Ph | 4-NHMe-Ph |
| 370. | 4-Cl-Ph | 4-NMe2-Ph |
| 371. | 4-Cl-Ph | 4-NHCOCH3-Ph |
| 372. | 4-Cl-Ph | 4-SO2NH2-Ph |
| 373. | 4-Cl-Ph | 4-SO2NHMe-Ph |
| 374. | 4-Cl-Ph | 4-CF3-Ph |
| 375. | 4-Cl-Ph | 4-OCH3-Ph |
| 376. | 4-Cl-Ph | 4-OPh-Ph |
| 377. | 4-Cl-Ph | 4-OCF3-Ph |
| 378. | 4-Cl-Ph | 4-SCH3-Ph |
| 379. | 4-Cl-Ph | 4-SOCH3-Ph |
| 380. | 4-Cl-Ph | 4-SO2CH3-Ph |
| 381. | 4-Cl-Ph | 4-OH-Ph |
| 382. | 4-Cl-Ph | 4-CH2OH-Ph |
| 383. | 4-Cl-Ph | 4-CHOHCH3-Ph |
| 384. | 4-Cl-Ph | 4-COH(CH3)2-Ph |
| 385. | 4-Cl-Ph | 4-CH3-Ph |
| 386. | 4-Cl-Ph | 4-C2H5-Ph |
| 387. | 4-Cl-Ph | 4-iPr-Ph |
| 388. | 4-Cl-Ph | 4-tBu-Ph |
| 389. | 4-Cl-Ph | 4-Ph-Ph |
| 390. | 4-Cl-Ph | 4-CH2Ph-Ph |
| 391. | 4-Cl-Ph | 4-CH2CO2Me-Ph |
| 392. | 4-Cl-Ph | 4-(1-piperidinyl)-Ph |
| 393. | 4-Cl-Ph | 4-(1-pyrrolidinyl)-Ph |
| 394. | 4-Cl-Ph | 4-(2-imidazolyl)-Ph |
| 395. | 4-Cl-Ph | 4-(1-imidazolyl)-Ph |
| 396. | 4-Cl-Ph | 4-(2-thiazolyl)-Ph |
| 397. | 4-Cl-Ph | 4-(3-pyrazolyl)-Ph |
| 398. | 4-Cl-Ph | 4-(1-pyrazolyl)-Ph |
| 399. | 4-Cl-Ph | 4-(1-tetrazolyl)-Ph |
| 400. | 4-Cl-Ph | 4-(5-tetrazolyl)-Ph |
| 401. | 4-Cl-Ph | 4-(2-pyridyl)-Ph |
| 402. | 4-Cl-Ph | 4-(2-thienyl)-Ph |
| 403. | 4-Cl-Ph | 4-(2-furanyl)-Ph |
| 404. | 4-Cl-Ph | 2-CN-Ph |
| 405. | 4-Cl-Ph | 2-COCH3-Ph |
| 406. | 4-Cl-Ph | 2-CO2Me-Ph |
| 407. | 4-Cl-Ph | 2-CO2Et-Ph |
| 408. | 4-Cl-Ph | 2-CO2H-Ph |
| 409. | 4-Cl-Ph | 2-CONH2-Ph |
| 410. | 4-Cl-Ph | 2-CONHMe-Ph |
| 411. | 4-Cl-Ph | 2-F-Ph |
| 412. | 4-Cl-Ph | 2-Cl-Ph |
| 413. | 4-Cl-Ph | 2-Br-Ph |
| 414. | 4-Cl-Ph | 2-NO2-Ph |
| 415. | 4-Cl-Ph | 2-NH2-Ph |
| 416. | 4-Cl-Ph | 2-NHMe-Ph |
| 417. | 4-Cl-Ph | 2-NMe2-Ph |
| 418. | 4-Cl-Ph | 2-NHCOCH3-Ph |
| 419. | 4-Cl-Ph | 2-SO2NH2-Ph |
| 420. | 4-Cl-Ph | 2-SO2NHMe-Ph |
| 421. | 4-Cl-Ph | 2-CF3-Ph |
| 422. | 4-Cl-Ph | 2-OCH3-Ph |
| 423. | 4-Cl-Ph | 2-OPh-Ph |
| 424. | 4-Cl-Ph | 2-OCF3-Ph |
| 425. | 4-Cl-Ph | 2-SCH3-Ph |
| 426. | 4-Cl-Ph | 2-SOCH3-Ph |
| 427. | 4-Cl-Ph | 2-SO2CH3-Ph |
| 428. | 4-Cl-Ph | 2-OH-Ph |
| 429. | 4-Cl-Ph | 2-CH2OH-Ph |
| 430. | 4-Cl-Ph | 2-CHOHCH3-Ph |
| 431. | 4-Cl-Ph | 2-COH(CH3)2-Ph |
| 432. | 4-Cl-Ph | 2-CHOHPh-Ph |
| 433. | 4-Cl-Ph | 2-CH3-Ph |
| 434. | 4-Cl-Ph | 2-C2H5-Ph |
| 435. | 4-Cl-Ph | 2-iPr-Ph |
| 436. | 4-Cl-Ph | 2-tBu-Ph |
| 437. | 4-Cl-Ph | 2-Ph-Ph |
| 438. | 4-Cl-Ph | 2-CH2Ph-Ph |
| 439. | 4-Cl-Ph | 2-CH2CO2Me-Ph |
| 440. | 4-Cl-Ph | 2-(1-piperidinyl)-Ph |
| 441. | 4-Cl-Ph | 2-(1-pyrrolidinyl)-Ph |
| 442. | 4-Cl-Ph | 2-(2-imidazolyl)-Ph |
| 443. | 4-Cl-Ph | 2-(1-imidazolyl)-Ph |
| 444. | 4-Cl-Ph | 2-(2-thiazolyl)-Ph |
| 445. | 4-Cl-Ph | 2-(3-pyrazolyl)-Ph |
| 446. | 4-Cl-Ph | 2-(1-pyrazolyl)-Ph |
| 447. | 4-Cl-Ph | 2-(1-tetrazolyl)-Ph |
| 448. | 4-Cl-Ph | 2-(5-tetrazolyl)-Ph |
| 449. | 4-Cl-Ph | 2-(2-pyridyl)-Ph |
| 450. | 4-Cl-Ph | 2-(2-thienyl)-Ph |
| 451. | 4-Cl-Ph | 2-(2-furanyl)-Ph |
| 452. | 4-Cl-Ph | 2,4-diF-Ph |
| 453. | 4-Cl-Ph | 2,5-diF-Ph |
| 454. | 4-Cl-Ph | 2,6-diF-Ph |
| 455. | 4-Cl-Ph | 3,4-diF-Ph |
| 456. | 4-Cl-Ph | 3,5-diF-Ph |
| 457. | 4-Cl-Ph | 2,4-diCl-Ph |
| 458. | 4-Cl-Ph | 2,5-diCl-Ph |
| 459. | 4-Cl-Ph | 2,6-diCl-Ph |
| 460. | 4-Cl-Ph | 3,4-diCl-Ph |
| 461. | 4-Cl-Ph | 3,5-diCl-Ph |
| 462. | 4-Cl-Ph | 3,4-diCF3-Ph |
| 463. | 4-Cl-Ph | 3,5-diCF3-Ph |
| 464. | 4-Cl-Ph | 5-Cl-2-MeO-Ph |
| 465. | 4-Cl-Ph | 5-Cl-2-Me-Ph |
| 466. | 4-Cl-Ph | 2-F-5-Me-Ph |
| 467. | 4-Cl-Ph | 2-F-5-NO2-Ph |
| 468. | 4-Cl-Ph | 3,4-OCH2O-Ph |
| 469. | 4-Cl-Ph | 3,4-OCH2CH2O-Ph |
| 470. | 4-Cl-Ph | 2-MeO-4-Me-Ph |
| 471. | 4-Cl-Ph | 2-MeO-5-Me-Ph |
| 472. | 4-Cl-Ph | 1-naphthyl |
| 473. | 4-Cl-Ph | 2-naphthyl |
| 474. | 4-Cl-Ph | 2-thienyl |
| 475. | 4-Cl-Ph | 3-thienyl |
| 476. | 4-Cl-Ph | 2-furanyl |
| 477. | 4-Cl-Ph | 3-furanyl |
| 478. | 4-Cl-Ph | 2-pyridyl |
| 479. | 4-Cl-Ph | 3-pyridyl |
| 480. | 4-Cl-Ph | 4-pyridyl |
| 481. | 4-Cl-Ph | 2-indolyl |
| 482. | 4-Cl-Ph | 3-indolyl |
| 483. | 4-Cl-Ph | 5-indolyl |
| 484. | 4-Cl-Ph | 6-indolyl |
| 485. | 4-Cl-Ph | 3-indazolyl |
| 486. | 4-Cl-Ph | 5-indazolyl |
| 487. | 4-Cl-Ph | 6-indazolyl |
| 488. | 4-Cl-Ph | 2-imidazolyl |
| 489. | 4-Cl-Ph | 3-pyrazolyl |
| 490. | 4-Cl-Ph | 2-thiazolyl |
| 491. | 4-Cl-Ph | 5-tetrazolyl |
| 492. | 4-Cl-Ph | 2-benzimidazolyl |
| 493. | 4-Cl-Ph | 5-benzimidazolyl |
| 494. | 4-Cl-Ph | 2-benzothiazolyl |
| 495. | 4-Cl-Ph | 5-benzothiazolyl |
| 496. | 4-Cl-Ph | 2-benzoxazolyl |
| 497. | 4-Cl-Ph | 5-benzoxazolyl |
| 498. | 4-Cl-Ph | 1-adamantyl |
| 499. | 4-Cl-Ph | 2-adamantyl |
| 500. | 4-Cl-Ph | t-Bu |
| 501. | 2-Cl-Ph | 3-CN-Ph |
| 502. | 2-Cl-Ph | 3-COCH3-Ph |
| 503. | 2-Cl-Ph | 3-CO2Me-Ph |
| 504. | 2-Cl-Ph | 3-CO2Et-Ph |
| 505. | 2-Cl-Ph | 3-CO2H-Ph |
| 506. | 2-Cl-Ph | 3-CONH2-Ph |
| 507. | 2-Cl-Ph | 3-F-Ph |
| 508. | 2-Cl-Ph | 3-Cl-Ph |
| 509. | 2-Cl-Ph | 3-NH2-Ph |

| # | Col A | Col B |
|---|---|---|
| 510. | 2-Cl-Ph | 3-SO2NH2-Ph |
| 511. | 2-Cl-Ph | 3-CF3-Ph |
| 512. | 2-Cl-Ph | 3-OCH3-Ph |
| 513. | 2-Cl-Ph | 3-OEt-Ph |
| 514. | 2-Cl-Ph | 3-OCF3-Ph |
| 515. | 2-Cl-Ph | 3-SO2CH3-Ph |
| 516. | 2-Cl-Ph | 3-OH-Ph |
| 517. | 2-Cl-Ph | 3-CH3-Ph |
| 518. | 2-Cl-Ph | 3-C2H5-Ph |
| 519. | 2-Cl-Ph | 4-CN-Ph |
| 520. | 2-Cl-Ph | 4-COCH3-Ph |
| 521. | 2-Cl-Ph | 4-CO2Me-Ph |
| 522. | 2-Cl-Ph | 4-CO2Et-Ph |
| 523. | 2-Cl-Ph | 4-CO2H-Ph |
| 524. | 2-Cl-Ph | 4-CONH2-Ph |
| 525. | 2-Cl-Ph | 4-F-Ph |
| 526. | 2-Cl-Ph | 4-Cl-Ph |
| 527. | 2-Cl-Ph | 4-NH2-Ph |
| 528. | 2-Cl-Ph | 4-SO2NH2-Ph |
| 529. | 2-Cl-Ph | 4-CF3-Ph |
| 530. | 2-Cl-Ph | 4-OCH3-Ph |
| 531. | 2-Cl-Ph | 4-OEt-Ph |
| 532. | 2-Cl-Ph | 4-OCF3-Ph |
| 533. | 2-Cl-Ph | 4-SO2CH3-Ph |
| 534. | 2-Cl-Ph | 4-OH-Ph |
| 535. | 2-Cl-Ph | 4-CH3-Ph |
| 536. | 2-Cl-Ph | 4-C2H5-Ph |
| 537. | 2-Cl-Ph | 2,4-diF-Ph |
| 538. | 2-Cl-Ph | 2,5-diF-Ph |
| 539. | 2-Cl-Ph | 3,4-diF-Ph |
| 540. | 2-Cl-Ph | 3,5-diF-Ph |
| 541. | 2-Cl-Ph | 2,4-diCl-Ph |
| 542. | 2-Cl-Ph | 2,5-diCl-Ph |
| 543. | 2-Cl-Ph | 3,4-diCl-Ph |
| 544. | 2-Cl-Ph | 3,5-diCl-Ph |
| 545. | 2-Cl-Ph | 3,4-OCH2O-Ph |
| 546. | 2-Cl-Ph | 3,4-OCH2CH2O-Ph |
| 547. | 2-Cl-Ph | 2-thienyl |
| 548. | 2-Cl-Ph | 2-furanyl |
| 549. | 2-Cl-Ph | 2-pyridyl |
| 550. | 2-Cl-Ph | 4-pyridyl |
| 551. | 2-Cl-Ph | 2-imidazolyl |
| 552. | 2-Cl-Ph | 3-pyrazolyl |
| 553. | 2-Cl-Ph | 2-thiazolyl |
| 554. | 2-Cl-Ph | 5-tetrazolyl |
| 555. | 2-Cl-Ph | 1-adamantyl |
| 556. | 2,4-diCl-Ph | 3-CN-Ph |
| 557. | 2,4-diCl-Ph | 3-COCH3-Ph |
| 558. | 2,4-diCl-Ph | 3-CO2Me-Ph |
| 559. | 2,4-diCl-Ph | 3-CO2Et-Ph |
| 560. | 2,4-diCl-Ph | 3-CO2H-Ph |
| 561. | 2,4-diCl-Ph | 3-CONH2-Ph |
| 562. | 2,4-diCl-Ph | 3-F-Ph |
| 563. | 2,4-diCl-Ph | 3-Cl-Ph |
| 564. | 2,4-diCl-Ph | 3-NH2-Ph |
| 565. | 2,4-diCl-Ph | 3-SO2NH2-Ph |
| 566. | 2,4-diCl-Ph | 3-CF3-Ph |
| 567. | 2,4-diCl-Ph | 3-OCH3-Ph |
| 568. | 2,4-diCl-Ph | 3-OEt-Ph |
| 569. | 2,4-diCl-Ph | 3-OCF3-Ph |
| 570. | 2,4-diCl-Ph | 3-SO2CH3-Ph |
| 571. | 2,4-diCl-Ph | 3-OH-Ph |
| 572. | 2,4-diCl-Ph | 3-CH3-Ph |
| 573. | 2,4-diCl-Ph | 3-C2H5-Ph |
| 574. | 2,4-diCl-Ph | 4-CN-Ph |
| 575. | 2,4-diCl-Ph | 4-COCH3-Ph |
| 576. | 2,4-diCl-Ph | 4-CO2Me-Ph |
| 577. | 2,4-diCl-Ph | 4-CO2Et-Ph |
| 578. | 2,4-diCl-Ph | 4-CO2H-Ph |
| 579. | 2,4-diCl-Ph | 4-CONH2-Ph |
| 580. | 2,4-diCl-Ph | 4-F-Ph |
| 581. | 2,4-diCl-Ph | 4-Cl-Ph |
| 582. | 2,4-diCl-Ph | 4-NH2-Ph |
| 583. | 2,4-diCl-Ph | 4-SO2NH2-Ph |
| 584. | 2,4-diCl-Ph | 4-CF3-Ph |
| 585. | 2,4-diCl-Ph | 4-OCH3-Ph |
| 586. | 2,4-diCl-Ph | 4-OEt-Ph |
| 587. | 2,4-diCl-Ph | 4-OCF3-Ph |
| 588. | 2,4-diCl-Ph | 4-SO2CH3-Ph |
| 589. | 2,4-diCl-Ph | 4-OH-Ph |
| 590. | 2,4-diCl-Ph | 4-CH3-Ph |
| 591. | 2,4-diCl-Ph | 4-C2H5-Ph |
| 592. | 2,4-diCl-Ph | 2,4-diF-Ph |
| 593. | 2,4-diCl-Ph | 2,5-diF-Ph |
| 594. | 2,4-diCl-Ph | 3,4-diF-Ph |
| 595. | 2,4-diCl-Ph | 3,5-diF-Ph |
| 596. | 2,4-diCl-Ph | 2,4-diCl-Ph |
| 597. | 2,4-diCl-Ph | 2,5-diCl-Ph |
| 598. | 2,4-diCl-Ph | 3,4-diCl-Ph |
| 599. | 2,4-diCl-Ph | 3,5-diCl-Ph |
| 600. | 2,4-diCl-Ph | 3,4-OCH2O-Ph |
| 601. | 2,4-diCl-Ph | 3,4-OCH2CH2O-Ph |
| 602. | 2,4-diCl-Ph | 2-thienyl |
| 603. | 2,4-diCl-Ph | 2-furanyl |
| 604. | 2,4-diCl-Ph | 2-pyridyl |
| 605. | 2,4-diCl-Ph | 4-pyridyl |
| 606. | 2,4-diCl-Ph | 2-imidazolyl |
| 607. | 2,4-diCl-Ph | 3-pyrazolyl |
| 608. | 2,4-diCl-Ph | 2-thiazolyl |
| 609. | 2,4-diCl-Ph | 5-tetrazolyl |
| 610. | 2,4-diCl-Ph | 1-adamantyl |
| 611. | 3-OCH3-Ph | 3-CN-Ph |
| 612. | 3-OCH3-Ph | 3-COCH3-Ph |
| 613. | 3-OCH3-Ph | 3-CO2Me-Ph |
| 614. | 3-OCH3-Ph | 3-CO2Et-Ph |
| 615. | 3-OCH3-Ph | 3-CO2H-Ph |
| 616. | 3-OCH3-Ph | 3-CONH2-Ph |
| 617. | 3-OCH3-Ph | 3-F-Ph |
| 618. | 3-OCH3-Ph | 3-Cl-Ph |
| 619. | 3-OCH3-Ph | 3-NH2-Ph |
| 620. | 3-OCH3-Ph | 3-SO2NH2-Ph |
| 621. | 3-OCH3-Ph | 3-CF3-Ph |
| 622. | 3-OCH3-Ph | 3-OCH3-Ph |
| 623. | 3-OCH3-Ph | 3-OEt-Ph |
| 624. | 3-OCH3-Ph | 3-OCF3-Ph |
| 625. | 3-OCH3-Ph | 3-SO2CH3-Ph |
| 626. | 3-OCH3-Ph | 3-OH-Ph |
| 627. | 3-OCH3-Ph | 3-CH3-Ph |
| 628. | 3-OCH3-Ph | 3-C2H5-Ph |
| 629. | 3-OCH3-Ph | 4-CN-Ph |
| 630. | 3-OCH3-Ph | 4-COCH3-Ph |
| 631. | 3-OCH3-Ph | 4-CO2Me-Ph |
| 632. | 3-OCH3-Ph | 4-CO2Et-Ph |
| 633. | 3-OCH3-Ph | 4-CO2H-Ph |
| 634. | 3-OCH3-Ph | 4-CONH2-Ph |
| 635. | 3-OCH3-Ph | 4-F-Ph |
| 636. | 3-OCH3-Ph | 4-Cl-Ph |
| 637. | 3-OCH3-Ph | 4-NH2-Ph |
| 638. | 3-OCH3-Ph | 4-SO2NH2-Ph |
| 639. | 3-OCH3-Ph | 4-CF3-Ph |
| 640. | 3-OCH3-Ph | 4-OCH3-Ph |
| 641. | 3-OCH3-Ph | 4-OEt-Ph |
| 642. | 3-OCH3-Ph | 4-OCF3-Ph |
| 643. | 3-OCH3-Ph | 4-SO2CH3-Ph |
| 644. | 3-OCH3-Ph | 4-OH-Ph |
| 645. | 3-OCH3-Ph | 4-CH3-Ph |
| 646. | 3-OCH3-Ph | 4-C2H5-Ph |
| 647. | 3-OCH3-Ph | 2,4-diF-Ph |
| 648. | 3-OCH3-Ph | 2,5-diF-Ph |
| 649. | 3-OCH3-Ph | 3,4-diF-Ph |
| 650. | 3-OCH3-Ph | 3,5-diF-Ph |
| 651. | 3-OCH3-Ph | 2,4-diCl-Ph |
| 652. | 3-OCH3-Ph | 2,5-diCl-Ph |
| 653. | 3-OCH3-Ph | 3,4-diCl-Ph |
| 654. | 3-OCH3-Ph | 3,5-diCl-Ph |
| 655. | 3-OCH3-Ph | 3,4-OCH2O-Ph |
| 656. | 3-OCH3-Ph | 3,4-OCH2CH2O-Ph |
| 657. | 3-OCH3-Ph | 2-thienyl |
| 658. | 3-OCH3-Ph | 2-furanyl |
| 659. | 3-OCH3-Ph | 2-pyridyl |
| 660. | 3-OCH3-Ph | 4-pyridyl |
| 661. | 3-OCH3-Ph | 2-imidazolyl |
| 662. | 3-OCH3-Ph | 3-pyrazolyl |
| 663. | 3-OCH3-Ph | 2-thiazolyl |
| 664. | 3-OCH3-Ph | 5-tetrazolyl |
| 665. | 3-OCH3-Ph | 1-adamantyl |
| 666. | 2-thienyl | 3-CN-Ph |
| 667. | 2-thienyl | 3-COCH3-Ph |
| 668. | 2-thienyl | 3-F-Ph |
| 669. | 2-thienyl | 3-Cl-Ph |
| 670. | 2-thienyl | 3-NH2-Ph |
| 671. | 2-thienyl | 3-OCH3-Ph |
| 672. | 2-thienyl | 3-OH-Ph |
| 673. | 2-thienyl | 4-CN-Ph |

| | | |
|---|---|---|
| 674. | 2-thienyl | 4-COCH3-Ph |
| 675. | 2-thienyl | 4-F-Ph |
| 676. | 2-thienyl | 4-Cl-Ph |
| 677. | 2-thienyl | 4-NH2-Ph |
| 678. | 2-thienyl | 4-OCH3-Ph |
| 679. | 2-thienyl | 4-OH-Ph |
| 680. | 2-thienyl | 3,4-diF-Ph |
| 681. | 2-thienyl | 3,5-diF-Ph |
| 682. | 2-thienyl | 3,4-diCl-Ph |
| 683. | 2-thienyl | 3,5-diCl-Ph |
| 684. | 2-thienyl | 3,4-OCH2O-Ph |
| 685. | 2-thienyl | 3,4-OCH2CH2O-Ph |
| 686. | 3-thienyl | 3-CN-Ph |
| 687. | 3-thienyl | 3-COCH3-Ph |
| 688. | 3-thienyl | 3-F-Ph |
| 689. | 3-thienyl | 3-Cl-Ph |
| 690. | 3-thienyl | 3-NH2-Ph |
| 691. | 3-thienyl | 3-OCH3-Ph |
| 692. | 3-thienyl | 3-OH-Ph |
| 693. | 3-thienyl | 4-CN-Ph |
| 694. | 3-thienyl | 4-COCH3-Ph |
| 695. | 3-thienyl | 4-F-Ph |
| 696. | 3-thienyl | 4-Cl-Ph |
| 697. | 3-thienyl | 4-NH2-Ph |
| 698. | 3-thienyl | 4-OCH3-Ph |
| 699. | 3-thienyl | 4-OH-Ph |
| 700. | 3-thienyl | 3,4-diF-Ph |
| 701. | 3-thienyl | 3,5-diF-Ph |
| 702. | 3-thienyl | 3,4-diCl-Ph |
| 703. | 3-thienyl | 3,5-diCl-Ph |
| 704. | 3-thienyl | 3,4-OCH2O-Ph |
| 705. | 3-thienyl | 3,4-OCH2CH2O-Ph |
| 706. | 2-furanyl | 3-CN-Ph |
| 707. | 2-furanyl | 3-COCH3-Ph |
| 708. | 2-furanyl | 3-F-Ph |
| 709. | 2-furanyl | 3-Cl-Ph |
| 710. | 2-furanyl | 3-NH2-Ph |
| 711. | 2-furanyl | 3-OCH3-Ph |
| 712. | 2-furanyl | 3-OH-Ph |
| 713. | 2-furanyl | 4-CN-Ph |
| 714. | 2-furanyl | 4-COCH3-Ph |
| 715. | 2-furanyl | 4-F-Ph |
| 716. | 2-furanyl | 4-Cl-Ph |
| 717. | 2-furanyl | 4-NH2-Ph |
| 718. | 2-furanyl | 4-OCH3-Ph |
| 719. | 2-furanyl | 4-OH-Ph |
| 720. | 2-furanyl | 3,4-diF-Ph |
| 721. | 2-furanyl | 3,5-diF-Ph |
| 722. | 2-furanyl | 3,4-diCl-Ph |
| 723. | 2-furanyl | 3,5-diCl-Ph |
| 724. | 2-furanyl | 3,4-OCH2O-Ph |
| 725. | 2-furanyl | 3,4-OCH2CH2O-Ph |
| 726. | 3-furanyl | 3-CN-Ph |
| 727. | 3-furanyl | 3-COCH3-Ph |
| 728. | 3-furanyl | 3-F-Ph |
| 729. | 3-furanyl | 3-Cl-Ph |
| 730. | 3-furanyl | 3-NH2-Ph |
| 731. | 3-furanyl | 3-OCH3-Ph |
| 732. | 3-furanyl | 3-OH-Ph |
| 733. | 3-furanyl | 4-CN-Ph |
| 734. | 3-furanyl | 4-COCH3-Ph |
| 735. | 3-furanyl | 4-F-Ph |
| 736. | 3-furanyl | 4-Cl-Ph |
| 737. | 3-furanyl | 4-NH2-Ph |
| 738. | 3-furanyl | 4-OCH3-Ph |
| 739. | 3-furanyl | 4-OH-Ph |
| 740. | 3-furanyl | 3,4-diF-Ph |
| 741. | 3-furanyl | 3,5-diF-Ph |
| 742. | 3-furanyl | 3,4-diCl-Ph |
| 743. | 3-furanyl | 3,5-diCl-Ph |
| 744. | 3-furanyl | 3,4-OCH2O-Ph |
| 745. | 3-furanyl | 3,4-OCH2CH2O-Ph |
| 746. | 2-pyridyl | 3-CN-Ph |
| 747. | 2-pyridyl | 3-COCH3-Ph |
| 748. | 2-pyridyl | 3-F-Ph |
| 749. | 2-pyridyl | 3-Cl-Ph |
| 750. | 2-pyridyl | 3-NH2-Ph |
| 751. | 2-pyridyl | 3-OCH3-Ph |
| 752. | 2-pyridyl | 3-OH-Ph |
| 753. | 2-pyridyl | 4-CN-Ph |
| 754. | 2-pyridyl | 4-COCH3-Ph |
| 755. | 2-pyridyl | 4-F-Ph |
| 756. | 2-pyridyl | 4-Cl-Ph |
| 757. | 2-pyridyl | 4-NH2-Ph |
| 758. | 2-pyridyl | 4-OCH3-Ph |
| 759. | 2-pyridyl | 4-OH-Ph |
| 760. | 2-pyridyl | 3,4-diF-Ph |
| 761. | 2-pyridyl | 3,5-diF-Ph |
| 762. | 2-pyridyl | 3,4-diCl-Ph |
| 763. | 2-pyridyl | 3,5-diCl-Ph |
| 764. | 2-pyridyl | 3,4-OCH2O-Ph |
| 765. | 2-pyridyl | 3,4-OCH2CH2O-Ph |
| 766. | 3-pyridyl | 3-CN-Ph |
| 767. | 3-pyridyl | 3-COCH3-Ph |
| 768. | 3-pyridyl | 3-F-Ph |
| 769. | 3-pyridyl | 3-Cl-Ph |
| 770. | 3-pyridyl | 3-NH2-Ph |
| 771. | 3-pyridyl | 3-OCH3-Ph |
| 772. | 3-pyridyl | 3-OH-Ph |
| 773. | 3-pyridyl | 4-CN-Ph |
| 774. | 3-pyridyl | 4-COCH3-Ph |
| 775. | 3-pyridyl | 4-F-Ph |
| 776. | 3-pyridyl | 4-Cl-Ph |
| 777. | 3-pyridyl | 4-NH2-Ph |
| 778. | 3-pyridyl | 4-OCH3-Ph |
| 779. | 3-pyridyl | 4-OH-Ph |
| 780. | 3-pyridyl | 3,4-diF-Ph |
| 781. | 3-pyridyl | 3,5-diF-Ph |
| 782. | 3-pyridyl | 3,4-diCl-Ph |
| 783. | 3-pyridyl | 3,5-diCl-Ph |
| 784. | 3-pyridyl | 3,4-OCH2O-Ph |
| 785. | 3-pyridyl | 3,4-OCH2CH2O-Ph |
| 786. | 4-pyridyl | 3-CN-Ph |
| 787. | 4-pyridyl | 3-COCH3-Ph |
| 788. | 4-pyridyl | 3-F-Ph |
| 789. | 4-pyridyl | 3-Cl-Ph |
| 790. | 4-pyridyl | 3-NH2-Ph |
| 791. | 4-pyridyl | 3-OCH3-Ph |
| 792. | 4-pyridyl | 3-OH-Ph |
| 793. | 4-pyridyl | 4-CN-Ph |
| 794. | 4-pyridyl | 4-COCH3-Ph |
| 795. | 4-pyridyl | 4-F-Ph |
| 796. | 4-pyridyl | 4-Cl-Ph |
| 797. | 4-pyridyl | 4-NH2-Ph |
| 798. | 4-pyridyl | 4-OCH3-Ph |
| 799. | 4-pyridyl | 4-OH-Ph |
| 800. | 4-pyridyl | 3,4-diF-Ph |
| 801. | 4-pyridyl | 3,5-diF-Ph |
| 802. | 4-pyridyl | 3,4-diCl-Ph |
| 803. | 4-pyridyl | 3,5-diCl-Ph |
| 804. | 4-pyridyl | 3,4-OCH2O-Ph |
| 805. | 4-pyridyl | 3,4-OCH2CH2O-Ph |
| 806. | 3-indolyl | 3-CN-Ph |
| 807. | 3-indolyl | 3-COCH3-Ph |
| 808. | 3-indolyl | 3-F-Ph |
| 809. | 3-indolyl | 3-Cl-Ph |
| 810. | 3-indolyl | 3-NH2-Ph |
| 811. | 3-indolyl | 3-OCH3-Ph |
| 812. | 3-indolyl | 3-OH-Ph |
| 813. | 3-indolyl | 4-CN-Ph |
| 814. | 3-indolyl | 4-COCH3-Ph |
| 815. | 3-indolyl | 4-F-Ph |
| 816. | 3-indolyl | 4-Cl-Ph |
| 817. | 3-indolyl | 4-NH2-Ph |
| 818. | 3-indolyl | 4-OCH3-Ph |
| 819. | 3-indolyl | 4-OH-Ph |
| 820. | 3-indolyl | 3,4-diF-Ph |
| 821. | 3-indolyl | 3,5-diF-Ph |
| 822. | 3-indolyl | 3,4-diCl-Ph |
| 823. | 3-indolyl | 3,5-diCl-Ph |
| 824. | 3-indolyl | 3,4-OCH2O-Ph |
| 825. | 3-indolyl | 3,4-OCH2CH2O-Ph |
| 826. | 5-indolyl | 3-CN-Ph |
| 827. | 5-indolyl | 3-COCH3-Ph |
| 828. | 5-indolyl | 3-F-Ph |
| 829. | 5-indolyl | 3-Cl-Ph |
| 830. | 5-indolyl | 3-NH2-Ph |
| 831. | 5-indolyl | 3-OCH3-Ph |
| 832. | 5-indolyl | 3-OH-Ph |
| 833. | 5-indolyl | 4-CN-Ph |
| 834. | 5-indolyl | 4-COCH3-Ph |
| 835. | 5-indolyl | 4-F-Ph |
| 836. | 5-indolyl | 4-Cl-Ph |
| 837. | 5-indolyl | 4-NH2-Ph |

| # | Group 1 | Group 2 |
|---|---|---|
| 838. | 5-indolyl | 4-OCH3-Ph |
| 839. | 5-indolyl | 4-OH-Ph |
| 840. | 5-indolyl | 3,4-diF-Ph |
| 841. | 5-indolyl | 3,5-diF-Ph |
| 842. | 5-indolyl | 3,4-diCl-Ph |
| 843. | 5-indolyl | 3,5-diCl-Ph |
| 844. | 5-indolyl | 3,4-OCH2O-Ph |
| 845. | 5-indolyl | 3,4-OCH2CH2O-Ph |
| 846. | 5-indazolyl | 3-CN-Ph |
| 847. | 5-indazolyl | 3-COCH3-Ph |
| 848. | 5-indazolyl | 3-F-Ph |
| 849. | 5-indazolyl | 3-Cl-Ph |
| 850. | 5-indazolyl | 3-NH2-Ph |
| 851. | 5-indazolyl | 3-OCH3-Ph |
| 852. | 5-indazolyl | 3-OH-Ph |
| 853. | 5-indazolyl | 4-CN-Ph |
| 854. | 5-indazolyl | 4-COCH3-Ph |
| 855. | 5-indazolyl | 4-F-Ph |
| 856. | 5-indazolyl | 4-Cl-Ph |
| 857. | 5-indazolyl | 4-NH2-Ph |
| 858. | 5-indazolyl | 4-OCH3-Ph |
| 859. | 5-indazolyl | 4-OH-Ph |
| 860. | 5-indazolyl | 3,4-diF-Ph |
| 861. | 5-indazolyl | 3,5-diF-Ph |
| 862. | 5-indazolyl | 3,4-diCl-Ph |
| 863. | 5-indazolyl | 3,5-diCl-Ph |
| 864. | 5-indazolyl | 3,4-OCH2O-Ph |
| 865. | 5-indazolyl | 3,4-OCH2CH2O-Ph |
| 866. | 5-benzimidazolyl | 3-CN-Ph |
| 867. | 5-benzimidazolyl | 3-COCH3-Ph |
| 868. | 5-benzimidazolyl | 3-F-Ph |
| 869. | 5-benzimidazolyl | 3-Cl-Ph |
| 870. | 5-benzimidazolyl | 3-NH2-Ph |
| 871. | 5-benzimidazolyl | 3-OCH3-Ph |
| 872. | 5-benzimidazolyl | 3-OH-Ph |
| 873. | 5-benzimidazolyl | 4-CN-Ph |
| 874. | 5-benzimidazolyl | 4-COCH3-Ph |
| 875. | 5-benzimidazolyl | 4-F-Ph |
| 876. | 5-benzimidazolyl | 4-Cl-Ph |
| 877. | 5-benzimidazolyl | 4-NH2-Ph |
| 878. | 5-benzimidazolyl | 4-OCH3-Ph |
| 879. | 5-benzimidazolyl | 4-OH-Ph |
| 880. | 5-benzimidazolyl | 3,4-diF-Ph |
| 881. | 5-benzimidazolyl | 3,5-diF-Ph |
| 882. | 5-benzimidazolyl | 3,4-diCl-Ph |
| 883. | 5-benzimidazolyl | 3,5-diCl-Ph |
| 884. | 5-benzimidazolyl | 3,4-OCH2O-Ph |
| 885. | 5-benzimidazolyl | 3,4-OCH2CH2O-Ph |
| 886. | 5-benzothiazolyl | 3-CN-Ph |
| 887. | 5-benzothiazolyl | 3-COCH3-Ph |
| 888. | 5-benzothiazolyl | 3-F-Ph |
| 889. | 5-benzothiazolyl | 3-Cl-Ph |
| 890. | 5-benzothiazolyl | 3-NH2-Ph |
| 891. | 5-benzothiazolyl | 3-OCH3-Ph |
| 892. | 5-benzothiazolyl | 3-OH-Ph |
| 893. | 5-benzothiazolyl | 4-CN-Ph |
| 894. | 5-benzothiazolyl | 4-COCH3-Ph |
| 895. | 5-benzothiazolyl | 4-F-Ph |
| 896. | 5-benzothiazolyl | 4-Cl-Ph |
| 897. | 5-benzothiazolyl | 4-NH2-Ph |
| 898. | 5-benzothiazolyl | 4-OCH3-Ph |
| 899. | 5-benzothiazolyl | 4-OH-Ph |
| 900. | 5-benzothiazolyl | 3,4-diF-Ph |
| 901. | 5-benzothiazolyl | 3,5-diF-Ph |
| 902. | 5-benzothiazolyl | 3,4-diCl-Ph |
| 903. | 5-benzothiazolyl | 3,5-diCl-Ph |
| 904. | 5-benzothiazolyl | 3,4-OCH2O-Ph |
| 905. | 5-benzothiazolyl | 3,4-OCH2CH2O-Ph |
| 906. | 5-benzoxazolyl | 3-CN-Ph |
| 907. | 5-benzoxazolyl | 3-COCH3-Ph |
| 908. | 5-benzoxazolyl | 3-F-Ph |
| 909. | 5-benzoxazolyl | 3-Cl-Ph |
| 910. | 5-benzoxazolyl | 3-NH2-Ph |
| 911. | 5-benzoxazolyl | 3-OCH3-Ph |
| 912. | 5-benzoxazolyl | 3-OH-Ph |
| 913. | 5-benzoxazolyl | 4-CN-Ph |
| 914. | 5-benzoxazolyl | 4-COCH3-Ph |
| 915. | 5-benzoxazolyl | 4-F-Ph |
| 916. | 5-benzoxazolyl | 4-Cl-Ph |
| 917. | 5-benzoxazolyl | 4-NH2-Ph |
| 918. | 5-benzoxazolyl | 4-OCH3-Ph |
| 919. | 5-benzoxazolyl | 4-OH-Ph |
| 920. | 5-benzoxazolyl | 3,4-diF-Ph |
| 921. | 5-benzoxazolyl | 3,5-diF-Ph |
| 922. | 5-benzoxazolyl | 3,4-diCl-Ph |
| 923. | 5-benzoxazolyl | 3,5-diCl-Ph |
| 924. | 5-benzoxazolyl | 3,4-OCH2O-Ph |
| 925. | 5-benzoxazolyl | 3,4-OCH2CH2O-Ph |
| 926. | 4-F-Ph | 3-(1-methyltetrazol-5-yl)-Ph |
| 927. | 4-F-Ph | 3-(5-methyltetrazol-1-yl)-Ph |
| 928. | 4-F-Ph | 3-(1-ethyltetrazol-5-yl)-Ph |
| 929. | 4-F-Ph | 3-(1-cyclopropylyltetrazol-5-yl)-Ph |
| 930. | 4-F-Ph | 3-(1-(2-methoxyethyl)tetrazol-5-yl)-Ph |
| 931. | 4-F-Ph | 3-(1-(2-cyanoethyl)tetrazol-5-yl)-Ph |
| 932. | 4-F-Ph | 3-(1-methyltetrazol-5-yl)-5-[(CH3)2N—CO]-Ph |
| 933. | 4-F-Ph | 3-(1-methyltetrazol-5-yl)-5-[(CH3)NH—CO]-Ph |
| 934. | 4-F-Ph | 3-(1-methyltetrazol-5-yl)-5-[H2N—CO]-Ph |
| 935. | 4-F-Ph | 3-(1-methyltetrazol-5-yl)-5-[COCH3]-Ph |
| 936. | 4-F-Ph | 3-(1-methyltetrazol-5-yl)-5-[morpholin-1-yl-CO]-Ph |
| 937. | 4-F-Ph | 3-(1-methyltetrazol-5-yl)-5-F-Ph |
| 938. | 4-F-Ph | 3-(1-methyltetrazol-5-yl)-5-Cl-Ph |
| 939. | 4-F-Ph | 3-(1-methyltetrazol-5-yl)-5-Br-Ph |
| 940. | 4-F-Ph | 3-(1-methyltetrazol-5-yl)-4-F-Ph |
| 941. | 4-F-Ph | 3-(1-methyltetrazol-5-yl)-4-Cl-Ph |
| 942. | 4-F-Ph | 3-(1-methyltetrazol-5-yl)-4-Br-Ph |
| 943. | 4-F-Ph | 3-(1-methyltetrazol-5-yl)-5-CF3-Ph |
| 944. | 4-F-Ph | 3-(1-methyltetrazol-5-yl)-4-CF3-Ph |
| 945. | 4-F-Ph | 3-(1-methyltetrazol-5-yl)-2-CH3O-Ph |
| 946. | 4-F-Ph | 3-(1-methyltetrazol-5-yl)-4-CH3O-Ph |
| 947. | 4-F-Ph | 3-(1-methyltetrazol-5-yl)-5-CH3O-Ph |
| 948. | 4-F-Ph | 3-(1-methyltetrazol-5-yl)-6-CH3O-Ph |
| 949. | 4-F-Ph | 3-(1-methyltetrazol-5-yl)-5-CH3-Ph |
| 950. | 4-F-Ph | 3-(1-methyltetrazol-5-yl)-5-CH3CH2-Ph |
| 951. | 4-F-Ph | 4-(1-methyltetrazol-5-yl)-5-[morpholin-1-yl-CO]-Ph |
| 952. | 4-F-Ph | 4-(1-methyltetrazol-5-yl)-5-F-Ph |
| 953. | 4-F-Ph | 4-(1-methyltetrazol-5-yl)-5-Cl-Ph |
| 954. | 4-F-Ph | 4-(1-methyltetrazol-5-yl)-5-Br-Ph |
| 955. | 4-F-Ph | 4-(1-methyltetrazol-5-yl)-3-CF3-Ph |
| 956. | 4-F-Ph | 4-(1-methyltetrazol-5-yl)-2-CH3O-Ph |
| 957. | 4-F-Ph | 4-(1-methyltetrazol-5-yl)-5-CH3O-Ph |
| 958. | 4-F-Ph | 3,5-bis(morpholin-1-yl)-Ph |
| 959. | 4-F-Ph | 3,5-bis(1,2,4-triazol-1-yl)-Ph |
| 960. | 4-F-Ph | 3,5-bis(pyrazol-1-yl)-Ph |
| 961. | 4-F-Ph | 3,5-bis(oxazol-2-yl)-Ph |
| 962. | 4-F-Ph | 3,5-bis(isoxazol-3-yl)-Ph |
| 963. | 4-F-Ph | 3,5-bis(isoxazol-5-yl)-Ph |
| 964. | 4-F-Ph | 3,5-bis(1,2,3-triazol-1-yl)-Ph |
| 965. | 4-F-Ph | 3,5-bis(COCH3)-Ph |
| 966. | 4-F-Ph | 3,5-bis(CH2OH)-Ph |
| 967. | 4-F-Ph | 3-(1-methyltetrazoly-5-yl)-(5-CN)-Ph |
| 968. | 4-F-Ph | 3-(1-methyltetrazoly-5-yl)-(5-CH2OH)-Ph |
| 969. | 4-F-Ph | 3-(1-methyltetrazoly-5-yl)-(5-CH(CH3)2)-Ph |

| | | |
|---|---|---|
| 970. | 4-F-Ph | 3-(1-methyltetrazoly-5-yl)-(5-COH(CH3)2)-Ph |
| 971. | 4-F-Ph | 3-(1-methyltetrazoly-5-yl)-(5-pyrazol-1-yl)-Ph |
| 972. | 4-F-Ph | 3,5-bis(CN)-Ph |
| 973. | 4-F-Ph | 3,5-bis(COCF3)-Ph |
| 974. | 2-F-Ph | 3-(1-methyltetrazol-5-yl)-Ph |
| 975. | 2-F-Ph | 3-(5-methyltetrazol-1-yl)-Ph |
| 976. | 2-F-Ph | 3-(1-ethyltetrazol-5-yl)-Ph |
| 977. | 2-F-Ph | 3-(1-cyclopropylyltetrazol-5-yl)-Ph |
| 978. | 2-F-Ph | 3-(1-(2-methoxyethyl)tetrazol-5-yl)-Ph |
| 979. | 2-F-Ph | 3-(1-(2-cyanoethyl)tetrazol-5-yl)-Ph |
| 980. | 2-F-Ph | 3-(1-methyltetrazol-5-yl)-5-[(CH3)2N—CO]-Ph |
| 981. | 2-F-Ph | 3-(1-methyltetrazol-5-yl)-5-[(CH3)NH—CO]-Ph |
| 982. | 2-F-Ph | 3-(1-methyltetrazol-5-yl)-5-[H2N—CO]-Ph |
| 983. | 2-F-Ph | 3-(1-methyltetrazol-5-yl)-5-[COCH3]-Ph |
| 984. | 2-F-Ph | 3-(1-methyltetrazol-5-yl)-5-[morpholin-1-yl-CO]-Ph |
| 985. | 2-F-Ph | 3-(1-methyltetrazol-5-yl)-5-F-Ph |
| 986. | 2-F-Ph | 3-(1-methyltetrazol-5-yl)-5-Cl-Ph |
| 987. | 2-F-Ph | 3-(1-methyltetrazol-5-yl)-5-Br-Ph |
| 988. | 2-F-Ph | 3-(1-methyltetrazol-5-yl)-4-F-Ph |
| 989. | 2-F-Ph | 3-(1-methyltetrazol-5-yl)-4-Cl-Ph |
| 990. | 2-F-Ph | 3-(1-methyltetrazol-5-yl)-4-Br-Ph |
| 991. | 2-F-Ph | 3-(1-methyltetrazol-5-yl)-5-CF3-Ph |
| 992. | 2-F-Ph | 3-(1-methyltetrazol-5-yl)-4-CF3-Ph |
| 993. | 2-F-Ph | 3-(1-methyltetrazol-5-yl)-2-CH3O-Ph |
| 994. | 2-F-Ph | 3-(1-methyltetrazol-5-yl)-4-CH3O-Ph |
| 995. | 2-F-Ph | 3-(1-methyltetrazol-5-yl)-5-CH3O-Ph |
| 996. | 2-F-Ph | 3-(1-methyltetrazol-5-yl)-6-CH3O-Ph |
| 997. | 2-F-Ph | 3-(1-methyltetrazol-5-yl)-5-CH3-Ph |
| 998. | 2-F-Ph | 3-(1-methyltetrazol-5-yl)-5-CH3CH2-Ph |
| 999. | 2-F-Ph | 4-(1-methyltetrazol-5-yl)-5-[morpholin-1-yl-CO]-Ph |
| 1000. | 2-F-Ph | 4-(1-methyltetrazol-5-yl)-5-F-Ph |
| 1001. | 2-F-Ph | 4-(1-methyltetrazol-5-yl)-5-Cl-Ph |
| 1002. | 2-F-Ph | 4-(1-methyltetrazol-5-yl)-5-Br-Ph |
| 1003. | 2-F-Ph | 4-(1-methyltetrazol-5-yl)-3-CF3-Ph |
| 1004. | 2-F-Ph | 4-(1-methyltetrazol-5-yl)-2-CH3O-Ph |
| 1005. | 2-F-Ph | 4-(1-methyltetrazol-5-yl)-5-CH3O-Ph |
| 1006. | 2-F-Ph | 3,5-bis(morpholin-1-yl)-Ph |
| 1007. | 2-F-Ph | 3,5-bis(1,2,4-triazol-1-yl)-Ph |
| 1008. | 2-F-Ph | 3,5-bis(pyrazol-1-yl)-Ph |
| 1009. | 2-F-Ph | 3,5-bis(oxazol-2-yl)-Ph |
| 1010. | 2-F-Ph | 3,5-bis(isoxazol-3-yl)-Ph |
| 1011. | 2-F-Ph | 3,5-bis(isoxazol-5-yl)-Ph |
| 1012. | 2-F-Ph | 3,5-bis(1,2,3-triazol-1-yl)-Ph |
| 1013. | 2-F-Ph | 3,5-bis(COCH3)-Ph |
| 1014. | 2-F-Ph | 3,5-bis(CH2OH)-Ph |
| 1015. | 2,4-diF-Ph | 3-(1-methyltetrazol-5-yl)-Ph |
| 1016. | 2,4-diF-Ph | 3-(5-methyltetrazol-1-yl)-Ph |
| 1017. | 2,4-diF-Ph | 3-(1-ethyltetrazol-5-yl)-Ph |
| 1018. | 2,4-diF-Ph | 3-(1-cyclopropylyltetrazol-5-yl)-Ph |
| 1019. | 2,4-diF-Ph | 3-(1-(2-methoxyethyl)tetrazol-5-yl)-Ph |
| 1020. | 2,4-diF-Ph | 3-(1-(2-cyanoethyl)tetrazol-5-yl)-Ph |
| 1021. | 2,4-diF-Ph | 3-(1-methyltetrazol-5-yl)-5-[(CH3)2N—CO]-Ph |
| 1022. | 2,4-diF-Ph | 3-(1-methyltetrazol-5-yl)-5-[(CH3)NH—CO]-Ph |
| 1023. | 2,4-diF-Ph | 3-(1-methyltetrazol-5-yl)-5-[H2N—CO]-Ph |
| 1024. | 2,4-diF-Ph | 3-(1-methyltetrazol-5-yl)-5-[COCH3]-Ph |
| 1025. | 2,4-diF-Ph | 3-(1-methyltetrazol-5-yl)-5-[morpholin-1-yl-CO]-Ph |
| 1026. | 2,4-diF-Ph | 3-(1-methyltetrazol-5-yl)-5-F-Ph |
| 1027. | 2,4-diF-Ph | 3-(1-methyltetrazol-5-yl)-5-Cl-Ph |
| 1028. | 2,4-diF-Ph | 3-(1-methyltetrazol-5-yl)-5-Br-Ph |
| 1029. | 2,4-diF-Ph | 3-(1-methyltetrazol-5-yl)-4-F-Ph |
| 1030. | 2,4-diF-Ph | 3-(1-methyltetrazol-5-yl)-4-Cl-Ph |
| 1031. | 2,4-diF-Ph | 3-(1-methyltetrazol-5-yl)-4-Br-Ph |
| 1032. | 2,4-diF-Ph | 3-(1-methyltetrazol-5-yl)-5-CF3-Ph |
| 1033. | 2,4-diF-Ph | 3-(1-methyltetrazol-5-yl)-4-CF3-Ph |
| 1034. | 2,4-diF-Ph | 3-(1-methyltetrazol-5-yl)-2-CH3O-Ph |
| 1035. | 2,4-diF-Ph | 3-(1-methyltetrazol-5-yl)-4-CH3O-Ph |
| 1036. | 2,4-diF-Ph | 3-(1-methyltetrazol-5-yl)-5-CH3O-Ph |
| 1037. | 2,4-diF-Ph | 3-(1-methyltetrazol-5-yl)-6-CH3O-Ph |
| 1038. | 2,4-diF-Ph | 3-(1-methyltetrazol-5-yl)-5-CH3-Ph |
| 1039. | 2,4-diF-Ph | 3-(1-methyltetrazol-5-yl)-5-CH3CH2-Ph |
| 1040. | 2,4-diF-Ph | 4-(1-methyltetrazol-5-yl)-5-[morpholin-1-yl-CO]-Ph |
| 1041. | 2,4-diF-Ph | 4-(1-methyltetrazol-5-yl)-5-F-Ph |
| 1042. | 2,4-diF-Ph | 4-(1-methyltetrazol-5-yl)-5-Cl-Ph |
| 1043. | 2,4-diF-Ph | 4-(1-methyltetrazol-5-yl)-5-Br-Ph |
| 1044. | 2,4-diF-Ph | 4-(1-methyltetrazol-5-yl)-3-CF3-Ph |
| 1045. | 2,4-diF-Ph | 4-(1-methyltetrazol-5-yl)-2-CH3O-Ph |
| 1046. | 2,4-diF-Ph | 4-(1-methyltetrazol-5-yl)-5-CH3O-Ph |
| 1047. | 2,4-diF-Ph | 3,5-bis(morpholin-1-yl)-Ph |
| 1048. | 2,4-diF-Ph | 3,5-bis(1,2,4-triazol-1-yl)-Ph |
| 1049. | 2,4-diF-Ph | 3,5-bis(pyrazol-1-yl)-Ph |
| 1050. | 2,4-diF-Ph | 3,5-bis(oxazol-2-yl)-Ph |
| 1051. | 2,4-diF-Ph | 3,5-bis(isoxazol-3-yl)-Ph |
| 1052. | 2,4-diF-Ph | 3,5-bis(isoxazol-5-yl)-Ph |
| 1053. | 2,4-diF-Ph | 3,5-bis(1,2,3-triazol-1-yl)-Ph |
| 1054. | 2,4-diF-Ph | 3,5-bis(COCH3)-Ph |
| 1055. | 2,4-diF-Ph | 3,5-bis(CH2OH)-Ph |
| 1056. | 4-Cl-Ph | 3-(1-methyltetrazol-5-yl)-Ph |
| 1057. | 4-Cl-Ph | 3-(5-methyltetrazol-1-yl)-Ph |
| 1058. | 4-Cl-Ph | 3-(1-ethyltetrazol-5-yl)-Ph |
| 1059. | 4-Cl-Ph | 3-(1-cyclopropylyltetrazol-5-yl)-Ph |
| 1060. | 4-Cl-Ph | 3-(1-(2-methoxyethyl)tetrazol-5-yl)-Ph |
| 1061. | 4-Cl-Ph | 3-(1-(2-cyanoethyl)tetrazol-5-yl)-Ph |
| 1062. | 4-Cl-Ph | 3-(1-methyltetrazol-5-yl)-5-[(CH3)2N—CO]-Ph |
| 1063. | 4-Cl-Ph | 3-(1-methyltetrazol-5-yl)-5-[(CH3)NH—CO]-Ph |
| 1064. | 4-Cl-Ph | 3-(1-methyltetrazol-5-yl)-5-[H2N—CO]-Ph |
| 1065. | 4-Cl-Ph | 3-(1-methyltetrazol-5-yl)-5-[COCH3]-Ph |

| # | R1 | R2 |
|---|---|---|
| 1066. | 4-Cl-Ph | 3-(1-methyltetrazol-5-yl)-5-[morpholin-1-yl-CO]-Ph |
| 1067. | 4-Cl-Ph | 3-(1-methyltetrazol-5-yl)-5-F-Ph |
| 1068. | 4-Cl-Ph | 3-(1-methyltetrazol-5-yl)-5-Cl-Ph |
| 1069. | 4-Cl-Ph | 3-(1-methyltetrazol-5-yl)-5-Br-Ph |
| 1070. | 4-Cl-Ph | 3-(1-methyltetrazol-5-yl)-4-F-Ph |
| 1071. | 4-Cl-Ph | 3-(1-methyltetrazol-5-yl)-4-Cl-Ph |
| 1072. | 4-Cl-Ph | 3-(1-methyltetrazol-5-yl)-4-Br-Ph |
| 1073. | 4-Cl-Ph | 3-(1-methyltetrazol-5-yl)-5-CF3-Ph |
| 1074. | 4-Cl-Ph | 3-(1-methyltetrazol-5-yl)-4-CF3-Ph |
| 1075. | 4-Cl-Ph | 3-(1-methyltetrazol-5-yl)-2-CH3O-Ph |
| 1076. | 4-Cl-Ph | 3-(1-methyltetrazol-5-yl)-4-CH3O-Ph |
| 1077. | 4-Cl-Ph | 3-(1-methyltetrazol-5-yl)-5-CH3O-Ph |
| 1078. | 4-Cl-Ph | 3-(1-methyltetrazol-5-yl)-6-CH3O-Ph |
| 1079. | 4-Cl-Ph | 3-(1-methyltetrazol-5-yl)-5-CH3-Ph |
| 1080. | 4-Cl-Ph | 3-(1-methyltetrazol-5-yl)-5-CH3CH2-Ph |
| 1081. | 4-Cl-Ph | 4-(1-methyltetrazol-5-yl)-5-[morpholin-1-yl-CO]-Ph |
| 1082. | 4-Cl-Ph | 4-(1-methyltetrazol-5-yl)-5-F-Ph |
| 1083. | 4-Cl-Ph | 4-(1-methyltetrazol-5-yl)-5-Cl-Ph |
| 1084. | 4-Cl-Ph | 4-(1-methyltetrazol-5-yl)-5-Br-Ph |
| 1085. | 4-Cl-Ph | 4-(1-methyltetrazol-5-yl)-3-CF3-Ph |
| 1086. | 4-Cl-Ph | 4-(1-methyltetrazol-5-yl)-2-CH3O-Ph |
| 1087. | 4-Cl-Ph | 4-(1-methyltetrazol-5-yl)-5-CH3O-Ph |
| 1088. | 4-Cl-Ph | 3,5-bis(morpholin-1-yl)-Ph |
| 1089. | 4-Cl-Ph | 3,5-bis(1,2,4-triazol-1-yl)-Ph |
| 1090. | 4-Cl-Ph | 3,5-bis(pyrazol-1-yl)-Ph |
| 1091. | 4-Cl-Ph | 3,5-bis(oxazol-2-yl)-Ph |
| 1092. | 4-Cl-Ph | 3,5-bis(isoxazol-3-yl)-Ph |
| 1093. | 4-Cl-Ph | 3,5-bis(isoxazol-5-yl)-Ph |
| 1094. | 4-Cl-Ph | 3,5-bis(1,2,3-triazol-1-yl)-Ph |
| 1095. | 4-Cl-Ph | 3,5-bis(COCH3)-Ph |
| 1096. | 4-Cl-Ph | 3,5-bis(CH2OH)-Ph |
| 1097. | 2-Cl-Ph | 3-(1-methyltetrazol-5-yl)-Ph |
| 1098. | 2-Cl-Ph | 3-(5-methyltetrazol-1-yl)-Ph |
| 1099. | 2-Cl-Ph | 3-(1-ethyltetrazol-5-yl)-Ph |
| 1100. | 2-Cl-Ph | 3-(1-cyclopropylyltetrazol-5-yl)-Ph |
| 1101. | 2-Cl-Ph | 3-(1-(2-methoxyethyl)tetrazol-5-yl)-Ph |
| 1102. | 2-Cl-Ph | 3-(1-(2-cyanoethyl)tetrazol-5-yl)-Ph |
| 1103. | 2-Cl-Ph | 3-(1-methyltetrazol-5-yl)-5-[(CH3)2N—CO]-Ph |
| 1104. | 2-Cl-Ph | 3-(1-methyltetrazol-5-yl)-5-[(CH3)NH—CO]-Ph |
| 1105. | 2-Cl-Ph | 3-(1-methyltetrazol-5-yl)-5-[H2N—CO]-Ph |
| 1106. | 2-Cl-Ph | 3-(1-methyltetrazol-5-yl)-5-[COCH3]-Ph |
| 1107. | 2-Cl-Ph | 3-(1-methyltetrazol-5-yl)-5-[morpholin-1-yl-CO]-Ph |
| 1108. | 2-Cl-Ph | 3-(1-methyltetrazol-5-yl)-5-F-Ph |
| 1109. | 2-Cl-Ph | 3-(1-methyltetrazol-5-yl)-5-Cl-Ph |
| 1110. | 2-Cl-Ph | 3-(1-methyltetrazol-5-yl)-5-Br-Ph |
| 1111. | 2-Cl-Ph | 3-(1-methyltetrazol-5-yl)-4-F-Ph |
| 1112. | 2-Cl-Ph | 3-(1-methyltetrazol-5-yl)-4-Cl-Ph |
| 1113. | 2-Cl-Ph | 3-(1-methyltetrazol-5-yl)-4-Br-Ph |
| 1114. | 2-Cl-Ph | 3-(1-methyltetrazol-5-yl)-5-CF3-Ph |
| 1115. | 2-Cl-Ph | 3-(1-methyltetrazol-5-yl)-4-CF3-Ph |
| 1116. | 2-Cl-Ph | 3-(1-methyltetrazol-5-yl)-2-CH3O-Ph |
| 1117. | 2-Cl-Ph | 3-(1-methyltetrazol-5-yl)-4-CH3O-Ph |
| 1118. | 2-Cl-Ph | 3-(1-methyltetrazol-5-yl)-5-CH3O-Ph |
| 1119. | 2-Cl-Ph | 3-(1-methyltetrazol-5-yl)-6-CH3O-Ph |
| 1120. | 2-Cl-Ph | 3-(1-methyltetrazol-5-yl)-5-CH3-Ph |
| 1121. | 2-Cl-Ph | 3-(1-methyltetrazol-5-yl)-5-CH3CH2-Ph |
| 1122. | 2-Cl-Ph | 4-(1-methyltetrazol-5-yl)-5-[morpholin-1-yl-CO]-Ph |
| 1123. | 2-Cl-Ph | 4-(1-methyltetrazol-5-yl)-5-F-Ph |
| 1124. | 2-Cl-Ph | 4-(1-methyltetrazol-5-yl)-5-Cl-Ph |
| 1125. | 2-Cl-Ph | 4-(1-methyltetrazol-5-yl)-5-Br-Ph |
| 1126. | 2-Cl-Ph | 4-(1-methyltetrazol-5-yl)-3-CF3-Ph |
| 1127. | 2-Cl-Ph | 4-(1-methyltetrazol-5-yl)-2-CH3O-Ph |
| 1128. | 2-Cl-Ph | 4-(1-methyltetrazol-5-yl)-5-CH3O-Ph |
| 1129. | 2-Cl-Ph | 3,5-bis(morpholin-1-yl)-Ph |
| 1130. | 2-Cl-Ph | 3,5-bis(1,2,4-triazol-1-yl)-Ph |
| 1131. | 2-Cl-Ph | 3,5-bis(pyrazol-1-yl)-Ph |
| 1132. | 2-Cl-Ph | 3,5-bis(oxazol-2-yl)-Ph |
| 1133. | 2-Cl-Ph | 3,5-bis(isoxazol-3-yl)-Ph |
| 1134. | 2-Cl-Ph | 3,5-bis(isoxazol-5-yl)-Ph |
| 1135. | 2-Cl-Ph | 3,5-bis(1,2,3-triazol-1-yl)-Ph |
| 1136. | 2-Cl-Ph | 3,5-bis(COCH3)-Ph |
| 1137. | 2-Cl-Ph | 3,5-bis(CH2OH)-Ph |
| 1138. | 2,4-diCl-Ph | 3-(1-methyltetrazol-5-yl)-Ph |
| 1139. | 2,4-diCl-Ph | 3-(5-methyltetrazol-1-yl)-Ph |
| 1140. | 2,4-diCl-Ph | 3-(1-ethyltetrazol-5-yl)-Ph |
| 1141. | 2,4-diCl-Ph | 3-(1-cyclopropylyltetrazol-5-yl)-Ph |
| 1142. | 2,4-diCl-Ph | 3-(1-(2-methoxyethyl)tetrazol-5-yl)-Ph |
| 1143. | 2,4-diCl-Ph | 3-(1-(2-cyanoethyl)tetrazol-5-yl)-Ph |
| 1144. | 2,4-diCl-Ph | 3-(1-methyltetrazol-5-yl)-5-[(CH3)2N—CO]-Ph |
| 1145. | 2,4-diCl-Ph | 3-(1-methyltetrazol-5-yl)-5-[(CH3)NH—CO]-Ph |
| 1146. | 2,4-diCl-Ph | 3-(1-methyltetrazol-5-yl)-5-[H2N—CO]-Ph |
| 1147. | 2,4-diCl-Ph | 3-(1-methyltetrazol-5-yl)-5-[COCH3]-Ph |
| 1148. | 2,4-diCl-Ph | 3-(1-methyltetrazol-5-yl)-5-[morpholin-1-yl-CO]-Ph |
| 1149. | 2,4-diCl-Ph | 3-(1-methyltetrazol-5-yl)-5-F-Ph |
| 1150. | 2,4-diCl-Ph | 3-(1-methyltetrazol-5-yl)-5-Cl-Ph |
| 1151. | 2,4-diCl-Ph | 3-(1-methyltetrazol-5-yl)-5-Br-Ph |
| 1152. | 2,4-diCl-Ph | 3-(1-methyltetrazol-5-yl)-4-F-Ph |
| 1153. | 2,4-diCl-Ph | 3-(1-methyltetrazol-5-yl)-4-Cl-Ph |
| 1154. | 2,4-diCl-Ph | 3-(1-methyltetrazol-5-yl)-4-Br-Ph |
| 1155. | 2,4-diCl-Ph | 3-(1-methyltetrazol-5-yl)-5-CF3-Ph |
| 1156. | 2,4-diCl-Ph | 3-(1-methyltetrazol-5-yl)-4-CF3-Ph |
| 1157. | 2,4-diCl-Ph | 3-(1-methyltetrazol-5-yl)-2-CH3O-Ph |
| 1158. | 2,4-diCl-Ph | 3-(1-methyltetrazol-5-yl)-4-CH3O-Ph |
| 1159. | 2,4-diCl-Ph | 3-(1-methyltetrazol-5-yl)-5-CH3O-Ph |

| | | |
|---|---|---|
| 1160. | 2,4-diCl-Ph | 3-(1-methyltetrazol-5-yl)-6-CH3O-Ph |
| 1161. | 2,4-diCl-Ph | 3-(1-methyltetrazol-5-yl)-5-CH3-Ph |
| 1162. | 2,4-diCl-Ph | 3-(1-methyltetrazol-5-yl)-5-CH3CH2-Ph |
| 1163. | 2,4-diCl-Ph | 4-(1-methyltetrazol-5-yl)-5-[morpholin-1-yl-CO]-Ph |
| 1164. | 2,4-diCl-Ph | 4-(1-methyltetrazol-5-yl)-5-F-Ph |
| 1165. | 2,4-diCl-Ph | 4-(1-methyltetrazol-5-yl)-5-Cl-Ph |
| 1166. | 2,4-diCl-Ph | 4-(1-methyltetrazol-5-yl)-5-Br-Ph |
| 1167. | 2,4-diCl-Ph | 4-(1-methyltetrazol-5-yl)-3-CF3-Ph |
| 1168. | 2,4-diCl-Ph | 4-(1-methyltetrazol-5-yl)-2-CH3O-Ph |
| 1169. | 2,4-diCl-Ph | 4-(1-methyltetrazol-5-yl)-5-CH3O-Ph |
| 1170. | 2,4-diCl-Ph | 3,5-bis(morpholin-1-yl)-Ph |
| 1171. | 2,4-diCl-Ph | 3,5-bis(1,2,4-triazol-1-yl)-Ph |
| 1172. | 2,4-diCl-Ph | 3,5-bis(pyrazol-1-yl)-Ph |
| 1173. | 2,4-diCl-Ph | 3,5-bis(oxazol-2-yl)-Ph |
| 1174. | 2,4-diCl-Ph | 3,5-bis(isoxazol-3-yl)-Ph |
| 1175. | 2,4-diCl-Ph | 3,5-bis(isoxazol-5-yl)-Ph |
| 1176. | 2,4-diCl-Ph | 3,5-bis(1,2,3-triazol-1-yl)-Ph |
| 1177. | 2,4-diCl-Ph | 3,5-bis(COCH3)-Ph |
| 1178. | 2,4-diCl-Ph | 3,5-bis(CH2OH)-Ph |
| 1179. | 3-OCH3-Ph | 3-(1-methyltetrazol-5-yl)-Ph |
| 1180. | 3-OCH3-Ph | 3-(5-methyltetrazol-1-yl)-Ph |
| 1181. | 3-OCH3-Ph | 3-(1-ethyltetrazol-5-yl)-Ph |
| 1182. | 3-OCH3-Ph | 3-(1-cyclopropylyltetrazol-5-yl)-Ph |
| 1183. | 3-OCH3-Ph | 3-(1-(2-methoxyethyl)tetrazol-5-yl)-Ph |
| 1184. | 3-OCH3-Ph | 3-(1-(2-cyanoethyl)tetrazol-5-yl)-Ph |
| 1185. | 3-OCH3-Ph | 3-(1-methyltetrazol-5-yl)-5-[(CH3)2N—CO]-Ph |
| 1186. | 3-OCH3-Ph | 3-(1-methyltetrazol-5-yl)-5-[(CH3)NH—CO]-Ph |
| 1187. | 3-OCH3-Ph | 3-(1-methyltetrazol-5-yl)-5-[H2N—CO]-Ph |
| 1188. | 3-OCH3-Ph | 3-(1-methyltetrazol-5-yl)-5-[COCH3]-Ph |
| 1189. | 3-OCH3-Ph | 3-(1-methyltetrazol-5-yl)-5-[morpholin-1-yl-CO]-Ph |
| 1190. | 3-OCH3-Ph | 3-(1-methyltetrazol-5-yl)-5-F-Ph |
| 1191. | 3-OCH3-Ph | 3-(1-methyltetrazol-5-yl)-5-Cl-Ph |
| 1192. | 3-OCH3-Ph | 3-(1-methyltetrazol-5-yl)-5-Br-Ph |
| 1193. | 3-OCH3-Ph | 3-(1-methyltetrazol-5-yl)-4-F-Ph |
| 1194. | 3-OCH3-Ph | 3-(1-methyltetrazol-5-yl)-4-Cl-Ph |
| 1195. | 3-OCH3-Ph | 3-(1-methyltetrazol-5-yl)-4-Br-Ph |
| 1196. | 3-OCH3-Ph | 3-(1-methyltetrazol-5-yl)-5-CF3-Ph |
| 1197. | 3-OCH3-Ph | 3-(1-methyltetrazol-5-yl)-4-CF3-Ph |
| 1198. | 3-OCH3-Ph | 3-(1-methyltetrazol-5-yl)-2-CH3O-Ph |
| 1199. | 3-OCH3-Ph | 3-(1-methyltetrazol-5-yl)-4-CH3O-Ph |
| 1200. | 3-OCH3-Ph | 3-(1-methyltetrazol-5-yl)-5-CH3O-Ph |
| 1201. | 3-OCH3-Ph | 3-(1-methyltetrazol-5-yl)-6-CH3O-Ph |
| 1202. | 3-OCH3-Ph | 3-(1-methyltetrazol-5-yl)-5-CH3-Ph |
| 1203. | 3-OCH3-Ph | 3-(1-methyltetrazol-5-yl)-5-CH3CH2-Ph |
| 1204. | 3-OCH3-Ph | 4-(1-methyltetrazol-5-yl)-5-[morpholin-1-yl-CO]-Ph |
| 1205. | 3-OCH3-Ph | 4-(1-methyltetrazol-5-yl)-5-F-Ph |
| 1206. | 3-OCH3-Ph | 4-(1-methyltetrazol-5-yl)-5-Cl-Ph |
| 1207. | 3-OCH3-Ph | 4-(1-methyltetrazol-5-yl)-5-Br-Ph |
| 1208. | 3-OCH3-Ph | 4-(1-methyltetrazol-5-yl)-3-CF3-Ph |
| 1209. | 3-OCH3-Ph | 4-(1-methyltetrazol-5-yl)-2-CH3O-Ph |
| 1210. | 3-OCH3-Ph | 4-(1-methyltetrazol-5-yl)-5-CH3O-Ph |
| 1211. | 3-OCH3-Ph | 3,5-bis(morpholin-1-yl)-Ph |
| 1212. | 3-OCH3-Ph | 3,5-bis(1,2,4-triazol-1-yl)-Ph |
| 1213. | 3-OCH3-Ph | 3,5-bis(pyrazol-1-yl)-Ph |
| 1214. | 3-OCH3-Ph | 3,5-bis(oxazol-2-yl)-Ph |
| 1215. | 3-OCH3-Ph | 3,5-bis(isoxazol-3-yl)-Ph |
| 1216. | 3-OCH3-Ph | 3,5-bis(isoxazol-5-yl)-Ph |
| 1217. | 3-OCH3-Ph | 3,5-bis(1,2,3-triazol-1-yl)-Ph |
| 1218. | 3-OCH3-Ph | 3,5-bis(COCH3)-Ph |
| 1219. | 3-OCH3-Ph | 3,5-bis(CH2OH)-Ph |
| 1220. | 2-thienyl | 3-(1-methyltetrazol-5-yl)-Ph |
| 1221. | 2-thienyl | 3-(5-methyltetrazol-1-yl)-Ph |
| 1222. | 2-thienyl | 3-(1-ethyltetrazol-5-yl)-Ph |
| 1223. | 2-thienyl | 3-(1-cyclopropylyltetrazol-5-yl)-Ph |
| 1224. | 2-thienyl | 3-(1-(2-methoxyethyl)tetrazol-5-yl)-Ph |
| 1225. | 2-thienyl | 3-(1-(2-cyanoethyl)tetrazol-5-yl)-Ph |
| 1226. | 2-thienyl | 3-(1-methyltetrazol-5-yl)-5-[(CH3)2N—CO]-Ph |
| 1227. | 2-thienyl | 3-(1-methyltetrazol-5-yl)-5-[(CH3)NH—CO]-Ph |
| 1228. | 2-thienyl | 3-(1-methyltetrazol-5-yl)-5-[H2N—CO]-Ph |
| 1229. | 2-thienyl | 3-(1-methyltetrazol-5-yl)-5-[COCH3]-Ph |
| 1230. | 2-thienyl | 3-(1-methyltetrazol-5-yl)-5-[morpholin-1-yl-CO]-Ph |
| 1231. | 2-thienyl | 3-(1-methyltetrazol-5-yl)-5-F-Ph |
| 1232. | 2-thienyl | 3-(1-methyltetrazol-5-yl)-5-Cl-Ph |
| 1233. | 2-thienyl | 3-(1-methyltetrazol-5-yl)-5-Br-Ph |
| 1234. | 2-thienyl | 3-(1-methyltetrazol-5-yl)-4-F-Ph |
| 1235. | 2-thienyl | 3-(1-methyltetrazol-5-yl)-4-Cl-Ph |
| 1236. | 2-thienyl | 3-(1-methyltetrazol-5-yl)-4-Br-Ph |
| 1237. | 2-thienyl | 3-(1-methyltetrazol-5-yl)-5-CF3-Ph |
| 1238. | 2-thienyl | 3-(1-methyltetrazol-5-yl)-4-CF3-Ph |
| 1239. | 3-thienyl | 3-(1-methyltetrazol-5-yl)-2-CH3O-Ph |
| 1240. | 3-thienyl | 3-(1-methyltetrazol-5-yl)-4-CH3O-Ph |
| 1241. | 3-thienyl | 3-(1-methyltetrazol-5-yl)-5-CH3O-Ph |
| 1242. | 3-thienyl | 3-(1-methyltetrazol-5-yl)-6-CH3O-Ph |
| 1243. | 3-thienyl | 3-(1-methyltetrazol-5-yl)-5-CH3-Ph |
| 1244. | 3-thienyl | 3-(1-methyltetrazol-5-yl)-5-CH3CH2-Ph |
| 1245. | 3-thienyl | 4-(1-methyltetrazol-5-yl)-5-[morpholin-1-yl-CO]-Ph |
| 1246. | 3-thienyl | 4-(1-methyltetrazol-5-yl)-5-F-Ph |
| 1247. | 3-thienyl | 4-(1-methyltetrazol-5-yl)-5-Cl-Ph |
| 1248. | 3-thienyl | 4-(1-methyltetrazol-5-yl)-5-Br-Ph |
| 1249. | 3-thienyl | 4-(1-methyltetrazol-5-yl)-3-CF3-Ph |
| 1250. | 3-thienyl | 4-(1-methyltetrazol-5-yl)-2-CH3O-Ph |
| 1251. | 3-thienyl | 4-(1-methyltetrazol-5-yl)-5-CH3O-Ph |
| 1252. | 3-thienyl | 3,5-bis(morpholin-1-yl)-Ph |
| 1253. | 3-thienyl | 3,5-bis(1,2,4-triazol-1-yl)-Ph |
| 1254. | 3-thienyl | 3,5-bis(pyrazol-1-yl)-Ph |
| 1255. | 3-thienyl | 3,5-bis(oxazol-2-yl)-Ph |

| | | |
|---|---|---|
| 1256. | 3-thienyl | 3,5-bis(isoxazol-3-yl)-Ph |
| 1257. | 3-thienyl | 3,5-bis(isoxazol-5-yl)-Ph |
| 1258. | 2-furanyl | 3,5-bis(1,2,3-triazol-1-yl)-Ph |
| 1259. | 2-furanyl | 3,5-bis(COCH3)-Ph |
| 1260. | 2-furanyl | 3,5-bis(CH2OH)-Ph |
| 1261. | 2-furanyl | 3-(1-methyltetrazol-5-yl)-Ph |
| 1262. | 2-furanyl | 3-(5-methyltetrazol-1-yl)-Ph |
| 1263. | 2-furanyl | 3-(1-ethyltetrazol-5-yl)-Ph |
| 1264. | 2-furanyl | 3-(1-cyclopropylyltetrazol-5-yl)-Ph |
| 1265. | 2-furanyl | 3-(1-(2-methoxyethyl)tetrazol-5-yl)-Ph |
| 1266. | 2-furanyl | 3-(1-(2-cyanoethyl)tetrazol-5-yl)-Ph |
| 1267. | 2-furanyl | 3-(1-methyltetrazol-5-yl)-5-[(CH3)2N—CO]-Ph |
| 1268. | 2-furanyl | 3-(1-methyltetrazol-5-yl)-5-[(CH3)NH—CO]-Ph |
| 1269. | 2-furanyl | 3-(1-methyltetrazol-5-yl)-5-[H2N—CO]-Ph |
| 1270. | 2-furanyl | 3-(1-methyltetrazol-5-yl)-5-[COCH3]-Ph |
| 1271. | 2-furanyl | 3-(1-methyltetrazol-5-yl)-5-[morpholin-1-yl-CO]-Ph |
| 1272. | 2-furanyl | 3-(1-methyltetrazol-5-yl)-5-F-Ph |
| 1273. | 2-furanyl | 3-(1-methyltetrazol-5-yl)-5-Cl-Ph |
| 1274. | 2-furanyl | 3-(1-methyltetrazol-5-yl)-5-Br-Ph |
| 1275. | 3-furanyl | 3-(1-methyltetrazol-5-yl)-4-F-Ph |
| 1276. | 3-furanyl | 3-(1-methyltetrazol-5-yl)-4-Cl-Ph |
| 1277. | 3-furanyl | 3-(1-methyltetrazol-5-yl)-4-Br-Ph |
| 1278. | 3-furanyl | 3-(1-methyltetrazol-5-yl)-5-CF3-Ph |
| 1279. | 3-furanyl | 3-(1-methyltetrazol-5-yl)-4-CF3-Ph |
| 1280. | 3-furanyl | 3-(1-methyltetrazol-5-yl)-2-CH3O-Ph |
| 1281. | 3-furanyl | 3-(1-methyltetrazol-5-yl)-4-CH3O-Ph |
| 1282. | 3-furanyl | 3-(1-methyltetrazol-5-yl)-5-CH3O-Ph |
| 1283. | 3-furanyl | 3-(1-methyltetrazol-5-yl)-6-CH3O-Ph |
| 1284. | 3-furanyl | 3-(1-methyltetrazol-5-yl)-5-CH3-Ph |
| 1285. | 3-furanyl | 3-(1-methyltetrazol-5-yl)-5-CH3CH2-Ph |
| 1286. | 3-furanyl | 4-(1-methyltetrazol-5-yl)-5-[morpholin-1-yl-CO]-Ph |
| 1287. | 3-furanyl | 4-(1-methyltetrazol-5-yl)-5-F-Ph |
| 1288. | 3-furanyl | 4-(1-methyltetrazol-5-yl)-5-Cl-Ph |
| 1289. | 3-furanyl | 4-(1-methyltetrazol-5-yl)-5-Br-Ph |
| 1290. | 3-furanyl | 4-(1-methyltetrazol-5-yl)-3-CF3-Ph |
| 1291. | 3-furanyl | 4-(1-methyltetrazol-5-yl)-2-CH3O-Ph |
| 1292. | 3-furanyl | 4-(1-methyltetrazol-5-yl)-5-CH3O-Ph |
| 1293. | 2-pyridyl | 3,5-bis(morpholin-1-yl)-Ph |
| 1294. | 2-pyridyl | 3,5-bis(1,2,4-triazol-1-yl)-Ph |
| 1295. | 2-pyridyl | 3,5-bis(pyrazol-1-yl)-Ph |
| 1296. | 2-pyridyl | 3,5-bis(oxazol-2-yl)-Ph |
| 1297. | 2-pyridyl | 3,5-bis(isoxazol-3-yl)-Ph |
| 1298. | 2-pyridyl | 3,5-bis(isoxazol-5-yl)-Ph |
| 1299. | 2-pyridyl | 3,5-bis(1,2,3-triazol-1-yl)-Ph |
| 1300. | 2-pyridyl | 3,5-bis(COCH3)-Ph |
| 1301. | 2-pyridyl | 3,5-bis(CH2OH)-Ph |
| 1302. | 3-pyridyl | 3-(1-methyltetrazol-5-yl)-Ph |
| 1303. | 3-pyridyl | 3-(5-methyltetrazol-1-yl)-Ph |
| 1304. | 3-pyridyl | 3-(1-ethyltetrazol-5-yl)-Ph |
| 1305. | 3-pyridyl | 3-(1-cyclopropylyltetrazol-5-yl)-Ph |
| 1306. | 3-pyridyl | 3-(1-(2-methoxyethyl)tetrazol-5-yl)-Ph |
| 1307. | 3-pyridyl | 3-(1-(2-cyanoethyl)tetrazol-5-yl)-Ph |
| 1308. | 3-pyridyl | 3-(1-methyltetrazol-5-yl)-5-[(CH3)2N—CO]-Ph |
| 1309. | 3-pyridyl | 3-(1-methyltetrazol-5-yl)-5-[(CH3)NH—CO]-Ph |
| 1310. | 3-pyridyl | 3-(1-methyltetrazol-5-yl)-5-[H2N—CO]-Ph |
| 1311. | 3-pyridyl | 3-(1-methyltetrazol-5-yl)-5-[COCH3]-Ph |
| 1312. | 3-pyridyl | 3-(1-methyltetrazol-5-yl)-5-[morpholin-1-yl-CO]-Ph |
| 1313. | 3-pyridyl | 3-(1-methyltetrazol-5-yl)-5-F-Ph |
| 1314. | 3-pyridyl | 3-(1-methyltetrazol-5-yl)-5-Cl-Ph |
| 1315. | 3-pyridyl | 3-(1-methyltetrazol-5-yl)-5-Br-Ph |
| 1316. | 3-pyridyl | 3-(1-methyltetrazol-5-yl)-4-F-Ph |
| 1317. | 3-pyridyl | 3-(1-methyltetrazol-5-yl)-4-Cl-Ph |
| 1318. | 3-pyridyl | 3-(1-methyltetrazol-5-yl)-4-Br-Ph |
| 1319. | 3-pyridyl | 3-(1-methyltetrazol-5-yl)-5-CF3-Ph |
| 1320. | 3-pyridyl | 3-(1-methyltetrazol-5-yl)-4-CF3-Ph |
| 1321. | 4-pyridyl | 3-(1-methyltetrazol-5-yl)-2-CH3O-Ph |
| 1322. | 4-pyridyl | 3-(1-methyltetrazol-5-yl)-4-CH3O-Ph |
| 1323. | 4-pyridyl | 3-(1-methyltetrazol-5-yl)-5-CH3O-Ph |
| 1324. | 4-pyridyl | 3-(1-methyltetrazol-5-yl)-6-CH3O-Ph |
| 1325. | 4-pyridyl | 3-(1-methyltetrazol-5-yl)-5-CH3-Ph |
| 1326. | 4-pyridyl | 3-(1-methyltetrazol-5-yl)-5-CH3CH2-Ph |
| 1327. | 4-pyridyl | 4-(1-methyltetrazol-5-yl)-5-(morpholin-1-yl-CO)-Ph |
| 1328. | 4-pyridyl | 4-(1-methyltetrazol-5-yl)-5-F-Ph |
| 1329. | 4-pyridyl | 4-(1-methyltetrazol-5-yl)-5-Cl-Ph |
| 1330. | 4-pyridyl | 4-(1-methyltetrazol-5-yl)-5-Br-Ph |
| 1331. | 4-pyridyl | 4-(1-methyltetrazol-5-yl)-3-CF3-Ph |
| 1332. | 4-pyridyl | 4-(1-methyltetrazol-5-yl)-2-CH3O-Ph |
| 1333. | 4-pyridyl | 4-(1-methyltetrazol-5-yl)-5-CH3O-Ph |
| 1334. | 4-pyridyl | 3,5-bis(morpholin-1-yl)-Ph |
| 1335. | 4-pyridyl | 3,5-bis(1,2,4-triazol-1-yl)-Ph |
| 1336. | 4-pyridyl | 3,5-bis(pyrazol-1-yl)-Ph |
| 1337. | 4-pyridyl | 3,5-bis(oxazol-2-yl)-Ph |
| 1338. | 4-pyridyl | 3,5-bis(isoxazol-3-yl)-Ph |
| 1339. | 4-pyridyl | 3,5-bis(isoxazol-5-yl)-Ph |
| 1340. | 3-indolyl | 3-(1-methyltetrazol-5-yl)-Ph |
| 1341. | 3-indolyl | 3-(5-methyltetrazol-1-yl)-Ph |
| 1342. | 3-indolyl | 3-(1-ethyltetrazol-5-yl)-Ph |
| 1343. | 3-indolyl | 3-(1-cyclopropylyltetrazol-5-yl)-Ph |
| 1344. | 3-indolyl | 3-(1-(2-methoxyethyl)tetrazol-5-yl)-Ph |
| 1345. | 3-indolyl | 3-(1-(2-cyanoethyl)tetrazol-5-yl)-Ph |
| 1346. | 3-indolyl | 3-(1-methyltetrazol-5-yl)-5-[(CH3)2N—CO]-Ph |
| 1347. | 3-indolyl | 3-(1-methyltetrazol-5-yl)-5-[(CH3)NH—CO]-Ph |
| 1348. | 3-indolyl | 3-(1-methyltetrazol-5-yl)-5-[H2N—CO]-Ph |
| 1349. | 3-indolyl | 3-(1-methyltetrazol-5-yl)-5-[COCH3]-Ph |
| 1350. | 3-indolyl | 3-(1-methyltetrazol-5-yl)-5-[morpholin-1-yl-CO]-Ph |
| 1351. | 3-indolyl | 3-(1-methyltetrazol-5-yl)-5-F-Ph |

| # | Col A | Col B |
|---|---|---|
| 1352. | 3-indolyl | 3-(1-methyltetrazol-5-yl)-5-Cl-Ph |
| 1353. | 3-indolyl | 3-(1-methyltetrazol-5-yl)-5-Br-Ph |
| 1354. | 3-indolyl | 3-(1-methyltetrazol-5-yl)-4-F-Ph |
| 1355. | 3-indolyl | 3-(1-methyltetrazol-5-yl)-4-Cl-Ph |
| 1356. | 5-indolyl | 3-(1-methyltetrazol-5-yl)-4-Br-Ph |
| 1357. | 5-indolyl | 3-(1-methyltetrazol-5-yl)-5-CF3-Ph |
| 1358. | 5-indolyl | 3-(1-methyltetrazol-5-yl)-4-CF3-Ph |
| 1359. | 5-indolyl | 3-(1-methyltetrazol-5-yl)-2-CH3O-Ph |
| 1360. | 5-indolyl | 3-(1-methyltetrazol-5-yl)-4-CH3O-Ph |
| 1361. | 5-indolyl | 3-(1-methyltetrazol-5-yl)-5-CH3O-Ph |
| 1362. | 5-indolyl | 3-(1-methyltetrazol-5-yl)-6-CH3O-Ph |
| 1363. | 5-indolyl | 3-(1-methyltetrazol-5-yl)-5-CH3-Ph |
| 1364. | 5-indolyl | 3-(1-methyltetrazol-5-yl)-5-CH3CH2-Ph |
| 1365. | 5-indolyl | 4-(1-methyltetrazol-5-yl)-5-[morpholin-1-yl-CO]-Ph |
| 1366. | 5-indolyl | 4-(1-methyltetrazol-5-yl)-5-F-Ph |
| 1367. | 5-indolyl | 4-(1-methyltetrazol-5-yl)-5-Cl-Ph |
| 1368. | 5-indolyl | 4-(1-methyltetrazol-5-yl)-5-Br-Ph |
| 1369. | 5-indolyl | 4-(1-methyltetrazol-5-yl)-3-CF3-Ph |
| 1370. | 5-indolyl | 4-(1-methyltetrazol-5-yl)-2-CH3O-Ph |
| 1371. | 5-indolyl | 4-(1-methyltetrazol-5-yl)-5-CH3O-Ph |
| 1372. | 5-indolyl | 3,5-bis(morpholin-1-yl)-Ph |
| 1373. | 5-indolyl | 3,5-bis(1,2,4-triazol-1-yl)-Ph |
| 1374. | 5-indolyl | 3,5-bis(pyrazol-1-yl)-Ph |
| 1375. | 5-indazolyl | 3,5-bis(oxazol-2-yl)-Ph |
| 1376. | 5-indazolyl | 3,5-bis(isoxazol-3-yl)-Ph |
| 1377. | 5-indazolyl | 3,5-bis(isoxazol-5-yl)-Ph |
| 1378. | 5-indazolyl | 3,5-bis(1,2,3-triazol-1-yl)-Ph |
| 1379. | 5-indazolyl | 3,5-bis(COCH3)-Ph |
| 1380. | 5-indazolyl | 3,5-bis(CH2OH)-Ph |
| 1381. | 5-benzimidazolyl | 3-(1-methyltetrazol-5-yl)-Ph |
| 1382. | 5-benzimidazolyl | 3-(5-methyltetrazol-1-yl)-Ph |
| 1383. | 5-benzimidazolyl | 3-(1-ethyltetrazol-5-yl)-Ph |
| 1384. | 5-benzimidazolyl | 3-(1-cyclopropylyltetrazol-5-yl)-Ph |
| 1385. | 5-benzimidazolyl | 3-(1-(2-methoxyethyl)tetrazol-5-yl)-Ph |
| 1386. | 5-benzimidazolyl | 3-(1-(2-cyanoethyl)tetrazol-5-yl)-Ph |
| 1387. | 5-benzimidazolyl | 3-(1-methyltetrazol-5-yl)-5-[(CH3)2N—CO]-Ph |
| 1388. | 5-benzimidazolyl | 3-(1-methyltetrazol-5-yl)-5-[(CH3)NH—CO]-Ph |
| 1389. | 5-benzimidazolyl | 3-(1-methyltetrazol-5-yl)-5-[H2N—CO]-Ph |
| 1390. | 5-benzimidazolyl | 3-(1-methyltetrazol-5-yl)-5-[COCH3]-Ph |
| 1391. | 5-benzimidazolyl | 3-(1-methyltetrazol-5-yl)-5-[morpholin-1-yl-CO]-Ph |
| 1392. | 5-benzimidazolyl | 3-(1-methyltetrazol-5-yl)-5-F-Ph |
| 1393. | 5-benzimidazolyl | 3-(1-methyltetrazol-5-yl)-5-Cl-Ph |
| 1394. | 5-benzimidazolyl | 3-(1-methyltetrazol-5-yl)-5-Br-Ph |
| 1395. | 5-benzimidazolyl | 3-(1-methyltetrazol-5-yl)-4-F-Ph |
| 1396. | 5-benzimidazolyl | 3-(1-methyltetrazol-5-yl)-4-Cl-Ph |
| 1397. | 5-benzimidazolyl | 3-(1-methyltetrazol-5-yl)-4-Br-Ph |
| 1398. | 5-benzimidazolyl | 3-(1-methyltetrazol-5-yl)-5-CF3-Ph |
| 1399. | 5-benzimidazolyl | 3-(1-methyltetrazol-5-yl)-4-CF3-Ph |
| 1400. | 5-benzothiazolyl | 3-(1-methyltetrazol-5-yl)-2-CH3O-Ph |
| 1401. | 5-benzothiazolyl | 3-(1-methyltetrazol-5-yl)-4-CH3O-Ph |
| 1402. | 5-benzothiazolyl | 3-(1-methyltetrazol-5-yl)-5-CH3O-Ph |
| 1403. | 5-benzothiazolyl | 3-(1-methyltetrazol-5-yl)-6-CH3O-Ph |
| 1404. | 5-benzothiazolyl | 3-(1-methyltetrazol-5-yl)-5-CH3-Ph |
| 1405. | 5-benzothiazolyl | 3-(1-methyltetrazol-5-yl)-5-CH3CH2-Ph |
| 1406. | 5-benzothiazolyl | 4-(1-methyltetrazol-5-yl)-5-[morpholin-1-yl-CO]-Ph |
| 1407. | 5-benzothiazolyl | 4-(1-methyltetrazol-5-yl)-5-F-Ph |
| 1408. | 5-benzothiazolyl | 4-(1-methyltetrazol-5-yl)-5-Cl-Ph |
| 1409. | 5-benzothiazolyl | 4-(1-methyltetrazol-5-yl)-5-Br-Ph |
| 1410. | 5-benzothiazolyl | 4-(1-methyltetrazol-5-yl)-3-CF3-Ph |
| 1411. | 5-benzothiazolyl | 4-(1-methyltetrazol-5-yl)-2-CH3O-Ph |
| 1412. | 5-benzothiazolyl | 4-(1-methyltetrazol-5-yl)-5-CH3O-Ph |
| 1413. | 5-benzothiazolyl | 3,5-bis(morpholin-1-yl)-Ph |
| 1414. | 5-benzothiazolyl | 3,5-bis(1,2,4-triazol-1-yl)-Ph |
| 1415. | 5-benzothiazolyl | 3,5-bis(pyrazol-1-yl)-Ph |
| 1416. | 5-benzothiazolyl | 3,5-bis(oxazol-2-yl)-Ph |
| 1417. | 5-benzothiazolyl | 3,5-bis(isoxazol-3-yl)-Ph |
| 1418. | 5-benzothiazolyl | 3,5-bis(isoxazol-5-yl)-Ph |
| 1419. | 5-benzoxazolyl | 3,5-bis(1,2,3-triazol-1-yl)-Ph |
| 1420. | 5-benzoxazolyl | 3,5-bis(COCH3)-Ph |
| 1421. | 5-benzoxazolyl | 3,5-bis(CH2OH)-Ph |
| 1422. | 4-F-Ph | 3-(imidazol-4-yl)-Ph |
| 1423. | 4-F-Ph | 3-(1-methyl-2-imidazolyl)-Ph |
| 1424. | 4-F-Ph | 3-(1-methyl-4-imidazolyl)-Ph |
| 1425. | 4-F-Ph | 3-(1-methyl-5-imidazolyl)-Ph |
| 1426. | 4-F-Ph | 3-(thiazol-4-yl)-Ph |
| 1427. | 4-F-Ph | 3-(thiazol-5-yl)-Ph |
| 1428. | 4-F-Ph | 3-(pyrazol-4-yl)-Ph |
| 1429. | 4-F-Ph | 3-(1-methyl-3-pyrazolyl)-Ph |
| 1430. | 4-F-Ph | 3-(1-methyl-4-pyrazolyl)-Ph |
| 1431. | 4-F-Ph | 3-(1-methyl-5-pyrazolyl)-Ph |
| 1432. | 4-F-Ph | 3-(3-pyridyl)-Ph |
| 1433. | 4-F-Ph | 3-(4-pyridyl)-Ph |
| 1434. | 4-F-Ph | 3-(3-thienyl)-Ph |
| 1435. | 4-F-Ph | 3-(3-furanyl)-Ph |
| 1436. | 4-F-Ph | 3-(1,2,4-triazol-1-yl)-Ph |
| 1437. | 4-F-Ph | 3-(1,2,4-triazol-4-yl)-Ph |
| 1438. | 4-F-Ph | 3-(1,2,3-triazol-1-yl)-Ph |
| 1439. | 4-F-Ph | 3-(1,2,3-triazol-4-yl)-Ph |
| 1440. | 4-F-Ph | 3-(1-methyl-1,2,4-triazol-3-yl)-Ph |
| 1441. | 4-F-Ph | 3-(1-methyl-1,2,4-triazol-5-yl)-Ph |
| 1442. | 4-F-Ph | 3-(1-methyl-1,2,3-triazol-4-yl)-Ph |
| 1443. | 4-F-Ph | 3-(1-methyl-1,2,3-triazol-5-yl)-Ph |
| 1444. | 4-F-Ph | 3-(3-isoxazolyl)-Ph |
| 1445. | 4-F-Ph | 3-(4-isoxazolyl)-Ph |
| 1446. | 4-F-Ph | 3-(5-isoxazolyl)-Ph |
| 1447. | 4-F-Ph | 3-(1-methyl-5-pyrazolyl)-Ph |
| 1448. | 4-F-Ph | 3-(1-ethyl-5-pyrazolyl)-Ph |
| 1449. | 4-F-Ph | 3-([1,3,4]-oxadiazol-2-yl)-Ph |
| 1450. | 4-F-Ph | 3-(CO—NH-(2-ethylpyrazol-3-yl))-Ph |
| 1451. | 4-F-Ph | 3-(CO—NH-(thiazol-2-yl))-Ph |
| 1452. | 4-F-Ph | 3-(CO—NH-(isoxazol-3-yl))-Ph |
| 1453. | 4-F-Ph | 5-acetyl-4-methylthiazol-2-yl |
| 1454. | 4-F-Ph | 5-acetyl-4-methyloxazol-2-yl |
| 1455. | 4-F-Ph | 5-acetyl-4-methylimidazol-2-yl |
| 1456. | 4-F-Ph | 3-acetyl-5-[(CH3)2N—CO]-Ph |
| 1457. | 4-F-Ph | 3-acetyl-5-[(CH3)NH—CO]-Ph |
| 1458. | 4-F-Ph | 3-acetyl-5-[H2N—CO]-Ph |
| 1459. | 4-F-Ph | 3-acetyl-5-[morpholin-1-yl-CO]-Ph |

| # | Col A | Col B |
|---|---|---|
| 1460. | 4-F-Ph | 3-acetyl-5-F-Ph |
| 1461. | 4-F-Ph | 3-acetyl-5-Cl-Ph |
| 1462. | 4-F-Ph | 3-acetyl-5-Br-Ph |
| 1463. | 4-F-Ph | 3-acetyl-4-F-Ph |
| 1464. | 4-F-Ph | 3-acetyl-4-Cl-Ph |
| 1465. | 4-F-Ph | 3-acetyl-4-Br-Ph |
| 1466. | 4-F-Ph | 3-acetyl-5-CF3-Ph |
| 1467. | 4-F-Ph | 3-acetyl-4-CF3-Ph |
| 1468. | 4-F-Ph | 3-acetyl-2-CH3O-Ph |
| 1469. | 4-F-Ph | 3-acetyl-4-CH3O-Ph |
| 1470. | 4-F-Ph | 3-acetyl-5-CH3O-Ph |
| 1471. | 4-F-Ph | 3-acetyl-6-CH3O-Ph |
| 1472. | 4-F-Ph | 3-acetyl-5-CH3-Ph |
| 1473. | 4-F-Ph | 3-acetyl-5-CH3CH2-Ph |
| 1474. | 4-F-Ph | 4-acetyl-5-[morpholin-1-yl-CO]-Ph |
| 1475. | 4-F-Ph | 4-acetyl-5-F-Ph |
| 1476. | 4-F-Ph | 4-acetyl-5-Cl-Ph |
| 1477. | 4-F-Ph | 4-acetyl-5-Br-Ph |
| 1478. | 4-F-Ph | 4-acetyl-3-CF3-Ph |
| 1479. | 4-F-Ph | 4-acetyl-2-CH3O-Ph |
| 1480. | 4-F-Ph | 4-acetyl-5-CH3O-Ph |
| 1481. | 4-F-Ph | 3-acetyl-5-(1-methyltetrazol-5-yl)-Ph |
| 1482. | 4-F-Ph | 3-acetyl-5-(1-ethyltetrazol-5-yl)-Ph |
| 1483. | 4-F-Ph | 3-acetyl-5-(1-cyclopropyltetrazol-5-yl)-Ph |
| 1484. | 4-F-Ph | 3-acetyl-5-(oxazol-2-yl)-Ph |
| 1485. | 4-F-Ph | 3-acetyl-5-(isoxazol-3-yl)-Ph |
| 1486. | 4-F-Ph | 3-acetyl-5-(isoxazol-5-yl)-Ph |
| 1487. | 4-F-Ph | 3-acetyl-5-(pyrazol-1-yl)-Ph |
| 1488. | 4-F-Ph | 3-acetyl-5-(1,2,4-triazol-1-yl)-Ph |
| 1489. | 4-F-Ph | 3-acetyl-5-(CH2OH)-Ph |
| 1490. | 4-F-Ph | 3-acetyl-5-(furan-2-yl)-Ph |
| 1491. | 4-F-Ph | 3-acetyl-5-(furan-3-yl)-Ph |
| 1492. | 4-F-Ph | 3-acetyl-5-(thien-2-yl)-Ph |
| 1493. | 4-F-Ph | 3-acetyl-5-(thien-3-yl)-Ph |
| 1494. | 4-F-Ph | 3-acetyl-5-CN-Ph |
| 1495. | 4-F-Ph | 3-acetyl-5-(CN)-Ph |
| 1496. | 4-F-Ph | 3-acetyl-5-(isopropyl)-Ph |
| 1497. | 4-F-Ph | 3-acetyl-5-(SO2NH2)-Ph |
| 1498. | 4-F-Ph | 3-acetyl-5-(CO-4-morpholine)-Ph |
| 1499. | 4-F-Ph | 3-isopropyl-5-(1-methyltetrazol-5-yl)-Ph |
| 1500. | 4-F-Ph | 3-SO2NH2-5-(1-methyltetrazol-5-yl)-Ph |
| 1501. | 4-F-Ph | 3,5-di(OMe)-Ph |
| 1502. | 4-F-Ph | 3,4,5-tri(Ome)-Ph |
| 1503. | 2-F-Ph | 3-(imidazol-4-yl)-Ph |
| 1504. | 2-F-Ph | 3-(1-methyl-2-imidazolyl)-Ph |
| 1505. | 2-F-Ph | 3-(1-methyl-4-imidazolyl)-Ph |
| 1506. | 2-F-Ph | 3-(1-methyl-5-imidazolyl)-Ph |
| 1507. | 2-F-Ph | 3-(thiazol-4-yl)-Ph |
| 1508. | 2-F-Ph | 3-(thiazol-5-yl)-Ph |
| 1509. | 2-F-Ph | 3-(pyrazol-4-yl)-Ph |
| 1510. | 2-F-Ph | 3-(1-methyl-3-pyrazolyl)-Ph |
| 1511. | 2-F-Ph | 3-(1-methyl-4-pyrazolyl)-Ph |
| 1512. | 2-F-Ph | 3-(1-methyl-5-pyrazolyl)-Ph |
| 1513. | 2-F-Ph | 3-(3-pyridyl)-Ph |
| 1514. | 2-F-Ph | 3-(4-pyridyl)-Ph |
| 1515. | 2-F-Ph | 3-(3-thienyl)-Ph |
| 1516. | 2-F-Ph | 3-(3-furanyl)-Ph |
| 1517. | 2-F-Ph | 3-(1,2,4-triazol-1-yl)-Ph |
| 1518. | 2-F-Ph | 3-(1,2,4-triazol-4-yl)-Ph |
| 1519. | 2-F-Ph | 3-(1,2,3-triazol-1-yl)-Ph |
| 1520. | 2-F-Ph | 3-(1,2,3-triazol-4-yl)-Ph |
| 1521. | 2-F-Ph | 3-(1-methyl-1,2,4-triazol-3-yl)-Ph |
| 1522. | 2-F-Ph | 3-(1-methyl-1,2,4-triazol-5-yl)-Ph |
| 1523. | 2-F-Ph | 3-(1-methyl-1,2,3-triazol-4-yl)-Ph |
| 1524. | 2-F-Ph | 3-(1-methyl-1,2,3-triazol-5-yl)-Ph |
| 1525. | 2-F-Ph | 3-(3-isoxazolyl)-Ph |
| 1526. | 2-F-Ph | 3-(4-isoxazolyl)-Ph |
| 1527. | 2-F-Ph | 3-(5-isoxazolyl)-Ph |
| 1528. | 2-F-Ph | 3-(1-methyl-5-pyrazolyl)-Ph |
| 1529. | 2-F-Ph | 3-(1-ethyl-5-pyrazolyl)-Ph |
| 1530. | 2-F-Ph | 3-([1,3,4]-oxadiazol-2-yl)-Ph |
| 1531. | 2-F-Ph | 3-(CO-NH-(2-ethylpyrazol-3-yl) )-Ph |
| 1532. | 2-F-Ph | 3-(CO-NH-(thiazol-2-yl))-Ph |
| 1533. | 2-F-Ph | 3-(CO-NH-(isoxazol-3-yl))-Ph |
| 1534. | 2-F-Ph | 5-acetyl-4-methylthiazol-2-yl |
| 1535. | 2-F-Ph | 5-acetyl-4-methyloxazol-2-yl |
| 1536. | 2-F-Ph | 5-acetyl-4-methylimidazol-2-yl |
| 1537. | 2-F-Ph | 3-acetyl-5-[(CH3)2N—CO]-Ph |
| 1538. | 2-F-Ph | 3-acetyl-5-[(CH3)NH—CO]-Ph |
| 1539. | 2-F-Ph | 3-acetyl-5-[H2N—CO]-Ph |
| 1540. | 2-F-Ph | 3-acetyl-5-[morpholin-1-yl-CO]-Ph |
| 1541. | 2-F-Ph | 3-acetyl-5-F-Ph |
| 1542. | 2-F-Ph | 3-acetyl-5-Cl-Ph |
| 1543. | 2-F-Ph | 3-acetyl-5-Br-Ph |
| 1544. | 2-F-Ph | 3-acetyl-4-F-Ph |
| 1545. | 2-F-Ph | 3-acetyl-4-Cl-Ph |
| 1546. | 2-F-Ph | 3-acetyl-4-Br-Ph |
| 1547. | 2-F-Ph | 3-acetyl-5-CF3-Ph |
| 1548. | 2-F-Ph | 3-acetyl-4-CF3-Ph |
| 1549. | 2-F-Ph | 2-F-Ph3-acetyl-2-CH3O-Ph |
| 1550. | 2-F-Ph | 3-acetyl-4-CH3O-Ph |
| 1551. | 2-F-Ph | 3-acetyl-5-CH3O-Ph |
| 1552. | 2-F-Ph | 3-acetyl-6-CH3O-Ph |
| 1553. | 2-F-Ph | 3-acetyl-5-CH3-Ph |
| 1554. | 2-F-Ph | 3-acetyl-5-CH3CH2-Ph |
| 1555. | 2-F-Ph | 4-acetyl-5-[morpholin-1-yl-CO]-Ph |
| 1556. | 2-F-Ph | 4-acetyl-5-F-Ph |
| 1557. | 2-F-Ph | 4-acetyl-5-Cl-Ph |
| 1558. | 2-F-Ph | 4-acetyl-5-Br-Ph |
| 1559. | 2-F-Ph | 4-acetyl-3-CF3-Ph |
| 1560. | 2-F-Ph | 4-acetyl-2-CH3O-Ph |
| 1561. | 2-F-Ph | 4-acetyl-5-CH3O-Ph |
| 1562. | 2-F-Ph | 3-acetyl-5-(1-methyltetrazol-5-yl)-Ph |
| 1563. | 2-F-Ph | 3-acetyl-5-(1-ethyltetrazol-5-yl)-Ph |
| 1564. | 2-F-Ph | 3-acetyl-5-(1-cyclopropyltetrazol-5-yl)-Ph |
| 1565. | 2-F-Ph | 3-acetyl-5-(oxazol-2-yl)-Ph |
| 1566. | 2-F-Ph | 3-acetyl-5-(isoxazol-3-yl)-Ph |
| 1567. | 2-F-Ph | 3-acetyl-5-(isoxazol-5-yl)-Ph |
| 1568. | 2-F-Ph | 3-acetyl-5-(pyrazol-1-yl)-Ph |
| 1569. | 2-F-Ph | 3-acetyl-5-(1,2,4-triazol-1-yl)-Ph |
| 1570. | 2-F-Ph | 3-acetyl-5-(CH2OH)-Ph |
| 1571. | 2-F-Ph | 3-acetyl-5-(furan-2-yl)-Ph |
| 1572. | 2-F-Ph | 3-acetyl-5-(furan-3-yl)-Ph |
| 1573. | 2-F-Ph | 3-acetyl-5-(thien-2-yl)-Ph |
| 1574. | 2-F-Ph | 3-acetyl-5-(thien-3-yl)-Ph |
| 1575. | 2-F-Ph | 3-acetyl-5-CN-Ph |
| 1576. | 2-F-Ph | 3-acetyl-5-(CN)-Ph |
| 1577. | 2-F-Ph | 3-acetyl-5-(isopropyl)-Ph |
| 1578. | 2-F-Ph | 3-acetyl-5-(SO2NH2)-Ph |
| 1579. | 2-F-Ph | 3-acetyl-5-(CO-4-morpholine)-Ph |
| 1580. | 2-F-Ph | 3-isopropyl-5-(1-methyltetrazol-5-yl)-Ph |
| 1581. | 2-F-Ph | 3-SO2NH2-5-(1-methyltetrazol-5-yl)-Ph |
| 1582. | 2-F-Ph | 3,5-di(OMe)-Ph |
| 1583. | 2-F-Ph | 3,4,5-tri(Ome)-Ph |
| 1584. | 2,4-diF-Ph | 3-(imidazol-4-yl)-Ph |
| 1585. | 2,4-diF-Ph | 3-(1-methyl-2-imidazolyl)-Ph |
| 1586. | 2,4-diF-Ph | 3-(1-methyl-4-imidazolyl)-Ph |
| 1587. | 2,4-diF-Ph | 3-(1-methyl-5-imidazolyl)-Ph |
| 1588. | 2,4-diF-Ph | 3-(thiazol-4-yl)-Ph |
| 1589. | 2,4-diF-Ph | 3-(thiazol-5-yl)-Ph |
| 1590. | 2,4-diF-Ph | 3-(pyrazol-4-yl)-Ph |
| 1591. | 2,4-diF-Ph | 3-(1-methyl-3-pyrazolyl)-Ph |
| 1592. | 2,4-diF-Ph | 3-(1-methyl-4-pyrazolyl)-Ph |
| 1593. | 2,4-diF-Ph | 3-(1-methyl-5-pyrazolyl)-Ph |
| 1594. | 2,4-diF-Ph | 3-(3-pyridyl)-Ph |
| 1595. | 2,4-diF-Ph | 3-(4-pyridyl)-Ph |
| 1596. | 2,4-diF-Ph | 3-(3-thienyl)-Ph |
| 1597. | 2,4-diF-Ph | 3-(3-furanyl)-Ph |
| 1598. | 2,4-diF-Ph | 3-(1,2,4-triazol-1-yl)-Ph |
| 1599. | 2,4-diF-Ph | 3-(1,2,4-triazol-4-yl)-Ph |
| 1600. | 2,4-diF-Ph | 3-(1,2,3-triazol-1-yl)-Ph |
| 1601. | 2,4-diF-Ph | 3-(1,2,3-triazol-4-yl)-Ph |

| # | Col1 | Col2 | | # | Col1 | Col2 |
|---|---|---|---|---|---|---|
| 1602. | 2,4-diF-Ph | 3-(1-methyl-1,2,4-triazol-3-yl)-Ph | | 1670. | 4-Cl-Ph | 3-(thiazol-5-yl)-Ph |
| 1603. | 2,4-diF-Ph | 3-(1-methyl-1,2,4-triazol-5-yl)-Ph | | 1671. | 4-Cl-Ph | 3-(pyrazol-4-yl)-Ph |
| 1604. | 2,4-diF-Ph | 3-(1-methyl-1,2,3-triazol-4-yl)-Ph | | 1672. | 4-Cl-Ph | 3-(1-methyl-3-pyrazolyl)-Ph |
| | | | | 1673. | 4-Cl-Ph | 3-(1-methyl-4-pyrazolyl)-Ph |
| 1605. | 2,4-diF-Ph | 3-(1-methyl-1,2,3-triazol-5-yl)-Ph | | 1674. | 4-Cl-Ph | 3-(1-methyl-5-pyrazolyl)-Ph |
| | | | | 1675. | 4-Cl-Ph | 3-(3-pyridyl)-Ph |
| 1606. | 2,4-diF-Ph | 3-(3-isoxazolyl)-Ph | | 1676. | 4-Cl-Ph | 3-(4-pyridyl)-Ph |
| 1607. | 2,4-diF-Ph | 3-(4-isoxazolyl)-Ph | | 1677. | 4-Cl-Ph | 3-(3-thienyl)-Ph |
| 1608. | 2,4-diF-Ph | 3-(5-isoxazolyl)-Ph | | 1678. | 4-Cl-Ph | 3-(3-furanyl)-Ph |
| 1609. | 2,4-diF-Ph | 3-(1-methyl-5-pyrazolyl)-Ph | | 1679. | 4-Cl-Ph | 3-(1,2,4-triazol-1-yl)-Ph |
| 1610. | 2,4-diF-Ph | 3-(1-ethyl-5-pyrazolyl)-Ph | | 1680. | 4-Cl-Ph | 3-(1,2,4-triazol-4-yl)-Ph |
| 1611. | 2,4-diF-Ph | 3-([1,3,4]-oxadiazol-2-yl)-Ph | | 1681. | 4-Cl-Ph | 3-(1,2,3-triazol-1-yl)-Ph |
| 1612. | 2,4-diF-Ph | 3-(CO—NH-(2-ethylpyrazol-3-yl)-Ph | | 1682. | 4-Cl-Ph | 3-(1,2,3-triazol-4-yl)-Ph |
| | | | | 1683. | 4-Cl-Ph | 3-(1-methyl-1,2,4-triazol-3-yl)-Ph |
| 1613. | 2,4-diF-Ph | 3-(CO—NH-(thiazol-2-yl))-Ph | | 1684. | 4-Cl-Ph | 3-(1-methyl-1,2,4-triazol-5-yl)-Ph |
| 1614. | 2,4-diF-Ph | 3-(CO—NH-(isoxazol-3-yl))-Ph | | | | |
| 1615. | 2,4-diF-Ph | 5-acetyl-4-methylthiazol-2-yl | | 1685. | 4-Cl-Ph | 3-(1-methyl-1,2,3-triazol-4-yl)-Ph |
| 1616. | 2,4-diF-Ph | 5-acetyl-4-methyloxazol-2-yl | | | | |
| 1617. | 2,4-diF-Ph | 5-acetyl-4-methylimidazol-2-yl | | 1686. | 4-Cl-Ph | 3-(1-methyl-1,2,3-triazol-5-yl)-Ph |
| 1618. | 2,4-diF-Ph | 3-acetyl-5-[(CH3)2N—CO]-Ph | | | | |
| 1619. | 2,4-diF-Ph | 3-acetyl-5-[(CH3)NH—CO]-Ph | | 1687. | 4-Cl-Ph | 3-(3-isoxazolyl)-Ph |
| 1620. | 2,4-diF-Ph | 3-acetyl-5-[H2N—CO]-Ph | | 1688. | 4-Cl-Ph | 3-(4-isoxazolyl)-Ph |
| 1621. | 2,4-diF-Ph | 3-acetyl-5-[morpholin-1-yl-CO]-Ph | | 1689. | 4-Cl-Ph | 3-(5-isoxazolyl)-Ph |
| | | | | 1690. | 4-Cl-Ph | 3-(1-methyl-5-pyrazolyl)-Ph |
| | | | | 1691. | 4-Cl-Ph | 3-(1-ethyl-5-pyrazolyl)-Ph |
| 1622. | 2,4-diF-Ph | 3-acetyl-5-F-Ph | | 1692. | 4-Cl-Ph | 3-([1,3,4]-oxadiazol-2-yl)-Ph |
| 1623. | 2,4-diF-Ph | 3-acetyl-5-Cl-Ph | | 1693. | 4-Cl-Ph | 3-(CO-NH-(2-ethylpyrazol-3-yl))-Ph |
| 1624. | 2,4-diF-Ph | 3-acetyl-5-Br-Ph | | | | |
| 1625. | 2,4-diF-Ph | 3-acetyl-4-F-Ph | | 1694. | 4-Cl-Ph | 3-(CO-NH-(thiazol-2-yl))-Ph |
| 1626. | 2,4-diF-Ph | 3-acetyl-4-Cl-Ph | | 1695. | 4-Cl-Ph | 3-(CO-NH-(isoxazol-3-yl))-Ph |
| 1627. | 2,4-diF-Ph | 3-acetyl-4-Br-Ph | | 1696. | 4-Cl-Ph | 5-acetyl-4-methylthiazol-2-yl |
| 1628. | 2,4-diF-Ph | 3-acetyl-5-CF3-Ph | | 1697. | 4-Cl-Ph | 5-acetyl-4-methyloxazol-2-yl |
| 1629. | 2,4-diF-Ph | 3-acetyl-4-CF3-Ph | | 1698. | 4-Cl-Ph | 5-acetyl-4-methylimidazol-2-yl |
| 1630. | 2,4-diF-Ph | 2-F-Ph 3-acetyl-2-CH3O-Ph | | 1699. | 4-Cl-Ph | 3-acetyl-5-[(CH3)2N—CO]-Ph |
| 1631. | 2,4-diF-Ph | 3-acetyl-4-CH3O-Ph | | 1700. | 4-Cl-Ph | 3-acetyl-5-[(CH3)NH—CO]-Ph |
| 1632. | 2,4-diF-Ph | 3-acetyl-5-CH3O-Ph | | 1701. | 4-Cl-Ph | 3-acetyl-5-[H2N—CO]-Ph |
| 1633. | 2,4-diF-Ph | 3-acetyl-6-CH3O-Ph | | 1702. | 4-Cl-Ph | 3-acetyl-5-[morpholin-1-yl-CO]-Ph |
| 1634. | 2,4-diF-Ph | 3-acetyl-5-CH3-Ph | | | | |
| 1635. | 2,4-diF-Ph | 3-acetyl-5-CH3CH2-Ph | | 1703. | 4-Cl-Ph | 3-acetyl-5-F-Ph |
| 1636. | 2,4-diF-Ph | 4-acetyl-5-[morpholin-1-yl-CO]-Ph | | 1704. | 4-Cl-Ph | 3-acetyl-5-Cl-Ph |
| | | | | 1705. | 4-Cl-Ph | 3-acetyl-5-Br-Ph |
| 1637. | 2,4-diF-Ph | 4-acetyl-5-F-Ph | | 1706. | 4-Cl-Ph | 3-acetyl-4-F-Ph |
| 1638. | 2,4-diF-Ph | 4-acetyl-5-Cl-Ph | | 1707. | 4-Cl-Ph | 3-acetyl-4-Cl-Ph |
| 1639. | 2,4-diF-Ph | 4-acetyl-5-Br-Ph | | 1708. | 4-Cl-Ph | 3-acetyl-4-Br-Ph |
| 1640. | 2,4-diF-Ph | 4-acetyl-3-CF3-Ph | | 1709. | 4-Cl-Ph | 3-acetyl-5-CF3-Ph |
| 1641. | 2,4-diF-Ph | 4-acetyl-2-CH3O-Ph | | 1710. | 4-Cl-Ph | 3-acetyl-4-CF3-Ph |
| 1642. | 2,4-diF-Ph | 4-acetyl-5-CH3O-Ph | | 1711. | 4-Cl-Ph | 2-F-Ph 3-acetyl-2-CH3O-Ph |
| 1643. | 2,4-diF-Ph | 3-acetyl-5-(1-methyltetrazol-5-yl)-Ph | | 1712. | 4-Cl-Ph | 3-acetyl-4-CH3O-Ph |
| | | | | 1713. | 4-Cl-Ph | 3-acetyl-5-CH3O-Ph |
| 1644. | 2,4-diF-Ph | 3-acetyl-5-(1-ethyltetrazol-5-yl)-Ph | | 1714. | 4-Cl-Ph | 3-acetyl-6-CH3O-Ph |
| | | | | 1715. | 4-Cl-Ph | 3-acetyl-5-CH3-Ph |
| 1645. | 2,4-diF-Ph | 3-acetyl-5-(1-cyclopropyltetrazol-5-yl)-Ph | | 1716. | 4-Cl-Ph | 3-acetyl-5-CH3CH2-Ph |
| | | | | 1717. | 4-Cl-Ph | 4-acetyl-5-[morpholin-1-yl-CO]-Ph |
| 1646. | 2,4-diF-Ph | 3-acetyl-5-(oxazol-2-yl)-Ph | | | | |
| 1647. | 2,4-diF-Ph | 3-acetyl-5-(isoxazol-3-yl)-Ph | | 1718. | 4-Cl-Ph | 4-acetyl-5-F-Ph |
| 1648. | 2,4-diF-Ph | 3-acetyl-5-(isoxazol-5-yl)-Ph | | 1719. | 4-Cl-Ph | 4-acetyl-5-Cl-Ph |
| 1649. | 2,4-diF-Ph | 3-acetyl-5-(pyrazol-1-yl)-Ph | | 1720. | 4-Cl-Ph | 4-acetyl-5-Br-Ph |
| 1650. | 2,4-diF-Ph | 3-acetyl-5-(1,2,4-triazol-1-yl)-Ph | | 1721. | 4-Cl-Ph | 4-acetyl-3-CF3-Ph |
| | | | | 1722. | 4-Cl-Ph | 4-acetyl-2-CH3O-Ph |
| 1651. | 2,4-diF-Ph | 3-acetyl-5-(CH2OH)-Ph | | 1723. | 4-Cl-Ph | 4-acetyl-5-CH3O-Ph |
| 1652. | 2,4-diF-Ph | 3-acetyl-5-(furan-2-yl)-Ph | | 1724. | 4-Cl-Ph | 3-acetyl-5-(1-methyltetrazol-5-yl)-Ph |
| 1653. | 2,4-diF-Ph | 3-acetyl-5-(furan-3-yl)-Ph | | | | |
| 1654. | 2,4-diF-Ph | 3-acetyl-5-(thien-2-yl)-Ph | | 1725. | 4-Cl-Ph | 3-acetyl-5-(1-ethyltetrazol-5-yl)-Ph |
| 1655. | 2,4-diF-Ph | 3-acetyl-5-(thien-3-yl)-Ph | | | | |
| 1656. | 2,4-diF-Ph | 3-acetyl-5-CN-Ph | | 1726. | 4-Cl-Ph | 3-acetyl-5-(1-cyclopropyltetrazol-5-yl)-Ph |
| 1657. | 2,4-diF-Ph | 3-acetyl-5-(CN)-Ph | | | | |
| 1658. | 2,4-diF-Ph | 3-acetyl-5-(isopropyl)-Ph | | 1727. | 4-Cl-Ph | 3-acetyl-5-(oxazol-2-yl)-Ph |
| 1659. | 2,4-diF-Ph | 3-acetyl-5-(SO2NH2)-Ph | | 1728. | 4-Cl-Ph | 3-acetyl-5-(isoxazol-3-yl)-Ph |
| 1660. | 2,4-diF-Ph | 3-acetyl-5-(CO-4-morpholine)-Ph | | 1729. | 4-Cl-Ph | 3-acetyl-5-(isoxazol-5-yl)-Ph |
| | | | | 1730. | 4-Cl-Ph | 3-acetyl-5-(pyrazol-1-yl)-Ph |
| 1661. | 2,4-diF-Ph | 3-isopropyl-5-(1-methyltetrazol-5-yl)-Ph | | 1731. | 4-Cl-Ph | 3-acetyl-5-(1,2,4-triazol-1-yl)-Ph |
| 1662. | 2,4-diF-Ph | 3-SO2NH2-5-(1-methyltetrazol-5-yl)-Ph | | 1732. | 4-Cl-Ph | 3-acetyl-5-(CH2OH)-Ph |
| | | | | 1733. | 4-Cl-Ph | 3-acetyl-5-(furan-2-yl)-Ph |
| 1663. | 2,4-diF-Ph | 3,5-di(OMe)-Ph | | 1734. | 4-Cl-Ph | 3-acetyl-5-(furan-3-yl)-Ph |
| 1664. | 2,4-diF-Ph | 3,4,5-tri(OMe)-Ph | | 1735. | 4-Cl-Ph | 3-acetyl-5-(thien-2-yl)-Ph |
| 1665. | 4-Cl-Ph | 3-(imidazol-4-yl)-Ph | | 1736. | 4-Cl-Ph | 3-acetyl-5-(thien-3-yl)-Ph |
| 1666. | 4-Cl-Ph | 3-(1-methyl-2-imidazolyl)-Ph | | 1737. | 4-Cl-Ph | 3-acetyl-5-CN-Ph |
| 1667. | 4-Cl-Ph | 3-(1-methyl-4-imidazolyl)-Ph | | 1738. | 4-Cl-Ph | 3-acetyl-5-(CN)-Ph |
| 1668. | 4-Cl-Ph | 3-(1-methyl-5-imidazolyl)-Ph | | 1739. | 4-Cl-Ph | 3-acetyl-5-(isopropyl)-Ph |
| 1669. | 4-Cl-Ph | 3-(thiazol-4-yl)-Ph | | 1740. | 4-Cl-Ph | 3-acetyl-5-(SO2NH2)-Ph |

| # | R | R' |
|---|---|---|
| 1741. | 4-Cl-Ph | 3-acetyl-5-(CO-4-morpholine)-Ph |
| 1742. | 4-Cl-Ph | 3-isopropyl-5-(1-methyltetrazol-5-yl)-Ph |
| 1743. | 4-Cl-Ph | 3-SO2NH2-5-(1-methyltetrazol-5-yl)-Ph |
| 1744. | 4-Cl-Ph | 3,5-di(OMe)-Ph |
| 1745. | 4-Cl-Ph | 3,4,5-tri(Ome)-Ph |
| 1746. | 2-Cl-Ph | 3-(imidazol-4-yl)-Ph |
| 1747. | 2-Cl-Ph | 3-(1-methyl-2-imidazolyl)-Ph |
| 1748. | 2-Cl-Ph | 3-(1-methyl-4-imidazolyl)-Ph |
| 1749. | 2-Cl-Ph | 3-(1-methyl-5-imidazolyl)-Ph |
| 1750. | 2-Cl-Ph | 3-(thiazol-4-yl)-Ph |
| 1751. | 2-Cl-Ph | 3-(thiazol-5-yl)-Ph |
| 1752. | 2-Cl-Ph | 3-(pyrazol-4-yl)-Ph |
| 1753. | 2-Cl-Ph | 3-(1-methyl-3-pyrazolyl)-Ph |
| 1754. | 2-Cl-Ph | 3-(1-methyl-4-pyrazolyl)-Ph |
| 1755. | 2-Cl-Ph | 3-(1-methyl-5-pyrazolyl)-Ph |
| 1756. | 2-Cl-Ph | 3-(3-pyridyl)-Ph |
| 1757. | 2-Cl-Ph | 3-(4-pyridyl)-Ph |
| 1758. | 2-Cl-Ph | 3-(3-thienyl)-Ph |
| 1759. | 2-Cl-Ph | 3-(3-furanyl)-Ph |
| 1760. | 2-Cl-Ph | 3-(1,2,4-triazol-1-yl)-Ph |
| 1761. | 2-Cl-Ph | 3-(1,2,4-triazol-4-yl)-Ph |
| 1762. | 2-Cl-Ph | 3-(1,2,3-triazol-1-yl)-Ph |
| 1763. | 2-Cl-Ph | 3-(1,2,3-triazol-4-yl)-Ph |
| 1764. | 2-Cl-Ph | 3-(1-methyl-1,2,4-triazol-3-yl)-Ph |
| 1765. | 2-Cl-Ph | 3-(1-methyl-1,2,4-triazol-5-yl)-Ph |
| 1766. | 2-Cl-Ph | 3-(1-methyl-1,2,3-triazol-4-yl)-Ph |
| 1767. | 2-Cl-Ph | 3-(1-methyl-1,2,3-triazol-5-yl)-Ph |
| 1768. | 2-Cl-Ph | 3-(3-isoxazolyl)-Ph |
| 1769. | 2-Cl-Ph | 3-(4-isoxazolyl)-Ph |
| 1770. | 2-Cl-Ph | 3-(5-isoxazolyl)-Ph |
| 1771. | 2-Cl-Ph | 3-(1-methyl-5-pyrazolyl)-Ph |
| 1772. | 2-Cl-Ph | 3-(1-ethyl-5-pyrazolyl)-Ph |
| 1773. | 2-Cl-Ph | 3-([1,3,4]-oxadiazol-2-yl)-Ph |
| 1774. | 2-Cl-Ph | 3-(CO—NH-(2-methylpyrazol-3-yl))-Ph |
| 1775. | 2-Cl-Ph | 3-(CO—NH-(thiazol-2-yl))-Ph |
| 1776. | 2-Cl-Ph | 3-(CO—NH-(isoxazol-3-yl))-Ph |
| 1777. | 2-Cl-Ph | 5-acetyl-4-methylthiazol-2-yl |
| 1778. | 2-Cl-Ph | 5-acetyl-4-methyloxazol-2-yl |
| 1779. | 2-Cl-Ph | 5-acetyl-4-methylimidazol-2-yl |
| 1780. | 2-Cl-Ph | 3-acetyl-5-[(CH3)2N—CO]-Ph |
| 1781. | 2-Cl-Ph | 3-acetyl-5-[(CH3)NH—CO]-Ph |
| 1782. | 2-Cl-Ph | 3-acetyl-5-[H2N—CO]-Ph |
| 1783. | 2-Cl-Ph | 3-acetyl-5-[morpholin-1-yl-CO]-Ph |
| 1784. | 2-Cl-Ph | 3-acetyl-5-F-Ph |
| 1785. | 2-Cl-Ph | 3-acetyl-5-Cl-Ph |
| 1786. | 2-Cl-Ph | 3-acetyl-5-Br-Ph |
| 1787. | 2-Cl-Ph | 3-acetyl-4-F-Ph |
| 1788. | 2-Cl-Ph | 3-acetyl-4-Cl-Ph |
| 1789. | 2-Cl-Ph | 3-acetyl-4-Br-Ph |
| 1790. | 2-Cl-Ph | 3-acetyl-5-CF3-Ph |
| 1791. | 2-Cl-Ph | 3-acetyl-4-CF3-Ph |
| 1792. | 2-Cl-Ph | 2-F-Ph 3-acetyl-2-CH3O-Ph |
| 1793. | 2-Cl-Ph | 3-acetyl-4-CH3O-Ph |
| 1794. | 2-Cl-Ph | 3-acetyl-5-CH3O-Ph |
| 1795. | 2-Cl-Ph | 3-acetyl-6-CH3O-Ph |
| 1796. | 2-Cl-Ph | 3-acetyl-5-CH3-Ph |
| 1797. | 2-Cl-Ph | 3-acetyl-5-CH3CH2-Ph |
| 1798. | 2-Cl-Ph | 4-acetyl-5-[morpholin-1-yl-CO]-Ph |
| 1799. | 2-Cl-Ph | 4-acetyl-5-F-Ph |
| 1800. | 2-Cl-Ph | 4-acetyl-5-Cl-Ph |
| 1801. | 2,4-diCl-Ph | 4-acetyl-5-Br-Ph |
| 1802. | 2,4-diCl-Ph | 4-acetyl-3-CF3-Ph |
| 1803. | 2,4-diCl-Ph | 4-acetyl-2-CH3O-Ph |
| 1804. | 2,4-diCl-Ph | 4-acetyl-5-CH3O-Ph |
| 1805. | 2,4-diCl-Ph | 3-acetyl-5-(1-methyltetrazol-5-yl)-Ph |
| 1806. | 2,4-diCl-Ph | 3-acetyl-5-(1-ethyltetrazol-5-yl)-Ph |
| 1807. | 2,4-diCl-Ph | 3-acetyl-5-(1-cyclopropyltetrazol-5-yl)-Ph |
| 1808. | 2,4-diCl-Ph | 3-acetyl-5-(oxazol-2-yl)-Ph |
| 1809. | 2,4-diCl-Ph | 3-acetyl-5-(isoxazol-3-yl)-Ph |
| 1810. | 2,4-diCl-Ph | 3-acetyl-5-(isoxazol-5-yl)-Ph |
| 1811. | 2,4-diCl-Ph | 3-acetyl-5-(pyrazol-1-yl)-Ph |
| 1812. | 2,4-diCl-Ph | 3-acetyl-5-(1,2,4-triazol-1-yl)-Ph |
| 1813. | 2,4-diCl-Ph | 3-acetyl-5-(CH2OH)-Ph |
| 1814. | 2,4-diCl-Ph | 3-acetyl-5-(furan-2-yl)-Ph |
| 1815. | 2,4-diCl-Ph | 3-acetyl-5-(furan-3-yl)-Ph |
| 1816. | 2,4-diCl-Ph | 3-acetyl-5-(thien-2-yl)-Ph |
| 1817. | 2,4-diCl-Ph | 3-acetyl-5-(thien-3-yl)-Ph |
| 1818. | 2,4-diCl-Ph | 3-acetyl-5-CN-Ph |
| 1819. | 2,4-diCl-Ph | 3-acetyl-5-(CN)-Ph |
| 1820. | 2,4-diCl-Ph | 3-acetyl-5-(isopropyl)-Ph |
| 1821. | 2,4-diCl-Ph | 3-acetyl-5-(SO2NH2)-Ph |
| 1822. | 2,4-diCl-Ph | 3-acetyl-5-(CO-4-morpholine)-Ph |
| 1823. | 2,4-diCl-Ph | 3-isopropyl-5-(1-methyltetrazol-5-yl)-Ph |
| 1824. | 2,4-diCl-Ph | 3-SO2NH2-5-(1-methyltetrazol-5-yl)-Ph |
| 1825. | 2,4-diCl-Ph | 3,5-di(OMe)-Ph |
| 1826. | 2,4-diCl-Ph | 3,4,5-tri(Ome)-Ph |
| 1827. | 3-OCH3-Ph | 3-(imidazol-4-yl)-Ph |
| 1828. | 3-OCH3-Ph | 3-(1-methyl-2-imidazolyl)-Ph |
| 1829. | 3-OCH3-Ph | 3-(1-methyl-4-imidazolyl)-Ph |
| 1830. | 3-OCH3-Ph | 3-(1-methyl-5-imidazolyl)-Ph |
| 1831. | 3-OCH3-Ph | 3-(thiazol-4-yl)-Ph |
| 1832. | 3-OCH3-Ph | 3-(thiazol-5-yl)-Ph |
| 1833. | 3-OCH3-Ph | 3-(pyrazol-4-yl)-Ph |
| 1834. | 3-OCH3-Ph | 3-(1-methyl-3-pyrazolyl)-Ph |
| 1835. | 3-OCH3-Ph | 3-(1-methyl-4-pyrazolyl)-Ph |
| 1836. | 3-OCH3-Ph | 3-(1-methyl-5-pyrazolyl)-Ph |
| 1837. | 3-OCH3-Ph | 3-(3-pyridyl)-Ph |
| 1838. | 3-OCH3-Ph | 3-(4-pyridyl)-Ph |
| 1839. | 3-OCH3-Ph | 3-(3-thienyl)-Ph |
| 1840. | 3-OCH3-Ph | 3-(3-furanyl)-Ph |
| 1841. | 3-OCH3-Ph | 3-(1,2,4-triazol-1-yl)-Ph |
| 1842. | 3-OCH3-Ph | 3-(1,2,4-triazol-4-yl)-Ph |
| 1843. | 3-OCH3-Ph | 3-(1,2,3-triazol-1-yl)-Ph |
| 1844. | 3-OCH3-Ph | 3-(1,2,3-triazol-4-yl)-Ph |
| 1845. | 3-OCH3-Ph | 3-(1-methyl-1,2,4-triazol-3-yl)-Ph |
| 1846. | 3-OCH3-Ph | 3-(1-methyl-1,2,4-triazol-5-yl)-Ph |
| 1847. | 3-OCH3-Ph | 3-(1-methyl-1,2,3-triazol-4-yl)-Ph |
| 1848. | 3-OCH3-Ph | 3-(1-methyl-1,2,3-triazol-5-yl)-Ph |
| 1849. | 3-OCH3-Ph | 3-(3-isoxazolyl)-Ph |
| 1850. | 3-OCH3-Ph | 3-(4-isoxazolyl)-Ph |
| 1851. | 3-OCH3-Ph | 3-(5-isoxazolyl)-Ph |
| 1852. | 3-OCH3-Ph | 3-(1-methyl-5-pyrazolyl)-Ph |
| 1853. | 3-OCH3-Ph | 3-(1-ethyl-5-pyrazolyl)-Ph |
| 1854. | 3-OCH3-Ph | 3-([1,3,4]-oxadiazol-2-yl)-Ph |
| 1855. | 3-OCH3-Ph | 3-(CO—NH-(2-ethylpyrazol-3-yl))-Ph |
| 1856. | 3-OCH3-Ph | 3-(CO—NH-(thiazol-2-yl))-Ph |
| 1857. | 3-OCH3-Ph | 3-(CO—NH-(isoxazol-3-yl))-Ph |
| 1858. | 3-OCH3-Ph | 5-acetyl-4-methylthiazol-2-yl |
| 1859. | 3-OCH3-Ph | 5-acetyl-4-methyloxazol-2-yl |
| 1860. | 3-OCH3-Ph | 5-acetyl-4-methylimidazol-2-yl |
| 1861. | 3-OCH3-Ph | 3-acetyl-5-[(CH3)2N—CO]-Ph |
| 1862. | 3-OCH3-Ph | 3-acetyl-5-((CH3)NH—CO]-Ph |
| 1863. | 3-OCH3-Ph | 3-acetyl-5-[H2N—CO]-Ph |
| 1864. | 3-OCH3-Ph | 3-acetyl-5-[morpholin-1-yl-CO]-Ph |
| 1865. | 3-OCH3-Ph | 3-acetyl-5-F-Ph |
| 1866. | 3-OCH3-Ph | 3-acetyl-5-Cl-Ph |
| 1867. | 3-OCH3-Ph | 3-acetyl-5-Br-Ph |
| 1868. | 3-OCH3-Ph | 3-acetyl-4-F-Ph |
| 1869. | 3-OCH3-Ph | 3-acetyl-4-Cl-Ph |
| 1870. | 3-OCH3-Ph | 3-acetyl-4-Br-Ph |
| 1871. | 3-OCH3-Ph | 3-acetyl-5-CF3-Ph |
| 1872. | 3-OCH3-Ph | 3-acetyl-4-CF3-Ph |
| 1873. | 3-OCH3-Ph | 2-F-Ph 3-acetyl-2-CH3O-Ph |
| 1874. | 3-OCH3-Ph | 3-acetyl-4-CH3O-Ph |
| 1875. | 3-OCH3-Ph | 3-acetyl-5-CH3O-Ph |
| 1876. | 3-OCH3-Ph | 3-acetyl-6-CH3O-Ph |
| 1877. | 3-OCH3-Ph | 3-acetyl-5-CH3-Ph |
| 1878. | 3-OCH3-Ph | 3-acetyl-5-CH3CH2-Ph |
| 1879. | 3-OCH3-Ph | 4-acetyl-5-[morpholin-1-yl-CO]-Ph |

| # | Col A | Col B |
|---|---|---|
| 1880. | 3-OCH3-Ph | 4-acetyl-5-F-Ph |
| 1881. | 3-OCH3-Ph | 4-acetyl-5-Cl-Ph |
| 1882. | 2-thienyl | 4-acetyl-5-Br-Ph |
| 1883. | 2-thienyl | 4-acetyl-3-CF3-Ph |
| 1884. | 2-thienyl | 4-acetyl-2-CH3O-Ph |
| 1885. | 2-thienyl | 4-acetyl-5-CH3O-Ph |
| 1886. | 2-thienyl | 3-acetyl-5-(1-methyltetrazol-5-yl)-Ph |
| 1887. | 2-thienyl | 3-acetyl-5-(1-ethyltetrazol-5-yl)-Ph |
| 1888. | 2-thienyl | 3-acetyl-5-(1-cyclopropyltetrazol-5-yl)-Ph |
| 1889. | 2-thienyl | 3-acetyl-5-(oxazol-2-yl)-Ph |
| 1890. | 2-thienyl | 3-acetyl-5-(isoxazol-3-yl)-Ph |
| 1891. | 2-thienyl | 3-acetyl-5-(isoxazol-5-yl)-Ph |
| 1892. | 2-thienyl | 3-acetyl-5-(pyrazol-1-yl)-Ph |
| 1893. | 2-thienyl | 3-acetyl-5-(1,2,4-triazol-1-yl)-Ph |
| 1894. | 2-thienyl | 3-acetyl-5-(CH2OH)-Ph |
| 1895. | 2-thienyl | 3-acetyl-5-(furan-2-yl)-Ph |
| 1896. | 2-thienyl | 3-acetyl-5-(furan-3-yl)-Ph |
| 1897. | 2-thienyl | 3-acetyl-5-(thien-2-yl)-Ph |
| 1898. | 2-thienyl | 3-acetyl-5-(thien-3-yl)-Ph |
| 1899. | 2-thienyl | 3-acetyl-5-CN-Ph |
| 1900. | 2-thienyl | 3-acetyl-5-(CN)-Ph |
| 1901. | 2-thienyl | 3-acetyl-5-(isopropyl)-Ph |
| 1902. | 2-thienyl | 3-acetyl-5-(SO2NH2)-Ph |
| 1903. | 2-thienyl | 3-acetyl-5-(CO-4-morpholine)-Ph |
| 1904. | 3-thienyl | 3-isopropyl-5-(1-methyltetrazol-5-yl)-Ph |
| 1905. | 3-thienyl | 3-SO2NH2-5-(1-methyltetrazol-5-yl)-Ph |
| 1906. | 3-thienyl | 3,5-di(OMe)-Ph |
| 1907. | 3-thienyl | 3,4,5-tri(Ome)-Ph |
| 1908. | 2-furanyl | 3-(imidazol-4-yl)-Ph |
| 1909. | 2-furanyl | 3-(1-methyl-2-imidazolyl)-Ph |
| 1910. | 2-furanyl | 3-(1-methyl-4-imidazolyl)-Ph |
| 1911. | 2-furanyl | 3-(1-methyl-5-imidazolyl)-Ph |
| 1912. | 2-furanyl | 3-(thiazol-4-yl)-Ph |
| 1913. | 2-furanyl | 3-(thiazol-5-yl)-Ph |
| 1914. | 2-furanyl | 3-(pyrazol-4-yl)-Ph |
| 1915. | 2-furanyl | 3-(1-methyl-3-pyrazolyl)-Ph |
| 1916. | 2-furanyl | 3-(1-methyl-4-pyrazolyl)-Ph |
| 1917. | 2-furanyl | 3-(1-methyl-5-pyrazolyl)-Ph |
| 1918. | 2-furanyl | 3-(3-pyridyl)-Ph |
| 1919. | 2-furanyl | 3-(4-pyridyl)-Ph |
| 1920. | 2-furanyl | 3-(3-thienyl)-Ph |
| 1921. | 2-furanyl | 3-(3-furanyl)-Ph |
| 1922. | 2-furanyl | 3-(1,2,4-triazol-1-yl)-Ph |
| 1923. | 2-furanyl | 3-(1,2,4-triazol-4-yl)-Ph |
| 1924. | 2-furanyl | 3-(1,2,3-triazol-1-yl)-Ph |
| 1925. | 2-furanyl | 3-(1,2,3-triazol-4-yl)-Ph |
| 1926. | 2-furanyl | 3-(1-methyl-1,2,4-triazol-3-yl)-Ph |
| 1927. | 2-furanyl | 3-(1-methyl-1,2,4-triazol-5-yl)-Ph |
| 1928. | 3-furanyl | 3-(1-methyl-1,2,3-triazol-4-yl)-Ph |
| 1929. | 3-furanyl | 3-(1-methyl-1,2,3-triazol-5-yl)-Ph |
| 1930. | 3-furanyl | 3-(3-isoxazolyl)-Ph |
| 1931. | 3-furanyl | 3-(4-isoxazolyl)-Ph |
| 1932. | 3-furanyl | 3-(5-isoxazolyl)-Ph |
| 1933. | 3-furanyl | 3-(1-methyl-5-pyrazolyl)-Ph |
| 1934. | 3-furanyl | 3-(1-ethyl-5-pyrazolyl)-Ph |
| 1935. | 3-furanyl | 3-([1,3,4]-oxadiazol-2-yl)-Ph |
| 1936. | 3-furanyl | 3-(CO—NH-(2-ethylpyrazol-3-yl))-Ph |
| 1937. | 3-furanyl | 3-(CO—NH-(thiazol-2-yl))-Ph |
| 1938. | 3-furanyl | 3-(CO—NH-(isoxazol-3-yl))-Ph |
| 1939. | 3-furanyl | 5-acetyl-4-methylthiazol-2-yl |
| 1940. | 3-furanyl | 5-acetyl-4-methyloxazol-2-yl |
| 1941. | 3-furanyl | 5-acetyl-4-methylimidazol-2-yl |
| 1942. | 3-furanyl | 3-acetyl-5-[(CH3)2N—CO]-Ph |
| 1943. | 3-furanyl | 3-acetyl-5-[(CH3)NH—CO]-Ph |
| 1944. | 3-furanyl | 3-acetyl-5-[H2N—CO]-Ph |
| 1945. | 3-furanyl | 3-acetyl-5-[morpholin-1-yl-CO]-Ph |
| 1946. | 3-furanyl | 3-acetyl-5-F-Ph |
| 1947. | 3-furanyl | 3-acetyl-5-Cl-Ph |
| 1948. | 2-pyridyl | 3-acetyl-5-Br-Ph |
| 1949. | 2-pyridyl | 3-acetyl-4-F-Ph |
| 1950. | 2-pyridyl | 3-acetyl-4-Cl-Ph |
| 1951. | 2-pyridyl | 3-acetyl-4-Br-Ph |
| 1952. | 2-pyridyl | 3-acetyl-5-CF3-Ph |
| 1953. | 2-pyridyl | 3-acetyl-4-CF3-Ph |
| 1954. | 2-pyridyl | 2-F-Ph3-acetyl-2-CH3O-Ph |
| 1955. | 2-pyridyl | 3-acetyl-4-CH3O-Ph |
| 1956. | 2-pyridyl | 3-acetyl-5-CH3O-Ph |
| 1957. | 2-pyridyl | 3-acetyl-6-CH3O-Ph |
| 1958. | 2-pyridyl | 3-acetyl-5-CH3-Ph |
| 1959. | 2-pyridyl | 3-acetyl-5-CH3CH2-Ph |
| 1960. | 2-pyridyl | 4-acetyl-5-[morpholin-1-yl-CO]-Ph |
| 1961. | 2-pyridyl | 4-acetyl-5-F-Ph |
| 1962. | 2-pyridyl | 4-acetyl-5-Cl-Ph |
| 1963. | 2-pyridyl | 4-acetyl-5-Br-Ph |
| 1964. | 2-pyridyl | 4-acetyl-3-CF3-Ph |
| 1965. | 2-pyridyl | 4-acetyl-2-CH3O-Ph |
| 1966. | 2-pyridyl | 4-acetyl-5-CH3O-Ph |
| 1967. | 2-pyridyl | 3-acetyl-5-(1-methyltetrazol-5-yl)-Ph |
| 1968. | 3-pyridyl | 3-acetyl-5-(1-ethyltetrazol-5-yl)-Ph |
| 1969. | 3-pyridyl | 3-acetyl-5-(1-cyclopropyltetrazol-5-yl)-Ph |
| 1970. | 3-pyridyl | 3-acetyl-5-(oxazol-2-yl)-Ph |
| 1971. | 3-pyridyl | 3-acetyl-5-(isoxazol-3-yl)-Ph |
| 1972. | 3-pyridyl | 3-acetyl-5-(isoxazol-5-yl)-Ph |
| 1973. | 3-pyridyl | 3-acetyl-5-(pyrazol-1-yl)-Ph |
| 1974. | 3-pyridyl | 3-acetyl-5-(1,2,4-triazol-1-yl)-Ph |
| 1975. | 3-pyridyl | 3-acetyl-5-(CH2OH)-Ph |
| 1976. | 3-pyridyl | 3-acetyl-5-(furan-2-yl)-Ph |
| 1977. | 3-pyridyl | 3-acetyl-5-(furan-3-yl)-Ph |
| 1978. | 3-pyridyl | 3-acetyl-5-(thien-2-yl)-Ph |
| 1979. | 3-pyridyl | 3-acetyl-5-(thien-3-yl)-Ph |
| 1980. | 3-pyridyl | 3-acetyl-5-CN-Ph |
| 1981. | 3-pyridyl | 3-acetyl-5-(CN)-Ph |
| 1982. | 3-pyridyl | 3-acetyl-5-(isopropyl)-Ph |
| 1983. | 3-pyridyl | 3-acetyl-5-(SO2NH2)-Ph |
| 1984. | 3-pyridyl | 3-acetyl-5-(CO-4-morpholine)-Ph |
| 1985. | 3-pyridyl | 3-isopropyl-5-(1-methyltetrazol-5-yl)-Ph |
| 1986. | 3-pyridyl | 3-SO2NH2-5-(1-methyltetrazol-5-yl)-Ph |
| 1987. | 3-pyridyl | 3,5-di(OMe)-Ph |
| 1988. | 4-pyridyl | 3-(imidazol-4-yl)-Ph |
| 1989. | 4-pyridyl | 3-(1-methyl-2-imidazolyl)-Ph |
| 1990. | 4-pyridyl | 3-(1-methyl-4-imidazolyl)-Ph |
| 1991. | 4-pyridyl | 3-(1-methyl-5-imidazolyl)-Ph |
| 1992. | 4-pyridyl | 3-(thiazol-4-yl)-Ph |
| 1993. | 4-pyridyl | 3-(thiazol-5-yl)-Ph |
| 1994. | 4-pyridyl | 3-(pyrazol-4-yl)-Ph |
| 1995. | 4-pyridyl | 3-(1-methyl-3-pyrazolyl)-Ph |
| 1996. | 4-pyridyl | 3-(1-methyl-4-pyrazolyl)-Ph |
| 1997. | 4-pyridyl | 3-(1-methyl-5-pyrazolyl)-Ph |
| 1998. | 4-pyridyl | 3-(3-pyridyl)-Ph |
| 1999. | 4-pyridyl | 3-(4-pyridyl)-Ph |
| 2000. | 4-pyridyl | 3-(3-thienyl)-Ph |
| 2001. | 4-pyridyl | 3-(3-furanyl)-Ph |
| 2002. | 4-pyridyl | 3-(1,2,4-triazol-1-yl)-Ph |
| 2003. | 4-pyridyl | 3-(1,2,4-triazol-4-yl)-Ph |
| 2004. | 4-pyridyl | 3-(1,2,3-triazol-1-yl)-Ph |
| 2005. | 4-pyridyl | 3-(1,2,3-triazol-4-yl)-Ph |
| 2006. | 4-pyridyl | 3-(1-methyl-1,2,4-triazol-3-yl)-Ph |
| 2007. | 4-pyridyl | 3-(1-methyl-1,2,4-triazol-5-yl)-Ph |
| 2008. | 3-indolyl | 3-(1-methyl-1,2,3-triazol-4-yl)-Ph |
| 2009. | 3-indolyl | 3-(1-methyl-1,2,3-triazol-5-yl)-Ph |
| 2010. | 3-indolyl | 3-(3-isoxazolyl)-Ph |
| 2011. | 3-indolyl | 3-(4-isoxazolyl)-Ph |
| 2012. | 3-indolyl | 3-(5-isoxazolyl)-Ph |
| 2013. | 3-indolyl | 3-(1-methyl-5-pyrazolyl)-Ph |
| 2014. | 3-indolyl | 3-(1-ethyl-5-pyrazolyl)-Ph |
| 2015. | 3-indolyl | 3-([1,3,4]-oxadiazol-2-yl)-Ph |
| 2016. | 3-indolyl | 3-(CO—NH-(2-ethylpyrazol-3-yl))-Ph |

| # | Col A | Col B |
|---|---|---|
| 2017. | 3-indolyl | 3-(CO—NH-(thiazol-2-yl))-Ph |
| 2018. | 3-indolyl | 3-(CO—NH-(isoxazol-3-yl))-Ph |
| 2019. | 3-indolyl | 5-acetyl-4-methylthiazol-2-yl |
| 2020. | 3-indolyl | 5-acetyl-4-methyloxazol-2-yl |
| 2021. | 3-indolyl | 5-acetyl-4-methylimidazol-2-yl |
| 2022. | 3-indolyl | 3-acetyl-5-[(CH3)2N—CO]-Ph |
| 2023. | 3-indolyl | 3-acetyl-5-[(CH3)NH—CO]-Ph |
| 2024. | 3-indolyl | 3-acetyl-5-[H2N—CO]-Ph |
| 2025. | 3-indolyl | 3-acetyl-5-[morpholin-1-yl-CO]-Ph |
| 2026. | 3-indolyl | 3-acetyl-5-F-Ph |
| 2027. | 3-indolyl | 3-acetyl-5-Cl-Ph |
| 2028. | 5-indolyl | 3-acetyl-5-Br-Ph |
| 2029. | 5-indolyl | 3-acetyl-4-F-Ph |
| 2030. | 5-indolyl | 3-acetyl-4-Cl-Ph |
| 2031. | 5-indolyl | 3-acetyl-4-Br-Ph |
| 2032. | 5-indolyl | 3-acetyl-5-CF3-Ph |
| 2033. | 5-indolyl | 3-acetyl-4-CF3-Ph |
| 2034. | 5-indolyl | 2-F-Ph 3-acetyl-2-CH3O-Ph |
| 2035. | 5-indolyl | 3-acetyl-4-CH3O-Ph |
| 2036. | 5-indolyl | 3-acetyl-5-CH3O-Ph |
| 2037. | 5-indolyl | 3-acetyl-6-CH3O-Ph |
| 2038. | 5-indolyl | 3-acetyl-5-CH3-Ph |
| 2039. | 5-indolyl | 3-acetyl-5-CH3CH2-Ph |
| 2040. | 5-indolyl | 4-acetyl-5-[morpholin-1-yl-CO]-Ph |
| 2041. | 5-indolyl | 4-acetyl-5-F-Ph |
| 2042. | 5-indolyl | 4-acetyl-5-Cl-Ph |
| 2043. | 5-indolyl | 4-acetyl-5-Br-Ph |
| 2044. | 5-indolyl | 4-acetyl-3-CF3-Ph |
| 2045. | 5-indolyl | 4-acetyl-2-CH3O-Ph |
| 2046. | 5-indolyl | 4-acetyl-5-CH3O-Ph |
| 2047. | 5-indolyl | 3-acetyl-5-(1-methyltetrazol-5-yl)-Ph |
| 2048. | 5-indazolyl | 3-acetyl-5-(1-ethyltetrazol-5-yl)-Ph |
| 2049. | 5-indazolyl | 3-acetyl-5-(1-cyclopropyltetrazol-5-yl)-Ph |
| 2050. | 5-indazolyl | 3-acetyl-5-(oxazol-2-yl)-Ph |
| 2051. | 5-indazolyl | 3-acetyl-5-(isoxazol-3-yl)-Ph |
| 2052. | 5-indazolyl | 3-acetyl-5-(isoxazol-5-yl)-Ph |
| 2053. | 5-indazolyl | 3-acetyl-5-(pyrazol-1-yl)-Ph |
| 2054. | 5-indazolyl | 3-acetyl-5-(1,2,4-triazol-1-yl)-Ph |
| 2055. | 5-indazolyl | 3-acetyl-5-(CH2OH)-Ph |
| 2056. | 5-indazolyl | 3-acetyl-5-(furan-2-yl)-Ph |
| 2057. | 5-indazolyl | 3-acetyl-5-(furan-3-yl)-Ph |
| 2058. | 5-indazolyl | 3-acetyl-5-(thien-2-yl)-Ph |
| 2059. | 5-indazolyl | 3-acetyl-5-(thien-3-yl)-Ph |
| 2060. | 5-indazolyl | 3-acetyl-5-CN-Ph |
| 2061. | 5-indazolyl | 3-acetyl-5-(CN)-Ph |
| 2062. | 5-indazolyl | 3-acetyl-5-(isopropyl)-Ph |
| 2063. | 5-indazolyl | 3-acetyl-5-(SO2NH2)-Ph |
| 2064. | 5-indazolyl | 3-acetyl-5-(CO-4-morpholine)-Ph |
| 2065. | 5-indazolyl | 3-isopropyl-5-(1-methyltetrazol-5-yl)-Ph |
| 2066. | 5-indazolyl | 3-SO2NH2-5-(1-methyltetrazol-5-yl)-Ph |
| 2067. | 5-indazolyl | 3,5-di(OMe)-Ph |
| 2068. | 5-benzimidazolyl | 3-(imidazol-4-yl)-Ph |
| 2069. | 5-benzimidazolyl | 3-(1-methyl-2-imidazolyl)-Ph |
| 2070. | 5-benzimidazolyl | 3-(1-methyl-4-imidazolyl)-Ph |
| 2071. | 5-benzimidazolyl | 3-(1-methyl-5-imidazolyl)-Ph |
| 2072. | 5-benzimidazolyl | 3-(thiazol-4-yl)-Ph |
| 2073. | 5-benzimidazolyl | 3-(thiazol-5-yl)-Ph |
| 2074. | 5-benzimidazolyl | 3-(pyrazol-4-yl)-Ph |
| 2075. | 5-benzimidazolyl | 3-(1-methyl-3-pyrazolyl)-Ph |
| 2076. | 5-benzimidazolyl | 3-(1-methyl-4-pyrazolyl)-Ph |
| 2077. | 5-benzimidazolyl | 3-(1-methyl-5-pyrazolyl)-Ph |
| 2078. | 5-benzimidazolyl | 3-(3-pyridyl)-Ph |
| 2079. | 5-benzimidazolyl | 3-(4-pyridyl)-Ph |
| 2080. | 5-benzimidazolyl | 3-(3-thienyl)-Ph |
| 2081. | 5-benzimidazolyl | 3-(3-furanyl)-Ph |
| 2082. | 5-benzimidazolyl | 3-(1,2,4-triazol-1-yl)-Ph |
| 2083. | 5-benzimidazolyl | 3-(1,2,4-triazol-4-yl)-Ph |
| 2084. | 5-benzimidazolyl | 3-(1,2,3-triazol-1-yl)-Ph |
| 2085. | 5-benzimidazolyl | 3-(1,2,3-triazol-4-yl)-Ph |
| 2086. | 5-benzimidazolyl | 3-(1-methyl-1,2,4-triazol-3-yl)-Ph |
| 2087. | 5-benzimidazolyl | 3-(1-methyl-1,2,4-triazol-5-yl)-Ph |
| 2088. | 5-benzothiazolyl | 3-(1-methyl-1,2,3-triazol-4-yl)-Ph |
| 2089. | 5-benzothiazolyl | 3-(1-methyl-1,2,3-triazol-5-yl)-Ph |
| 2090. | 5-benzothiazolyl | 3-(3-isoxazolyl)-Ph |
| 2091. | 5-benzothiazolyl | 3-(4-isoxazolyl)-Ph |
| 2092. | 5-benzothiazolyl | 3-(5-isoxazolyl)-Ph |
| 2093. | 5-benzothiazolyl | 3-(1-methyl-5-pyrazolyl)-Ph |
| 2094. | 5-benzothiazolyl | 3-(1-ethyl-5-pyrazolyl)-Ph |
| 2095. | 5-benzothiazolyl | 3-([1,3,4]-oxadiazol-2-yl)-Ph |
| 2096. | 5-benzothiazolyl | 3-(CO—NH-(2-ethylpyrazol-3-yl))-Ph |
| 2097. | 5-benzothiazolyl | 3-(CO—NH-(thiazol-2-yl))-Ph |
| 2098. | 5-benzothiazolyl | 3-(CO—NH-(isoxazol-3-yl))-Ph |
| 2099. | 5-benzothiazolyl | 5-acetyl-4-methylthiazol-2-yl |
| 2100. | 5-benzothiazolyl | 5-acetyl-4-methyloxazol-2-yl |
| 2101. | 5-benzothiazolyl | 5-acetyl-4-methylimidazol-2-yl |
| 2102. | 5-benzothiazolyl | 3-acetyl-5-[(CH3)2N—CO]-Ph |
| 2103. | 5-benzothiazolyl | 3-acetyl-5-[(CH3)NH—CO]-Ph |
| 2104. | 5-benzothiazolyl | 3-acetyl-5-[H2N—CO]-Ph |
| 2105. | 5-benzothiazolyl | 3-acetyl-5-[morpholin-1-yl-CO]-Ph |
| 2106. | 5-benzothiazolyl | 3-acetyl-5-F-Ph |
| 2107. | 5-benzothiazolyl | 3-acetyl-5-Cl-Ph |
| 2108. | 5-benzoxazolyl | 3-acetyl-5-Br-Ph |
| 2109. | 5-benzoxazolyl | 3-acetyl-4-F-Ph |
| 2110. | 5-benzoxazolyl | 3-acetyl-4-Cl-Ph |
| 2111. | 5-benzoxazolyl | 3-acetyl-4-Br-Ph |
| 2112. | 5-benzoxazolyl | 3-acetyl-5-CF3-Ph |
| 2113. | 5-benzoxazolyl | 3-acetyl-4-CF3-Ph |
| 2114. | 5-benzoxazolyl | 2-F-Ph 3-acetyl-2-CH3O-Ph |
| 2115. | 5-benzoxazolyl | 3-acetyl-4-CH3O-Ph |
| 2116. | 5-benzoxazolyl | 3-acetyl-5-CH3O-Ph |
| 2117. | 5-benzoxazolyl | 3-acetyl-6-CH3O-Ph |
| 2118. | 5-benzoxazolyl | 3-acetyl-5-CH3-Ph |
| 2119. | 5-benzoxazolyl | 3-acetyl-5-CH3CH2-Ph |
| 2120. | 5-benzoxazolyl | 4-acetyl-5-[morpholin-1-yl-CO]-Ph |
| 2121. | 5-benzoxazolyl | 4-acetyl-5-F-Ph |
| 2122. | 5-benzoxazolyl | 4-acetyl-5-Cl-Ph |
| 2123. | 5-benzoxazolyl | 4-acetyl-5-Br-Ph |
| 2124. | 5-benzoxazolyl | 4-acetyl-3-CF3-Ph |
| 2125. | 5-benzoxazolyl | 4-acetyl-2-CH3O-Ph |
| 2126. | 5-benzoxazolyl | 4-acetyl-5-CH3O-Ph |
| 2127. | 5-benzoxazolyl | 3-acetyl-5-(1-methyltetrazol-5-yl)-Ph |

Utility

The utility of the compounds in accordance with the present invention as modulators of chemokine receptor activity may be demonstrated by methodology known in the art, such as the assays for CCR-2 and CCR-3 ligand binding, as disclosed by Ponath et al., J. Exp. Med., 183, 2437–2448 (1996) and Uguccioni et al., J. Clin. Invest., 100, 1137–1143 (1997). Cell lines for expressing the receptor of interest include those naturally expressing the chemokine receptor, such as EOL-3 or THP-1, those induced to express the chemokine receptor by the addition of chemical or protein agents, such as HL-60 or AML14.3D10 cells treated with, for example, butyric acid with interleukin-5 present, or a cell engineered to express a recombinant chemokine receptor, such as CHO or HEK-293. Finally, blood or tissue cells, for example human peripheral blood eosinophils, isolated using methods as described by Hansel et al., J. Immunol. Methods, 145, 105–110 (1991), can be utilized in such assays. In particular, the compound of the present invention have activity in binding to the CCR-3 receptor in the aforementioned assays. As used herein, "activity" is intended to mean a compound demonstrating an $IC_{50}$ of 10 $\mu$M or lower in concentration when measured in the aforementioned assays. Such a result is indicative of the intrinsic activity of the compounds as modulators of chemokine receptor activity. A general binding protocol is described below.

CCR3-Receptor Binding Protocol

Millipore filter plates (#MABVN1250) are treated with 5 $\mu$g/ml protamine in phosphate buffered saline, pH 7.2, for ten minutes at room temperature. Plates are washed three times with phosphate buffered saline and incubated with phosphate buffered saline for thirty minutes at room temperature. For binding, 50 μl of binding buffer (0.5% bovine serum albumen, 20 mM HEPES buffer and 5 mM magnesium chloride in RPMI 1640 media) with or without a test concentration of a compound present at a known concentration is combined with 50 μl of 125-I labeled human eotaxin (to give a final concentration of 150 pM radioligand) and 50 μl of cell suspension in binding buffer containing $5 \times 10^5$ total cells. Cells used for such binding assays can include cell lines transfected with a gene expressing CCR3 such as that described by Daugherty et al. (1996), isolated human eosinophils such as described by Hansel et al. (1991) or the AML14.3D10 cell line after differentiation with butyric acid as described by Tiffany et al. (1998). The mixture of compound, cells and radioligand are incubated at room temperature for thirty minutes. Plates are placed onto a vacuum manifold, vacuum applied, and plates washed three times with binding buffer with 0.5M NaCl added. The plastic skirt is removed from the plate, the plate allowed to air dry, the wells punch out and CPM counted. The percent inhibition of binding is calculated using the total count obtained in the absence of any competing compound or chemokine ligand and the background binding determined by addition of 100 nM eotaxin in place of the test compound.

The utility of the compounds in accordance with the present invention as inhibitors of the migration of eosinophils or cell lines expressing the chemokine receptors may be demonstrated by methodology known in the art, such as the chemotaxis assay disclosed by Bacon et al., Brit. J. Pharmacol., 95, 966–974 (1988). In particular, the compound of the present invention have activity in inhibition of the migration of eosinophils in the aforementioned assays. As used herein, "activity" is intended to mean a compound demonstrating an $IC_{50}$ of 10 μm or lower in concentration when measured in the aforementioned assays. Such a result is indicative of the intrinsic activity of the compounds as modulators of chemokine receptor activity. A human eosinophil chemotaxis assay protocol is described below.

Human Eosinophil Chemotaxis Assay

Neuroprobe MBA96 96-well chemotaxis chambers with Neuroprobe polyvinylpyrrolidone-free polycarbonate PFD5 5-micron filters in place are warmed in a 37° C. incubator prior to assay. Freshly isolated human eosinophils, isolated according to a method such as that described by Hansel et al. (1991), are suspended in RPMI 1640 with 0.1% bovine serum albumin at 1×106 cells/ml and warmed in a 37° C. incubator prior to assay. A 20 nM solution of human eotaxin in RPMI 1640 with 0.1% bovine serum albumin is warmed in a 37° C. incubator prior to assay. The eosinophil suspension and the 20 nM eotaxin solution are each mixed 1:1 with prewarmed RPMI 1640 with 0.1% bovine serum albumin with or without a dilution of a test compound that is at two fold the desired final concentration. These mixtures are warmed in a 37° C. incubator prior to assay. The filter is separated from the prewarmed Neuroprobe chemotaxis chamber and the eotaxin/compound mixture is placed into a Polyfiltronics MPC 96 well plate that has been placed in the bottom part of the Neuro Probe chemotaxis chamber. The approximate volume is 370 microliters and there should be a positive meniscus after dispensing. The filter is replaced above the 96 well plate, the rubber gasket is attached to the bottom of the upper chamber, and the chamber assembled. A 200 μl volume of the cell suspension/compound mixture is added to the appropriate wells of the upper chamber. The upper chamber is covered with a plate sealer, and the assembled unit placed in a 37° C. incubator for 45 minutes. After incubation, the plate sealer is removed and all remaining cell suspension is aspirated off. The chamber is disassembled and, while holding the filter by the sides at a 90-degree angle, unmigrated cells are washed away using a gentle stream of phosphate buffered saline dispensed from a squirt bottle and then the filter wiped with a rubber tipped squeegee. The filter is allowed to completely dry and immersed completely in Wright Giemsa stain for 30–45 seconds. The filter is rinsed with distilled water for 7 minutes, rinsed once with water briefly, and allowed to dry. Migrated cells are enumerated by microscopy.

Mammalian chemokine receptors provide a target for interfering with or promoting immune cell function in a mammal, such as a human. Compounds that inhibit or promote chemokine receptor function are particularly useful for modulating immune cell function for therapeutic purposes. Accordingly, the present invention is directed to compounds which are useful in the prevention and/or treatment of a wide variety of inflammatory, infectious, and immunoregulatory disorders and diseases, including asthma and allergic diseases, infection by pathogenic microbes (which, by definition, includes viruses), as well as autoimmune pathologies such as the rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation or infectious disease. As a result, one or more inflammatory process, such as leukocyte emigration, adhesion, chemotaxis, exocytosis (e.g., of enzymes, histamine) or inflammatory mediator release, is inhibited. For example, eosinophilic infiltration to inflammatory sites (e.g., in asthma or allergic rhinitis) can be inhibited according to the present method. In particular, the compound of the following examples has activity in blocking the migration of cells expressing the CCR-3 receptor using the appropriate chemokines in the aforementioned assays. As used herein, "activity" is intended to mean a compound demonstrating an $IC_{50}$ of 10 μM or lower in concentration when measured in the aforementioned assays. Such a result is also indicative of the intrinsic activity of the compounds as modulators of chemokine receptor activity.

Similarly, an instant compound which promotes one or more functions of the mammalian chemokine receptor (e.g., a human chemokine) as administered to stimulate (induce or enhance) an immune or inflammatory response, such as leukocyte emigration, adhesion, chemotaxis, exocytosis (e.g., of enzymes, histamine) or inflammatory mediator release, resulting in the beneficial stimulation of inflammatory processes. For example, eosinophils can be recruited to combat parasitic infections. In addition, treatment of the aforementioned inflammatory, allergic and autoimmune diseases can also be contemplated for an instant compound which promotes one or more functions of the mammalian chemokine receptor if one contemplates the delivery of sufficient compound to cause the loss of receptor expression on cells through the induction of chemokine receptor internalization or the delivery of compound in a manner that results in the misdirection of the migration of cells.

In addition to primates, such as humans, a variety of other mammals can be treated according to the method of the present invention. For instance, mammals, including but not limited to, cows, sheep, goats, horses, dogs, cats, guinea pigs, rats or other bovine, ovine, equine, canine, feline, rodent or murine species can be treated. However, the method can also be practiced in other species, such as avian species. The subject treated in the methods above is a mammal, male or female, in whom modulation of chemokine receptor activity is desired. "Modulation" as used herein is intended to encompass antagonism, agonism, partial antagonism and/or partial agonism.

Diseases or conditions of human or other species which can be treated with inhibitors of chemokine receptor function, include, but are not limited to: inflammatory or allergic diseases and conditions, including respiratory allergic diseases such as asthma, allergic rhinitis, hypersensitivity lung diseases, hypersensitivity pneumonitis, eosinophilic cellulitis (e.g., Well's syndrome), eosinophilic pneumonias (e.g., Loeffler's syndrome, chronic eosinophilic pneumonia), eosinophilic fasciitis (e.g., Shulman's syndrome), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), eosinophilia-myalgia syndrome due to the ingestion of contaminated tryptophan, insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such as an dermatitis, eczema, atopic dermatitis, allergic contact dermatitis, urticaria; vasculitis (e.g., necrotizing, cutaneous, and hypersensitivity vasculitis); eosinophilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, certain hematologic malignancies, cytokine-induced toxicity (e.g., septic shock, endotoxic shock), polymyositis, dermatomyositis. Infectious diseases or conditions of human or other species which can be treated with inhibitors of chemokine receptor function, include, but are not limited to, HIV.

Diseases or conditions of humans or other species which can be treated with promoters of chemokine receptor function, include, but are not limited to: immunosuppression, such as that in individuals with immunodeficiency syndromes such as AIDS or other viral infections, individuals undergoing radiation therapy, chemotherapy, therapy for autoimmune disease or drug therapy (e.g., corticosteroid therapy), which causes immunosuppression; immunosuppression due to congenital deficiency in receptor function or other causes; and infections diseases, such as parasitic diseases, including, but not limited to helminth infections, such as nematodes (round worms); (Trichuriasis, Enterobiasis, Ascariasis, Hookworm, Strongyloidiasis, Trichinosis, filariasis); trematodes (flukes) (Schistosomiasis, Clonorchiasis), cestodes (tape worms) (Echinococcosis, *Taeniasis saginata*, Cysticercosis); visceral worms, visceral larva migraines (e.g., Toxocara), eosinophilic gastroenteritis (e.g., *Anisaki* sp., *Phocanema* sp.), cutaneous larva migraines (*Ancylostona braziliense, Ancylostoma caninum*). The compounds of the present invention are accordingly useful in the prevention and treatment of a wide variety of inflammatory, infectious and immunoregulatory disorders and diseases. In addition, treatment of the aforementioned inflammatory, allergic and autoimmune diseases can also be contemplated for promoters of chemokine receptor function if one contemplates the delivery of sufficient compound to cause the loss of receptor expression on cells through the induction of chemokine receptor internalization or delivery of compound in a manner that results in the misdirection of the migration of cells.

In another aspect, the instant invention may be used to evaluate the putative specific agonists or antagonists of a G protein coupled receptor. The present invention is directed to the use of these compounds in the preparation and execution of screening assays for compounds that modulate the activity of chemokine receptors. Furthermore, the compounds of this invention are useful in establishing or determining the binding site of other compounds to chemokine receptors, e.g., by competitive inhibition or as a reference in an assay to compare its known activity to a compound with an unknown activity. When developing new assays or protocols, compounds according to the present invention could be used to test their effectiveness. Specifically, such compounds may be provided in a commercial kit, for example, for use in pharmaceutical research involving the aforementioned diseases. The compounds of the instant invention are also useful for the evaluation of putative specific modulators of the chemokine receptors. In addition, one could utilize compounds of this invention to examine the specificity of G protein coupled receptors that are not thought to be chemokine receptors, either by serving as examples of compounds which do not bind or as structural variants of compounds active on these receptors which may help define specific sites of interaction.

Combined therapy to prevent and treat inflammatory, infectious and immunoregulatory disorders and diseases, including asthma and allergic diseases, as well as autoimmune pathologies such as rheumatoid arthritis and atherosclerosis, and those pathologies noted above is illustrated by the combination of the compounds of this invention and other compounds which are known for such utilities. For example, in the treatment or prevention of inflammation, the present compounds may be used in conjunction with an anti-inflammatory or analgesic agent such as an opiate agonist, a lipoxygenase inhibitor, a cyclooxygenase-2 inhibitor, an interleukin inhibitor, such as an interleukin-1 inhibitor, a tumor necrosis factor inhibitor, an NMDA antagonist, an inhibitor or nitric oxide or an inhibitor of the synthesis of nitric oxide, a non-steroidal anti-inflammatory agent, a phosphodiesterase inhibitor, or a cytokine-suppressing anti-inflammatory agent, for example with a compound such as acetaminophen, aspirin, codeine, fentaynl, ibuprofen, indomethacin, ketorolac, morphine, naproxen, phenacetin, piroxicam, a steroidal analgesic, sufentanyl, sunlindac, interferon alpha and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levodesoxy-ephedrine; and antitussive such as codeine, hydrocodone, caramiphen, carbetapentane, or dextramethorphan; a diuretic; and a sedating or non-sedating antihistamine. Likewise, compounds of the present invention may be used in combination with other drugs that are used in the treatment/prevention/suppression or amelioration of the diseases or conditions for which compound of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention. Examples of other active ingredients that may be combined with a compound of the present invention, either administered separately or in the same pharmaceutical compositions, include, but are not limited to: (a) integrin antagonists such as those for selectins, ICAMs and VLA-4; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as b2-agonists (terbutaline, metaproterenol, fenoterol, isoetharine, albuteral, bitolterol, and pirbuterol), theophylline, cromolyn sodium, atropine, ipratropium bromide, leukotriene antagonists (zafirlukast, montelukast, pranlukast, iralukast, pobilukast, SKB-102, 203), leukotriene biosynthesis inhibitors (zileuton, BAY-1005); (f) non-steroidal antiinflammatory agents (NSAIDs) such as propionic acid derivatives (alminoprofen, benxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (I) other antagonists of the chemokine receptors; (j) cholesterol lowering agents such as HMG-COA reductase inhibitors (lovastatin, simvastatin and pravastatin, fluvastatin, atorvsatatin, and other statins), sequestrants (cholestyramine and colestipol), nicotonic acid, fenofibric acid derivatives (gemfibrozil, clofibrat, fenofibrate and benzafibrate), and probucol; (k) anti-diabetic agents such as insulin, sulfonylureas, biguanides (metformin), a-glucosidase inhibitors (acarbose) and glitazones (troglitazone ad pioglitazone); (1) preparations of interferons (interferon alpha-2a, interferon-2B, interferon alpha-N3, interferon beta-1a, interferon beta-1b, interferon gamma-1b); (m) antiviral compounds such as efavirenz, nevirapine, indinavir, ganciclovir, lamivudine, famciclovir, and zalcitabine; (o) other compound such as 5-aminosalicylic acid an prodrugs thereof, antimetabolites such as azathioprine and 6-mercaptopurine, and cytotoxic cancer chemotherapeutic agents. The weight ratio of the compound of the present invention to the second active ingredient may be varied and will depend upon the effective doses of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

The compounds are administered to a mammal in a therapeutically effective amount. By "therapeutically effective amount" it is meant an amount of a compound of Formula I that, when administered alone or in combination with an additional therapeutic agent to a mammal, is effective to prevent or ameliorate the thromboembolic disease condition or the progression of the disease.

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

Where the compounds of this invention are combined with other anticoagulant agents, for example, a daily dosage may be about 0.1 to 100 milligrams of the compound of Formula I and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where two or more of the foregoing second therapeutic agents are administered with the compound of Formula I, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

As will be apparent to one skilled in the art, numerous modifications and variations of the present invention are possible in light of the above teachings. It is therefore to be understood that within the scope of the appended claims, the invention may be practiced otherwise than as specifically described herein.

What is claimed is:

1. A compound of formula (I):

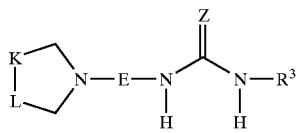

or stereoisomers or pharmaceutically acceptable salts thereof, wherein:

K is selected from $CH_2$, $CHR^5$ and $CHR^6$;

L is selected from $CH_2$, $CHR^5$, $CHR^6$, $CR^6R^6$ and $CR^5R^6$;

J is selected from $CH_2$, $CHR^5$, $CHR^{13}$, and $CR^5R^{13}$;

with the proviso:

at least one of K or L contains an $R^5$

Z is selected from O, S, $NR^{1a}$, $C(CN)_2$, $CH(NO_2)$, and CHCN;

$R^{1a}$ is selected from H, $C_{1-6}$ alkyl, $C_{3-6}$ cycloalkyl, $CONR^{1b}R^{1b}$, $OR^{1b}$, CN, $NO_2$, and $(CH_2)_w$phenyl;

$R^{1b}$ is independently selected from H, $C_{1-3}$ alkyl, $C_{3-6}$ cycloalkyl, and phenyl;

E is —(C=O)—$(CR^9R^{10})_v$—$(CR^{11}R^{12})_r$—, —$(SO_2)$—$(CR^9R^{10})_v$—$(CR^{11}R^{12})_r$—,

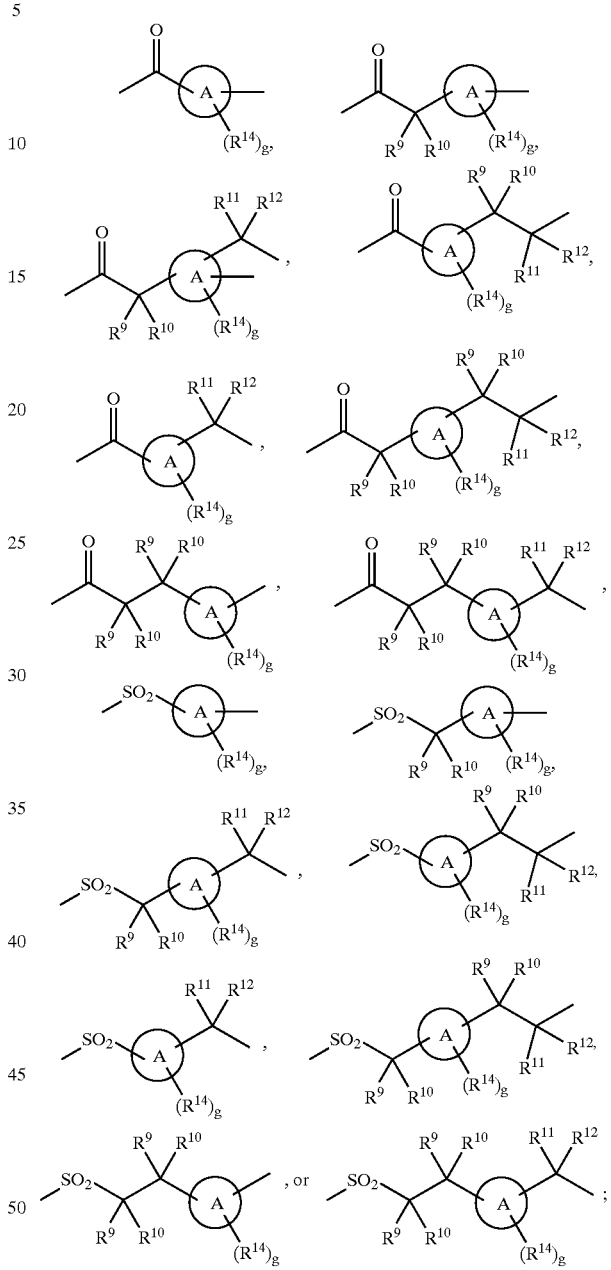

Ring A is a $C_{3-8}$ carbocyclic residue;

$R^2$ is selected from H, $C_{1-8}$ alkyl, $C_{3-8}$ alkenyl, $C_{3-8}$ alkynyl, and a $(CH_2)_r$—$C_{3-10}$ carbocyclic residue substituted with 0–5 $R^a$;

$R^a$, at each occurrence, is selected from $C_{1-4}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rNR^bR^b$, $(CH_2)_rOH$, $(CH_2)_rOR^c$, $(CH_2)_rSH$, $(CH_2)_rSR^c$, $(CH_2)_rC(O)R^b$, $(CH_2)_rC(O)NR^bR^b$, $(CH_2)_rNR^bC(O)R^b$, $(CH_2)_rC(O)OR^b$, $(CH_2)_rOC(O)R^c$, $(CH_2)_rCH(=NR^b)NR^bR^b$, $(CH_2)_rNHC(=NR^b)NR^bR^b$, $(CH_2)_rS(O)_pR^c$, $(CH_2)_rS(O)_2NR^bR^b$, $(CH_2)_rNR^bS(O)_2R^c$, and $(CH_2)_r$phenyl;

$R^b$, at each occurrence, is selected from H, $C_{1-6}$ alkyl, $C_{3-6}$ cycloalkyl, and phenyl;

$R^c$, at each occurrence, is selected from $C_{1-6}$ alkyl, $C_{3-6}$ cycloalkyl, and phenyl;

$R^3$ is selected from $(CH_2)_rN(CH_3)_2$, a $(CR^{3'}R^{3''})_r$—$C_{3-8}$ carbocyclic residue substituted with 0–5 $R^{15}$; a $(CR^{3'}R^{3''})_r$—$C_{9-10}$ carbocyclic residue substituted with 0–4 $R^{15}$; and a $(CR^{3'}R^{3''})_r$-5–10 membered heterocyclic system containing 1–4 heteroatoms selected from N, O, and S, substituted with 0–3 $R^{15}$;

$R^{3'}$ and $R^{3''}$, at each occurrence, are selected from H, $C_{1-6}$ alkyl, $(CH_2)_rC_{3-6}$ cycloalkyl, and phenyl;

$R^5$ is selected from a $(CR^{5'}R^{5''})_r$—$C_{3-10}$ carbocyclic residue substituted with 0–5 $R^{16}$ and a $(CR^{5'}R^{5''})_r$-5–10 membered heterocyclic system containing 1–4 heteroatoms selected from N, O, and S, substituted with 0–3 $R^{16}$;

$R^{5'}$ and $R^{5''}$, at each occurrence, are selected from H, $C_{1-6}$ alkyl, $(CH_2)_rC_{3-6}$ cycloalkyl, and phenyl;

$R^6$, at each occurrence, is selected from $C_{1-6}$ alkyl, $C_{2-8}$ alkenyl, $C_{2-8}$ alkynyl, $(CH_2)_rC_{3-6}$ cycloalkyl, $(CF_2)_r$ $CF_3$, CN, $(CH_2)_rNR^{6a}R^{6a'}$, $(CH_2)_rOH$, $(CH_2)_rOR^{6b}$, $(CH_2)_rSH$, $(CH_2)_rSR^{6b}$, $(CH_2)_rC(O)OH$, $(CH_2)_rC(O)R^{6b}$, $(CH_2)_rC(O)NR^{6a}R^{6a'}$, $(CH_2)_rNR^{6d}C(O)R^{6a}$, $(CH_2)_rC(O)OR^{6b}$, $(CH_2)_rOC(O)R^{6b}$, $(CH_2)_rS(O)_pR^{6b}$, $(CH_2)_rS(O)_2NR^{6a}R^{6a'}$, $(CH_2)_rNR^{6d}S(O)_2R^{6b}$, and $(CH_2)_r$phenyl substituted with 0–3 $R^{6c}$;

$R^{6a}$ and $R^{6a'}$, at each occurrence, are selected from H, $C_{1-6}$ alkyl, $C_{3-6}$ cycloalkyl, and phenyl substituted with 0–3 $R^{6c}$;

$R^{6b}$, at each occurrence, is selected from $C_{1-6}$ alkyl, $C_{3-6}$ cycloalkyl, and phenyl substituted with 0–3 $R^{6c}$;

$R^{6c}$, at each occurrence, is selected from $C_{1-6}$ alkyl, $C_{3-6}$ cycloalkyl, Cl, F, Br, I, CN, $NO_2$, $(CF_2)_rCF_3$, $(CH_2)_rOC_{1-5}$ alkyl, $(CH_2)_rOH$, $(CH_2)_rSC_{1-5}$ alkyl, and $(CH_2)_rNR^{6d}R^{6d}$;

$R^{6d}$, at each occurrence, is selected from H, $C_{1-6}$ alkyl, and $C_{3-6}$ cycloalkyl;

with the proviso that when any of J, K, or L is $CR^6R^6$ and $R^6$ is halogen, cyano, nitro, or bonded to the carbon to which it is attached through a heteroatom, the other $R^6$ is not halogen, cyano, or bonded to the carbon to which it is attached through a heteroatom;

$R^9$, is selected from H, $C_{1-6}$ alkyl, $C_{2-8}$ alkenyl, $C_{2-8}$ alkynyl, F, Cl, Br, I, $NO_2$, CN, $(CHR')_rOH$, $(CH_2)_rOR^{9d}$, $(CH_2)_rSR^{9d}$, $(CH_2)_rNR^{9a}R^{9a'}$, $(CH_2)_rC(O)OH$, $(CH_2)_rC(O)R^{9b}$, $(CH_2)_rC(O)NR^{9a}R^{9a'}$, $(CH_2)_rNR^{9a}C(O)R^{9a}$, $(CH_2)_rNR^{9a}C(O)H$, $(CH_2)_rC(O)OR^{9b}$, $(CH_2)_rOC(O)R^{9b}$, $(CH_2)_rOC(O)NR^{9a}R^{9a'}$, $(CH_2)_rNR^{9a}C(O)OR^{9b}$, $(CH_2)_rS(O)_pR^{9b}$, $(CH_2)_rS(O)_2NR^{9a}R^{9a'}$, $(CH_2)_rNR^{9a}S(O)_2R^{9b}$, $C_{1-6}$ haloalkyl, a $(CH_2)_r$—$C_{3-10}$ carbocyclic residue substituted with 0–5 $R^{9c}$, and a $(CH_2)_r$-5–10 membered heterocyclic system containing 1–4 heteroatoms selected from N, O, and S, substituted with 0–3 $R^{9c}$;

$R^{9a}$ and $R^{9a'}$, at each occurrence, are selected from H, $C_{1-6}$ alkyl, $C_{3-8}$ alkenyl, $C_{3-8}$ alkynyl, a $(CH_2)_r$—$C_{3-10}$ carbocyclic residue substituted with 0–5 $R^{9e}$, and a $(CH_2)_r$-5–10 membered heterocyclic system containing 1–4 heteroatoms selected from N, O, and S, substituted with 0–3 $R^{9e}$;

alternatively, $R^{9a}$ and $R^{9a'}$, along with the N to which they are attached, join to form a 5–6 membered heterocyclic system containing 1–2 heteroatoms selected from $NR^{9g}$, O, and S and optionally fused with a benzene ring or a 6-membered aromatic heterocycle;

$R^{9b}$, at each occurrence, is selected from $C_{1-6}$ alkyl, $C_{3-8}$ alkenyl, $C_{3-8}$ alkynyl, a $(CH_2)_r$—$C_{3-6}$ carbocyclic residue substituted with 0–2 $R^{9e}$, and a $(CH_2)_r$-5–6 membered heterocyclic system containing 1–4 heteroatoms selected from N, O, and S, substituted with 0–3 $R^{9e}$;

$R^{9c}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rNR^{9f}R^{9f}$, $(CH_2)_rOH$, $(CH_2)_rOR^{9b}$, $(CH_2)_rSR^{9b}$, $(CH_2)_rC(O)OH$, $(CH_2)_rC(O)R^{9b}$, $(CH_2)_rC(O)NR^{9f}R^{9f}$, $(CH_2)_rNR^{9f}C(O)R^{9a}$, $(CH_2)_rC(O)OR^{9b}$, $(CH_2)_rOC(O)R^{9b}$, $(CH_2)_rC(=NR^{9f})NR^{9f}R^{9f}$, $(CH_2)_rS(O)_pR^{9b}$, $(CH_2)_rNHC(=NR^{9f})NR^{9f}R^{9f}$, $(CH_2)_rS(O)_2NR^{9f}R^{9f}$, $(CH_2)_rNR^{9f}S(O)_2R^{9b}$, and $(CH_2)_r$phenyl substituted with 0–3 $R^{9e}$;

$R^{9d}$, at each occurrence, is selected from $C_{1-6}$ alkyl, $C_{3-6}$ alkenyl, $C_{3-6}$ alkynyl, a $C_{3-10}$ carbocyclic residue substituted with 0–3 $R^{9c}$, and a 5–6 membered heterocyclic system containing 1–4 heteroatoms selected from the group consisting of N, O, and S substituted with 0–3 $R^{9c}$;

$R^{9e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{9f}R^{9f}$, and $(CH_2)_r$phenyl, wherein the phenyl on the $(CH_2)_r$phenyl is substituted with 0–5 substituents selected from F, Cl, Br, I, $NO_2$, $C_{1-6}$alkyl, OH, and $NR^{9f}R^{9f}$;

$R^{9f}$, at each occurrence, is selected from H, $C_{1-6}$ alkyl, and $C_{3-6}$ cycloalkyl;

$R^{9g}$, is selected from H, $C_{1-6}$ alkyl, $C_{3-6}$ cycloalkyl, $(CH_2)_r$phenyl, $C(O)R^{9f}$, $C(O)OR^{9h}$, and $SO_2R^{9h}$;

$R^{9h}$, at each occurrence, is selected from $C_{1-6}$ alkyl, and $C_{3-6}$ cycloalkyl;

$R^{10}$, is selected from H, $C_{1-6}$ alkyl, $C_{2-8}$ alkenyl, $C_{2-8}$ alkynyl, F, Cl, Br, I, $NO_2$, CN, $(CHR')_rOH$, $(CH_2)_rOR^{10d}$, $(CH_2)_rSR^{10d}$, $(CH_2)_rNR^{10a}R^{10a'}$, $(CH_2)_rC(O)OH$, $(CH_2)_rC(O)R^{10b}$, $(CH_2)_rC(O)NR^{10a}R^{10a'}$, $(CH_2)_rNR^{10a}C(O)R^{10a}$, $(CH_2)_rNR^{10a}C(O)H$, $(CH_2)_rC(O)OR^{10b}$, $(CH_2)_rOC(O)R^{10b}$, $(CH_2)_rOC(O)NR^{10a}R^{10a'}$, $(CH_2)_rNR^{10a}C(O)OR^{10b}$, $(CH_2)_rS(O)_pR^{10b}$, $(CH_2)_rS(O)_2NR^{10a}R^{10a'}$, $(CH_2)_rNR^{10a}S(O)_2R^{10b}$, $C_{1-6}$ haloalkyl, a $(CH_2)_r$—$C_{3-10}$ carbocyclic residue substituted with 0–5 $R^{10c}$, and a $(CH_2)_r$-5–10 membered heterocyclic system containing 1–4 heteroatoms selected from N, O, and S, substituted with 0–3 $R^{10c}$;

$R^{10a}$ and $R^{10a'}$, at each occurrence, are selected from H, $C_{1-6}$ alkyl, $C_{3-8}$ alkenyl, $C_{3-8}$ alkynyl, a $(CH_2)_r$—$C_{3-10}$ carbocyclic residue substituted with 0–5 $R^{10e}$, and a $(CH_2)_r$-5–10 membered heterocyclic system containing 1–4 heteroatoms selected from N, O, and S, substituted with 0–3 $R^{10e}$;

alternatively, $R^{10a}$ and $R^{10a'}$, along with the N to which they are attached, join to form a 5–6 membered heterocyclic system containing 1–2 heteroatoms selected from $NR^{10g}$, O, and S and optionally fused with a benzene ring or a 6-membered aromatic heterocycle;

$R^{10b}$, at each occurrence, is selected from $C_{1-6}$ alkyl, $C_{3-8}$ alkenyl, $C_{3-8}$ alkynyl, a $(CH_2)_r$—$C_{3-6}$ carbocyclic residue substituted with 0–2 $R^{10e}$, and a $(CH_2)_r$-5–6 membered heterocyclic system containing 1–4 heteroatoms selected from N, O, and S, substituted with 0–3 $R^{10e}$;

$R^{10c}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rNR^{10f}R^{10f}$, $(CH_2)_rOH$, $(CH_2)_rOR^{10b}$, $(CH_2)_rSR^{10b}$, $(CH_2)_rC(O)OH$, $(CH_2)_rC(O)R^{10b}$, $(CH_2)_rC(O)NR^{10f}R^{10f}$, $(CH_2)_rNR^{10f}C(O)R^{10a}$, $(CH_2)_rC(O)OR^{10b}$, $(CH_2)_rOC(O)R^{10b}$, $(CH_2)_rC$ (=NR$^{10f}$)NR$^{10f}$R$^{10f}$, (CH$_2$)$_r$S(O)$_p$R$^{10b}$, (CH$_2$)$_r$NHC(=NR$^{10f}$)NR$^{10f}$R$^{10f}$, (CH$_2$)$_r$S(O)$_2$NR$^{10f}$R$^{10f}$, (CH$_2$)$_r$NR$^{10f}$S(O)$_2$R$^{10b}$, and (CH$_2$)$_r$phenyl substituted with 0–3 R$^{10e}$;

R$^{10d}$, at each occurrence, is selected from C$_{1-6}$ alkyl, C$_{3-6}$ alkenyl, C$_{3-6}$ alkynyl, and a C$_{3-10}$ carbocyclic residue substituted with 0–3 R$^{10c}$;

R$^{10e}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{10f}$R$^{10f}$, and (CH$_2$)$_r$phenyl;

R$^{10f}$, at each occurrence, is selected from H, C$_{1-6}$ alkyl, and C$_{3-6}$ cycloalkyl;

R$^{10g}$ is selected from H, C$_{1-6}$ alkyl, C$_{3-6}$ cycloalkyl, (CH$_2$)$_r$phenyl, C(O)R$^{10f}$, SO$_2$R$^{10h}$, and C(O)O R$^{10h}$;

R$^{10h}$, at each occurrence, is selected from H, C$_{1-6}$ alkyl, C$_{3-6}$ cycloalkyl;

alternatively, R$^9$ and R$^{10}$ join to form =O, a C$_{3-10}$ cycloalkyl, a 5–6-membered lactone or lactam, or a 4–6-membered saturated heterocycle containing 1–2 heteroatoms selected from O, S, and NR$^{10g}$ and optionally fused with a benzene ring or a 6-membered aromatic heterocycle;

with the proviso that when either of R$^9$ or R$^{10}$ is bonded to the carbon to which it is attached through a heteroatom, then the other of R$^9$ or R$^{10}$ is not halogen, cyano, or bonded to the carbon to which it is attached through a heteroatom;

R$^{11}$, is selected from H, C$_{1-6}$ alkyl, C$_{2-8}$ alkenyl, C$_{2-8}$ alkynyl, (CR'R$^{17}$)$_q$OH, (CH$_2$)$_q$SH, (CR'R$^{17}$)$_q$OR$^{11d}$, (CH$_2$)$_q$SR$^{11d}$, (CR'R$^{17}$)$_q$NR$^{11a}$R$^{11a'}$, (CH$_2$)$_r$C(O)OH, (CH$_2$)$_r$C(O)R$^{11b}$, (CH$_2$)$_r$C(O)NR$^{11a}$R$^{11a'}$, (CH$_2$)$_q$NR$^{11a}$C(O)R$^{11a}$, (CH$_2$)$_q$OC(O)NR$^{11a}$R$^{11a'}$, (CH$_2$)$_q$NR$^{11a}$C(O)OR$^{11b}$, (CH$_2$)$_q$NR$^{11a}$C(O)NHR$^{11a'}$, (CH$_2$)$_r$C(O)OR$^{11b}$, (CH$_2$)$_q$OC(O)R$^{11b}$, (CH$_2$)$_q$S(O)$_p$R$^{11b}$, (CH$_2$)$_q$S(O)$_2$NR$^{11a}$R$^{11a'}$, (CH$_2$)$_q$NR$^{11a}$S(O)$_2$R$^{11b}$, C$_{1-6}$ haloalkyl, a (CH$_2$)$_r$—C$_{3-10}$ carbocyclic residue substituted with 0–5 R$^{11c}$, and a (R'R$^{17}$)$_r$-5–10 membered heterocyclic system containing 1–4 heteroatoms selected from N, O, and S, substituted with 0–3 R$^{11c}$;

R$^{11a}$ and R$^{11a'}$, at each occurrence, are selected from H, C$_{1-6}$ alkyl, C$_{3-8}$ alkenyl, C$_{3-8}$ alkynyl, a (CH$_2$)$_r$—C$_{3-10}$ carbocyclic residue substituted with 0–5 R$^{11e}$, and a (CH$_2$)$_r$-5–10 membered heterocyclic system containing 1–4 heteroatoms selected from N, O, and S, substituted with 0–3 R$^{11e}$;

alternatively, R$^{11a}$ and R$^{11a'}$ along with the N to which they are attached, join to form a 5–6 membered heterocyclic system containing 1–2 heteroatoms selected from NR$^{11g}$, O, and S and optionally fused with a benzene ring or a 6-membered aromatic heterocycle;

R$^{11b}$, at each occurrence, is selected from C$_{1-6}$ alkyl, C$_{3-8}$ alkenyl, C$_{3-8}$ alkynyl, a (CH$_2$)$_r$—C$_{3-6}$ carbocyclic residue substituted with 0–2 R$^{11e}$, and a (CH$_2$)$_r$-5–6 membered heterocyclic system containing 1–4 heteroatoms selected from N, O, and S, substituted with 0–3 R$^{11e}$;

R$^{11c}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, Br, I, F, (CF$_2$)$_r$CF$_3$, NO$_2$, CN, (CH$_2$)$_r$NR$^{11f}$R$^{11f}$, (CH$_2$)$_r$OH, (CH$_2$)$_r$OC$_{1-4}$ alkyl, (CH$_2$)$_r$SC$_{1-4}$ alkyl, (CH$_2$)$_r$C(O)OH, (CH$_2$)$_r$C(O)R$^{11b}$, (CH$_2$)$_r$C(O)NR$^{11f}$R$^{11f}$, (CH$_2$)$_r$NR$^{11f}$C(O)R$^{11a}$, (CH$_2$)$_r$C(O)OC$_{1-4}$ alkyl, (CH$_2$)$_r$OC(O)R$^{11b}$, (CH$_2$)$_r$C(=NR$^{11f}$)NR$^{11f}$R$^{11f}$, (CH$_2$)$_r$NHC(=NR$^{11f}$)NR$^{11f}$R$^{11f}$, (CH$_2$)$_r$S(O)$_p$R$^{11b}$, (CH$_2$)$_r$S(O)$_2$NR$^{11f}$R$^{11f}$, (CH$_2$)$_r$NR$^{11f}$S(O)$_2$R$^{11b}$, and (CH$_2$)$_r$phenyl substituted with 0–3 R$^{11e}$;

R$^{11d}$, at each occurrence, is selected from C$_{1-6}$ alkyl, C$_{3-6}$ alkenyl, C$_{3-6}$ alkynyl, and a C$_{3-10}$ carbocyclic residue substituted with 0–3 R$^{11c}$;

R$^{11e}$, at each occurrence, is selected from C$_{1-6}$ alkyl, C$_{2-8}$ alkenyl, C$_{2-8}$ alkynyl, C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{11f}$R$^{11f}$, and (CH$_2$)$_r$phenyl, wherein the phenyl on the (CH$_2$)$_r$phenyl is substituted with 0–5 substituents selected from F, Cl, Br, I, NO$_2$, C$_{1-6}$alkyl, OH, and NR$^{9f}$R$^{9f}$;

R$^{11f}$, at each occurrence, is selected from H, C$_{1-6}$ alkyl, and C$_{3-6}$ cycloalkyl;

R$^{11g}$ is selected from H, C$_{1-6}$ alkyl, C$_{3-6}$ cycloalkyl, (CH$_2$)$_r$phenyl, C(O)R$^{11f}$, C(O)OR$^{11h}$, and SO$_2$R$^{11h}$;

R$^{11h}$, at each occurrence, is selected from C$_{1-6}$ alkyl, and C$_{3-6}$ cycloalkyl;

R$^{12}$, is selected from H, C$_{1-6}$ alkyl, C$_{2-8}$ alkenyl, C$_{2-8}$ alkynyl, (CHR')$_q$OH, (CH$_2$)$_q$SH, (CHR')$_q$OR$^{12d}$, (CH$_2$)$_q$ SR$^{12d}$, (CHR')$_q$NR$^{12a}$R$^{12a'}$, (CH$_2$)$_r$C(O)OH, (CH$_2$)$_r$C(O)R$^{12b}$, (CH$_2$)$_r$C(O)NR$^{12a}$R$^{12a'}$, (CH$_2$)$_q$NR$^{12a}$C(O)R$^{12a}$, (CH$_2$)$_r$OC(O)NR$^{12a}$R$^{12a'}$, (CH$_2$)$_r$NR$^{12a}$C(O)OR$^{12b}$, (CH$_2$)$_q$NR$^{12a}$C(O)NHR$^{12a}$, C(O)OR$^{12b}$, (CH$_2$)$_q$OC(O)R$^{12b}$, (CH$_2$)$_q$S(O)$_p$R$^{12b}$, (CH$_2$)$_q$S(O)$_2$ NR$^{12a}$R$^{12a'}$, (CH$_2$)$_q$NR$^{12a}$S(O)$_2$R$^{12b}$, C$_{1-6}$ haloalkyl, a (CH$_2$)$_r$—C$_{3-10}$ carbocyclic residue substituted with 0–5 R$^{12c}$, and a (R'R$^{17}$)$_r$-5–10 membered heterocyclic system containing 1–4 heteroatoms selected from N, O, and S, substituted with 0–3 R$^{12c}$;

R$^{12a}$ and R$^{12a'}$, at each occurrence, are selected from H, C$_{1-6}$ alkyl, C$_{3-8}$ alkenyl, C$_{3-8}$ alkynyl, a (CH$_2$)$_r$—C$_{3-10}$ carbocyclic residue substituted with 0–5 R$^{12e}$, and a (CH$_2$)$_r$-5–10 membered heterocyclic system containing 1–4 heteroatoms selected from N, O, and S, substituted with 0–3 R$^{12e}$;

alternatively, R$^{12a}$ and R$^{12a'}$, along with the N to which they are attached, join to form a 5–6 membered heterocyclic system containing 1–2 heteroatoms selected from NR$^{12g}$, O, and S and optionally fused with a benzene ring or a 6-membered aromatic heterocycle;

R$^{12b}$, at each occurrence, is selected from C$_{1-6}$ alkyl, C$_{3-8}$ alkenyl, C$_{3-8}$ alkynyl, a (CH$_2$)$_r$—C$_{3-6}$ carbocyclic residue substituted with 0–2 R$^{12e}$, and a (CH$_2$)$_r$-5–6 membered heterocyclic system containing 1–4 heteroatoms selected from N, O, and S, substituted with 0–3 R$^{12e}$;

R$^{12c}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, Br, I, F, (CF$_2$)$_r$CF$_3$, NO$_2$, CN, (CH$_2$)$_r$NR$^{12f}$R$^{12f}$, (CH$_2$)$_r$OH, (CH$_2$)$_r$OC$_{1-4}$ alkyl, (CH$_2$)$_r$SC$_{1-4}$ alkyl, (CH$_2$)$_r$C(O)OH, (CH$_2$)$_r$C(O)R$^{12b}$, (CH$_2$)$_r$C(O)NR$^{12f}$R$^{12f}$, (CH$_2$)$_r$NR$^{12f}$C(O)R$^{12a}$, (CH$_2$)$_r$C(O)OC$_{1-4}$ alkyl, (CH$_2$)$_r$OC(O)R$^{12b}$, (CH$_2$)$_r$C(=NR$^{12f}$)NR$^{12f}$R$^{12f}$, (CH$_2$)$_r$NHC(=NR$^{12f}$)NR$^{12f}$R$^{12f}$, (CH$_2$)$_r$S(O)$_p$R$^{12b}$, (CH$_2$)$_r$S(O)$_2$NR$^{12f}$R$^{12f}$, (CH$_2$)$_r$NR$^{12f}$S(O)$_2$R$^{12b}$, and (CH$_2$)$_r$phenyl substituted with 0–3 R$^{12e}$;

R$^{12d}$, at each occurrence, is selected from methyl, CF$_3$, C$_{2-6}$ alkyl substituted with 0–3 R$^{12e}$, C$_{3-6}$ alkenyl, C$_{3-6}$ alkynyl, and a C$_{3-10}$ carbocyclic residue substituted with 0–3 R$^{12c}$;

R$^{12e}$, at each occurrence, is selected from C$_{1-6}$ alkyl, C$_{2-8}$ alkenyl, C$_{2-8}$ alkynyl, C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{12f}$R$^{12f}$, and (CH$_2$)$_r$phenyl;

$R^{12f}$, at each occurrence, is selected from H, $C_{1-6}$ alkyl, and $C_{3-6}$ cycloalkyl;

$R^{12g}$ is selected from H, $C_{1-6}$ alkyl, $C_{3-6}$ cycloalkyl, $(CH_2)_r$phenyl, $C(O)R^{12f}$, $C(O)OR^{12h}$, and $SO_2R^{12h}$;

$R^{12h}$, at each occurrence, is selected from $C_{1-6}$ alkyl, and $C_{3-6}$ cycloalkyl;

alternatively, $R^{11}$ and $R^{12}$ join to form a $C_{3-10}$ cycloalkyl, a 5–6-membered lactone or lactam, or a 4–6-membered saturated heterocycle containing 1–2 heteroatoms selected from O, S, and $NR^{11g}$ and optionally fused with a benzene ring or a 6-membered aromatic heterocycle;

$R^{13}$, at each occurrence, is selected from $C_{1-6}$ alkyl, $C_{2-8}$ alkenyl, $C_{2-8}$ alkynyl, $C_{3-6}$ cycloalkyl, $(CF_2)_wCF_3$, $(CH_2)_qNR^{13a}R^{13a'}$, $(CHR')_qOH$, $(CH_2)_qOR^{13b}$, $(CH_2)_q$SH, $(CH_2)_qSR^{13b}$, $(CH_2)_wC(O)OH$, $(CH_2)_wC(O)R^{13b}$, $(CH_2)_wC(O)NR^{13a}R^{13a'}$, $(CH_2)_qNR^{13d}C(O)R^{13a}$, $(CH_2)_wC(O)OR^{13b}$, $(CH_2)_qOC(O)R^{13b}$, $(CH_2)_wS(O)_pR^{13b}$, $(CH_2)_wS(O)_2NR^{13a}R^{13a'}$, $(CH_2)_qNR^{13d}S(O)_2R^{13b}$, and $(CH_2)_w$-phenyl substituted with 0–3 $R^{13c}$;

$R^{13a}$ and $R^{13a'}$, at each occurrence, are selected from H, $C_{1-6}$ alkyl, $C_{3-6}$ cycloalkyl, and phenyl substituted with 0–3 $R^{13c}$;

$R^{13b}$, at each occurrence, is selected from $C_{1-6}$ alkyl, $C_{3-6}$ cycloalkyl, and phenyl substituted with 0–3 $R^{13c}$;

$R^{13c}$, at each occurrence, is selected from $C_{1-6}$ alkyl, $C_{3-6}$ cycloalkyl, Cl, F, Br, I, CN, $NO_2$, $(CF_2)_rCF_3$, $(CH_2)_rOC_{1-5}$ alkyl, $(CH_2)_rOH$, $(CH_2)_rSC_{1-15}$ alkyl, and $(CH_2)_r$ $NR^{13d}R^{13d}$;

$R^{13d}$, at each occurrence, is selected from H, $C_{1-6}$ alkyl, and $C_{3-6}$ cycloalkyl;

$R^{14}$, at each occurrence, is selected from H, $C_{1-6}$ alkyl, $C_{2-8}$ alkenyl, $C_{2-8}$ alkynyl, $(CH_2)_rC_{3-6}$ cycloalkyl, Cl, Br, I, F, $NO_2$, CN, $(CHR')_rNR^{14a}R^{14a'}$, $(CHR')_rOH$, $(CHR')_rO(CHR')_rR^{14d}$, $(CHR')_rSH$, $(CHR')_rC(O)H$, $(CHR')_rS(CHR')_rR^{14d}$, $(CHR')_rC(O)OH$, $(CHR')_rC(O)(CHR')_rR^{14b}$, $(CHR')_rC(O)NR^{14a}R^{14a'}$, $(CHR')_rNR^{14f}C(O)(CHR')_rR^{14b}$, $(CHR')_rOC(O)NR^{14a}R^{14a'}$, $(CHR')_rNR^{14f}C(O)O(CHR')_rR^{14b}$, $(CHR')_rC(O)O(CHR')_rR^{14d}$, $(CHR')_rOC(O)(CHR')_rR^{14b}$, $(CHR')_rC(=NR^{14f})NR^{14a}R^{14a'}$, $(CHR')_rNHC(=NR^{14f})NR^{14f}R^{14f}$, $(CHR')_rS(O)_p(CHR')_rR^{14b}$, $(CHR')_rS(O)_2NR^{14a}R^{14a'}$, $(CHR')_rNR^{14f}S(O)_2(CHR')_rR^{14b}$, $C_{1-6}$ haloalkyl, $C_{2-8}$ alkenyl substituted with 0–3 R', $C_{2-8}$ alkynyl substituted with 0–3 R', $(CHR')_r$phenyl substituted with 0–3 $R^{14e}$, and a $(CH_2)_r$-5–10 membered heterocyclic system containing 1–4 heteroatoms selected from N, O, and S, substituted with 0–2 $R^{15e}$, or two $R^{14}$ substituents on adjacent atoms on ring A form to join a 5–6 membered heterocyclic system containing 1–3 heteroatoms selected from N, O, and S substituted with 0–2 $R^{15e}$;

$R^{14a}$ and $R^{14a'}$, at each occurrence, are selected from H, $C_{1-6}$ alkyl, $C_{3-8}$ alkenyl, $C_{3-8}$ alkynyl, a $(CH_2)_r$—$C_{3-10}$ carbocyclic residue substituted with 0–5 $R^{14e}$, and a $(CH_2)_r$-5–10 membered heterocyclic system containing 1–4 heteroatoms selected from N, O, and S, substituted with 0–2 $R^{14e}$;

$R^{14b}$, at each occurrence, is selected from $C_{1-6}$ alkyl, $C_{3-8}$ alkenyl, $C_{3-8}$ alkynyl, a $(CH_2)_r$—$C_{3-6}$ carbocyclic residue substituted with 0–3 $R^{14e}$, and a $(CH_2)_r$-5–6 membered heterocyclic system containing 1–4 heteroatoms selected from N, O, and S, substituted with 0–2 $R^{14e}$;

$R^{14d}$, at each occurrence, is selected from $C_{3-8}$ alkenyl, $C_{3-8}$ alkynyl, methyl, $CF_3$, $C_{2-6}$ alkyl substituted with 0–3 $R^{14e}$, a $(CH_2)_r$—$C_{3-10}$ carbocyclic residue substituted with 0–3 $R^{14e}$, and a $(CH_2)_r$-5–6 membered heterocyclic system containing 1–4 heteroatoms selected from N, O, and S, substituted with 0–3 $R^{14e}$;

$R^{14e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{14f}R^{14f}$, and $(CH_2)_r$ phenyl;

$R^{14f}$, at each occurrence, is selected from H, $C_{1-6}$ alkyl, $C_{3-6}$ cycloalkyl, and phenyl;

$R^{15}$, at each occurrence, is selected from $C_{1-8}$ alkyl, $(CH_2)_rC_{3-6}$ cycloalkyl, Cl, Br, I, F, $NO_2$, CN, $(CR'R^{17})_r$ $NR^{15a}R^{15a'}$, $(CR'R^{17})_rOH$, $(CR'R^{17})_rO(CHR')_rR^{15d}$, $(CR'R^{17})_rSH$, $(CR'R^{17})_rC(O)H$, $(CR'R^{17})_rS(CHR')_r$ $R^{15d}$, $(CR'R^{17})_rC(O)OH$, $(CR'R^{17})_rC(O)(CHR')_rR^{15b}$, $(CR'R^{17})_rC(O)NR^{15a}R^{15a'}$, $(CR'R^{17})_rNR^{15f}C(O)$ $(CHR')_rR^{15b}$, $(CR'R^{17})_rOC(O)NR^{15a}R^{15a'}$, $(CR'R^{17})_r$ $NR^{15f}C(O)O(CHR')_rR^{15b}$, $(CR'R^{17})_rNR^{15f}C(O)$ $NR^{15f}R^{15f}$, $(CR'R^{17})_rC(O)O(CHR')_rR^{15d}$, $(CR'R^{17})_rOC$ $(O)(CHR')_rR^{15b}$, $(CR'R^{17})_rC(=NR^{15f})NR^{15a}R^{15a'}$, $(CR'R^{17})_rNHC(=NR^{15f})NR^{15f}R^{15f}$, $(CR'R^{17})_rS(O)_p$ $(CHR')_rR^{15b}$, $(CR'R^{17})_rS(O)_2NR^{15a}R^{15a'}$, $(CR'R^{17})_r$ $NR^{15f}S(O)_2(CHR')_rR^{15b}$, $C_{1-6}$ haloalkyl, $C_{2-8}$ alkenyl substituted with 0–3 R', $C_{2-8}$ alkynyl substituted with 0–3 R', $(CR'R^{17})_r$phenyl substituted with 0–3 $R^{15e}$, and a $(CH_2)_r$-5–10 membered heterocyclic system containing 1–4 heteroatoms selected from N, O, and S, substituted with 0–2 $R^{15e}$;

$R^{15a}$ and $R^{15a'}$, at each occurrence, are selected from H, $C_{1-6}$ alkyl, $C_{3-8}$ alkenyl, $C_{3-8}$ alkynyl, a $(CH_2)_r$—$C_{3-10}$ carbocyclic residue substituted with 0–5 $R^{15e}$, and a $(CH_2)_r$-5–10 membered heterocyclic system containing 1–4 heteroatoms selected from N, O, and S, substituted with 0–2 $R^{15e}$;

alternatively, $R^{15a}$ and $R^{15a'}$, along with the N to which they are attached, join to form a 5–6 membered heterocyclic system containing 1–2 heteroatoms selected from $NR^{15h}$, O, and S and optionally fused with a benzene ring or a 6-membered aromatic heterocycle;

$R^{15b}$, at each occurrence, is selected from $C_{1-6}$ alkyl, $C_{3-8}$ alkenyl, $C_{3-8}$ alkynyl, a $(CH_2)_r$—$C_{3-6}$ carbocyclic residue substituted with 0–3 $R^{15e}$, and a $(CH_2)_r$-5–6 membered heterocyclic system containing 1–4 heteroatoms selected from N, O, and S, substituted with 0–2 $R^{15e}$;

$R^{15d}$, at each occurrence, is selected from $C_{3-8}$ alkenyl, $C_{3-8}$ alkynyl, methyl, $CF_3$, $C_{2-6}$ alkyl substituted with 0–3 $R^{15e}$, a $(CH_2)_r$—$C_{3-10}$ carbocyclic residue substituted with 0–3 $R^{15e}$, and a $(CH_2)_r$-5–6 membered heterocyclic system containing 1–4 heteroatoms selected from N, O, and S, substituted with 0–3 $R^{15e}$;

$R^{15e}$, at each occurrence, is selected from $C_{1-6}$ alkyl, 2-cyanoethyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{15f}R^{15a}$, $(CH_2)_r$phenyl, and a heterocycle substituted with 0–1 $R^{15g}$, wherein the heterocycle is selected from imidazole, thiazole, oxazole, pyrazole, 1,2,4-triazole, 1,2,3-triazole, isoxazole, and tetrazole, $R^{15f}$, at each occurrence, is selected from H, $C_{1-6}$ alkyl, $C_{3-6}$ cycloalkyl, and phenyl;

$R^{15g}$ is selected from methyl, ethyl, acetyl, and $CF_3$;

$R^{15h}$ is selected from H, $C_{1-6}$ alkyl, $C_{3-6}$ cycloalkyl, $(CH_2)_r$phenyl, $C(O)R^{15f}$, $C(O)OR^{15i}$, and $SO_2R^{15i}$;

$R^{15i}$, at each occurrence, is selected from $C_{1-6}$ alkyl, $C_{3-6}$ cycloalkyl;

$R^{16}$, at each occurrence, is selected from $C_{1-8}$ alkyl, $C_{2-8}$ alkenyl, $C_{2-8}$ alkynyl, $(CH_2)_rC_{3-6}$ cycloalkyl, Cl, Br, I, F, $NO_2$, CN, $(CHR')_rNR^{16a}R^{16a'}$, $(CHR')_rOH$, $(CHR')_r$ $O(CHR')_rR^{16d}$, $(CHR')_rSH$, $(CHR')_rC(O)H$, $(CHR')_rS$ $(CHR')_rR^{16d}$, $(CHR')_rC(O)OH$, $(CHR')_rC(O)(CHR')_r$ $R^{16b}$, $(CHR')_rC(O)NR^{16a}R^{16a'}$, $(CHR')_rNR^{16f}C(O)$ $(CHR')_rR^{16b}$, $(CHR')_rC(O)O(CHR')_rR^{16d}$, $(CHR')_rOC$ $(O)(CHR')_rR^{16b}$, $(CHR')_rC(=NR^{16f})NR^{16a}R^{16a'}$, $(CHR')_rNHC(=NR^{16f})NR^{16f}R^{16f}$, $(CHR')_rS(O)_p$ $(CHR')_rR^{16b}$, $(CHR')_rS(O)_2NR^{16a}R^{16a'}$, $(CHR')_r$ $NR^{16f}S(O)_2(CHR')_rR^{16b}$, $C_{1-6}$ haloalkyl, $C_{2-8}$ alkenyl substituted with 0–3 R', $C_{2-8}$ alkynyl substituted with 0–3 R', and $(CHR')_r$phenyl substituted with 0–3 $R^{16e}$;

$R^{16a}$ and $R^{16a'}$, at each occurrence, are selected from H, $C_{1-6}$ alkyl, $C_{3-8}$ alkenyl, $C_{3-8}$ alkynyl, a $(CH_2)_r$—$C_{3-10}$ carbocyclic residue substituted with 0–5 $R^{16e}$, and a $(CH_2)_r$-5–10 membered heterocyclic system containing 1–4 heteroatoms selected from N, O, and S, substituted with 0–2 $R^{16e}$;

$R^{16b}$, at each occurrence, is selected from $C_{1-6}$ alkyl, $C_{3-8}$ alkenyl, $C_{3-8}$ alkynyl, a $(CH_2)_rC_{3-6}$ carbocyclic residue substituted with 0–3 $R^{16e}$, and a $(CH_2)_r$-5–6 membered heterocyclic system containing 1–4 heteroatoms selected from N, O, and S, substituted with 0–2 $R^{16e}$;

$R^{16d}$, at each occurrence, is selected from $C_{3-8}$ alkenyl, $C_{3-8}$ alkynyl, methyl, $CF_3$, $C_{2-6}$ alkyl substituted with 0–3 $R^{16e}$, a $(CH_2)_r$—$C_{3-10}$ carbocyclic residue substituted with 0–3 $R^{16e}$, and a $(CH_2)_r$-5–6 membered heterocyclic system containing 1–4 heteroatoms selected from N, O, and S, substituted with 0–3 $R^{16e}$;

$R^{16e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{16f}R^{16f}$, and $(CH_2)_r$ phenyl;

$R^{16f}$, at each occurrence, is selected from H, $C_{1-5}$ alkyl, and $C_{3-6}$ cycloalkyl, and phenyl;

$R^{17}$, at each occurrence, is independently selected from H and methyl;

R', at each occurrence, is selected from H, $C_{1-6}$ alkyl, $C_{3-8}$ alkenyl, $C_{3-8}$ alkynyl, $(CH_2)_rC_{3-6}$ cycloalkyl, and $(CH_2)_r$phenyl substituted with $R^{15e}$;

g is selected from 0, 1, 2, 3, and 4;
v is selected from 0, 1, and 2;
t is selected from 1 and 2;
w is selected from 0 and 1;
r is selected from 0, 1, 2, 3, 4, and 5;
q is selected from 1, 2, 3, 4, and 5; and
p is selected from 0, 1, and 2.

2. The compound of claim 1, wherein:
Z is selected from O, S, N(CN), and N(CONH$_2$);
$R^2$ is selected from H and $C_{1-4}$ alkyl;
$R^6$, at each occurrence, is selected from $C_{1-4}$ alkyl, $C_{2-8}$ alkenyl, $C_{2-8}$ alkynyl, $(CH_2)_rC_{3-6}$ cycloalkyl, $(CF_2)_r$ $CF_3$, CN, $(CH_2)_rOH$, $(CH_2)_rOR^{6b}$, $(CH_2)_rC(O)R^{6b}$, $(CH_2)_rC(O)NR^{6a}R^{6a'}$, $(CH_2)_rNR^{6d}C(O)R^{6a}$, and $(CH_2)_t$ phenyl substituted with 0–3 $R^{6c}$;

$R^{6a}$ and $R^{6a'}$, at each occurrence, are selected from H, $C_{1-6}$ alkyl, $C_{3-6}$ cycloalkyl, and phenyl substituted with 0–3 $R^{6c}$;

$R^{6b}$, at each occurrence, is selected from $C_{1-6}$ alkyl, $C_{3-6}$ cycloalkyl, and phenyl substituted with 0–3 $R^{6c}$;

$R^{6c}$, at each occurrence, is selected from $C_{1-6}$ alkyl, $C_{3-6}$ cycloalkyl, Cl, F, Br, I, CN, $NO_2$, $(CF_2)_rCF_3$, $(CH_2)_r$ $OC_{1-5}$ alkyl, $(CH_2)_rOH$, $(CH_2)_rSC_{1-5}$ alkyl, and $(CH_2)_r$ $NR^{6d}R^{6d}$;

$R^{6d}$, at each occurrence, is selected from H, $C_{1-6}$ alkyl, and $C_{3-6}$ cycloalkyl;

$R^{13}$, at each occurrence, is selected from $C_{1-4}$ alkyl, $C_{3-6}$ cycloalkyl, $(CH_2)NR^{13a}R^{13a'}$, $(CHR')OH$, $(CH_2)$ $OR^{13b}$, $(CH_2)_wC(O)R^{13b}$, $(CH_2)_nC(O)NR^{13a}R^{13a'}$, $(CH_2)NR^{13d}C(O)R^{13a}$, $(CH_2)_nS(O)_2NR^{13a}R^{13a'}$, $(CH_2)$ $NR^{13d}S(O)_2R^{13b}$, and $(CH_2)_w$-phenyl substituted with 0–3 $R^{13c}$;

$R^{13a}$ and $R^{13a'}$, at each occurrence, are selected from H, $C_{1-6}$ alkyl, $C_{3-6}$ cycloalkyl, and phenyl substituted with 0–3 $R^{13c}$;

$R^{13b}$, at each occurrence, is selected from $C_{1-6}$ alkyl, $C_{3-6}$ cycloalkyl, and phenyl substituted with 0–3 $R^{13c}$;

$R^{13c}$, at each occurrence, is selected from $C_{1-6}$ alkyl, $C_{3-6}$ cycloalkyl, Cl, F, Br, I, CN, $NO_2$, $(CF_2)_rCF_3$, $(CH_2)_r$ $OC_{1-5}$ alkyl, $(CH_2)_rOH$, and $(CH_2)_rNR^{13d}R^{13d}$;

$R^{13d}$, at each occurrence, is selected from H, $C_{1-6}$ alkyl, and $C_{3-6}$ cycloalkyl;

v is selected from 0, 1 and 2;
q is selected from 1, 2, and 3; and
r is selected from 0, 1, 2, and 3.

3. The compound of claim 2, wherein:
E is —(C=O)—$(CR^9R^{10})_v$—$(CR^{11}R^{12})$—, —$(SO_2)$— $(CR^9R^{10})_v$—$(CR^{11}R^{12})$—,

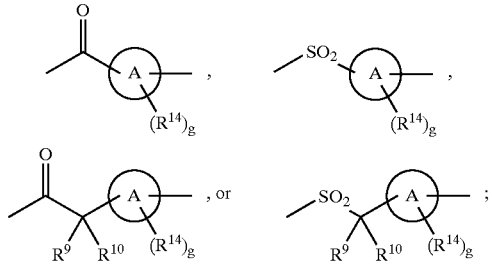

$R^3$ is selected from $(CH_2)_2N(CH_3)_2$, a $(CR^{3'}H)_r$-carbocyclic residue substituted with 0–5 $R^{15}$, wherein the carbocyclic residue is selected from phenyl, $C_{3-6}$ cycloalkyl, naphthyl, and adamantyl; and a $(CR^{3'}H)_r$-heterocyclic system substituted with 0–3 $R^{15}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl; and $R^5$ is selected from $(CR^{5'}H)_r$-phenyl substituted with 0–5 $R^{16}$; and a $(CR^{5'}H)_r$-heterocyclic system substituted with 0–3 $R^{16}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl.

4. The compound of claim 3, wherein
$R^{16}$, at each occurrence, is selected from $C_{1-8}$ alkyl, $(CH_2)_rC_{3-6}$ cycloalkyl, $CF_3$, Cl, Br, I, F, $(CH_2)_r$ $NR^{16a}R^{16a'}$, $NO_2$, CN, OH, $(CH_2)_rOR^{16d}$, $(CH_2)_rC(O)$ $R^{16b}$, $(CH_2)_rC(O)NR^{16a}R^{16a'}$, $(CH_2)_rNR^{16f}C(O)R^{16b}$, $(CH_2)_rS(O)_pR^{16b}$, $(CH_2)_rS(O)_2NR^{16a}R^{16a'}$, $(CH_2)_rNR^{16f}S(O)_2R^{16b}$, and $(CH_2)_r$phenyl substituted with 0–3 $R^{16e}$;

$R^{16a}$ and $R^{16a'}$, at each occurrence, are selected from H, $C_{1-6}$ alkyl, $C_{3-6}$ cycloalkyl, and $(CH_2)_r$phenyl substituted with 0–3 $R^{16e}$;

$R^{16b}$, at each occurrence, is selected from $C_{1-6}$ alkyl, $C_{3-6}$ cycloalkyl, and $(CH_2)_r$phenyl substituted with 0–3 $R^{16e}$;

$R^{16d}$, at each occurrence, is selected from $C_{1-6}$ alkyl and phenyl;

$R^{16e}$, at each occurrence, is selected from $C_{1-6}$ alkyl, Cl, F, Br, I, CN, $NO_2$, $(CF_2)_rCF_3$, OH, and $(CH_2)_rOC_{1-5}$ alkyl; and $R^{16f}$, at each occurrence, is selected from H, and $C_{1-5}$ alkyl.

5. The compound of claim 4, wherein:

E is —(C=O)—$(CR^9R^{10})_v$—$(CR^{11}R^{12})$—, or

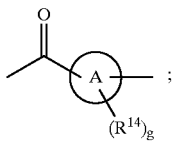

$R^5$ is $CH_2$phenyl substituted with 0–3 $R^{16}$; and r is selected from 0, 1, and 2.

6. The compound of claim 5, wherein:

K is selected from $CH_2$ and $CHR^5$;

L is selected from $CH_2$ and $CHR^5$; and $R^3$ is a $(CH_2)_r$—$C_{3-10}$ carbocyclic residue substituted with 0–3 $R^{15}$, wherein the carbocyclic residue is selected from cyclopropyl, cyclobutyl, cyclopentyl, cyclohexyl, phenyl, naphthyl and adamantyl, and a $(CR^3H)_r$-heterocyclic system substituted with 0–3 $R^{15}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl.

7. The compound of claim 3, wherein:

K and L are independently selected from $CH_2$ and $CHR^5$;

Z is O, S, NCN, or $NCONH_2$;

$R^1$ is H;

$R^2$ is H;

$R^3$ is selected from a $(CH_2)_rN(CH_3)_2$, a $(CH_2)_r$—$C_{3-10}$ carbocyclic residue substituted with 0–3 $R^{15}$, wherein the carbocyclic residue is selected from cyclopropyl, cyclobutyl, cyclopentyl, cyclohexyl, phenyl, naphthyl and adamantyl, and a $(CR^3H)_r$-heterocyclic system substituted with 0–3 $R^{15}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl; and $R^5$ is selected from a $CH_2$-phenyl substituted with 0–5 $R^{16}$ and a $CH_2$-heterocyclic system substituted with 0–3 $R^{16}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl.

8. A pharmaceutical composition, comprising a pharmaceutically acceptable carrier and a therapeutically effective amount of a compound according to claim 1.

9. A method for treating or preventing asthma, comprising administering to a patient in need thereof a therapeutically effective amount of a compound according to claim 1.

10. A pharmaceutical composition comprising a pharmaceutically acceptable carrier and a therapeutically effective amount of a compound according to claim 1, or a pharmaceutically acceptable salt thereof.

11. A method for treating inflammation in an inflammatory disorders comprising administering to a patient in need thereof a therapeutically effective amount of a compound according to claim 7, or a pharmaceutically acceptable salt thereof, wherein the disorder is selected from asthma, allergic rhinitis, atopic dermatitis, inflammatory bowel diseases, idiopathic pulmonary fibrosis, bullous pemphigoid, allergic eczema, conjunctivitis, transplantation, familial eosinophilia, eosinophilic cellulitis, eosinophilic pneumonias, eosinophilic fasciitis, and eosinophilic gastroenteritis.

12. The method according to claim 11, wherein the disorder is selected from asthma, allergic rhinitis, atopic dermatitis, and inflammatory bowel diseases.

13. The method according to claim 12, wherein the disorder is asthma.

* * * * *

UNITED STATES PATENT AND TRADEMARK OFFICE
CERTIFICATE OF CORRECTION

PATENT NO.         : 6,984,651 B2
APPLICATION NO.    : 10/635946
DATED              : January 10, 2006
INVENTOR(S)        : John V. Duncia et al.

It is certified that error appears in the above-identified patent and that said Letters Patent is hereby corrected as shown below:

Title Page:
Related U.S. Application Data, delete "Division of application No. 09/885,550, filed on June 29, 2001," and insert -- Division of application No. 09/885,550, filed on June 20, 2001, --;

Column 200:
Line 5, delete the "$(CH_2)_nC(O)NR^{13a}R^{13a'}$" and insert
-- $(CH_2)_wC(O)NR^{13a}R^{13a'}$, --;
Line 6, delete the "$(CH_2)_nS(O)_2NR^{13a}R^{13a'}$," and insert
-- $(CH_2)_wS(O)_2NR^{13a}R^{13a'}$, --;

Column 202:
Lines 42-43, delete the "bullous pemphigoid, allergic eczema, conjunctivitis," and insert -- bullous pemphigoid, allergic collitis, eczema, conjunctivitis, --.

Signed and Sealed this

Third Day of October, 2006

JON W. DUDAS
*Director of the United States Patent and Trademark Office*